(12) United States Patent
Thurston et al.

(10) Patent No.: US 6,608,192 B1
(45) Date of Patent: Aug. 19, 2003

(54) COLLECTIONS OF COMPOUNDS

(75) Inventors: David Edwin Thurston, University Park (GB); Philip Wilson Howard, University Park (GB)

(73) Assignee: Spirogen Limited, Ryde (GB)

( * ) Notice: Subject to any disclaimer, the term of this patent is extended or adjusted under 35 U.S.C. 154(b) by 0 days.

(21) Appl. No.: 09/763,768

(22) PCT Filed: Aug. 27, 1999

(86) PCT No.: PCT/GB99/02836

§ 371 (c)(1),
(2), (4) Date: Feb. 26, 2001

(87) PCT Pub. No.: WO00/12506

PCT Pub. Date: Mar. 9, 2000

(30) Foreign Application Priority Data

Aug. 27, 1998 (GB) ............................................. 9818730

(51) Int. Cl.[7] .......................................... C07D 487/00
(52) U.S. Cl. ....................................................... 540/496
(58) Field of Search ......................................... 540/496

(56) References Cited

U.S. PATENT DOCUMENTS

| | | | | |
|---|---|---|---|---|
| 3,523,941 A | * | 8/1970 | Leimgruber et al. | 260/239.3 |
| 3,524,849 A | | 8/1970 | Batcho et al. | 260/239.3 |
| 4,239,683 A | | 12/1980 | Takanabe et al. | 260/239.3 T |
| 4,309,437 A | * | 1/1982 | Ueda et al. | 424/274 |
| 5,545,568 A | | 8/1996 | Ellman | 436/518 |

FOREIGN PATENT DOCUMENTS

| | | |
|---|---|---|
| FR | 2 586 683 | 3/1987 |
| GB | 1 299 198 | 12/1972 |
| JP | 57 131 791 | 8/1982 |
| JP | 58 180 487 | 10/1983 |
| WO | WO 92/19620 | 11/1992 |
| WO | WO 97/01560 | 1/1997 |

OTHER PUBLICATIONS

Lown et al., Biochem. Pharmacol. (1979), 28 (13), 2017–26; Abstract.*
Leimgruber et al., Am. Chem. Soc., 87, 5793–5795 (1965).
Leimgruber et al., J. Am. Chem. Soc., 87, 5791–5793 (1965).
Thurston et al., Chem. Rev., 1994, 433–465 (1994).
Hochlowski et al., J. Antibiotics, 40, 145–148 (1987).
Konishi et al., J. Antibiotics, 37, 200–206 (1984).
Thurston et al., Chem. Brit., 26, 767–772 (1990).
Bose et al., Tetrahedron, 48, 751–758 (1992).
Kunimoto et al., J. Antibiotics, 33, 665–667 (1980).
Takeuchi et al., J. Antibiotics, 29, 93–96 (1976).
Tsunakawa, et al., J. Antibiotics, 41, 1366–1373 (1988).
Shimizu et al., J. Antiobiotics, 29, 2492–2503 (1982).
Langley and Thurston, J. Org. Chem., 52, 91–97 (1987).
Hara et al., J. Antibiotics, 41, 702,704 (1988).
Itoh et al., J. Antibiotics, 41, 1281–1284 (1988).
Leber et al., J. Am. Chem. Soc., 110, 2992–2993 (1988).

Arima et al., J. Antibiotics, 25, 437–444 (1972).
Kohn, Antibiotics III, Springer–Verlag, NY, 3–11 (1975).
Hurley and Needham–VanDevanter, Acc. Chem. Res., 19, 230–237 (1986).
Baraldi, P. G. et al., "Design, synthesis and biological activity of a pyrrolo [2,1-c][1,4]benzodiazepine (PBD)–distamycin hybrid", Bioorganic & Medicinal Chemistry Letters, vol. 8, No. 21, 3019–3024 (1998).
Monks, A. et al., Journal of National Cancer Institute, 83, 757 (1991).
Schreiber et al., JACS, 120, 23–29 (1998).
Soth, M. J. and Nowick, J. S., "Unnatural oligomer libraries", Curr. Opin. Chem. Biol., 1, 120–129 (1997).
Zuckermann et al., "Discovery of Nanomolecular Ligands for 7–Transmembrane G–Protein–Coupled Receptors from a Diverse N–(Substituted) glycine Peptoid Library", Journal of Medicinal Chemistry, 37, 2678–85 (1994).
Figliozzi, GMR et al., "Synthesis of N–substituted Glycine Peptoid Libraries", Methods in Enzymology, 267, 437–47 (1996).
Simon, R. J. et al., Peptoids: A Modular Approach to Drug Discovery, Proc. Natl. Acad. Sci. USA, 89, 9367–71 (1992).
P E Nielson et al., Science, 254, 1497 (1991).
M Egholm et al., Nature, 365, 566 (1993).
M Egholm et al., JACS, 114, 1895 (1992).
S C Brown et al., Science, 265, 777 (1994).
K Saha et al., JOC, 58, 7827 (1993).
K Burgess et al., "Solid Phase Synthesis of Unnatural Biopolymers Containing Repeating Urea Units" Agnew Chem. Int. Ed. Engl, 34, No. 8:907 (1995).
K Burgess et al., "Solid Phase Synthesis of Oligoureas", Journal of the American Chemical Society, 119: 1556–64 (1997).
E J Moran et al., "Novel Biopolymers for Drug Discovery. Biopolymers", Peptide Science, John Wiley and Sons, 37: 213–19 (1995).
Cho, C Y et al., "An Unnatural Biopolymer", Science, 261: 1303–5 (1993).

(List continued on next page.)

Primary Examiner—Bruck Kifle
(74) Attorney, Agent, or Firm—Michael Best & Friedrich LLP; Grady J. Frenchick; Charlene Yager

(57) ABSTRACT

A compound of formula (IV): O is a solid support; L is a linking group or a single bond; X' is selected from CO, NH, S, or O; A is O, S, NH, or a single bond; $R_2$ and $R_3$ are independently selected from: H, R, OH, OR, =O, =CH—R, =CH$_2$, CH$_2$—CO$_2$R', CH$_2$—CO$_2$H, CH$_2$—SO$_2$R, O—SO$_2$R, CO$_2$R, COR, CN and there is optionally a double bond between C1 and C2 or C2 and C3; $R_6$, $R_7$, and $R_9$ are independently selected from H, R, OH, OR, halo, nitro, amino, Me$_3$Sn; $R_{11}$ is either H or R; Q is S, O or NH; $R_{10}$ is a nitrogen protecting group; and Y is a divalent group such that HY=R, and other related compounds and collections of compounds.

12 Claims, 49 Drawing Sheets

OTHER PUBLICATIONS

Paikoff S F et al., "The Solid Phase Synthesis of N–Alkylcarbamate Oligomers", *Tetrahedron Letters*, 37, No. 32: 5653–56 (1996).

Boger et al., *Chem. Rev.*, 97, 787–828 (1997).

Cava et al., Drost, K. J., Cava, M. P., *J. Org. Chem.*, 56, 2240–2244 (1991).

Rawal, V. H., Jones, R. J., Cava, M. P., *J. Org. Chem.*, 52, 19–28 (1987).

Aristoff, *J. Org. Chem.*, 57, 6234–6239 (1992).

Thurston, D. E. et al., "Synthesis of a novel GC–specific covalent–binding DNA affinity–cleavage agent based on pyrrolobenzodiazepines", *Chemical Communications*, 563–565 (1996).

Chemical Abstracts, Yingzhi, Bi. et al., "Building blocks for peptide and carbamate libraries", *Chemical Abstracts*, vol. 125, No. 23, 1013 (1996).

Furka, A. et al., *International Journal of Peptide and Protein Research*, 37, 487–493 (1991).

Lescrinier, et al., *Chem. Eur. J.*, 425–433 (1998).

Edman, P. and Begg, G., *Eur. J. Biochem.*, 1, 80 (1967).

Althuis, T.H. and Hess, H.J.,*J. Medicinal Chem.*, 20(1), 146–149 (1977).

Thurston, D.E., "Advances in the study of Pyrrolo[2,1–c][4,1] benzodiazepine (PBD) Antitumour Antibiotics", *Molecular Aspects of Anticancer Drug–DNA interactions*, Neidle, S., Waring, M.J. eds., Macmillan Press Ltd., 1: 54–88 (1993).

Nagasaka, T. et al.,. "Stereoselective synthesis of Tilivalline", *Tetrahedron Letters*, vol. 30, No. 14, 1871–72 (1989).

Fukuyama, T. et al., "Total synthesis of (+)–porothramycin B", *Tetrahedron Letters*, vol. 34, No. 16, 2577–2580 (1993).

Wilson, S. C. et al., "Design and Synthesis of a Novel Epoxide–Containing Pyrrolo[2,1–c][1,4]benzodiazepine (PBD) via a New Cyclization Procedure", *Tetrahedron Letters*, vol. 36, No. 35, 6333–6336 (1995).

Nagasaka, T. et al.,. "Stereoselective synthesis of tilivalline", *Journal of Organic Chemistry*, vol. 36, No. 20, 6797–6801 (1998).

Guiotto A. et al., "Synthesis of novel C7–aryl substituted pyrrolo [2,1–c][1,4]benzodiazepines (PBDs) via Pro–N10–troc protection and suzuki coupling", *Bioorgnainc & Medicinal Chemistry Letters*, vol. 8, No. 21, 3017–3018 (1998).

Gregson, S. J. et al., "Synthesis of a novel C2/C2'–exo unsaturated pyrrolobenzodiazepine cross–linking agent with remarkable DNA binding affinity and cytotoxicity", *Chemical Communications*, 797–798 (1999).

Chemical Abstract No. 4427a, Umezawa, "Mazethramycins" *Chemical Abstracts*, vol. 90, No. 1, 428 (1979).

Chemical Abstract No. 72145x, Fujisawa, "Benzodiazepine derivatives", *Chemical Abstracts*, vol. 98, No. 9, 638 (1983).

Chemical Abstract No. 171573p, O'Neil, "The synthesis of Functionalized Pyrrolo–[2,1–c][1,4]–Benzodiazepines", *Chemical Abstracts*, vol. 126, No. 13, 618 (1997) and entire article.

Chemical Abstract No. 239940r, Farmer, "DNA binding properties of a new class of linked anthramycin analogs", *Chemical Abstracts*, vol. 114, No. 25, 25 (1991) and entire article.

Courtney, S. M. et al., "A new convenient procedure for the synthesis of pyrrolo[2,1–c][1,4]benzodiazepines", *Tetrahedron Letters*, vol. 34, No. 33, 5327–28 (1993).

O'Neil, I. A. et al., "DPPE: A Convenient Replacement for Triphenylphosphine in the Staudinger and Mitsunobu Reactions", *Tetrahedron Letters*, vol. 39, No. 42, 7787–7790 (1998).

Thurston, D. E., et al., "Effect of A–ring modifications on the DNA–binding behavior and cytotoxicity of pyrrolo[2,1–c][1,4]benzodiazepines", *Journal of Medicinal Chemistry*, vol. 42, 1951–1964 (1999).

Bi, Y., et al., *Bioorganic & Medicinal Chemistry Letters*, vol. 6, No. 19, 2299–2300 (1996).

Chemical Abstracts No. 139983k, Fujisawa, *Chemical Abstracts*, vol. 99, No. 17, 603 (1983).

Bose, D.S., et al., J.Am.Chem.Soc. 1992, 114, 4939–4941.

Jenkins, T.C., et al., J. Med.Chem. 1994, 37, 4529–4537.

Foloppe, M.P., et al., "DNA–binding properties of pyrrolo [2,1–c][1,4]benzodiazepine N10–C11 amidines" *Eur. J. Med. Chem.*,31, 407–410 (1996).

\* cited by examiner 5a, 6a, 7a: R₁₀ = Nvoc
5b, 6b, 7b: R₁₀ = Fmoc
5c, 6c, 7c: R₁₀ = Teoc a: 20% piperidine/DMF; b: (i) Fmoc.glycine,
TBTU, DIPEA, DMF; (ii) 20% Ac₂O, 30% pyridine, 50% CH₂Cl₂ a: (i) TBTU, DIPEA, DMF (ii) 20% Ac2O, 30% pyridine, 50% CH2Cl2;
b: 20% piperidine/DMF; c:hn a: 20% piperidine/DMF; b: (i) Fmoc.glycine, valine, phenylalanine, TBTU, DIPEA, DMF; (ii) 20% Ac₂O, 30% pyridine, 50% CH₂Cl₂

38 R = H, CH₃ OR CH₂Ph a: (i) TBTU, DIPEA; DMF (ii) 20% Ac₂O, 30% pyridine, 50% CH₂Cl₂;
b: 20% piperidine/DMF

COLLECTIONS OF COMPOUNDS

This invention relates to collections of pyrrolobenzodiazepines, to methods of synthesizing these compounds on solid supports, and to compounds of utility therein. This invention further relates to methods for identifying and isolating pyrrolobenzodiazepine compounds with useful and diverse activities from such collections.

BACKGROUND TO THE INVENTION

Compounds having biological activity can be identified by screening collections of compounds (i.e. libraries of compounds) produced through synthetic chemical techniques. Such screening methods include methods wherein the library comprises a plurality of compounds synthesized at specific locations on the surface of a solid support where a receptor is appropriately labelled to identify binding to the compound, e.g., fluorescent or radioactive labels. Correlation of the labelled receptor bound to the support with its location on the support identifies the binding compound (U.S. Pat. No. 5,143,854).

Central to these methods is the screening of a multiplicity of compounds in the library and the ability to identify the structures of the compounds which have a requisite biological activity. In order to facilitate synthesis and identification, the compounds in the library are typically formed on solid supports. Usually each such compound is covalently attached to the support via a cleavable or non-cleavable linking arm. The libraries of compounds can be screened either on the solid support or as cleaved products to identify compounds having good biological activity.

BACKGROUND TO THE INVENTION

A large number of both synthetic and naturally occurring low molecular weight ligands are known that interact with DNA via a number of different mechanisms, including covalent or non-covalent interaction in the minor or major grooves, intercalation between base pairs or other types of non-specific interactions.

A particular class of compounds which interacts with the minor groove are the pyrrolobenzodiazepines (PBDs). PBDs have the ability to recognise and bond to specific sequences of DNA; the most preferred sequence is PuGPu (Purine-Guanine-Purine). The first PBD antitumour antibiotic, anthramycin, was discovered in 1965 (Leimgruber et al., 1965 J. Am. Chem. Soc., 87, 5793–5795; Leimgruber et al., 1965 J. Am. Chem. Soc., 87, 5791–5793). Since then, a number of naturally occurring PBDs have been reported, and over 10 synthetic routes have been developed to a variety of analogues (Thurston et al., 1994 Chem. Rev. 1994, 433–465). Family members include abbeymycin (Hochlowski et al., 1987 J. Antibiotics, 40, 145–148), chicamycin (Konishi et al., 1984 J. Antibiotics, 37, 200–206), DC-81 (Japanese Patent 58-180 487; Thurston et al., 1990, Chem. Brit., 26, 767–772; Bose et al., 1992 Tetrahedron, 48, 751–758), mazethramycin (Kuminoto et al., 1980 J. Antibiotics, 33, 665–667), neothramycins A and B (Takeuchi et al., 1976 J. Antibiotics, 29, 93–96), porothramycin (Tsunakawa et al., 1988 J. Antibiotics, 41, 1366–1373), prothracarcin (Shimizu et al., 1982 J. Antibiotics, 29, 2492–2503; Langley and Thurston, 1987 J. Org. Chem., 52, 91–97), sibanomicin (DC-102)(Hara et al., 1988 J. Antibiotics, 41, 702–704; Itoh et al., 1988 J. Antibiotics, 41, 1281–1284), sibiromycin (Leber et al., 1988 J. Am. Chem. Soc., 110, 2992–2993) and tomamycin (Arima et al., 1972 J. Antibiotics, 25, 437–444).

PBDs are of the general structure:

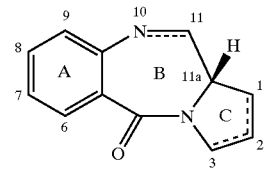

They differ in the number, type and position of substituents, in both their aromatic A rings and pyrrolo C rings, and in the degree of saturation of the C ring. There is either an imine (N=C), carbinolamine (NH—CH(OH)) or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In Antibiotics III. Springer-Verlag, New York, pp. 3–11; Hurley and Needham-VanDevanter, 1986 Acc. Chem. Res., 19, 230–237). Their ability to form an adduct in the minor groove enables them to interfere with DNA processing, hence their use as antitumour agents.

DISCLOSURE OF THE INVENTION

A first aspect of the present invention relates to compounds of formula (I):

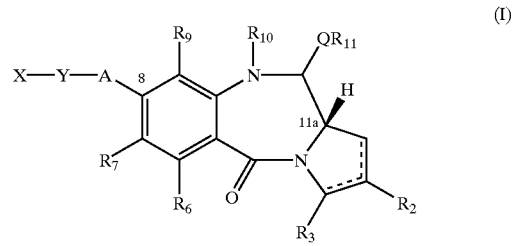

wherein:

X is selected from COOH, NHZ, SH, or OH, where Z is either H or an amine protecting group;

A is O, S, NH, or a single bond;

$R_2$ and $R_3$ are independently selected from: H, R, OH, OR, =O, =CH—R, =$CH_2$, $CH_2$—$CO_2R$, $CH_1$—$CO_2H$, $CH_2$—$SO_2R$, O—$SO_2R$, $CO_2R$, COR and CN, and there is optionally a double bond between $C_1$ and $C_2$ or $C_2$ and $C_3$;

$R_6$, $R_7$, and $R_9$ are independently selected from H, R, OH, OR, halo, nitro, amino, $Me_3Sn$;

$R_{11}$, is either H or R;

Q is S, O or NH;

$R_{10}$ is a nitrogen protecting group;

where R is a lower alkyl group having 1 to 10 carbon atoms, or an aralkyl group (i.e. an alkyl group with one or more aryl substituents), preferably of up to 12 carbon atoms, whereof the alkyl group optionally contains one or more carbon-carbon double or triple bonds, which may form part of a conjugated system, or an aryl group, preferably of up to 12 carbon atoms; and is optionally substituted by one or more halo, hydroxy, amino, or nitro groups, and optionally contains one or more hetero atoms, which may form part of, or be, a functional group; and Y is a divalent group such that HY=R.

These compounds are useful in the synthesis of collections of pyrrolobenzodiazepines. Compounds of formula I can be attached to a solid support, e.g. via a connecting link which may comprise a chain of combinatorial units. Without N10-protection, the risk of undesirable side reactions with the imine bond during the coupling step would be greater.

If R is an aryl group, and contains a hetero atom, then R is a heterocyclic group. If R is an alkyl chain, and contains a hetero atom, the hetero atom may be located anywhere in the alkyl chain, e.g. —O—$C_2H_5$, —$CH_2$—S—$CH_3$, or may form part of, or be, a functional group, e.g. carbonyl, hydroxy.

R and HY groups are preferably independently selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R and HY groups are independently selected from lower alkyl groups having 1 to 10 carbon atoms optionally substituted by one or more halo, hydroxy, amino, or nitro groups. It is particularly preferred that R or HY are unsubstituted straight or branched chain alkyl groups, having 1 to 10, preferably 1 to 6, and more preferably 1 to 4, carbon atoms, e.g. methyl, ethyl, propyl, butyl.

Alternatively, $R_6$, $R_7$, and $R_9$, may preferably be independently selected from R groups with the following structural characteristics:

(i) an optionally substituted phenyl group;

(ii) an optionally substituted ethenyl group;

(iii) an ethenyl group conjugated to an electron sink. The term 'electron sink' means a moiety covalently attached to a compound which is capable of reducing electron density in other parts of the compound. Examples of electron sinks include cyano, carbonyl and ester groups.

The term 'nitrogen protecting group' (or 'amine protecting group') has the meaning usual in synthetic chemistry, particularly synthetic peptide chemistry. It means any group which may be covalently bound to the nitrogen atom of the pyrrolobenzodiazepine (or amine) grouping, and permits reactions to be carried out upon the molecule containing this grouping without its removal. Nevertheless, it is able to be removed from the nitrogen atom without affecting the remainder of the molecule. Suitable nitrogen protecting groups for the present invention include Fmoc (9-fluorenylmethoxycarbonyl), Nvoc (6-nitroveratryloxycarbonyl), Teoc (2-trimethylsilylethyloxycarbonyl), Troc (2,2,2-trichloroethyloxycarbonyl), Boc (t-butyloxycarbonyl), CBZ (benzyloxycarbonyl), Alloc (allyloxycarbonyl), and Psec (2(-phenylsulphonyl)ethyloxycarbonyl). Other suitable groups are described in Protective Groups in Organic Synthesis, T Green and P Wuts, published by Wiley, 1991, which is incorporated herein by reference. It is preferred that the nitrogen protecting group has a carbamate functionality where it binds to the nitrogen atom at the 10 position of the PBD ring structure.

$R_7$ is preferably an electron donating group. 'Electron donating group' means a moiety covalently attached to a compound which is capable of increasing electron density in other parts of the molecule. Examples of electron donating groups useful in the present invention include alkyl, amine, hydroxyl, alkoxy and the like.

In compounds of formula I, Q is preferably O, and $R_{11}$ is preferably H. Independently, $R_6$ and $R_9$ are preferably H, and $R_7$ is preferably an alkoxy group, and more preferably methoxy or ethoxy. It is further preferred that if there is a double bond in the C ring, it is between C2 and C3. In this case, $R_2$ and $R_3$ are preferably H.

—Y—A— is preferably an alkoxy chain, preferably an ethoxy chain.

A second aspect of the present invention relates to compounds of formula II:

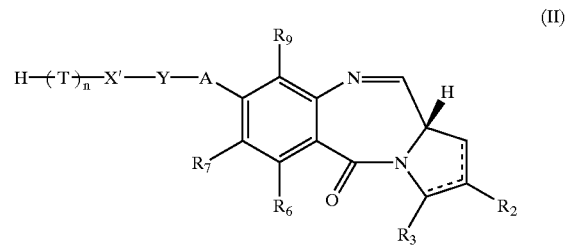

(II)

wherein

Y, A, $R_7$, $R_2$, $R_3$, $R_6$, and $R_9$ are as defined in the first aspect of the invention;

X' is CO, NH, S or O;

T is a combinatorial unit;

and n is a positive integer, where if n is greater than 1, each T may be different.

It is preferred that X' is either CO or NH. n may preferably be from 1 to 16, and more preferably from 3 to 14.

A third aspect of the present invention relates to compounds of the formula III:

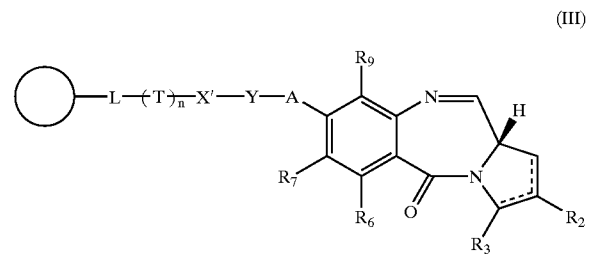

(III)

wherein

X', Y, A, $R_7$, $R_2$, $R_3$, $R_6$, $R_9$, and T are as defined in the second aspect of the invention;

n is zero or a positive integer;

L is a linking group, or less preferably a single bond;

and ○ is a solid support, where if n is greater than 1, each T may be different.

A fourth aspect of the present invention relates to compounds of the formula IV:

(IV)

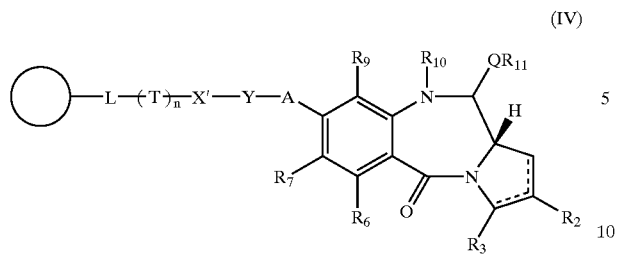

wherein X', Y, A, $R_7$, $R_2$, $R_3$, $R_6$, $R_9$, T, n, L and ◯ are as defined in the third aspect of the invention, and $R_{10}$, $R_{11}$, and Q are as defined in the first aspect of the invention.

A fifth aspect of the present invention relates to a method of making compounds of formula IV as described in the fourth aspect of the invention by reacting compounds of formula I with compounds of formula V:

(V)

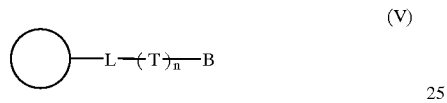

wherein ◯, L, T and n are as defined in the fourth aspect of the invention, and B is H or an atom or group for providing a functional group capable of reaction with X.

A sixth aspect of the present invention relates to compounds of formula VI:

(VI)

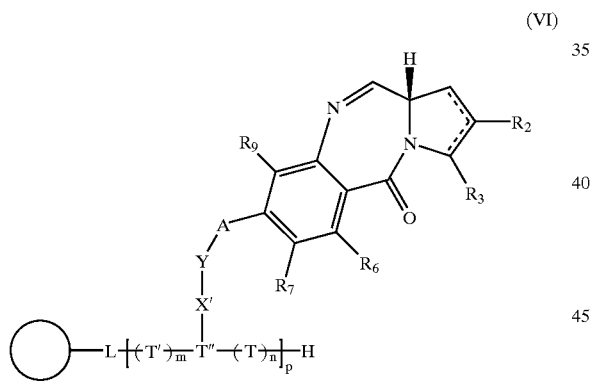

wherein

◯, L, X', Y, A, $R_2$, $R_3$, $R_6$, $R_7$, $R_9$ and T are as defined in the second aspect of the invention;

n and m are positive integers, or one of them may be zero;

T' is a combinatorial unit, where each T' may be different if m is greater than 1;

T" is a combinatorial unit which provides a site for the attachment of X'; and p is a positive integer, where if p is greater than 1, for each repeating unit, the meaning of X', Y, A, $R_2$, $R_3$, $R_6$, $R_7$, $R_9$, T, T', T" and the values of n and m are independently selected.

For example, if X' is CO then the site on T" may be NH, and if X' is NH, S or O, then the site on T" may be CO.

In a preferred aspect of the sixth aspect of the present invention, the compound is of formula (VIa):

(VIa)

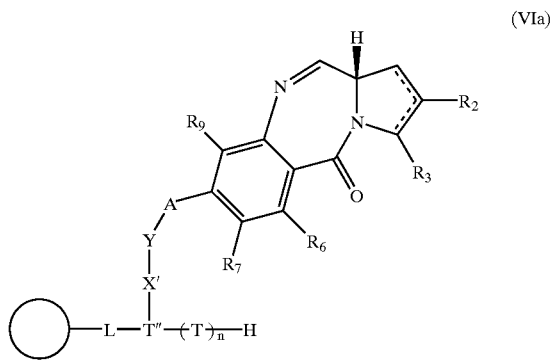

wherein ◯, L, X', Y, A, $R_2$, $R_3$, $R_6$, $R_7$, $R_9$, T, T" are as defined above.

A seventh aspect of the present invention relates to compounds of formula VII:

(VII)

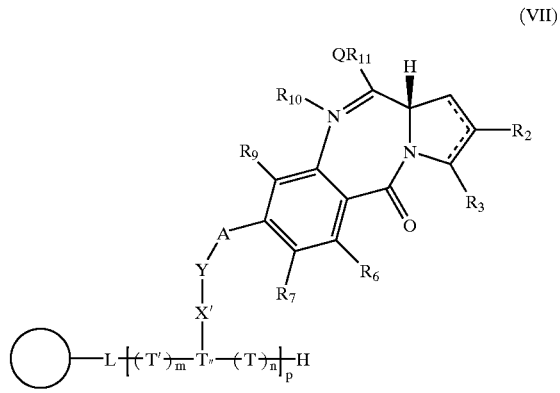

wherein ◯, L, X', Y, A, $R_2$, $R_3$, $R_6$, $R_7$, $R_9$, T, T', T", n, m and p are as defined in the sixth aspect and Q, $R_{10}$, and $R_{11}$, are as defined in the first aspect of the invention, where if p is greater than 1, for each repeating unit the meanings of X', Y, A, $R_2$, $R_3$, $R_6$, $R_7$, $R_9$, T, T', T", Q, $R_{10}$, $R_{11}$ and the values of n and m are independently selected.

An eighth aspect of the present invention relates to compounds of formula VIII:

(VIII)

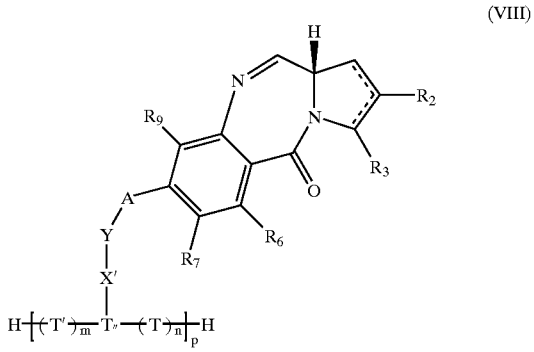

wherein X', Y, A, $R_2$, $R_3$, $R_6$, $R_7$, $R_9$, T, T', T", n, m and p are as defined in the sixth aspect of the invention, where if p is greater than 1, for each repeating unit the meanings of X', Y, A, $R_2$, $R_3$, $R_6$, $R_7$, $R_9$, T, T', T" and values of n and m are independently selected.

A ninth aspect of the present invention relates to compounds of formula IX:

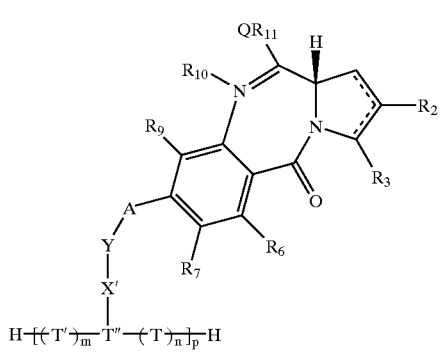

(IX)

wherein X', Y, A, $R_2$, $R_3$, $R_6$, $R_7$, $R_9$, Q, $R_{10}$, $R_{11}$, T, T', T", n, m and p are as defined in the seventh aspect of the invention, where if p is greater than 1, for each repeating unit the meanings of X', Y, A, $R_7$, $R_2$, $R_3$, $R_6$, $R_9$, T, T', T",Q, $R_{10}$, $R_{11}$ and values of n and m are independently selected.

A tenth aspect of the present invention relates to compounds of formula X:

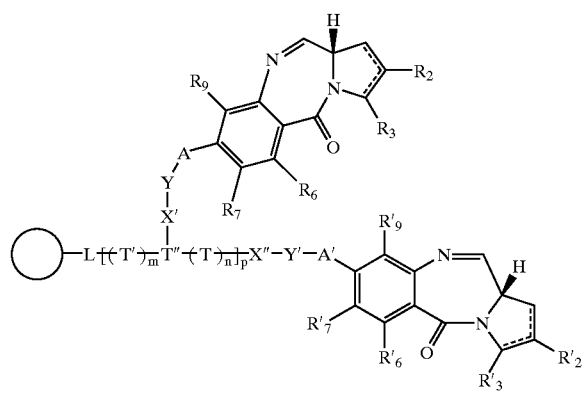

(X)

wherein ○, L, X', Y, A, $R_2$, $R_3$, $R_6$, $R_7$, $R_9$, T, T', T", n, m and p are as defined in the sixth aspect of the invention, and X", Y', A', $R'_2$, $R'_3$, $R'_6$, $R'_7$ and $R'_9$ are selected from the same possibilities as X', Y, A, $R_2$, $R_3$, $R_6$, $R_7$ and $R_9$ respectively, and where if p is greater than 1, for each repeating unit the meaning of X', Y, A, $R_2$, $R_3$, $R_6$, $R_7$, $R_9$, T, T', T" and the values of n and m may be independently selected.

An eleventh aspect of the present invention relates to compounds of formula XI:

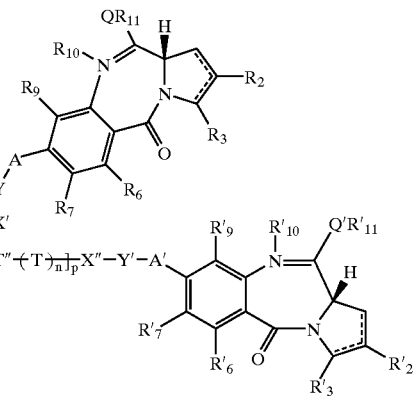

(XI)

wherein ○, L, X', Y, A, $R_2$, $R_3$, $R_6$, $R_7$, $R_9$, X", Y', A', $R'_2$, $R'_3$, $R'_6$, $R'_7$, $R'_9$, T, T', T", n, m and p are as defined in the tenth aspect of the invention, Q, $R_{10}$, and $R_{11}$, are as defined in the first aspect of the invention, and Q', $R'_{10}$, $R'_{11}$, have the same definitions as Q, $R_{10}$, $R_{11}$, respectively, and where if p is greater than 1, for each repeating unit the meanings of X', Y, A, $R_2$, $R_3$, $R_6$, $R_7$, $R_9$, T, T', T", Q, $R_{10}$, $R_{11}$ and the values of n and m are independently selected.

A twelfth aspect of the present invention relates to compounds of formula XII:

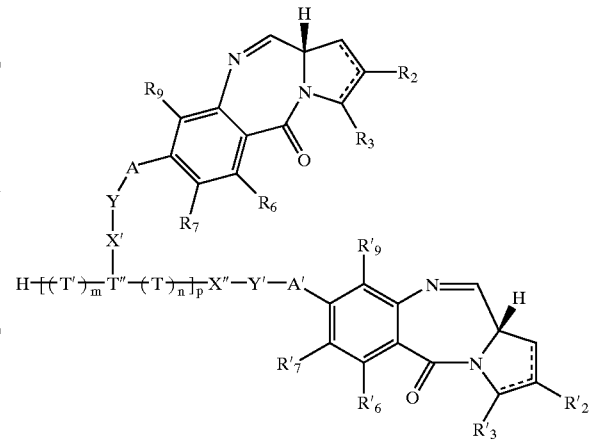

(XII)

wherein X', Y, A, $R_7$, $R_2$, $R_3$, $R_6$, $R_9$, X", Y', A', $R'_7$, $R'_2$, $R'_3$, $R'_6$, $R'_9$, T, T', T", n, m and p are as defined in the tenth aspect of the invention, and where if p is greater than 1, for each repeating unit the meanings of X', Y, A, $R_2$, $R_3$, $R_6$, $R_7$, $R_9$, T, T', and T" and the values of n and m may be independently selected.

A thirteenth aspect of the present invention relates to compounds of formula XIII:

(XIII)

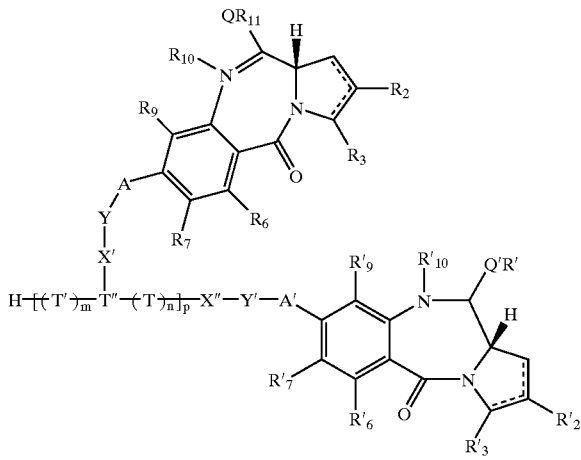

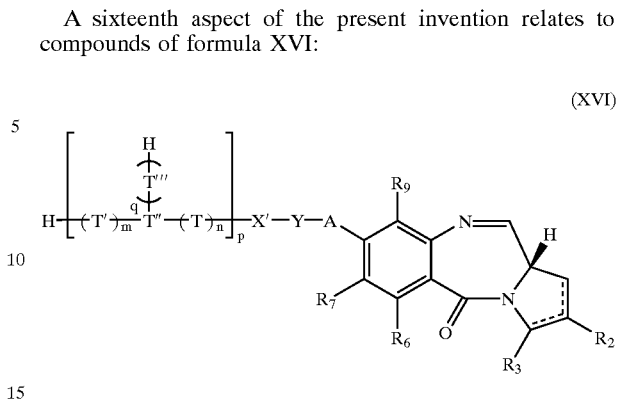

wherein X', Y, A, R$_2$, R$_3$, R$_6$, R$_7$, R$_9$, Q, R$_{10}$, R$_{11}$, X", Y', A', R'$_2$, R'$_3$, R'$_6$, R'$_7$, R'$_9$, Q', R'$_{10}$, R'$_{11}$, T, T', T", n, m and p are as defined in the eleventh aspect of the invention, and where if p is greater than 1, for each repeating unit the meanings of X', Y, A, R$_2$, R$_3$, R$_6$, R$_7$, R$_9$, T, T', T", Q, R$_{10}$, R$_{11}$ and the values of n and m may be independently selected.

A fourteenth aspect of the present invention relates to compounds of formula XIV:

(XIV)

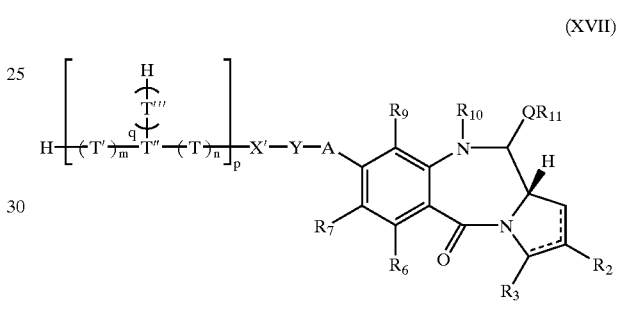

wherein ○, L, X', Y, A, R$_2$, R$_3$, R$_6$, R$_7$, R$_9$, T, T', T", n, m and p are as defined in the sixth aspect of the invention, and T'" and q are selected from the same possibilities as T and n respectively, and where if p is greater than 1, for each repeating unit the meaning of T, T', T", T'" and the values of n, m and q may be independently selected.

A fifteenth aspect of the present invention relates to compounds of formula XV:

(XV)

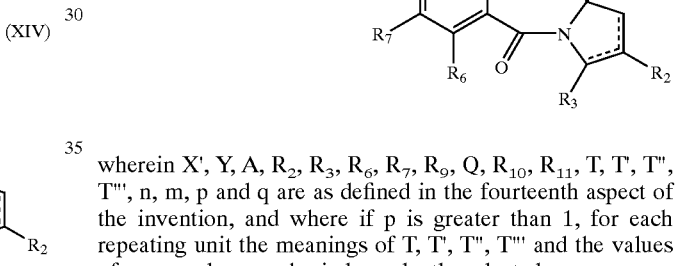

wherein ○, L, X', Y, A, R$_2$ , R$_3$, R$_6$, R$_7$, R$_9$, T, T', T", T'", n, m, p and q are as defined in the fourteenth aspect of the invention, Q, R$_{10}$, and R$_{11}$, are as defined in the first aspect of the invention, and where if p is greater than 1, for each repeating unit the meanings of T, T', T",T'" and the values of n, m and q may be independently selected.

A sixteenth aspect of the present invention relates to compounds of formula XVI:

(XVI)

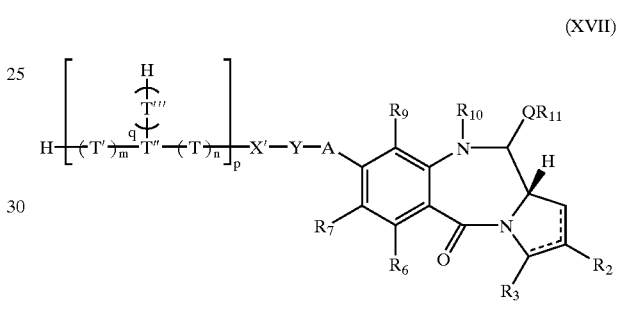

wherein X', Y, A, R$_7$, R$_2$, R$_3$, R$_6$, R$_9$,T, T', T", T'" , n, m, p and q are as defined in the fourteenth aspect of the invention, and where if p is greater than 1, the meanings of T, T', T", T'" and values of n, m and q may be independently selected.

A seventeenth aspect of the present invention relates to compounds of formula XVII:

(XVII)

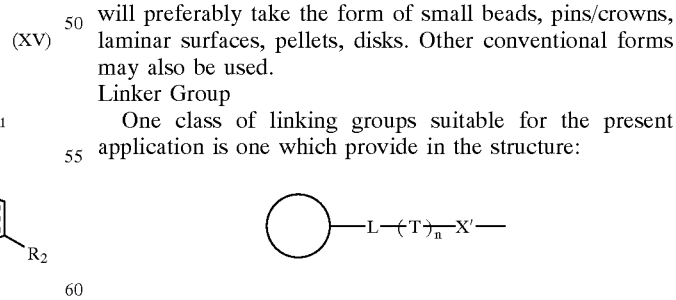

wherein X', Y, A, R$_2$, R$_3$, R$_6$, R$_7$, R$_9$, Q, R$_{10}$, R$_{11}$, T, T', T", T'", n, m, p and q are as defined in the fourteenth aspect of the invention, and where if p is greater than 1, for each repeating unit the meanings of T, T', T", T'" and the values of n, m and q may be independently selected.

Solid Support

The term 'solid support' refers to a material having a rigid or semi-rigid surface which contains or can be derivatized to contain reactive functionalities which can serve for covalently linking a compound to the surface thereof. Such materials are well known in the art and include, by way of example, silicon dioxide supports containing reactive Si-OH groups, polyacrylamide supports, polystyrene supports, polyethyleneglycol supports, and the like. Such supports will preferably take the form of small beads, pins/crowns, laminar surfaces, pellets, disks. Other conventional forms may also be used.

Linker Group

One class of linking groups suitable for the present application is one which provide in the structure:

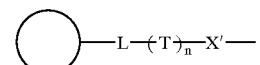

at least one covalent bond which can be readily broken by specific chemical reactions (or by light or changes in pH) thereby providing for liberation of compounds free from the solid support. The methods employed to break the covalent bond are selected so as to be specific for the desired bond breakage thereby preventing unintended reactions from occurring elsewhere on the complex. The linking group is selected relative to the synthesis of the compounds to be formed on the solid support so as to prevent premature cleavage of this compound from the solid support as well as to limit interference by any of the procedures employed during compound synthesis on the support.

Examples of resins incorporating linking groups are set out in the table below, which also indicates the groups that can be immobilised thereon, along with the suggested cleavage methods for the linking group. Such resins are commercially available (e.g. from NovaBiochem). The table also indicates which of the linker groups are suitable for compounds where the N10 position is not protected, i.e. where the cleavage methods would not affect an N10-C11 imine bond.

| Linker/Resin Type | Immobilises | Cleavage Method | Compatible with Non-Protected PBD |
|---|---|---|---|
| 2-Chlorotrityl chloride | $RNH_2$, $RCO_2H$, ROH, RSH | 1 . 50% TFA | Possibly |
| Trityl chloride | $RNH_2$, $RCO_2H$, ROH, RSH | 1–5% TFA | Yes |
| 2-Methoxytrityl chloride | $RNH_2$, $RCO_2H$, ROH, RSH | 1–5% | Yes |
| Rink amide resin | $RCO_2H$ | 95% TFA | Yes |
| Sieber amide resin | $RCO_2H$ | 1% TFA | Yes |
| 4-Sulfamyl-benzoyl | $RCO_2H$ | Alkylation/ amines | YES |
| Wang resin | ROH, ArOH, $RNH_2$, $RCO_2H$ | 15–95% TFA or DDQ or CAN | Possibly |
| HMPB-BHA | ROH, ArOH, $RCO_2H$ | 1% TFA | Possibly |
| Bromoethyl photolinker | $RNH_2$, $RCO_2H$, ROH, RSH | hv | YES |
| Hydroxy ethyl photolinker | $RCO_2H$ | hv | YES |
| Aminoethyl photolinker | $RCO_2H$ | hv | YES |

Structures

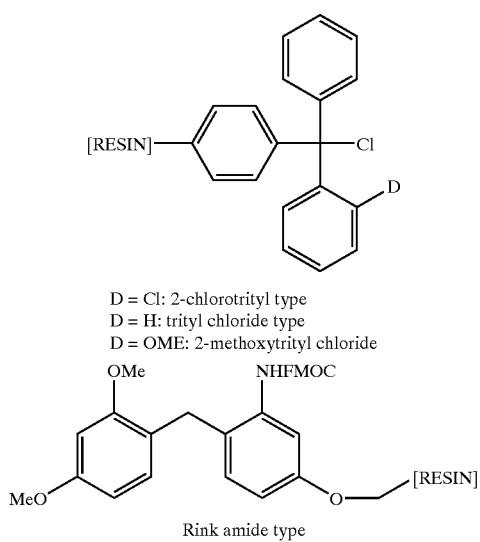

D = Cl: 2-chlorotrityl type
D = H: trityl chloride type
D = OME: 2-methoxytrityl chloride

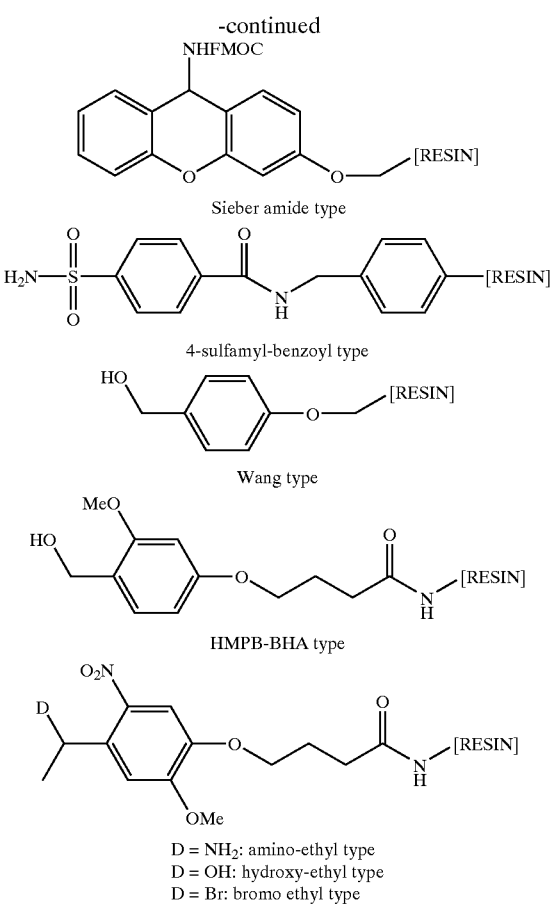

Rink amide type

Sieber amide type 4-sulfamyl-benzoyl type

Wang type

HMPB-BHA type

D = $NH_2$: amino-ethyl type
D = OH: hydroxy-ethyl type
D = Br: bromo ethyl type For protected PBDs the most preferred linking group is the Rink linker, which is cleavable by TFA. The N-protected PBDs can then be deprotected using photolysis. For unprotected PBDs the linking groups of choice are those which are photolabile.

It is also possible that the linking group is a simple functionality provided on the solid support, e.g. amine, and in this case the linking group may not be readily cleavable. This type of linking group is useful in the synthesis of large split and mix libraries which will be subjected to on-bead screening (see below), where cleavage is unnecessary. Such resins are commercially available from a large number of companies including NovaBiochem, Advanced ChemTech and Rapp Polymere. These resins include amino-Tentagel, and amino methylated polystyrene resin.

Combinatorial Unit

The term 'combinatorial unit' means any monomer unit which can be used to build a chain attached to the solid support, usually by a linking group. Examples of molecules suitable for such chain building are found in Schreiber et al. (*JACS*, 120. 1998, pp.23–29), which is incorporated herein by reference. An important example of a unit is an amino acid residue. Chains may be synthesised by means of amine-protected amino acids. Fmoc protected amino-acids are available from a number of sources, such as Sigma and Nova Biochem. Both natural and unnatural amino acids can be used, e.g. D- and L-amino acids and heterocyclic amino acids. In particular, heterocyclic amino acids of the type found in the construction of netropsin and distamycin are of interest because of their DNA-recognition properties.

Amine units can be used to make up peptoids: see Soth, M. J. and Nowick, J. S. 1997, Unnatural oligomer libraries, Curr. Opin, Chem. Biol. 1, no. 1: 120–129; Zuckermann et al., 1994, Discovery of Nanomolecular Ligands for 7-Transmembrane G-Protein-Coupled Receptors from a Diverse N-(Substituted)glycine Peptoid Library, *Journal of Medicinal Chemistry* 37: 2678–85; Figliozzi, GMR et al., 1996, Synthesis of N-substituted Glycine Peptoid Libraries, *Methods in Enzymology,* 267: 437–47; Simon, R J et al. , 1992, Peptoids: A Modular Approach to Drug Discovery, *Proc. Natl. Acad. Sci. USA,* 89:9367–71; which are all incorporated herein by reference.

Other combinatorial units include PNAs (peptidonucleic acids): P E Nielsen, et al, *Science,* 1991, 254, 1497; M Egholm, et al, *Nature,* 1993, 365, 566; M Egholm et al, *JACS,* 1992, 114, 1895; S C Brown, et al, *Science,* 1994, 265, 777; 5. K Saha, et al, *JOC,* 1993, 58, 7827; oligoureas: Burgess K, et al, 1995, Solid Phase Synthesis of Unnatural Biopolymers Containing Repeating Urea Units. *Agnew. Chem. Int. Examining Division. Engl* 34, no. 8:907; Burgess K, et al, 1997, Solid Phase Synthesis of Oligoureas; *Journal of the American Chemical Society* 119: 1556–64; and oligocarbamates: Moran E J et al, 1995, Novel Biopolymers for Drug Discovery. *Biopolymers (Peptide Science);* John Wiley and Sons 37: 213–19; Cho C Y et al, 1993, An unnatural Biopolymer. *Science* 261: 1303–5; Paikoff S F et al, 1996, The Solid Phase Synthesis of N-Alkylcarbamate Oligomers. *Tetrahedron Letters* 37, no. 32: 5653–56. All of these documents are incorporated herein by reference.

A type of combinatorial unit of particular relevance to the present invention is one based on the pyrrolobenzodiazepine structures; these are of general formulae XVIIIa and XVIIIb:

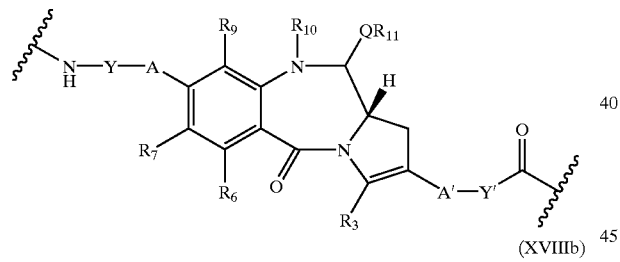

(XVIIIa)

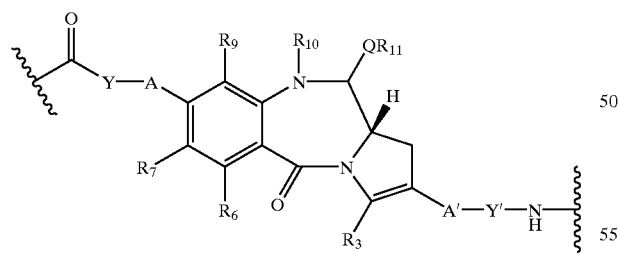

(XVIIIb)

wherein $R_3$, $R_6$, $R_7$, $R_9$, $R_{10}$, $R_{11}$, Q, A and Y are as defined in the first aspect of the invention, and A', and Y' are independently selected from the possible groups for A and Y respectively.

A further type of particularly relevant combinatorial unit is one based on a cyclopropyl indole ("a CPI unit"). Such units are known to interact covalently with the minor groove of DNA, being specific for AT. These units are of general formulae XIXa and XIXb:

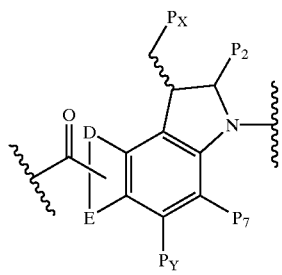

(XIXa)

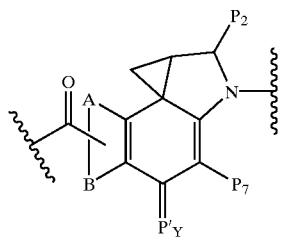

(XIXb)

wherein $P_x$ (if present) is an electrophilic leaving group;

$P_y$ (if present) is selected from NH-Prot, O-Prot, S-Prot, $NO_2$, NHOH, $N_3$, NHR, NRR, N=NR, N(O)RR, $NHSO_2R$, N=NPhR, SR or SSR, where Prot represents a protecting group;

$P'_y$ (if present) is selected from NH, O and S;

D and E collectively represent a fused benzene or pyrrole ring (in either orientation), which is optionally substituted by up to respectively 3 or 1 additional groups independently selected from R, OH, OR, halo, nitro, amino, $Me_3Sn$, $CO_2H$, $CO_2R$; $P_2$ and $P_7$ are independently selected from H, R, OH, OR, halo, nitro, amino, $Me_3Sn$.

The preferences for R are as above. $P_y$ is preferably NH-Prot, O-Prot, S-Prot and $P_x$ is preferably halogen or $OSO_2R$. It is further preferred that the —$CO_2$— substituent is in the 2 or 3 position of the benzene ring or the 2 position of the pyrrole ring. $P_2$ and $P_7$ are preferably H.

These compounds may be synthesised using the techniques described by Boger et al, *Chem. Rev.* 1997, 97, 787–828; Cava et al, Drost, K. J.; Cava, M. P. *J. Org. Chem.* 1991, 56, 2240–2244; Rawal, V. H.; Jones, R. J.; Cava, M. P. *J. Org. Chem.* 1987, 52, 19–28; and Aristoff *J. Med. Chem.* 1993, 1992, 57, 6234–6239.

The following synthesis is provided as an example of the application of the Boger method.

Synthesis of a CPI Combinational Unit

The synthesis starts with a Wadsworth-Horner-Emmons condensation of 3-bromo-benzaldehyde with the Sargent phosphonate which predominantly provides the E-isomer, which in turn undergoes acid-catalyzed deprotection and Friedel-Crafts acylation. This generates the functionalised precursor, which is followed by 5-exo-trig aryl radical-alkene cyclization.

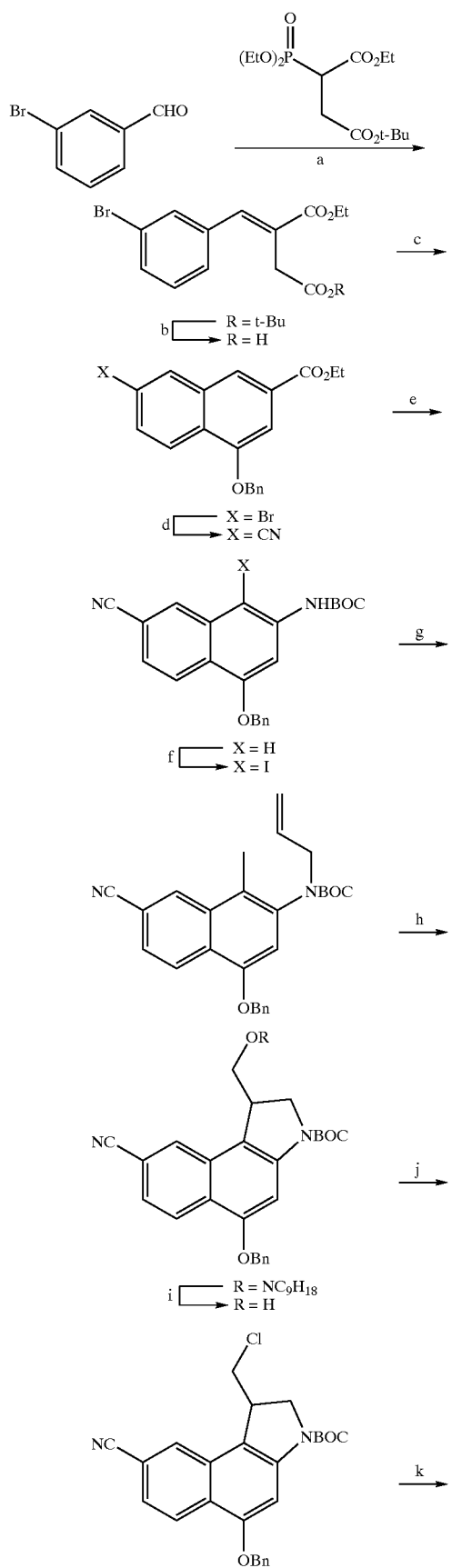

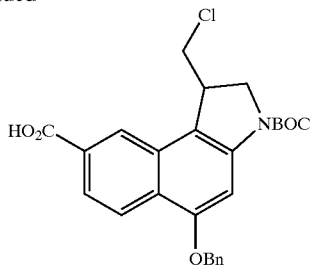

Reagents and conditions: a: NaH, Sargent phosphate; b: TFA; c: 1) Ac₂O—KOAc; 2) K₂CO₃; 3) BnBr, K₂CO₃; d: CuCN; e: 1) LiOh; 2) DPPA, t-BuOH; f: NIS; g: allyl Br, NaH; h: Bu₃SnH, TEMPO; i: Zn—HOAc; j: Ph₃P—CCl; k: NaOH.

Aromatic nucleophilic substitution, ester hydrolysis and Curtius rearrangements effected by treatment with DPPA are followed by regioselective C4 iodination and N-alkylation with allyl bromide. The aryl radical-alkene cyclization by means of TEMPO as radical trap, as described in Boger synthesis of CBI, provides the tricyclic system that, after conversion to the primary chloride and base-catalyzed hydrolysis of the cyano group, gives the desired combinatorial unit. The present invention relates to libraries, or collections, of compounds all of which are represented by a single one of the formulae I to IV, and VI to XVII. The diversity of the compounds in a library may reflect the presence of compounds differing in the identities of one or more of the substituent groups and/or in the identities of the combinatorial units T (when present). The number of members in the library depends on the number of variants, and the number of possibilities for each variant. For example, if it is the combinatorial units which are varied, and there are 3 combinatorial units, with 3 possibilities for each unit the library will have 27 compounds. 4 combinatorial units and 5 possibilities for each unit gives a library of 625 compounds. If for instance there is a chain of 5 combinatorial units with 17 possibilities for each unit, the total number of members in the library would be 1.4 million. A library may therefore comprise more than 1 000, 5 000, 10 000, 100 000 or a million compounds, which may be arranged as described below.

In the case of free compounds (formulae I, II, VIII, IX, XII, XIII, XVI, and XVII) the individual compounds are preferably in discrete volumes of solvents, e.g. in tubes or wells. In the case of bound compounds (formulae III, IV, VI, VII, X, XI, XIV and XV) the individual compounds are preferably bound at discrete locations, e.g. on respective pins/crowns or beads. The library of compounds may be provided on a plate which is of a suitable size for the library, or may be on a number of plates of a standard size, e.g. 96 well plates. If the number of members of the library is large, it is preferable that each well on a plate contains a number of related compounds from the library, e.g. from 10 to 100. One possibility for this type of grouping of compounds is where only a subset of the combinatorial units, or substituents, are known and the remainder are randomised; this arrangement is useful in iterative screening processes (see below). The library may be presented in other forms that are well-known.

A further aspect of the present invention is a method of preparing a diverse collection, or library of compounds as discussed above. If the diversity of the library is in the combinatorial units, then the library may be synthesised by the stepwise addition of protected combinatorial units to a PBD core, each step being interposed by a deprotection step. Such a method is exemplified later. Libraries of this type can be prepared by the method known as "split and mix" which is described in Furka, A; Sebestyen, F; Asgedom, M and Dibo, G; General Method of Rapid Synthesis of Multicomponent Peptide Mixtures; International Journal of Peptide and Protein Research; 1991, 37, 487–193, which is incorporated herein by reference. If the diversity of the library is in the substituent groups, the library may be synthesised by carrying out the same synthetic methods on a variety of starting materials or key intermediates, which already possess the necessary substituent patterns.

The present invention also relates to a method of screening the compounds of formula II, III, VI, VIII, X, XII, XIV and XVI to discover biologically active compounds. The screening can be to assess the binding interaction with nucleic acids, e.g. DNA or RNA, or proteins, or to assess the affect of the compounds against protein-protein or nucleic acid-protein interactions, e.g. transcription factor DP-1 with E2F-1, or estrogen response element (ERE) with human estrogen receptor (a 66 kd protein which functions as hormone-activated transcription factor, the sequence of which is published in the art and is generally available). The screening can be carried out by bringing the target macromolecules into contact with individual compounds or the arrays or libraries described above, and selecting those compounds, or wells with mixtures of compounds, which show the strongest effect.

This effect may simply be the cytotoxicity of the compounds in question against cells or the binding of the compounds to nucleic acids. In the case of protein-protein or nucleic acid-protein interaction, the effect may be the disruption of the interaction studied.

The binding of the compounds to nucleic acids may be assessed by labelling oligomers which contain a target sequence, and measuring the amount of labelled oligomers that bind to the compounds tested. The labelling may either be radio-labelling, or alternatively be labels detectable under visible or ultra-violet light. If this latter form of screening is carried out on compounds bound to solid supports which are in separate locations, the screening for results can be carried out visually under a microscope. A similar technique is described in detail in "DNA-Binding ligands from peptide libraries containing unnatural amino acids", Lescrinier et al., *Chem Eur J*, 1998, 425–433. These techniques are particularly suited to a one-step screening of a complete library of compounds, especially a large library made by the "split and mix" method described above.

Protein-protein interactions can be measured in a number of ways, e.g. FRET (fluorescence resonance energy transfer) which involves labelling one of the proteins with a fluorescent donor moiety and the other with an acceptor which is capable of absorbing the emission from the donor; the fluorescence signal of the donor will be altered depending on the interaction between the two proteins. Another method of measuring protein-protein interactions is by enzymatic labelling, using, for example, horseradish peroxidase.

The screening process may undergo several iterations by selecting the most active compounds, or group of compounds, tested in each iteration; this is particular useful when testing arrays of wells which include mixtures of related compounds. Furthermore, if the wells contain compounds for which only a subset of the combinatorial units, or substituents, are known, but the rest are randomised, subsequent iterations can be carried out by synthesising compounds possessing the selected known (and successful) combinatorial unit, or substituent, pattern, but with further specified combinatorial units, or substituents, replacing the previously randomised combinatorial units, or substituents, adjacent the already known pattern; the remaining combinatorial units, or substituents, are randomised as in the previous iteration. This iterative method enables the identification of active members of large libraries without the need to isolate every member of the library.

A further feature of this aspect is formulation of selected compound or compounds with pharmaceutically acceptable carriers or diluents.

In yet further aspects, the invention provides a pharmaceutical composition comprising a compound of formula II, VIII, XII or XVI and a pharmaceutically acceptable carrier or diluent; and the use of a compound of formula II, VIII, XII or XVI in the manufacture of a medicament for the treatment of a gene-based disease, or a bacterial, parasitic or viral infection. Gene-based disease include neoplastic disease, and Alzheimer's disease, and also include any disease susceptible to regulation of gene-expression.

Compounds of formula II, VIII, XII or XVI may be used in a method of therapy against a gene-based disease, such as cancer or Alzheimer's disease, or a viral, parasitic or bacterial infection.

Another aspect of the present invention relates to the use of compounds of formula III, VI, X or XIV in diagnostic methods. A compound of formula III, VI, X, XIV which binds to an identified sequence of DNA or a protein known to be an indicator of a medical condition can be used in a method of diagnosis. The method may involve passing a sample, e.g. of appropriately treated blood or tissue extract, over an immobilised compound of formula III, VI X, XIV, for example in a column, and subsequently determining whether any binding of target DNA to the compound of formula III, VI or X has taken place. Such a determination could be carried out by passing a known amount of labelled target DNA known to bind to compound III, VI or X through the column, and calculating the amount of compound III, VI, X or XIV that has remained unbound.

A further aspect of the present invention relates to the use of compounds of formula II, VIII, XII or XVI in target validation. Target validation is the disruption of an identified DNA sequence to ascertain the function of the sequence, and a compound of formula II, VIII, XII or XVI can be used to selectively bind an identified sequence, and thus disrupt its function, i.e. functional genomics Preferred Synthetic Strategies A key step in a preferred route to compounds of formula I is a cyclisation process to produce the B-ring, involving generation of an aldehyde (or functional equivalent thereof) at what will be the 11-position, and attack thereon by the pro-10-nitrogen:

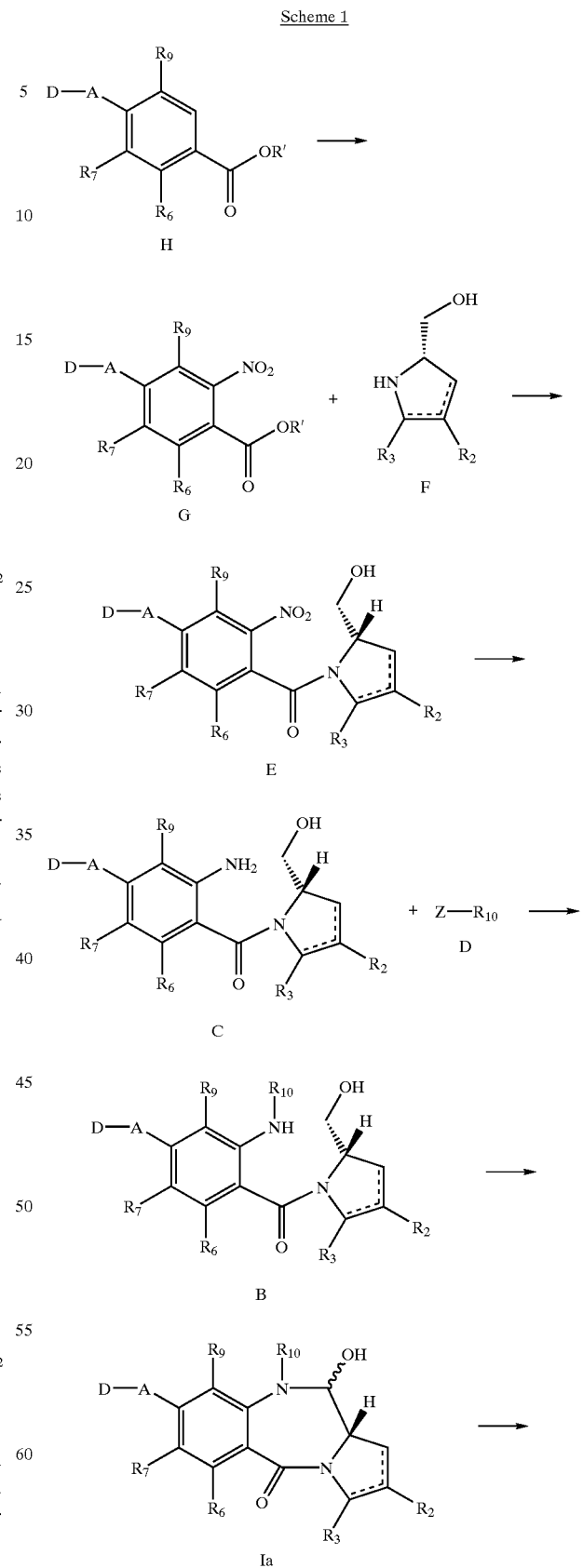

Scheme 1

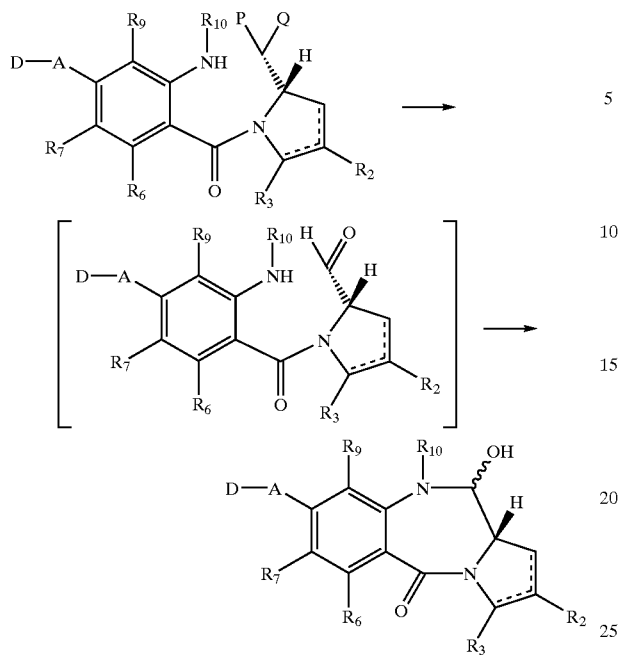

In this structure, D represents XY, or a masked form thereof. The "masked aldehyde" —CPQ may be an acetal or thioacetal, in which case the cyclisation involves unmasking. Alternatively, the masked aldehyde may be an aldehyde precursor, such as an alcohol —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

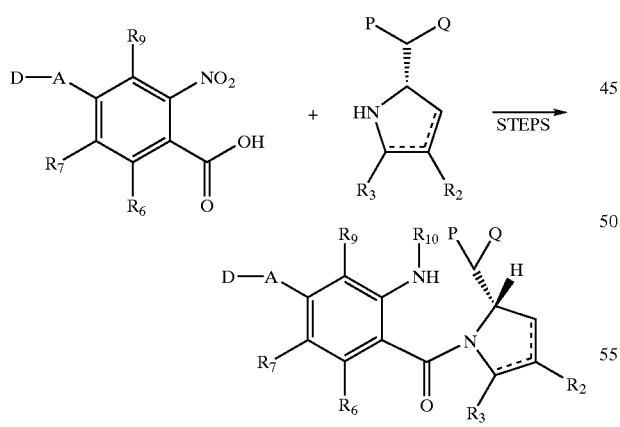

The nitro group can then be reduced to —NH$_2$ and protected by reaction with a suitable agent, e.g. a chloroformate, which provides the removable nitrogen protecting group in the compound of formula I.

A process involving the oxidation-cyclization procedure is illustrated in scheme 1 (an alternative type of cyclisation will be described later with reference to scheme 2).

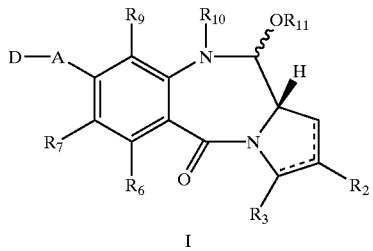

I

If $R_{11}$ is other than hydrogen, the compound of formula I, may be prepared by direct etherification of the alcohol Ia. Compounds with Q=S can be prepared by treatment of the corresponding alcohol Ia with $R_{11}SH$, and a catalyst (usually an acidic solution HCl, and sometimes a Lewis Acid such as $Al_2O_3$). If Q=NH, then these compounds can be prepared by reacting Ia with an amine $R_{11}NH$ and a catalyst (usually an aqueous acid or a Lewis Acid).

Exposure of the alcohol B (in which the 10-nitrogen is generally protected as a carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol B may be prepared by the addition of a nitrogen protecting reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO_3$ at −25° C. under a $N_2$ atmosphere. Compounds of formula F can be readily prepared, for example by olefination of the ketone derived from L-trans-4-hydroxy proline. The ketone intermediate can also be exploited by conversion to the enol triflate for use in palladium mediated coupling reactions.

The o-nitrobenzoyl chloride is synthesised from the o-nitrobenzoic acid (or, after hnydrolysis, the alkyl ester) of formula G, which itself is prepared from the vanillic acid (or alkyl ester) derivative H. Many of these are commercially available and some are disclosed in Althuis, T. H. and Hess, H. J., *J. Medicinal Chem,* 20(1), 146–266 (1977).

Scheme 2

Alternative Cyclisation (Scheme 2)

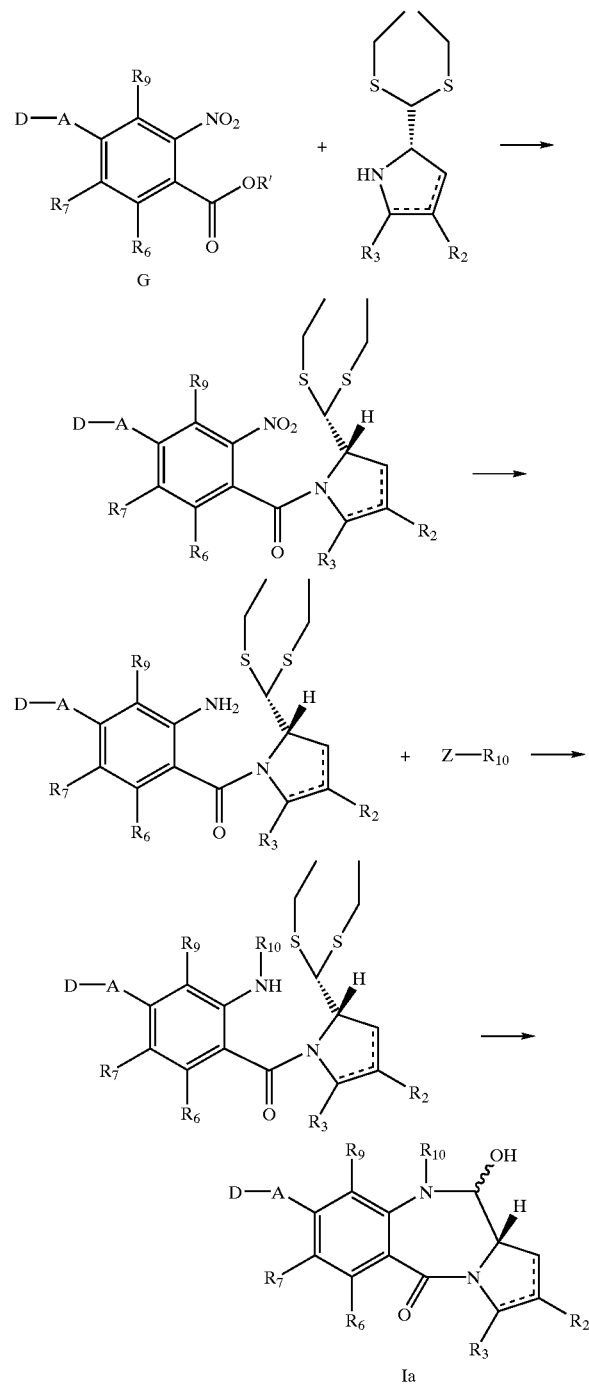

In scheme 1, the final or penultimate step was an oxidative cyclisation. An alternative approach, using thioacetal coupling, is shown in scheme 2. Mercury-mediated unmasking causes cyclisation to the desired compound (Ia).

The thioacetal intermediates may be prepared as shown in scheme 2: the thioacetal protected C-ring [prepared via a literature method: Langley, D. R. & Thurston, D. E., *J. Organic Chemistry,* 52, 91–97 (1987)] is coupled to the o-nitrobenzoic acid (or, after hydrolysis, the alkyl ester) G using a literature procedure. The resulting nitro compound cannot be reduced by hydrogenation, because of the thioacetal group, so the tin (II) chloride method is used to afford the amine. This is then N-protected, e.g., by reaction with a chloroformate or acid chloride, such as p-nitrobenzylchloroformate.

Acetal-containing C-rings can be used as an alternative in this type of route with deprotection involving other methods including the use of Lewis Acid conditions.

In the above synthesis schemes, the derivatisation of the A-ring is shown as being complete before the compounds are attached to the solid support. This is preferred if the substituents are groups such as alkoxy or nitro. On the other hand, substituent groups such as alkyl or alkenyl could be added to the A-ring after the coupling of the compound to the solid support. This may be achieved by $R_6$, $R_7$, or $R_9$ being easily replaceable groups, such as halogen atoms.

An alternative synthesis approach to those detailed above is to protect the pro N10 position on the component which will form the A-ring, before joining the component which will for the C-ring.

Embodiments of the present invention will now be described by way of example with reference to the accompanying drawings in which.

Figure 10A:
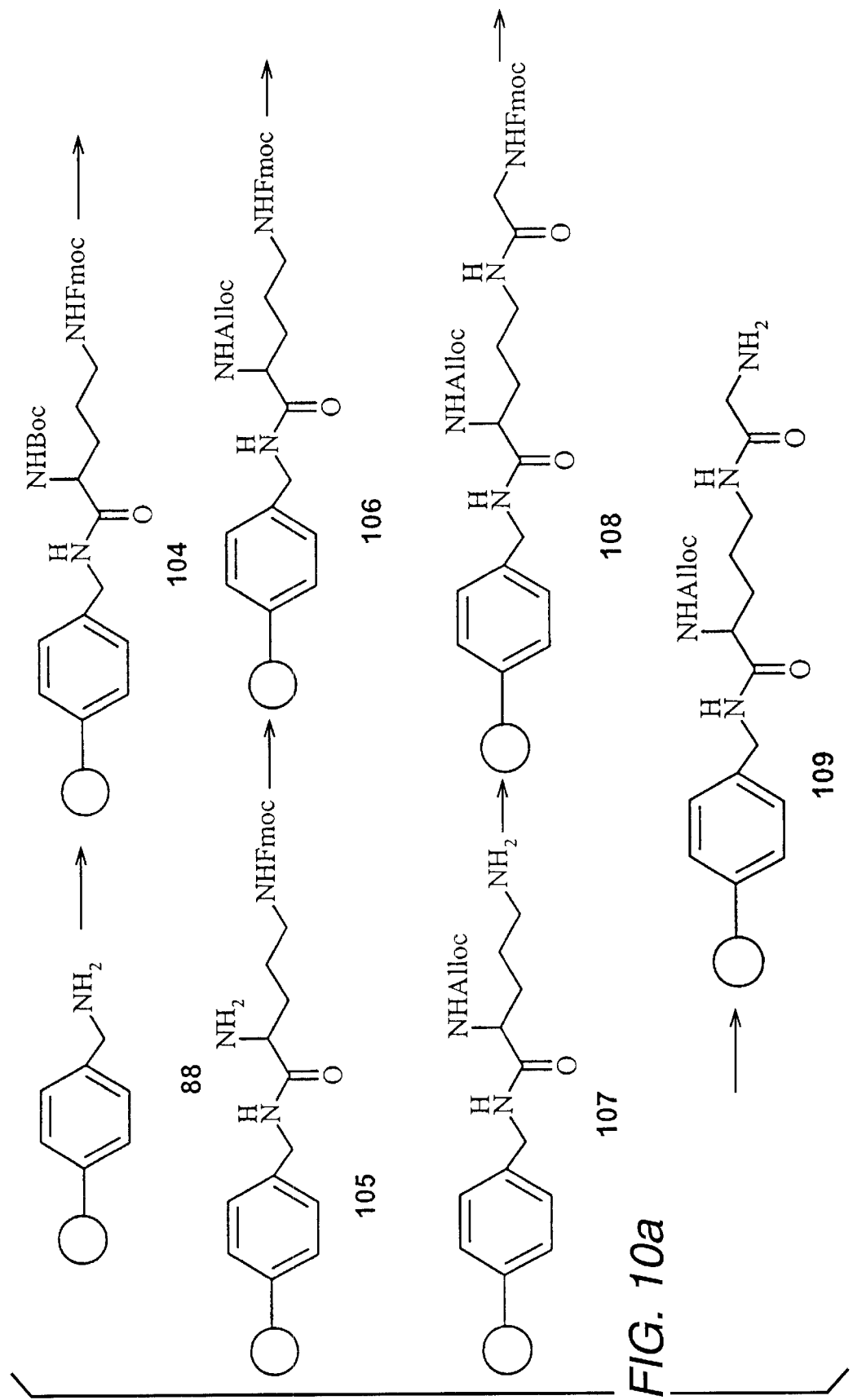
Figure 11A:
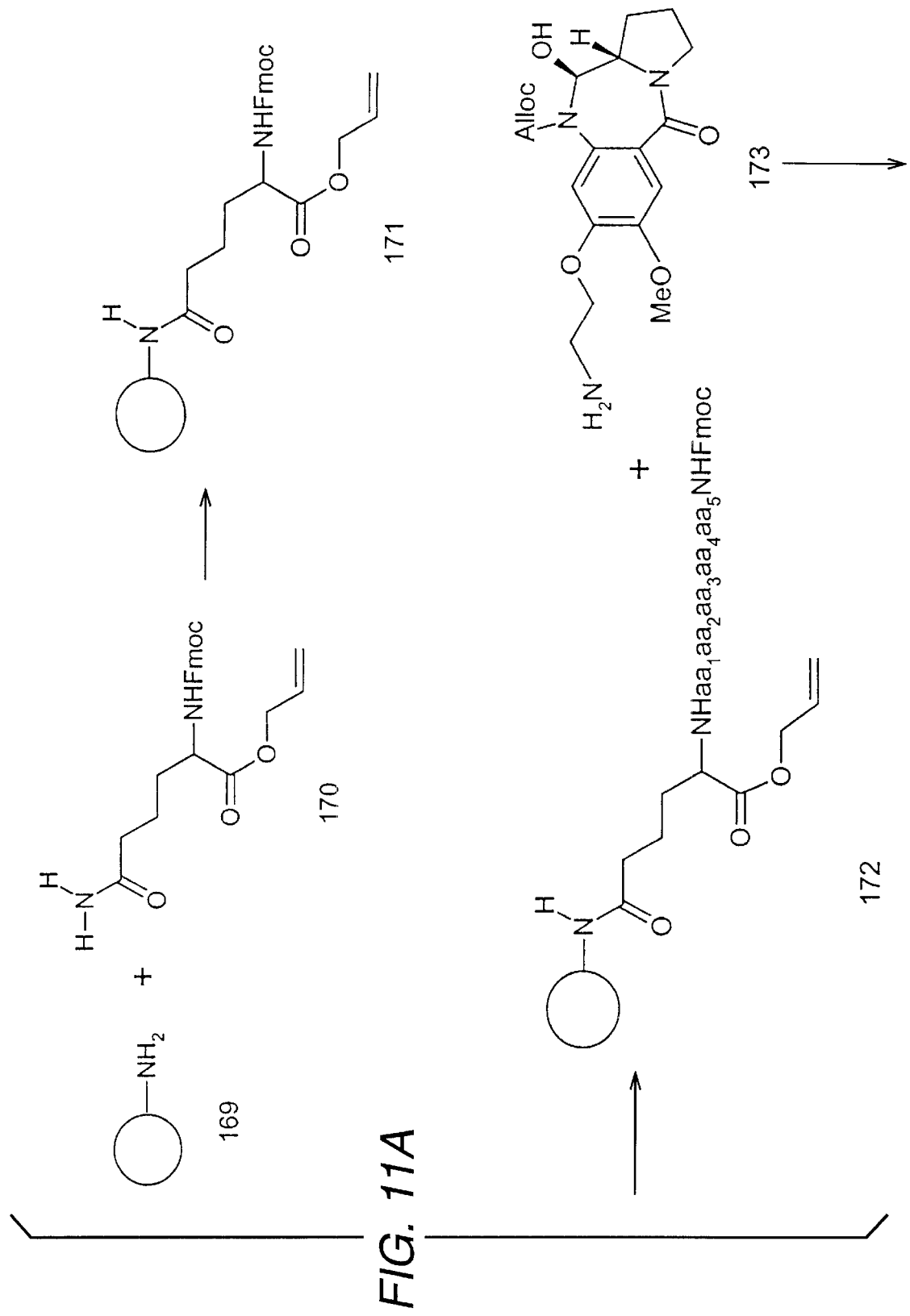
Figure 11B:
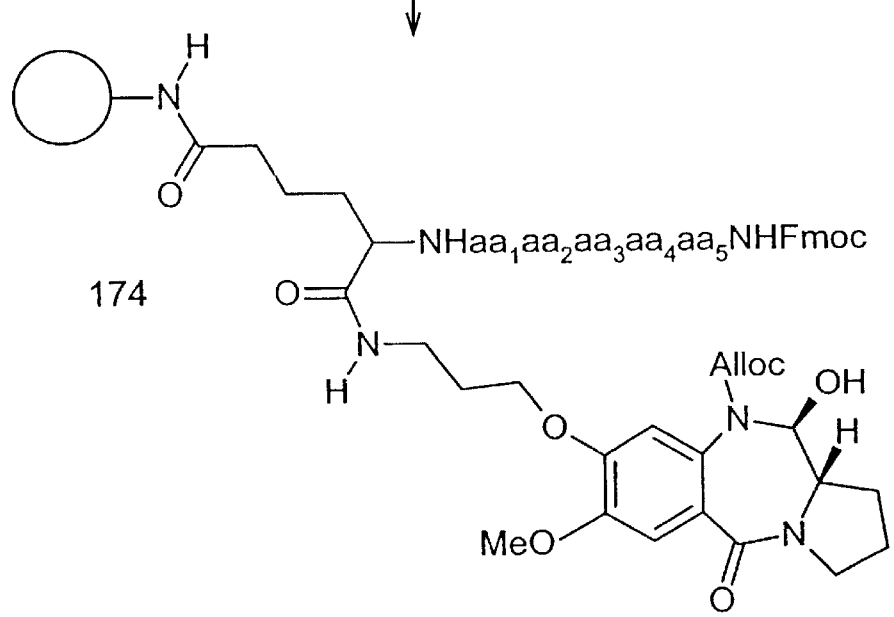
Figure 11B:
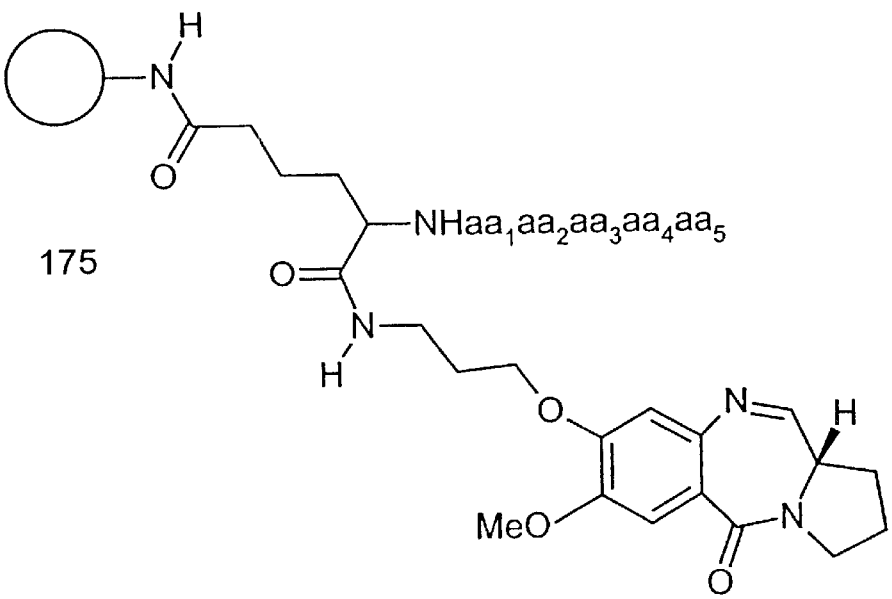

FIGS. 10a, b and c are a reaction scheme for the synthesis of compounds of formula X and XI;

FIG. 11 is reaction schemes for the synthesis of compounds of formula XIII and XIV; and FIGS. 12 to 15 are reaction schemes for the synthesis of compounds of formula III and IV.

GENERAL METHODS

Melting points (mp) were determined on an Electrothermal 9100 digital melting point apparatus and are uncorrected. Infrared (IR) spectra were recorded using a Perkin-Elmer Spectrum 1000 spectrophotometer. $^1$H- and $^3$C-NMR spectra were recorded on a Jeol GSX 270 MHz FT-NMR spectrometer operating at 20° C.+/−1° C. Chemical shifts are reported in parts per million ($\delta$) downfield from tetramethylsilane (TMS). Spin multiplicities are described as: s (singlet), bs (broad singlet), d (doublet), dd (doublet of doublets), t (triplet), q (quartet), p (pentuplet) or m (multiplet). Mass spectra (MS) were recorded using a Jeol JMS-DX 303 GC Mass Spectrometer (EI mode: 70 eV, source 117–147° C.). Accurate molecular masses (HRMS) were determined by peak matching using perfluorokerosene (PFK) as an internal mass marker, and FAB mass spectra were obtained from a glycerol/thioglycerol/trifluoroacetic acid (1:1:0.1) matrix with a source temperature of 180° C. Optical rotations at the Na-D line were obtained at ambient temperature using an ADP 220 Automatic Polarimeter (Bellingham & Stanley). Flash chromatography was performed using Aldrich flash chromatography "Silica Gel-60" (E. Merck, 230–400 mesh). Thin-layer chromatography (TLC) was performed using $GF_{254}$ silica gel (with fluorescent indicator) on glass plates. All solvents and reagents, unless otherwise stated, were supplied by the Aldrich Chemical Company Ltd. and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40–60° C.

EXAMPLE 1

Figure 1A:
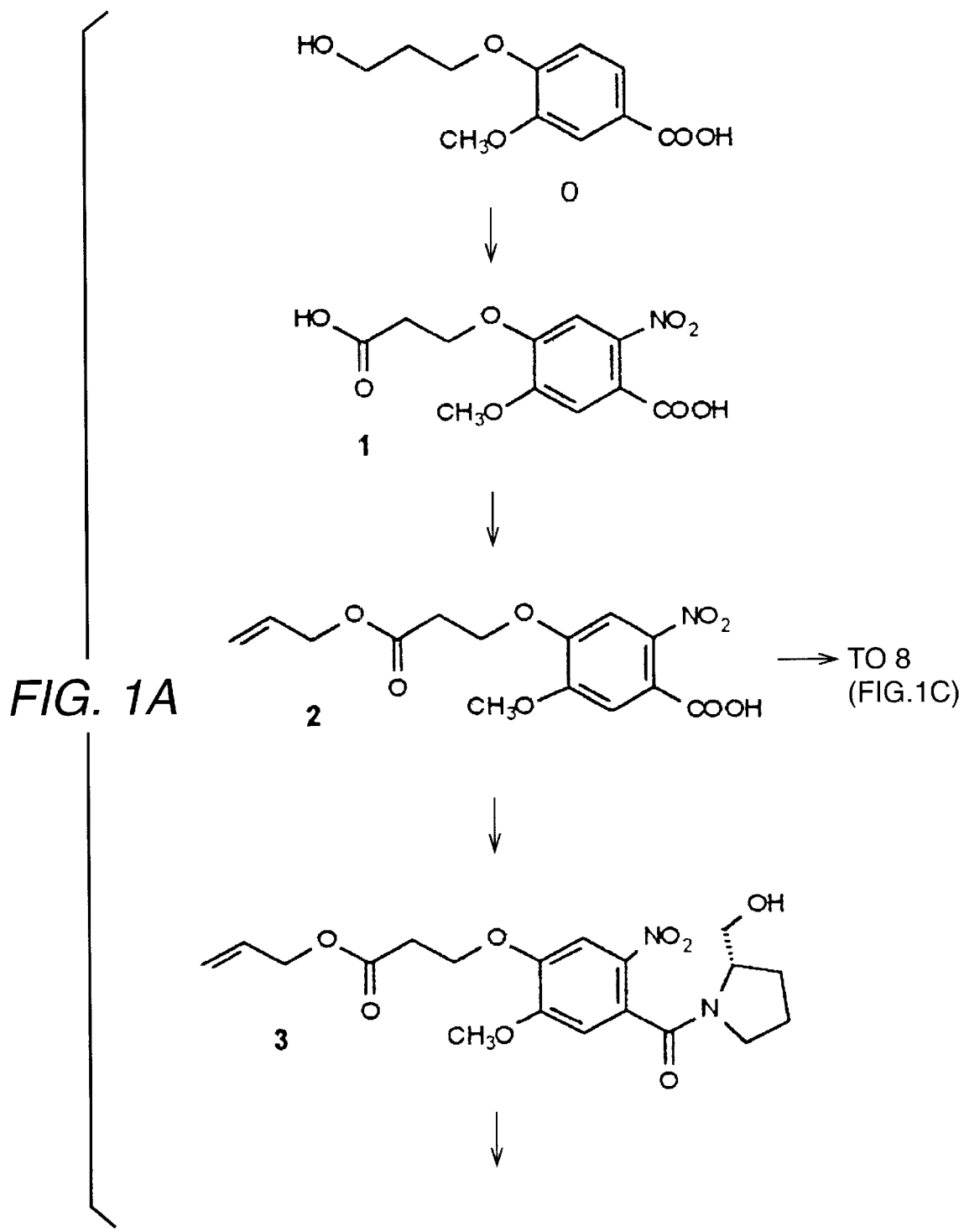
FIG. 1 is a reaction scheme for the synthesis of compounds of formula I.
Figure 1B:
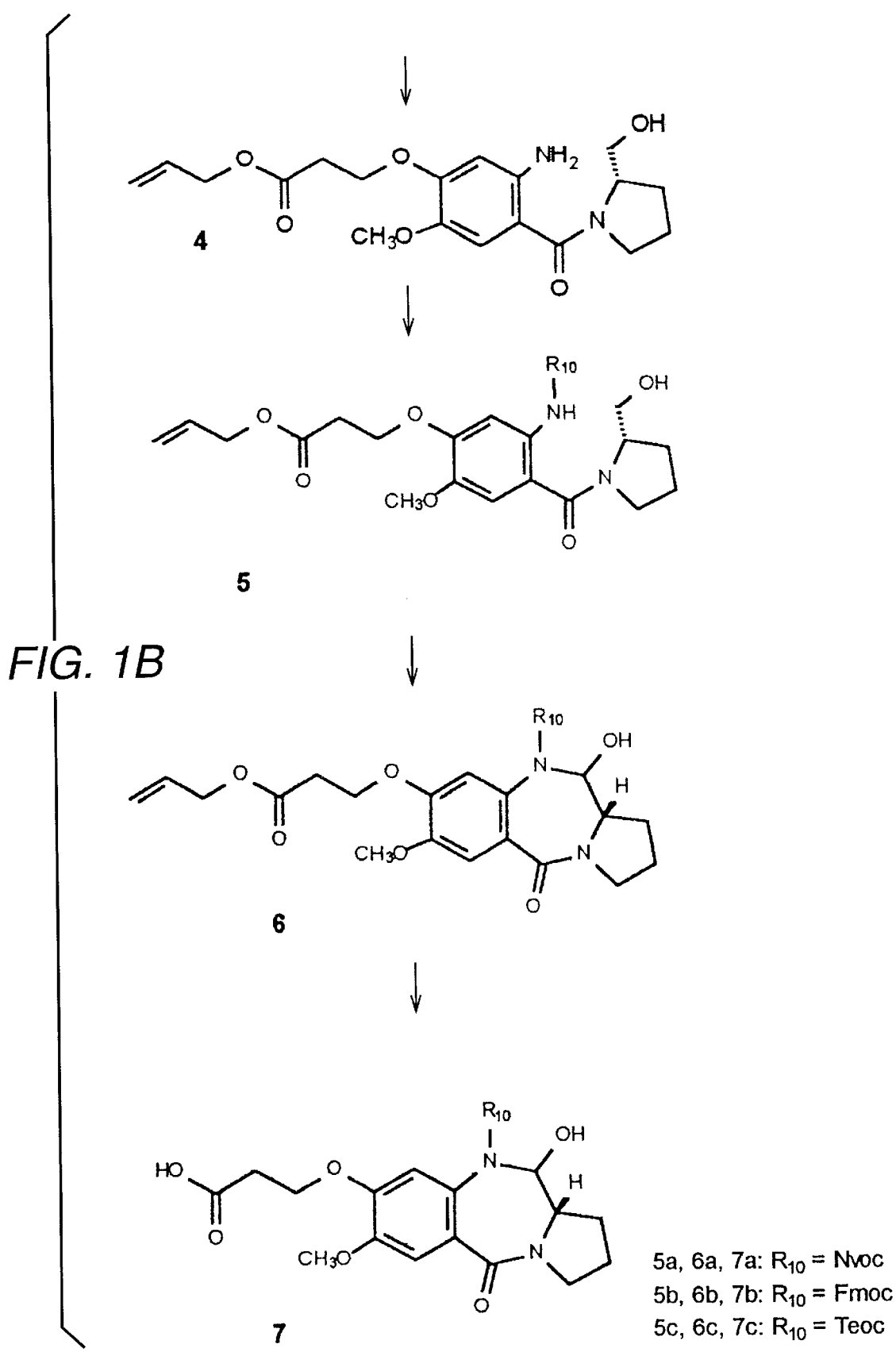
Figure 1C:
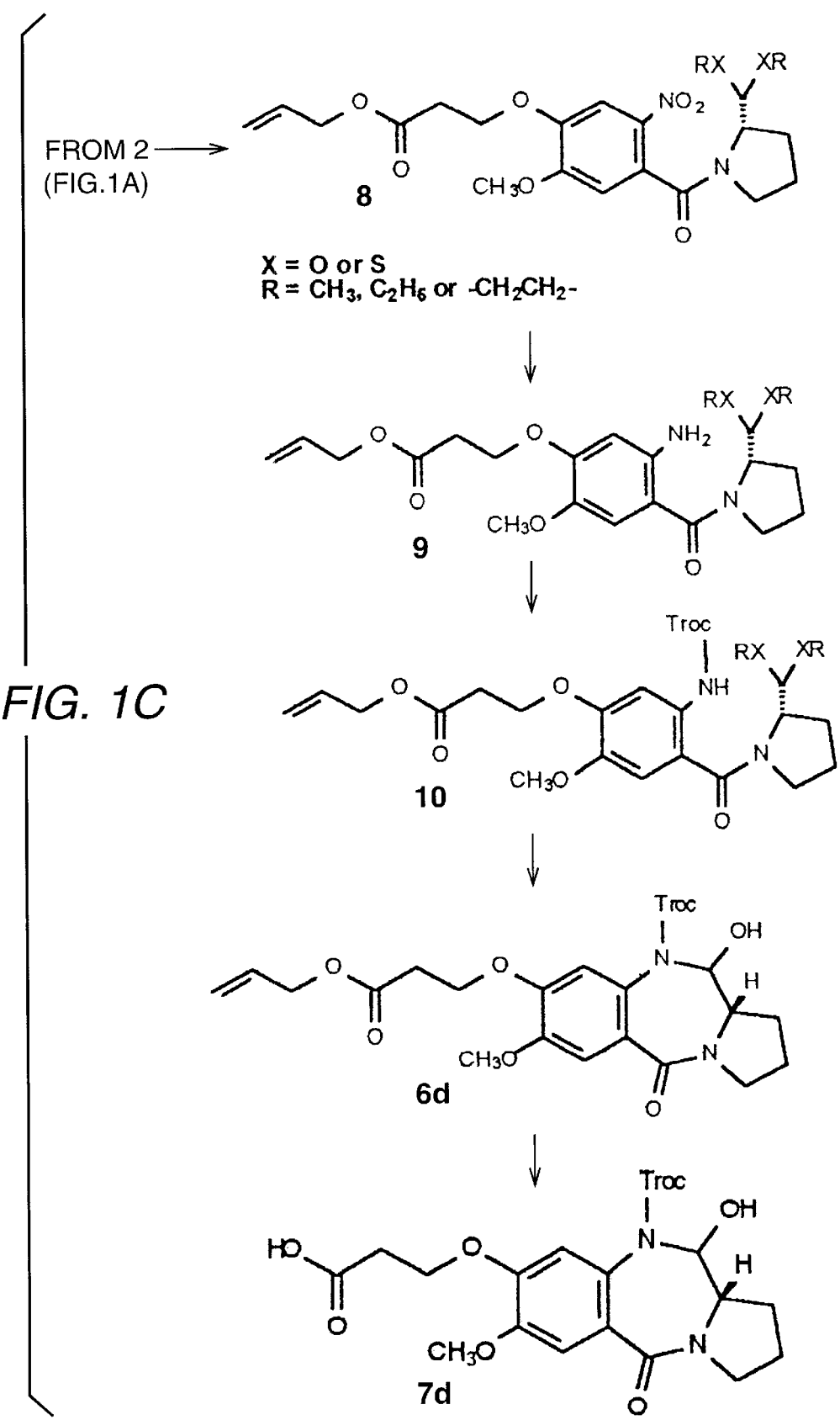

Synthesis of PBDs of Formula I (FIG. 1)

Overall Synthesis

The compounds with an acid-terminating side chain, 7a–c ($R_{10}$=Nvoc, Fmoc, Teoc), were prepared by palladium-mediated de-esterification of the appropriate allyl esters. The esters were in turn prepared by Swern oxidation (oxidation of the primary alcohol to an aldehyde which provokes spontaneous B-ring closure) of the Nvoc, Fmoc and Teoc protected amino alcohols. The carbamate-protected amino alcohols were prepared by treating the common amino alcohol intermediate 4 with the appropriate chloroformate in the presence of pyridine. The amino alcohol was obtained by reduction of the nitro compound 3, which in turn was assembled by coupling pyrrolidine methanol to the o-nitrobenzoic acid 2. Compound 2 was prepared by selective esterification of the diacid 1 at the aliphatic acid. Finally, the diacid was obtained by simultaneous nitration and oxidation of the known hydroxypropyloxy vanillic acid derivative 0.

The Troc-protected compound 7d was prepared by an alternative synthetic strategy involving the use of acetals. The ring closed allyl ester 6d was prepared by unmasking the acetal protected aldehyde in the presence of the Troc protected amine. The Troc protected amine was obtained through exposure of the free amine 9 to Troc-Cl in the presence of pyridine. Reduction with tin chloride furnished the amine 9 from the nitro acetal 8, which in turn was obtained by coupling 2 to the appropriate acetal-protected prolinal.

Allyl Amino Alcohol Intermediate (4)

3-(4-carboxy-2-methoxy-5-nitrophenoxy)propanoic acid (1)

The alcohol 0 (50 g, 0.22 mol) was added portionwise over 1 hour to nitric acid (70%, 400 ml) cooled to 0° C. Once addition was complete, the solution was stirred at 0° C. for 1 hour, then allowed to warm to RT. The semisolid formed was collected by filtration and washed with a minimum of ice/water. The resulting pale yellow solid was redissolved in EtOAc, the solution dried ($MgSO_4$) and then concentrated to afford the diacid 1 (31 g, 49%). $^1$H NMR (270 MHZ): $\delta$2.83–2.79 (t, J=6, 12.5 HZ, 2H), 3.94 (s, 3H), 4.37–4.33 (t, J=6, 12.5 MHZ, 2H), 7.18 (s, 1H), 7.46 (s, 1H), 10.38 (br.s, 2H).

2-Propene 3-(4-carboxy-2-methoxy-5-nitrophenoxy) propanoate (2)

A mixture of 3-(4-carboxy-2-methoxy-5-nitrophenoxy) propanoic acid 1 (20 g, 74.3 mmol) and p-toluene sulphonic acid monohydrate (2.3 g, 7.4 mmol) in allyl alcohol (240 mL, 3.5 mol) was refluxed for 7 hours then allowed to cool. The allyl alcohol was then removed in vacuo, and the residue triturated with dilute HCl acid (3×75 ml) and collected by filtration. This solid was taken up in EtOAc, and the resulting solution washed with water (3×50 ml) and brine (3×50 ml) and dried over sodium sulphate. Evaporation in vacuo afforded 2 as a white solid (19.27 g, 84%): mp 128–130° C.; $^1$H-NMR (270 MHZ, CDCl$_3$) δ2.92 (t, 2H, J=6.35 Hz); 3.94 (s, 3H); 4.38 (t, 2H, J=6.41 Hz); 4.65 (d, 2H, J=5.61 Hz); 5.27 (dd, 1H, J$_1$=1.28 Hz, J$_2$=19.42 Hz); 5.33 (dd, 1H, J$_1$=1.28 Hz, J$_2$=17.04 Hz); 5.92 (m, 1H); 7.15 (s, 1H); 7.45 (s, 1H); $^{13}$C NMR (67.8 MHZ, CDCl$_3$): δ34.1, 56.5, 65.0, 65.4, 108.5, 111.3, 118.3, 122.9, 131.8, 141.1, 149.1, 152.6, 167.1, 170.0; IR (Nujol); ν 1730, 1630, 1550, 1430, 1390, 1290, 1230, 1190, 1170, 1070, 1030, 1010 cm$^{-1}$; MS (EI) m/z (relative intensity): 325 (M$^{+\bullet}$, 19), 251 (3), 213 (2), 196 (3), 211 (3), 113 (19), 91 (4), 71 (9), 55 (6); HRMS: calcd. for C$_{14}$H$_{15}$NO$_8$ 325.0798, found 232.0773.

2-Propene 3-(4-[2'-hydroxymethylpyrrolidinecarboxy]-2-methoxy-5-nitrophenoxy)propanoate (3)

Oxalyl chloride (2.7 ml, 31.0 mmol) was added dropwise to a suspension of the nitro acid 2 (9 g, 28.0 mmol) and DMF (0.05 ml) in CH$_2$Cl$_2$ (150 ml), followed by stirring at room temperature for 16 hours The resulting solution was added dropwise to a stirred solution of pyrrolidine methanol (3 ml, 31.0 mmol) and triethylamine (8.5 ml, 61.0 mmol) in CH$_2$Cl$_2$ (80 ml) at −20° C. (liquid N$_2$/acetone) followed by stirring at room temperature for 16 hours under N$_2$. After quenching with aqueous HCl (1.0 N, 50 ml), the separated organic phase was washed with H$_2$O (3×25 ml) and brine (3×10 ml), dried over magnesium sulphate and evaporated in vacuo to afford a crude orange oil. Purification by flash column chromatography (5% MeOH/EtOAc) afforded 3 as a pale yellow oil (7.9 g, 70%): $^1$H NMR (270 MHZ, CDCl$_3$): δ2.22–1.71 (m, 6H); 2.94 (t, J=6.4 Hz, 2H); 3.15 (d×d, J=6.5 Hz, 2H); 3.92–3.76 (m, 1H); 3.96 (s, 3H); 4.4 (t, J=6.2 Hz, 2H); 4.67–4.64 (m, 2H); 5.39–5.23 (m, 2H); 6.0–5.86 (m, 1H); 6.81 (s, 1H); 7.75 (s, 1H); $^{13}$C NMR (67.8 MHz, CDCl$_3$): δ24.4, 28.5, 34.1, 49.5, 56.7, 61.6, 64.9, 65.6, 108.9, 109.3, 118.6, 128.2, 131.8, 148.2, 154.9, 170.1; IR (film): ν 3394, 2947, 2882, 1735, 1689, 1618, 1577, 1521, 1454, 1431, 1386, 1334, 1276, 1221, 1178, 1059, 1002 cm$^{-1}$; MS (EI) M/Z (relative intensity): 408 (M$^+$, 1), 390(4), 377(20), 308(86), 296(3), 278(9), 265(35), 252(3), 118(74), 111(3), 108(8), 98(4), 83(14). HRMS: calcd. for C$_{19}$H$_{25}$O$_6$N$_2$ 377.416, found 377.1711

2-Propene 3-(5-amino-4-[2'-hydroxymethylpyrrolidinecarboxy]-2-methoxyphenoxy)propanoate (4)

Solid SnCl$_2$.2H$_2$O (21.3 g, 0.095 mol) was added to a stirred solution of the nitro alcohol 3 (7.7 g, 0.02 mol) in MeOH (100 ml), and the mixture heated at reflux for 45 min. The solvent was then evaporated in vacuo, and the residual oil partitioned between EtOAc (50 ml) and aqueous saturated NaHCO$_3$ (50 ml) followed by vigorous stirring for 16 hours to aid separation. The combined layers were filtered through Celite and washed with EtOAc (25 ml). The layers were separated and the resulting organic phase was washed with H$_2$O (3×25 ml) and brine (3×10 ml) and then dried over magnesium sulphate. Evaporation in vacuo afforded the amine 4 as a dark orange oil (5.6 g, 78%): $^1$H NMR (270 MHZ, CDCl$_3$) δ2.17–1.65 (m, 6H); 2.9 (t, J=6.6 Hz, 2H); 3.72–3.46 (m, 3H); 3.75 (s, 3H); 4.2 (t, J=6.8 Hz, 2H); 4.4 (br. d×d, J=9.7 Hz, 2H); 4.65–4.62 (m, 2H); 5.37–5.22 (m, 2H); 6.0–5.85 (m, 1H); 6.3 (s, 1H); 6.76 (s, 1H). $^{13}$C NMR (67.8 MHZ, CDCl$_3$): δ24.9, 28.7, 34.3, 57.3, 61.2, 64.2, 65.5, 67.4, 102.6, 113.5, 118.5, 131.9, 141.1, 150.9, 170.5. IR (film): ν 3354, 2940, 2880, 1734, 1621, 1589, 1514, 1453, 1429, 1407, 1265, 1230, 1173, 1110, 1023. MS(EI) M/Z (relative intensity): 378 (M$^+$, 60), 278(100), 266(5), 252(9), 238(3), 220(4), 206(6), 194(4), 178(3), 166(40), 150(5), 137(20), 123(4), 113(4), 107(4), 100(8), 94(12), 84(9). HRMS: calcd. for C$_{19}$H$_{26}$O$_6$N$_2$ 378.424, found 378.1760.

Example 1(a)

Nvoc-PBD Acid (7a)

Nvoc Chloroformate 4,5-Dimethoxynitrobenzyl alcohol (2 g, 9.4 mmol) and triphosgene (0.93 g, 3.13 mmol) were dissolved in CH$_2$Cl$_2$ (50 ml), and the resulting red suspension stirred vigorously and cooled to 0° C. Pyridine (260 μl, 3.13 mmol) was added dropwise, and the resulting green solution stirred at room temperature for 16 hours to afford a solution of the chloroformate that was used directly in the next step.

Allyl Nvoc Alcohol (5a)

A solution of freshly prepared (see above) Nvoc chloroformate (9.4 mmol) and pyridine (1.3 ml, 9.5 mmol) was added dropwise to a stirred solution of the amino alcohol 4 (3 g, 7.9 mmol) in CH$_2$Cl$_2$ (60 ml) at 0° C. The mixture was allowed to return to room temperature and stirring continued for 3 hours. Evaporation in vacuo afforded an oil which was redissolved in CH$_2$Cl$_2$ (50 ml). The resulting solution was washed with HCl (1.0 N, 3×25 ml), H$_2$O (3×25 ml) and brine (3×10 ml), dried over magnesium sulphate and evaporated in vacuo to give a dark yellow foam. This was purified by flash column chromatography (EtOAc) to afford the carbamate 5a as a pale yellow foam (3.7 g, 76%): $^1$H NMR (270 MHZ, CDCl$_3$): δ1.6–2.2 (m, 6H); 2.9 (t, J=6.2, 2H); 3.4–3.9 (m, 3H); 3.81 (s, 3H); 3.97 and 4.01 (2×s, 6H); 4.3 (t, J=6.4 Hz, 2H); 4.63 (d, J=5.9 Hz, 2H); 5.22–5.36 (m, 2H); 5.5–5.67 (m, 2H); 5.85–6.0 (m, 1H); 6.84 (s, 1H); 7.09 (s, 1H); 7.74 (s, 1H); 8.93 (br. s, 1H). $^{13}$C NMR (67.8 MHz, CDCl$_3$): δ25.1, 28.3, 34.3, 51.5, 56.4, 56.6, 56.8, 61.0, 63.8, 64.4, 65.4, 66.4, 106.3, 108.2, 110.0, 111.9, 118.5, 127.8, 131.5, 131.9, 139.6, 144.4, 148.1, 150.3, 153.2, 153.7, 170.3, 170.7. IR (reflectance): ν 3329, 3110, 2937, 1728, 1581, 1523, 1453, 1323, 1270, 1175, 1129, 1070, 1031, 1011. MS(FAB) M/Z (relative intensity): 618 (M$^+$+1(3)), 473(2), 439(1), 405(1), 378(3), 304(7), 278(16), 196(100), 166(28), 151(15), 102(27), 70(9).

Allyl Nvoc PBD (6a)

A solution of DMSO (1.45 ml, 0.02 mol) in CH$_2$Cl$_2$ (40 ml) was added over 45 minutes to a stirring solution of oxalyl chloride (5.1 ml, 0.01 mol) in CH$_2$Cl$_2$ (20 ml) cooled to −40° C. (liquid N$_2$/chlorobenzene). Stirring was continued for a further 15 minutes at −40° C., and then a solution of the NVOC alcohol 5a (3.5 g, 5.7 mmol) in CH$_2$Cl$_2$ (45 ml) was added dropwise over 1 hour. Stirring was continued at −40° C. for a further 45 min, and then a solution of Et$_3$N (3.4 ml, 0.024 mol) in CH$_2$Cl$_2$ (20 ml) was added dropwise over 30 minutes and stirring continued for 1 hour. The mixture was then allowed to warm to room temperature before diluting with CH$_2$Cl$_2$ (20 ml). The organic phase was washed with HCl (1.0 N) (3×50 ml), H$_2$O (3×50 ml) and brine (3×25 ml), dried over magnesium sulphate and then evaporated in vacuo to give a yellow foam. This was purified by flash column chromatography (1% MeOH/CHCl$_3$) to afford 6a as a pale yellow foam (3.2 g, 91%): $^1$H NMR (270 MHZ, CDCl$_3$): δ1.9–2.2 (m, 6H); 2.86 (t, J=6.9 Hz, 2H); 3.45–3.6 (m, 3H); 3.81 (s, 3H); 3.88 and 3.91 (2×s, 6H); 4.2–4.4 (m, 3H); 4.61 (m, 2H); 5.19–5.35 (m, 2H); 5.49 (s, 2H); 5.7 (br d, J=9.9 Hz, 1H); 5. 82–5.97 (m, 1H); 6.51 (s, 1H); 6.86 (s, 1H); 7.25 (s, 1H); 7.66 (s, 1H); $^{13}$C NMR (67.8 MHZ, CDCl$_3$): δ23.1, 28.7, 30.6, 34.1, 46.5, 56.2, 60.1, 64.6, 65.3, 65.5, 86.1, 107.9, 109.2, 110.8, 114.3, 118.4, 126.7, 127.0, 128.1, 131.8, 138.9, 147.9, 148.9, 149.9, 153.8, 155.4, 166.8, 170.3. IR (reflectance): v 3329, 3084, 2940, 1713, 1633, 1519, 1454, 1276, 1105, 1067. MS (EI) M/Z (relative intensity) 615 (M$^+$, 12), 503(100), 358(4), 261(3), 246(37), 231(4), 196(32), 180(24), 166(4), 150(4), 136(6), 70(31).

Acid Nvoc PBD (7a)

Tetrakis(triphenylphosphine) palladium (0.583 g, 0.504 mmol) and morpholine (4.4 ml, 50.4 mmol) were added to a solution of the allyl carbinolamine 6a (3.1 g, 5.04 mmol) in THF (30 ml) and the mixture stirred for 16 hours. After evaporation in vacuo, the resulting oil was redissolved in CH$_2$Cl$_2$, and the solution washed with HCl (1.0 N) (3×25 ml), H$_2$O (3×25 ml) and brine (3×10 ml), dried over magnesium sulphate and then evaporated in vacuo to give an orange foam. This was purified by flash column chromatography (1% MeOH/CHCl$_3$) to afford 7a as a pale yellow foam (2.25 g, 78%): $^1$H NMR (270 MHZ, CDCl$_3$): δ1.9–2.3 (m, 4H); 2.85 (t, J=6.7 Hz, 2H); 3.4–3.6 (m, 3H); 3.68 (s, 3H); 3.87 and 3.9 (2×s, 6H); 4.2–4.4 (m, 3H); 5.4–5.48 (m, 2H); 5.7 (br d, J=9.9 Hz, 1H); 6.5 (s, 1H); 6.89 (s, 1H); 7.26 (s, 1H); 7.64 (s, 1H); $^{13}$C NMR (67.8 MHZ, CDCl$_3$): δ23.0, 28.5, 33.9, 46.6, 56.2, 60.4, 64.6, 65.4, 86.1, 107.9, 109.3, 110.8, 114.7, 126.5, 126.9, 128.2, 138.9, 147.9, 148.9, 149.9, 153.8, 155.5, 167.1, 174.5. IR (reflectance): v 2939, 2252, 1712, 1599, 1522, 1459, 1277, 1221, 1137, 1105, 1066, MS (FAB) M/Z (relative intensity): 576 (M$^{30}$+1, 15), 514(3), 381(3), 363(3), 336(3), 319(9), 303(2), 293(3), 289(2), 279(4), 266(6), 264(14), 253(3), 245(4), 238(10), 215(4), 206(4), 196(100), 192(16), 180(23), 166(32), 151 (18), 136(10), 123(7), 117(14), 93(28), 73(15), 70(20).

Example 1(b)

Fmoc-PBD Acid (7b)

Allyl Fmoc Alcohol (5b)

9-Fluorenylmethyl chloroformate (5.65 g, 0.022 mol) was added portionwise to a stirred solution of the amino alcohol 4 (7.5 g, 0.02 mol) and Na$_2$CO$_3$ (5.26 g, 0.05 mol) in a mixture of THF (150 ml) and water H$_2$O (150 ml) at 0° C. The reaction mixture was allowed to return to room temperature, stirred for a further 2 h, and then extracted with EtOAc (3×50 ml). The combined organic phase was washed with H$_2$O (3×50 ml) and brine (3×25 ml), dried over magnesium sulphate and evaporated in vacuo to give a dark red oil. This was purified by flash column chromatography (petroleum ether 40–60/EtOAc, 1:1) to afford 5b as a pale yellow oil (8.11 g, 68%): $^1$H NMR (270 MHZ, CDCl$_3$): δ1.72–2.18 (m, 6H); 2.9 (t, J=6.4, 2H); 3.43–3.91 (m, 3H); 3.81 (s, 3H); 4.25–4.54 (m, 5H); 4.61–4.65 (m, 2H); 5.21–5.37 (m, 2H); 5.85–6.0 (m, 1H); 6.85 (s, 1H); 7.31–7.79 (m, 9H); 8.77 (br s, 1H); $^{13}$C NMR (67.8 MHZ, CDCl$_3$): δ25.1, 28.4, 35.3, 47.0, 56.7, 60.9, 64.3, 65.4, 66.3, 67.1, 106.4, 111.7, 118.3, 120.0, 125.2, 127.1, 127.2, 127.8, 131.5, 131.9, 141.3, 143.7, 144.4, 150.2, 153.8, 170.3; MS (FAB): 601 (M$^{+\cdot}$1); HRMS: calcd for C$_{34}$H$_{36}$N$_2$O$_8$ 600.667, found 600.2175. IR (film): v 3315, 2952, 1727, 1597, 1522, 1452, 1392, 1322, 1174, 1117, 1017.

Fmoc Allyl Carbinolamine Cyclised (6b)

A solution of DMSO (3.4 ml, 0.048 mol) in CH$_2$Cl$_2$ (100 ml) was added dropwise over 45 minutes to a stirred solution of oxalyl chloride (12 ml, 0.024 mol) in CH$_2$Cl$_2$ (50 ml) at −40° C. (liquid N$_2$/chlorobenzene). The mixture was stirred at −40° C. for a further 15 minutes and then a solution of the FMOC alcohol 5b (8 g, 0.013 mol) in CH$_2$Cl$_2$ (135 ml) was added over 1 hour. After stirring for a further 45 minutes at −40° C., a solution of DIPEA (10 ml, 0.057 mol) in CH$_2$Cl$_2$ (55 ml) was added over 30 minutes and stirring continued for 1 hour. The solution was then allowed to warm to room temperature, diluted with CH$_2$Cl$_2$ (100 ml), and the organic phase washed with HCl (1.0 N) (3×50 ml), H$_2$O (3×50 ml) and brine (3×25 ml), dried over magnesium sulphate and evaporated in vacuo to afford 6b as a pale cream foam (6.4 g, 80%): $^1$H NMR (270 MHZ, CDCl$_3$): δ1.99–2.1 (m, 4H); 2.83–2.87 (m, 2H); 3.51–3.6 (m, 2H); 3.6–3.8 (m, 1H); 3.95 (s, 3H); 4.0–4.58 (m, 7H); 5.17–5.31 (m, 2H); 5.68 (d, J=9.7 Hz, 1H); 5.84–5.87 (m, 1H); 6.75 (s, 1H); 7.02–7.75 (m, 9H); $^{13}$C NMR (67.8 MHZ, CDCl$_3$) δ23.0, 28.7, 34.2, 46.5, 53.5, 56.2, 59.5, 60.1, 64.4, 65.4, 68.4, 86.0, 111.2, 114.7, 118.4, 119.9, 124.9, 125.4, 126.8, 127.1, 127.8, 128.3, 131.8, 131.9, 141.1, 141.2, 143.1, 143.5, 148.9, 149.9, 156.1, 166.9, 170.3; MS (FAB) 599 (M$^{+\cdot}$+1). IR (reflectance): v 3318, 2950, 1713, 1603, 1517, 1386, 1290, 1177, 1037.

Fmoc Acid Carbinolamine (7b)

Phenylsilane (2.5 ml, 0.02 mol) and tetrakis (triphenylphosphine) palladium(0.232 g, 0.2 mmol) were added to a solution of the FMOC carbinolamine 6b (6 g, 0.01 mol) in CH$_2$Cl$_2$ (80 ml) followed by stirring at room temperature for 16 hours. The reaction was quenched with H$_2$O (50 ml) and extracted with CH$_2$Cl$_2$ (3×30 ml). The combined organic phase was washed with water (3×30 ml), brine (3×25 ml), dried over magnesium sulphate and evaporated in vacuo to give a dark brown foam. This was purified by flash column chromatography (MeOH/CHCl$_3$, 1:99) to afford 7b as a pale beige foam (4.3 g, 77%): $^1$H NMR (270 MHZ, CDCl$_3$): δ1.9–2.2 (m, 4H); 2.65–2.85 (m, 2H); 3.4–3.6 (m, 2H); 3.6–3.8 (m, 1H); 3.91 (s, 3H); 4.0–4.25 (m, 4H); 4.45–4.5 (m, 1H); 5.68 (d, J=9.5 Hz, 1H); 6.75 (s, 1H); 6.9–7.7 (m, 9H); $^{13}$C NMR (67.8 MHZ, CDCl$_3$) δ23.0, 28.6, 33.9, 46.5, 56.2, 60.3, 64.6, 68.5, 86.0, 111.2, 115.2, 119.8, 124.9, 126.8, 127.1, 127.7, 128.2, 140.9, 141.1, 142.9, 143.4, 149.1, 149.9, 156.3, 167.0, 174.6. IR (reflectance); v 3316, 2955, 2609, 2249, 1713, 1601, 1514, 1453, 1279, 1036. MS (FAB) M/Z (relative intensity) 560 (M$^+$+1).

Example 1(c)

Teoc-PBD Acid (7c)

Allyl Teoc Alcohol (5c)

Pyridine (0.165 ml, 2.04 mmol) was added dropwise to a solution of triphosgene (0.605 g, 2.04 mmol) and 2-trimethylsilyl ethanol (1.082 g, 9.15 mol) in anhydrous CH$_2$Cl$_2$ (100 ml), and the mixture allowed to stir at room temperature for 16 hours. This solution was added dropwise to a stirred solution of the amino alcohol 4 (2.30 g, 6.10 mmol) and pyridine (0.987 mL, 0.0122 mol) in anhydrous $CH_2Cl_2$ (50 mL) at 0° C. (ice bath) under a nitrogen atmosphere. After reaction was complete as indicated by TLC (petroleum ether/ethyl acetate, 1:1), the mixture was washed with copper (II) sulphate (2×100 mL) and brine (100 mL), dried ($MgSO_4$) and evaporated in vacuo to give a brown oil. This was purified by flash column chromatography (chlororform/methanol, 99:1) to afford 5c as a brown solid (2.5 g, 78%): $^1$H NMR (270 MHz, $CDCl_3$): δ–0.06 (s, 9H), 1.01 (m, 2H), 1.82–2.30 (m, 4H), 2.86 (m, 2H), 3.40–3.75 (m, 7H), 4.15–4.31 (m, 4H), 4.6 (m, 2H), 5.15–5.31 (m, 2H), 5.80–5.94 (m, 1H), 6.76 (s, 1H), 7.76 (s, 1H), 8.52 (s, 1H); $^{13}$C NMR (67.8 MHz, $CDCl_3$) δ–1.47, 17.7, 25.1, 28.4, 34.3, 51.6, 56.8, 61.2, 63.5, 64.3, 65.4, 66.8, 106.2, 112.1, 113.8, 118.3, 132.0, 132.2, 144.0, 154.1, 170.3; MS (EI): 522 ($M^+$, 12.8), 435 (7), 350 (13), 319 (77), 262 (27), 206 (13), 149 (88), 83 (32), 70 (100); HRMS: Calcd 522.2397, found 522.2351.

Allyl Teoc Carbinolamine PBD (6c)

A solution of DMSO (1.02 mL, 0.014 mol) in dry $CH_2Cl_2$ (30 mL) was added to a solution of oxalyl chloride (3.59 mL, 7.185 mmol) in $CH_2Cl_2$ (25 mL) at –43° C. (chlorobenzene/liq. $N_2$) under a nitrogen atmosphere. After stirring at –43° C. for 45 min, a solution of the TEOC alcohol 5c (2.50 g, 4.79 mmol) in dry $CH_2Cl_2$ (30 mL) was added dropwise to the reaction mixture and stirring continued at –43° C. for a further 45 min. A solution of triethylamine (3.34 mL, 0.024 mol) in dry DCM (25 mL) was then added dropwise, and the vessel allowed to warm to 0° C. The reaction mixture was diluted with $CH_2Cl_2$ (150 mL), washed with 1N HCl (100 mL), water (100 mL) and brine (100 mL), dried ($MgSO_4$) and then evaporated in vacuo to give crude 6c. This was purified by flash column chromatography (silica gel, chloroform) to afford 6c as a yellow oil (1.72 g, 69%): $^1$H NMR (270 MHz, $CDCl_3$): δ–0.08 (s, 9H), 0.92 (m, 2H), 2.04–2.33 (m, 4H), 3.14 (m, 2H), 3.50–3.75 (m, 4H), 3.93 (s, 3H), 4.00–4.40 (m, 4H), 4.67 (m, 2H), 5.26–5.40 (m, 2H), 5.65 (d, 1H, J=9.52 Hz), 5.89–5.99 (m, 1H), 6.72 (bs, 1H), 7.23 (s, 1H); $^{13}$C NMR (67.8 MHz, $CDCl_3$) δ–1.47, 17.6, 23.0, 28.7, 34.2, 46.4, 56.2, 59.9, 64.3, 65.4, 65.5, 85.9, 111.0, 114.7, 118.3, 126.4, 131.8, 132.0, 148.7, 149.7, 154.2, 170.0, 170.4; MS (FAB): 629 (0.8), 593 (0.91), 536 (1.5), 493 (4.6), 465 (1.0), 449 (1.7), 431 (6.8), 394 (8.1), 368 (1.3), 338 (1.5), 304 (5.8), 264 (3.6), 238 (2.2), 204 (1.6), 192 (9.1), 166 (2.5), 149 (6.8), 98 (4.3), 73 (100).

Acid Teoc PBD Carbinolamine (7c)

Tetrakis(triphenylphosphine)palladium(0) (190 mg, 0.165 mmol) was added to a solution of the Teoc-protected carbinolamine 6c (1.72 g, 3.30 mmol) in ethanol (50 mL), and the mixture heated at reflux for 60 minutes after which time TLC (AcOH/MeOH/chloroform, 1:10:100) indicated that reaction was complete. The reaction mixture was allowed to cool and was then filtered through Celite. Evaporation of the solvent in vacuo afforded 7c as a yellow solid (1.08 g, 68%): $^1$H NMR (270 MHz, $CDCl_3$): δ–0.06 (s, 9H), 0.86 (m, 2H), 1.98–2.20 (m, 4H), 2.8–3.0 (m, 2H), 3.40–3.70 (m, 3H), 3.75 (s, 3H), 4.00–4.40 (m, 2H), 5.65 (d, J=8.63 Hz, 1H), 6.78 (bs, 1H), 7.21 (s, 1H): $^{13}$C NMR (67.8 MHz, $CDCl_3$) δ, –1.5, 18.3 , 23.1, 28.7, 34.5, 46.4, 56.1, 58.4, 64.8, 64.9, 85.9, 110.8, 115.0, 126.3, 128.7, 148.6, 149.6, 167.2.

Example 1(d)

Synthesis of Troc-PBD Acid 7d

Prop-2-enyl 4-(N-2S-Diethylthiomethylpyrrolidinecarboxy)-2-methoxy-5-nitrophenyl)propanoate (8)

2-Propene 3-(4-carboxy-2-methoxy-5-nitrophenyloxy) propanoate 2: 5 g, 15.34 mmol), oxalyl chloride (2 mL, 23 mmol) and 5 drops of DMF were stirred in dry THF (100 mL) for 18 hours. The solvent was then removed in vacuo and the residue dissolved in dry THF (50 mL). This was added dropwise to a vigorously stirred mixture of (2S)-pyrrolidine-2-carboxaldehyde diethyl thioacetal (3.15 g, 15.34 mmol) and triethylamine (1.86 g, 18.41 mmol). The stirring was continued for 18 hours. The solvent was then removed in vacuo and the product purified by flash column chromatography (ethyl acetate) to give 8 (7.48 g, 95%) as a yellow oil. $^1$H NMR (270 MHZ, $CDCl_3$): δ7.74 (s, 1H, OCCHC), 6.83 (s, 1H, MeOCCHC), 5.98–5.86 (m, 1H, $CH_2CHCH_2$, 5.33 (d, 1H, J=26.56 Hz, $OCH_2CHCH_2$), 5.28 (d, 1H, J=20.24 Hz, $OCH_2CHCH_2$), 4.88 (d, 1H, J=3.85 Hz, NCHCH), 4.74–4.65 (m, 2H, $OCH_2CHCH_2$) 4.42 (t, 2H, J=7.69 Hz, $CH_2CH_2OC$), 3.94 (s, 3H, $OCH_3$), 3.29–3.21 (m, 2H, $NCH_2$), 2.96 (p, 2H, J=3.12 Hz, $CH_2CH_2O$), 2.87–2.67 (m, 4H, $SCH_2CH_3$), 2.32–1.78 (m, 4H, $NCH_2CH_2CH_2$) 1.38–1.31 (m, 6H, $SCH_2CH_3$). $^{13}$C-NMR ($CDCl_3$): δ15.00, 15.13 ($SCH_2CH_3$), 24.63 ($NCH_2CH_2CH_2$), 26.28, 26.59, 27.22 ($NCH_2CH_2CH_2$), 34.13 ($CH_2CH_2O$), 50.19 ($NCH_2$), 52.80 (NCHCH), 56.60 ($OCH_3$), 61.08 (NCH), 65.13 ($CH_2CH_2O$), 65.64 ($OCH_2CHCH_2$), 108.70 (arom. CH), 109.47 (arom. CH), 118.55 ($OCH_2CHCH_2$), 128.58 (CCON), 131.73 ($OCH_2CHCH_2$), 137.17 ($CNO_2$), 147.98 ($CH_2CH_2OC$), 154.57 ($COCH_3$), 166.61 (CON), 170.14 (COO). IR (Nujol) ν=3550–2720, 3000, 2630, 2200, 1740, 1640, 1580, 1530, 1340, 1280, 1220, 1180, 1050 cm$^{-1}$. MS (EI): m/e (relative intensity): 527 ($M^{+\bullet}$, 1), 377 (10), 310 (12), 309 (72), 308 (94), 268 (20), 142 (4). HRMS calcd. for $C_{24}H_{35}O_7N_2S_2$=527.1875, found=527.1885.

5-Amino-3-(4-(2-diethylthiomethyl-(2S)-perhydro-1-pyrroloylcarbonyl)-2-methoxyphenyloxy)2-propenylpropanoate (9)

A solution of 8 (7.21 g, 14.05 mmol) and in(II) chloride (15.85 g, 76 mmol) was refluxed for 40 minutes in ethyl acetate (100 mL) then allowed to cool. The solvent was then removed in vacuo and the residue was triturated with saturated bicarbonate solution at 0° C. EtOAc (50 mL) was added and the reaction stirred overnight. The reaction mixture was then filtered through Celite and the filter cake washed with ethyl acetate. The combined organics were then washed with water and brine, dried with sodium sulphate and the solvent removed in vacuo. The product was purified using flash column chromatography (5% MeOH/dichloromethane) to give a yellow oil, (5.87 g, 86%). $^1$H NMR (270 MHZ, $CDCl_3$): δ6.82 (s, 1H, arom. CH), 6.28 (s, 1H, arom.CH), 5.99–5.85 (m, 1H, $OCH_2CHCH_2$), 5.31 (dd, 1H, J=1.28 Hz, 27.66 Hz, $OCH_2CHCH_2$), 5.26 (dd, 1H, J=1.28 Hz, 20.70 Hz, $OCH_2CHCH_2$), 4.71–4.62 (m, 5H, including doublet at 4.62, 2H, J=5.49 Hz, $NH_2$+NCHCH, $OCH_2CHCH_2$), 4.27 (t, 2H, J=6.59 Hz, $CH_2CH_2O$), 3.92, (m, 1H, NCH), 3.74 (s, 3H, $OCH_3$), 3.66–3.57 (m, 2H, $NCH_2$) 2.89 (t, 2H, J=6.6 Hz, $CH_2CH_2O$), 2.83–2.64 (m, 4H, $SCH_2CH_3$), 2.28–1.80 (m, 4H, $NCH_2CH_2CH_2$), 1.25 (m, 6H, $SCH_2CH_3$);$^{13}$C NMR ($CDCl_3$) δ14.20 ($SCH_2CH_3$), 26.55, 27.23 ($NCH_2CH_2CH_2$), 34.27 ($CH_2CH_2O$), 53.20 (NCHCH), 56.08 ($OCH_3$), 60.10 (NCH), 60.39 ($NCH_2$), 64.20 ($CH_2CH_2O$), 64.41 ($OCH_2CHCH_2$), 102.26 (arom. CH), 113.71 (arom. CH), 118.40 ($OCH_2CHCH_2$), 131.93 ($OCH_2CHCH_2$), 141.03 ($CNH_2$), 141.74 ($CH_2CH_2OC$), 154.56 ($COCH_3$), 169.69 (CON), 170.53 (COO). IR (neat liquid film) 3500–3000, 3460, 3400, 2970, 1740, 1650, 1535, 1470, 1345, 1290, 1225, 1190 cm$^{-1}$; MS (EI): m/e (relative intensity): 482 ($M^{+\bullet}$; 4), 347 (2), 278 (31), 137 (1), 70 (3); HRMS calcd. for $C_{23}H_{34}O_5N_2S_2$=482.1909, found= 482.1925.

3-(4-(2-Diethylthiomethyl-(2S)-perhydro-1-pyrrolylcarbonyl)-2-methoxy-5-(2,2,2-trichloroethyloxycarbonylamino)phenyloxy)2-propenylpropanoate (10)

To a solution of 9 (5.67 g, 11.74 mmol) in dichloromethane (200 mL) was add ed pyridine (2.02 mL, 23.48 mmol). To this was added dropwise at 0° C. a solution of trichloroethyl chloroformate(1.616 mL, 11.74 mmol). The solution was stirred for a further 1 hour at 0° C. The organics were washed with 1 N HCl (3×100 mL), water (3×100 mL) brine (100 mL), dried over magnesium sulphate and the solvent removed in vacuo to give a brown oil (6.8 g, 88%) $^1$H NMR (270 MHZ, CDCl$_3$): δ9.14 (bs, 1H, NH), 7.88 (bs, 1H, CHCNH), 6.93 (s, 1H, MeOCCHC), 5.99–5.86 (m, 1H, OCH$_2$CHCH$_2$), 5.31 (dt, 1H, J=1.47 Hz, 27.84 Hz OCH$_2$CHCH$_2$), 5.25 (dt, 1H, J=1.29 Hz, 21.61 Hz, CH$_2$CHCH$_2$),4.89–4.77 (m, 4H, including doublet 1H, J=1.28 Hz, CHCHSEt, NH, CH$_2$-TrOC), 4.62 (d, 2H, J=1.28 Hz, OCH$_2$CHCH$_2$), 3.81 (s, 3H, OCH$_3$), 3.60 (m, 2H, NCH$_2$), 2.91 (d, 2H, J=6.42 Hz, CH$_2$CH$_2$O), 2.84–2.61 (m, 4H, SCH$_2$CH$_3$), 1.37–1.23 (m, 6H, SCH$_2$CH$_3$); $^{13}$C NMR (CDCl$_3$): δ170.33 (ester CO), 168.50 (CON), 151.94 (OCO), 150.29 (COCH$_3$), 144.52 (COCH$_2$CH$_2$), 131.93 (OCH$_2$CHCH$_2$), 131.35 (CNH), 118.29 (OCH$_2$CHCH$_2$), 112.21 (arom. CH), 105.51 (arom. CH), 95.27 (CCl$_3$), 76.24 (CH$_2$TrOC), 74.39 (CH$_2$TrOC), 65.42 (CH$_2$CH$_2$O), 61.14 (NCH), 56.30 (OCH$_3$), 53.00 (NCHCHSEt), 34.27 (CH$_2$CH$_2$O), 27.30, 26.71, 26.43, 25.24 (NCH$_2$CH$_2$CH$_2$), 15.27, 14.87, 14.18 (SCH$_2$CH$_3$). MS (EI): m/e (relative intensity): 658, 656 (M$^{+\cdot}$, 1), 508 (1), 373 (6), 305 (5), 304 (27), 192 (5), 70 (12).

3-(11-Hydroxy-5-oxo-10-(2,2,2-trichloroethyloxocarbonylamino)-(11aS)-2,3,5,10,11,11a-hexahydro-1H-benzo[e]pyrrolo[2,1-a][1,4]diazepin-8-yloxy-2-propenylpropanoate (6d)

A solution of 10 (6.8 g, 10.34 mmol) in acetonitrile/water (4:1, 200 mL) was treated with calcium carbonate (2.585 g, 25.85 mmol) and mercuric(II) chloride (7.00 g, 25.85 mmol) and the solution was stirred for 18 hours. The reaction was then filtered through Celite and the filter pad washed with ethyl acetate. The organics were collected and washed with water (3×50 mL), brine (100 mL) and dried over magnesium sulphate. The solvent was removed in vacuo and the resulting product was purified by flash column chromatography (ethyl acetate) to give the product as a yellow oil (3.67 g, 64%) $^1$H NMR (270 MHZ, CDCl$_3$): δ7.25 (arom. CH), 6.86 (s, 1H, arom. CH), 6.00–5.85 (m, 1H, CH$_2$CHCH$_2$), 5.67 (d, 1H, J=9.71 Hz, TrOC-CH$_2$) 5.37–5.20 (m, 3H, TrOC-CH$_2$+OCH$_2$CHCH$_2$), 4.65 (d, 2H, J=5.67 Hz, CH$_2$CHCH$_2$O), 4.36–4.22 (m, 3H, CH$_2$CH$_2$O+NCHOH), 3.90 (s, 3H, OCH$_3$), 3.72–3.47 (m, 3H, NCH+NCH$_2$), 2.91 (t, J=6.41 Hz, CH$_2$CH$_2$O) 2.29–2.00 (m, 4H, NCH$_2$CH$_2$CH$_2$) $^{13}$C NMR (67.8 MHZ, CDCl$_3$): δ170.33 (ester carbonyl CO), 166.17 (CON), 154.4 (OCO), 149.88 (COCH$_3$), 148.93 (COCH$_2$CH$_2$), 131.86 (CH$_2$CHCH$_2$), 127.48 (arom. CN), 126.24 (CCON), 118.42 (OCH$_2$CHCH$_2$), 114.48 (arom. CH), 110.82 (arom. CH), 95.09 (CCl$_3$), 86.42 (NCHOH), 74.96 (TrOC-CH$_2$), 65.47 (OCH$_2$CHCH$_2$), 64.43 (CH$_2$CH$_2$O), 60.13 (NCH), 56.14 (OCH$_3$), 46.44 (NCH$_2$), 34.26 (CH$_2$CH$_2$O), 28.64 (NCH$_2$CH$_2$CH$_2$), MS (EI) m/z (relative intensity):=552 (M$^+$10), 550 (10), 374 (2), 368 (5), 304 (15), 192 (8), 70 (24), 55(24). HRMS calcd. for C$_{22}$H$_{25}$N$_2$O$_8$Cl$_3$=552.0651, found 3 peaks due to chlorine 552.0646, 550.676, 554.0617.

3-(11-Hydroxy-5-oxo-7-methoxy-10-(2,2,2-trichloroethyloxocarbonylamino)-(11aS)-2,3,5,10,11,11a-hexahydro-1H-benzo[e]pyrrolo[2,1-a][1,4]diazepin-8-yloxypropanoic acid (7d).

A solution of 6d (3.5 g, 6.35 mmol) was dissolved in ethanol (100 mL). To this was added Tetrakis (triphenylphospine) palladium(0) (350 mg; 0.303 mmol) and the solution refluxed for 30 minutes until the reaction was complete by TLC monitoring. The reaction was then allowed to cool and the filtered through Celite. The EtOH was then removed in vacuo to give the crude material as a yellow solid which was used directly in the next steps. $^1$H-NMR (220 MHZ, CDCl$_3$): δ7.22 (s, 1H, OCCHCN), 7.01 (s, 1H, MeOCCHC), 6.27 (bs, COOH), 5.67 (d, 1H, J=9.5 Hz, TrOC-CH$_2$), 5.06 (d, 1H, J=12.09 Hz, TrOC-CH$_2$), 4.29–4.11 (m, 2H, CHOH), 3.85 (s, 3H, OCH$_3$), 3.71 (t, 2H, J=6.97 Hz, CH$_2$CH$_2$O), 3.51 (m, 1H, NCH), 2.80 (m, 2H, NCH$_2$), 2.12–1.99 (m, 4H, NCH$_2$CH$_2$CH$_2$), 1.21 (t, 2H, J=6.96 Hz, CH$_2$CH$_2$O); $^{13}$C NMR (67.8 MHZ, CDCl$_3$): δ=174.27 (acid CH), 167.34 (CON), 154.20 (OCO), 149.78 (COCH$_3$), 148.74 (COCH2CH2), 133.79 (arom. CH), 132.16 (arom. CH), 128.66 (arom. CN), 125.87 (CCON), 95.06 (CCl$_3$), 86.53 (NCHCHOH), 74.95 (CH$_2$-TrOC), 60.67 (NCH), 58.24 (CH$_2$CH$_2$O), 56.04 (OCH$_3$), 46.44 (NCH$_2$), 35.24 (NCH$_2$CH$_2$CH$_2$), 28.59 (NCH$_2$CH$_2$CH$_2$), 23.08 (CH$_2$CH$_2$O).

Example 1(e)

Synthesis of Resin-bound Protected PBD (JGB-285)

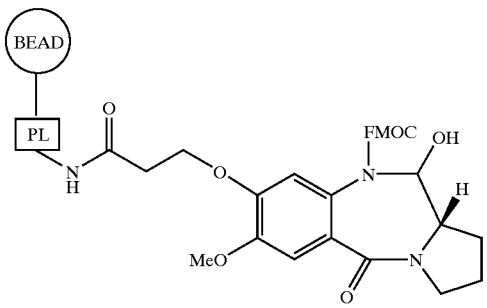

JGB-285

DMF (500 µl) was added to amino Tentagel resin (0.056 g, 0.26 mmol/g loading) in an Alltech tube (8 ml) and the resulting suspension shaken for 30 min. A solution of Fmoc-PBD-acid 7b(66.6 mg, 0.12 mmol), TBTU (0.038 g, 0.012 mmol) and DIPEA (21 µl, 0.012 mmol) in DMF (1 ml) was added and shaking continued for 16 hours. The resin was filtered and rinsed with DMF (5 ml), CH$_2$Cl$_2$ (5 ml) and MeOH (5 ml). This procedure was repeated twice to ensure complete reaction and the resin was then dried in vacuo to afford JGB-285.

Example 1(f)

Synthesis of Resin-bound Unprotected PBD (JGB-286)

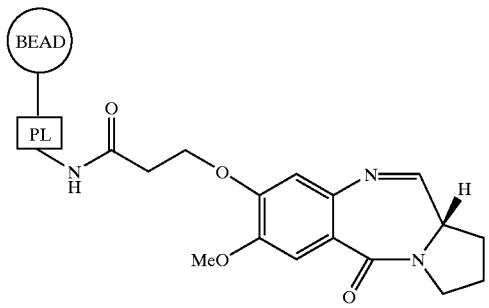

A solution of piperidine in DMF (20%, 500 μl) was added to the resin JGB-285 and the suspension shaken for 16 hours. The resin was filtered and rinsed with DMF (5 ml), CH$_2$Cl$_2$ (5 ml) and MeOH (5 ml). This procedure was repeated twice and the resin was dried in vacuo to afford JGB-286.

EXAMPLE 2

Figure 2A:
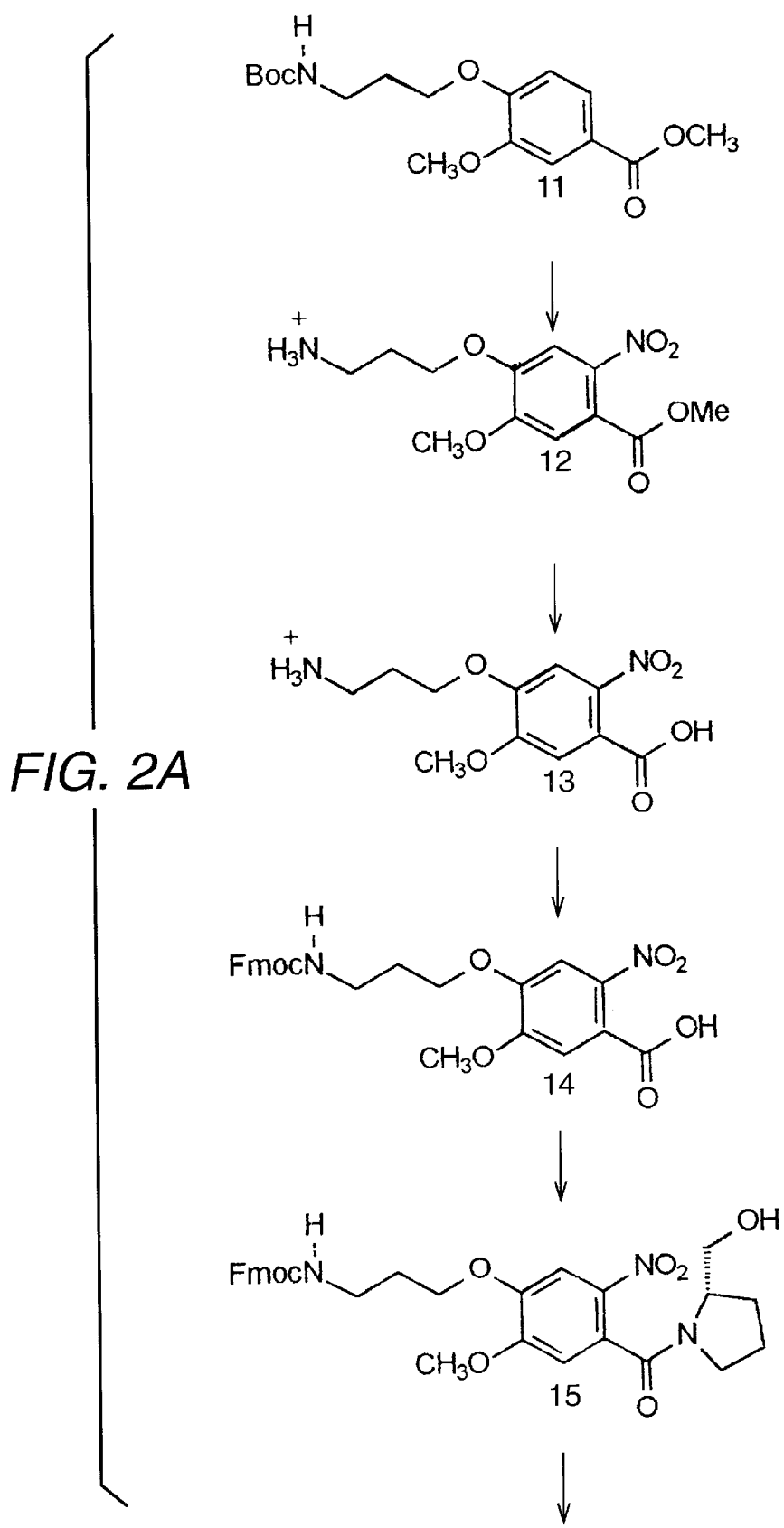
FIG. 2 is a reaction scheme for the synthesis of alternative compounds of fomula I.
Figure 2B:
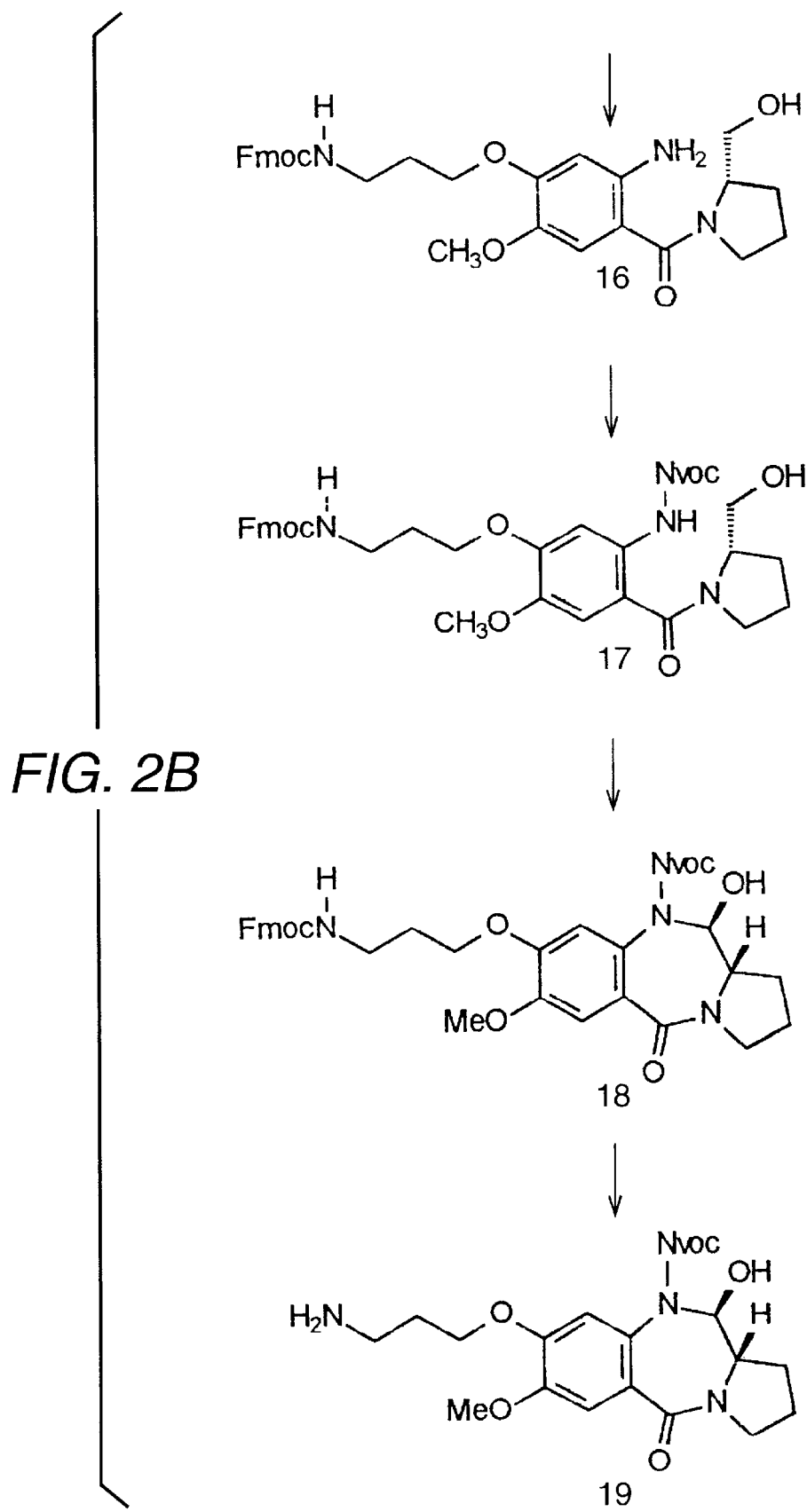

Synthesis of 8-aminopropyl PBD of Formula I (See FIG. 2)

Overall Synthesis

The compound 19 was prepared by removal of Fmoc from 18 under standard conditions (piperidine/DMF). The Fmoc carbamate was obtained via Swern oxidation of the alcohol 17, which resulted in spontaneous closure of the pyrrolobenzodiazepine B-ring. A number of other oxidation methods should also prove effective in promoting the oxidation/cyclization reaction, for example, the Dess Martin reagent, the TPAP/NMO system or Pyridine Sulphur trioxide in DMSO. The alcohol 17 was furnished by treatment of the amino alcohol 16 with Nvoc-Cl in the presence of pyridine. As before this is a general procedure applicable to any chloroformate, the choice limited only by compatibility with the PBD and Fmoc cleavage conditions. The amine group can also be protected with numerous other carbamate protecting groups, the most useful in this instance being Alloc, Teoc and Noc due to their compatibility with Fmoc cleavage conditions. It should be noted that Fmoc itself could be employed for N-10 protection in which case it would obviously be necessary to employ a different protecting group for the aliphatic nitrogen (see below). The amino alcohol was prepared by tin chloride reduction of the nitro alcohol, which in turn was prepared by coupling pyrrolidine methanol to the o-nitrobenzoic acid 14 under standard conditions. The o-nitrobenzoic acid was prepared by Fmoc protection of the amino acid 13. Again, it would be possible to substitute Fmoc with a number of other protecting groups for example Boc, Alloc, Noc etc. due to their compatibility with the N10 Nvoc group. It should be noted that if Fmoc was used to protect the aromatic N10 group, Boc, Alloc, Teoc and Nvoc could be used to protect the aliphatic nitrogen. The amino acid 13 was prepared by hydrolysis of the ester 12, which in turn was obtained by simultaneous nitration and deprotection of the Boc protected amine 11, which was obtained by a Mitsunobu etherification of methyl vanillate with Boc aminopropanol.

Boc Amino Ester (11)

A solution diethylazidodicarboxylate (3.38 g, 19.4 mmol) in THF (50 ml) was added dropwise to a solution of methylvanillate (3.53 g, 19.4 mmol), N-Boc-propanolamine (3.4 g, 19.4 mmol) and triphenylphosphine (5.09 g, 19.4 mmol) in THF (50 ml) at 0° C. The reaction mixture was allowed to warm to room temperature and stir overnight. Excess solvent was removed by rotary evaporation under reduced pressure and the residue triturated with toluene. Precipitated triphenylphosphine oxide was removed by vacuum filtration and the filtrate concentrated in vacuo. The residue was subjected to flash column chromatography (silica gel, petroleum ether 40–60/ethyl acetate, 80/20) and removal of excess eluent afforded the pure product 11 (4.8 g, 73% yield.). $^1$H NMR (270 MHZ, CDCl$_3$) δ7.65 (dd, J=8.43, 2.02 Hz, 1H), 7.54 (d, J=2.02 Hz, 1H), 6.86 (d, J=8.43 Hz, 1H), 5.55 (bs, 1H), 4.15 (t, J=5.87 Hz, 2H), 3.93 (s, 3H), 3.90 (s, 3H), 3.41–3.35 (m, 2H), 2.09–2.00 (m, 2H) and 1.46 (s, 9H). $^{13}$C NMR (68.7 MHZ, CDCl$_3$) δ166.9, 156.1, 152.1, 148.8, 123.5, 122.8, 112.0, 111.2, 79.0, 68.2, 55.9, 52.0, 38.9, 29.2 and 28.5.

Amino Nitro Ester (12)

The Boc-protected amine 11 (10 g) was added portionwise to cold nitric acid (30 ml, 70%, ice bath), the reaction mixture was allowed warm to room temperature and stir overnight. The reaction mixture was poured onto crushed ice (100 g) and the resulting aqueous solution reduced to half its original volume by rotary evaporation under reduced pressure. The resulting precipitate was collected by vacuum filtration and recrystallised from absolute ethanol to afford the product as a yellow crystalline solid 12 (8.9 g, 87%). $^1$H NMR (270 MHZ, CDCl$_3$) δ7.47 (s, 1H), 7.08 (s, 1H), 4.24 (t, J=5.86 Hz, 2H) 3.96, (s, 3H), 3.89 (s, 3H), 3.24 (t, J=6.78 Hz, 2H) and 2.32–2.23 (m, 2H).

Amino Nitro Acid (13)

A solution of potassium hydroxide (0.5 g, 8.7 mmol) and the nitrobenzoic acid 12 (1 g, 2.9 mmol) in aqueous methanol (H$_2$O, 10 ml; methanol, 20 ml) was allowed to stir at room temperature for 1 hour and then heated at reflux until TLC (AcOEt, MeOH, TEA, 1:10:100) revealed the complete consumption of starting material. Excess methanol was removed by rotary evaporation and the residual solution diluted with water and neutralised with 1N HCl. The neutralised aqueous solution was used directly, without further purification, in the next synthetic step.

Fmoc Nitro Acid (14)

Fluorenylmethyl chloroformate (0.78 g, 3 mmol) was added portionwise to the aqueous solution from the previous reaction which had been diluted with THF (50 ml) and aqueous sodium carbonate (2.15 g, 50 ml water). The reaction mixture was then allowed to stir overnight. Excess organic solvent was removed by rotary evaporation under reduced pressure from the reaction mixture, the residual aqueous solution was then washed with ethyl acetate (3×20 ml) (to remove excess Fmoc-Cl). The aqueous phase was acidified with conc. HCl and extracted with ethyl acetate (2×50 ml). The organic phase was dried over magnesium sulphate, filtered and evaporated in vacuo to afford the product 14 (1 g, 70% yield). $^1$H NMR (270 MHZ, CDCl$_3$) δ(Rotamers) 8.21 (bs, 2H), 7.73 (d, J=7.14 Hz, 2H), 7.59 (d, J=7.33 Hz, 2H) 7.40–7.13 (m, 5H), 6.47 and 5.70 (2×bs, 1H), 4.54–3.88 (m, 5H), 3.77 (s, 3H), 3.44–3.42 (m, 2H) and 2.04–1.90 (m, 2H). $^{13}$C NMR (68.7 MHZ, CDCl$_3$) δ168.7, 156.9, 152.1, 149.8, 143.7, 141.9, 141.3, 127.7, 127.0, 124.9, 120.6, 120.0, 111.1, 107.8, 68.5, 66.4, 56.4, 47.3, 39.1 and 28.4.

Fmoc Nitro Alcohol (15)

A catalytic amount of DMF (2 drops) was added to a solution of the acid 14 (1.16 g, 2.36 mmol) and oxalyl chloride (0.33 g, 2.6 mmol) in dry dichloromethane (20 ml) and the reaction mixture was allowed to stir overnight. The resulting acid chloride solution was cooled to 0° C. and treated dropwise with a solution of pyrrolidinemethanol (0.26 g, 2.57 mmol) and triethylamine (0.52 g, 5.14 mmol) in dry dichloromethane (15 ml). Thin layer chromatography, performed shortly after the end of the addition of amine, revealed that reaction had gone to completion. The reaction mixture was washed with HCl (1N, 1×50 ml) and water (2×20 ml) and dried over magnesium sulphate. Removal of excess solvent afforded the crude product which was subjected to flash column chromatography (silica gel, gradient elution,1% methanol in chloroform to 2% methanol in chloroform) to afford the required amide 15 (1.1 g, 81%). $^1$H NMR (270 MHZ, CDCl$_3$) δ7.75 (d, J=7.33 Hz, 2H), 7.67 (s, 1H), 7.60 (d, J=6.96 Hz, 2H), 7.41–7.26 (m, 4H), 6.78 (s, 1H), 5.66 (bs, 1H), 4.48–4.39 (m, 3H), 4.23–4.13 (m, 3H), 3.91–3.79 (m, 5H), 3.45–3.42 (m, 2H), 3.18–3.13 (m, 2H) and 2.08–1.70 (m, 6H). $^{13}$C NMR (68.7 MHZ, CDCl$_3$) δ168.5, 156.5, 154.7, 148.2, 143.9, 141.3, 137.0, 128.0, 127.7, 127.0, 124.9, 120, 108.9, 108.0, 68.4, 66.2, 66.0, 61.5, 56.6, 53.5, 47.3, 39.0, 28.9, 28.4 and 24.4.

Fmoc Amino Alcohol (16)

A solution of the nitroamide 15 (3 g, 5.22 mmol) and SnCl$_2$ 2H$_2$O (6.15 g, 27.15 mmol) in methanol (60 ml) was heated at reflux for 2 hours. The reaction mixture was concentrated to ⅓ of its original volume and carefully treated with saturated aqueous sodium bicarbonate solution (vigorous effervescence!) until pH8 was obtained. The mixture was allowed to stir vigorously with ethyl acetate (100 ml) overnight and then filtered through celite to remove precipitated tin salts. The aqueous phase was extracted with ethyl acetate (50 ml) and the combined organic phase was dried over magnesium sulphate. Removal of excess solvent afforded the desired amine as a dark yellow oil 16 (1.93 g, 68%). $^1$H NMR (270 MHZ, CDCl$_3$) δ7.75 (d, J=7.51 Hz, 2H), 7.61 (d, J=7.33 Hz, 2H), 7.40–7.26 (m, 4H), 6.72 (s, 1H), 6.25 (s, 1H), 5.95 (bs, 1H), 4.43–4.04 (m, 6H), 3.67–3.42 (m, 9H) and 2.11–1.7 (m, 6H). $^{13}$C NMR (68.7 MHZ, CDCl$_3$) δ171.7, 156.6, 150.8, 144.0, 141.3, 140.6, 127.6, 127.0, 125.0, 119.9, 112.0, 102.2, 68.0, 66.6, 66.4, 61.0, 56.6, 51.0, 47.3, 39.5, 29.1, 28.5 and 24.9.

Fmoc Nvoc Alcohol (17)

A solution of 4,5-dimethoxy-2-nitrobenzylchloroformate (1.44 g, 5.23 mmol) in dichloromethane (40 ml) was added dropwise to a solution of the amine 16 (2.59 g, 4.75 mmol) and pyridine (0.41 g, 5.23 mmol) in dichloromethane (60 ml) at 0°C. After 3 hours the reaction mixture was washed with HCl (1N, 2×100 ml), water (2×100 ml) and brine (1×100 ml). The organic phase was dried over magnesium sulphate and removal of excess solvent gave the crude product, which was subjected to flash column chromatography (silica gel, ethyl acetate followed by 1% methanol in ethyl acetate) to afford the pure carbamate 17 (3.2 g, 86%). $^1$H NMR (270 MHZ, CDCl$_3$) δ8.94 (br,s 1H) 7.74 (d, J=7.51 Hz, 2H), 7.71 (s, 1H), 7.61 (d J=7.33 Hz, 2H), 7.40–7.25 (m, 4H), 7.08 (s, 1H), 6.80 (s, 1H), 5.62 (d, J=15.02 Hz, 1H), 5.50 (d, J=15.02, 1H), 4.44–4.41 (m, 3H), 4.24–4.13 (m,3H), 3.99 (s, 3H), 3.94 (s, 3H), 3.70–3.44 (m, 9H), and 2.17–1.72 (m, 6H). $^{13}$C NMR (68.7 MHZ, CDCl$_3$) δ171.7, 164.0, 156.6, 153.7, 153.3, 150.1, 148.1, 144.3, 144.0, 141.3, 139.6, 131.3, 127.6, 127.0, 125.0, 119.9, 110.7, 110 1, 108.2, 105.5, 68.1, 66.4, 66.1, 63.9, 60.9, 56.6, 56.4, 56.2, 47.3, 39.5, 28.9, 28.3 and 25.1.

Fmoc Nvoc Carbinolamine (18)

A solution of DMSO (0.8 ml, 11.4 mmol) in dry dichloromethane (15 ml) was added dropwise, over 30 minutes, to a solution of oxalyl chloride (0.72 g, 5.71 mmol) in dry dichloromethane (15 ml) at −45° C. under a nitrogen atmosphere. The reaction mixture was allowed to stir for 30 minutes before the addition of the substrate 17 (3.2 g, 4.08 mmol) in dry dichloromethane (35 ml) over 50 minutes whilst maintaining the temperature of the reaction at −45° C. The reaction mixture was then allowed to stir at −45° C. for a further 45 minutes. A solution of triethylamine (2.15 ml, 16.2 mmol) in dry dichloromethane (10 ml) was added dropwise over 25 minutes at −45° C. and the reaction mixture allowed to stir for a further 30 minutes at −45° C. before being allowed to warm to room temperature. The reaction mixture was washed with 1N HCl (1×75 ml), water (1×75 ml), brine (1×75 ml) and dried over magnesium sulphate. Removal of excess solvent furnished the crude product which was subjected to flash column chromatography (silica gel, ethyl acetate) to afford the cyclized product 18 (1.92 g, 60% yield). $^1$H NMR (270 MHZ, CDCl$_3$) δ7.74 (d, J=7.51 Hz, 2H), 7.60–7.59 (m, 3H), 7.40–7.23 (m, 4H), 7.22 (s, 1H), 6.83 (s, 1H), 6.50 (s, 1H), 5.88 (bs, 1H), 5.72 (d, J=9.34 Hz, 1H), 5.45–5.38 (m, 2H), 4.59 (bs, 1H), 4.42 (d, J=7.14 Hz, 2H), 4.22–4.08 (m, 3H), 3.86 (s, 3H), 3.76 (s, 3H), 3.68 (s, 3H), 3.59–3.44 (m, 4H) and 2.12–2.02 (m, 6H). $^{13}$C NMR (68.7 MHZ, CDCl$_3$) δ166.9, 156.6, 155.4, 153.8, 150.1, 148.8, 148.1,144.0, 141.3, 139, 128.2, 127.7, 127.0, 126.7,126.5, 125.0, 120.0, 113.7, 110.5, 109.7,108.1, 86.2, 68.4, 66.3, 65.4, 60.3, 56.3, 56.2, 56.0, 47.3, 46.5, 39.4, 29.7, 28.7 and 23.1.

Amino Nvoc Carbinolamine (19)

The Fmoc protected amine 18 (0.5 g, 0.64 mmol) was added to a solution of piperidine (1 g, 11.7 mmol) in dichloromethane (10 ml). After 2 hours TLC revealed the continued presence of starting material DMF was added as a co-solvent and reaction proceeded to completion over the next 30 minutes. The reaction mixture was diluted with ethyl acetate (50 ml), washed with water (25 ml), brine (25 ml) and dried over magnesium sulphate. Removal of excess solvent afforded a yellow crystalline product which was recrystallised from ethyl acetate and petroleum ether 40–60 (0.123 g, 34% yield). $^1$H NMR (270 MHZ, CDCl$_3$) δ7.61 (s, 1H), 7.21 (s, 1H), 6.90 (s, 1H), 6.50 (s, 1H), 5.70 (d, J=9.70 Hz, 1H), 5.44 (bs, 2H), 4.13–4.11 (m, 1H), 3.96–3.40 (m, 13H), and.2.18–1.90 (m, 6H). $^{13}$C NMR (68.7 MHZ, CDCl$_3$) δ167.1, 155.1, 153.8, 150.0, 148.7, 147.9, 138.8, 128.5, 127.3, 126.5, 114.3, 110.4, 109.5, 107.9, 86.0, 67.1, 65.1, 60.7, 56.3, 56.1, 53.3, 38.7, 28.7, 28.0 and 23.1.

Example 3a

Figure 3A:
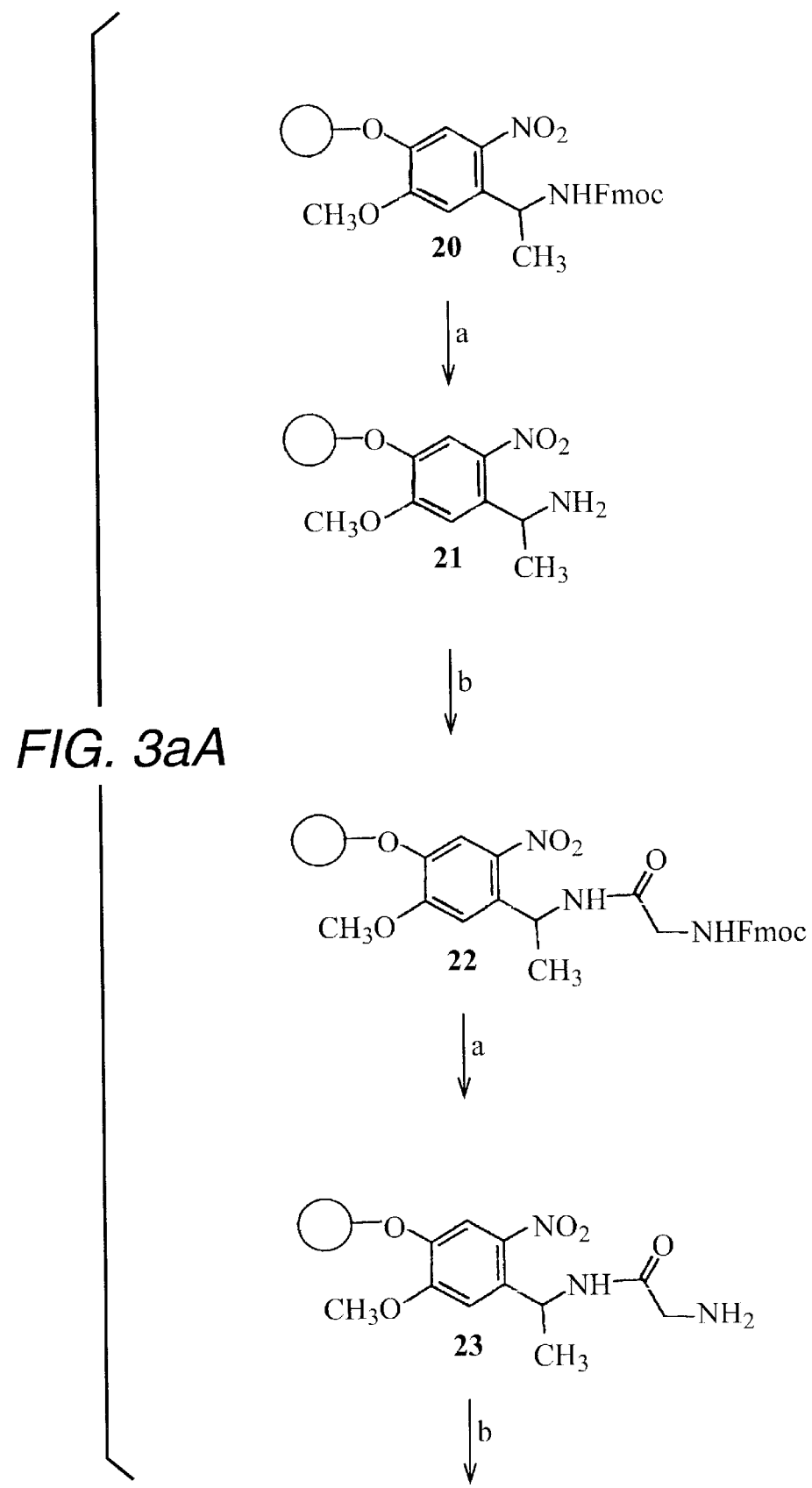
FIGS. 3a and 3b are a reaction scheme for the synthesis of compounds of formulae V, IV, III, and II.
Figure 3A:
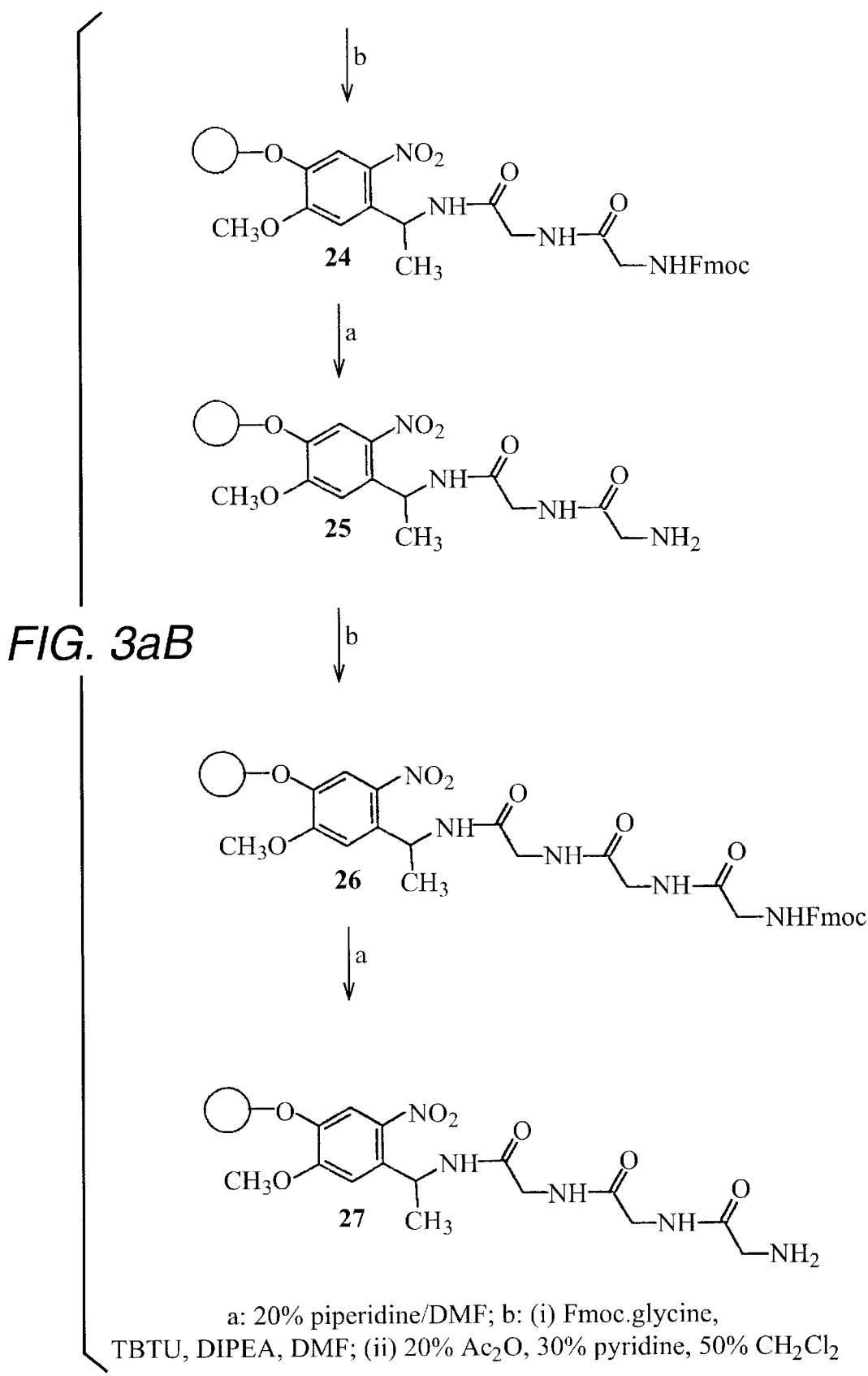
Figure 3B:
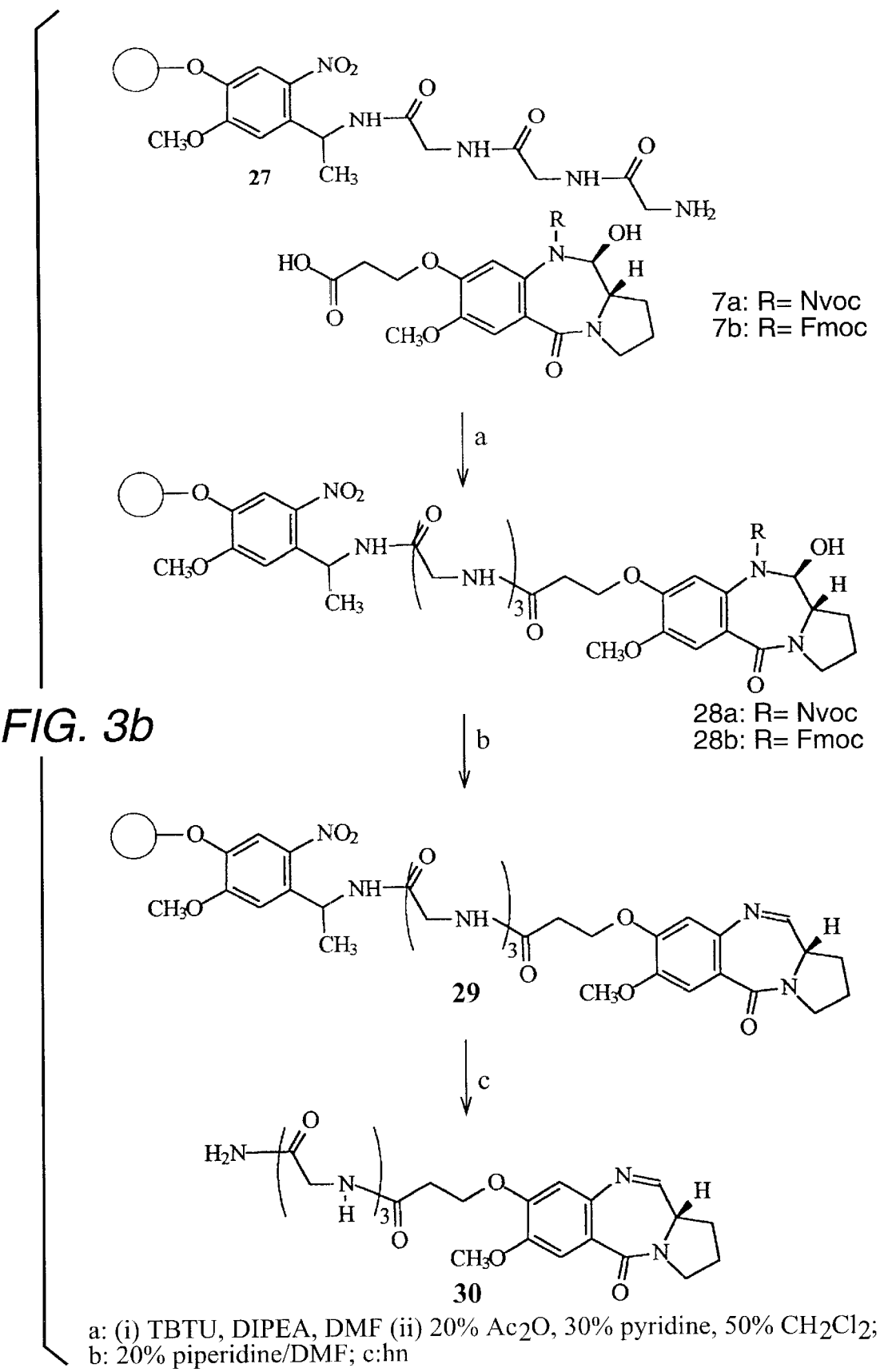

Synthesis of PBD-Triglycine 30 (FIGS. 3a & 3b)

This example was carried out to prove the general method of synthesis.

Resin Deprotection

Fmoc-aminoethyl photolinker NovaSyn TG resin 20 (0.35 g, 0.23 mmol/g loading) was placed in a peptide vessel, fitted with a sinter. After the addition of 20% piperidine in DMF (3 ml), the vessel was shaken for 3 hours. The deprotected resin 21 was then separated by filtration and rinsed with NMP (3 ml), MeOH (3 ml) and $CH_2Cl_2$ (3 ml). The whole procedure was repeated twice before drying the resin in vacuo.

Coupling Conditions

DMF (2 ml) was added to resin 21 and the suspension shaken for 30 min. A solution of Fmoc-glycine (0.24 g, 0.805 mmol), TBTU (0.26 g, 0.805 mmol) and DIPEA (140 µl, 0.805 mmol) in DMF (2 ml) was added and shaking continued for 20 hours. The coupled resin 22 was then filtered and rinsed with NMP (5 ml), MeOH (5 ml) and $CH_2Cl_2$ (5 ml). The whole procedure was repeated once before drying the resin in vacuo. The coupling efficiency was monitored by the addition of bromophenol blue in DMF (0.2 ml).

Acetylation (Endcapping) Conditions $Ac_2O$ (20%) and pyridine (30%) in $CH_2Cl_2$ (5 ml) was added to resin 22 and the suspension was shaken for 2 hours. The acetylated resin was filtered and washed with $CH_2Cl_2$ (5 ml), EtOH (5 ml) and a further aliquot of $CH_2Cl_2$ (2 ml). The whole procedure was repeated once before drying the resin in vacuo. The effectiveness of acetylation was monitored by the addition of bromophenol blue in DMF (0.5 ml).

Deprotection Conditions

Piperidine (20%) in DMF (2 ml) was added to the acetylated resin 22 and the suspension was shaken for 12 hours. The deprotected resin 23 was collected by filtration and rinsed with NMP (5 ml), MeOH (5 ml) and $CH_2Cl_2$ (5 ml). The whole procedure was repeated twice before drying the resin in vacuo.

Addition of Two Further Glycine Units

The previous coupling (21–22), acetylation and deprotection (22–23) steps were repeated twice (23–27) until the resin-bound tripeptide 27 was obtained.

Coupling to the PBD Unit (Fmoc-PBD)

Triglycine resin 27 (0.12 g, 0.235 mmol/g loading) was placed in a peptide synthesis vessel fitted with a sinter. DMF (3 ml) was added and the vessel was shaken for 30 min. A solution of the Fmoc-PBD acid 7b (0.15 g, 0.28 mmol), TBTU (0.09 g, 0.28 mmol) and DIPEA (50 µl, 0.28 mmol) in DMF (3 ml) was added, and shaking continued for 20 hours. Bromophenol blue indicator (30 µl) was added to monitor the progress of the reaction. The coupled resin 28b was collected by filtration and rinsed with DMF (5 ml), NMP (5 ml) and $CH_2Cl_2$ (5 ml). The whole procedure was repeated twice before drying the resin in vacuo.

Acetylation (Endcapping) Conditions $Ac_2O$ (20%) and pyridine (30%) in $CH_2Cl_2$ (5 ml) was added to resin 28b and the vessel shaken for 2 hours. The acetylated resin was filtered and washed with $CH_2Cl_2$ (5 ml), EtOH (5 ml) and further $CH_2Cl_2$ (2 ml). The whole procedure was repeated once and the resin 29 dried in vacuo. The effectiveness of acetylation was monitored by the addition of bromophenol blue in DMF (0.5 ml).

Deprotection to Free PBD

Piperidine (20%) in DMF (2 ml) was added to the acetylated resin 28a and the vessel shaken for 12 hours. The resin 29 was collected by filtration and rinsed with NMP (5 ml), MeOH (5 ml) and $CH_2Cl_2$ (5 ml). This procedure was repeated twice and the resin dried in vacuo.

Synthesis of Nvoc-PBD Triglycine 28a (FIG. 3b)

Triglycine resin 27 (0.16 g, 0.235 mmol/g loading) was placed in a peptide vessel fitted with a sinter. DMF (3 ml) was added and the vessel shaken for 30 min. A solution of the Nvoc-PBD acid 7a (0.22 g, 0.38 mmol), TBTU (0.12 g, 0.38 mmol) and DIPEA (65 µl, 0.38 mmol) in DMF (3 ml) was added, and shaking continued for 20 hours. Bromophenol blue indicator (30 µl) was added to monitor the progress of the reaction. Resin 28a was collected by filtration and rinsed with DMF (5 ml), NMP (5 ml) and $CH_2Cl_2$ (5 ml). The whole procedure was repeated twice before drying the resin in vacuo.

Acetylation (Endcapping) Conditions $Ac_2O$ (20%) and pyridine (30%) in $Ch_2Cl_2$ (5 ml) was added to resin 28a and the vessel shaken for 2 hours. The acetylated resin was collected by filtration and washed with $CH_2Cl_2$ (5 ml), EtOH (5 ml) and further $CH_2Cl_2$ (2 ml). The whole procedure was repeated once before drying the resin 29 in vacuo. The effectiveness of acetylation was monitored by the addition of bromophenol blue in DMF (0.5 ml).

Photolysis

A suspension of beads bearing the Nvoc-PBD in DMF was simultaneously N10-deprotected and cleaved from the resin by irradiating at 365 nm for 2 hours (Spectrolinker XL 1000 UV Crosslinker, Spectronics Corporation) to afford a 1 mmol stock solution of 30 which was used directly in the MTT assay (Example 3b).

Example 3(b)

General MTT Assay Method

The ability of agents to inhibit the growth of U937 chronic human histiocytic leukemia cells or K562 human chronic myeloid leukemia cells in culture was measured using the MTT assay (Mosmann, 1983). This is based on the ability of viable cells to reduce a yellow soluble tetrazolium salt, 3-(4,5-dimethylthiazolyl)-2,5-diphenyltetrazolium bromide (MTT; Sigma Chemical Co.), to an insoluble purple formazan precipitate. Following drug treatment, the cells were transferred to 96-well microtitre plates with $10^4$ cells per well and 8 wells per sample. The plates were incubated at 37° C. in a humidified atmosphere containing 5% $CO_2$. Following incubation of the plates for 4 days (to allow control cells to increase in number by 10-fold), 20 µL of a 5 mg/mL solution of MTT in phosphate-buffered saline was added to each well and the plates incubated further for 5 hours. The plates were then centrifuged for 5 minutes at 300 g and the bulk of the medium removed from the cell pellet, leaving 10–20 µL per well. DMSO (200 µL) was added to each well, and the samples agitated to ensure complete mixing. The optical density was then read at a wavelength of 550 nm on a Titertek Multiscan ELISA plate reader and the dose-response curve constructed. The $IC_{50}$ value was read as the dose required to reduce the final optical density to 50% of the control value.

MTT Assay of PBD-Triglycine

The MTT assay was used to evaluate the cytoxicity of the previously prepared PBD-Triglycine (compound 30), from Example 3a. The assay found the $IC_{50}$ to be 0.59 μM.

Example 4(a)

Figure 4A:
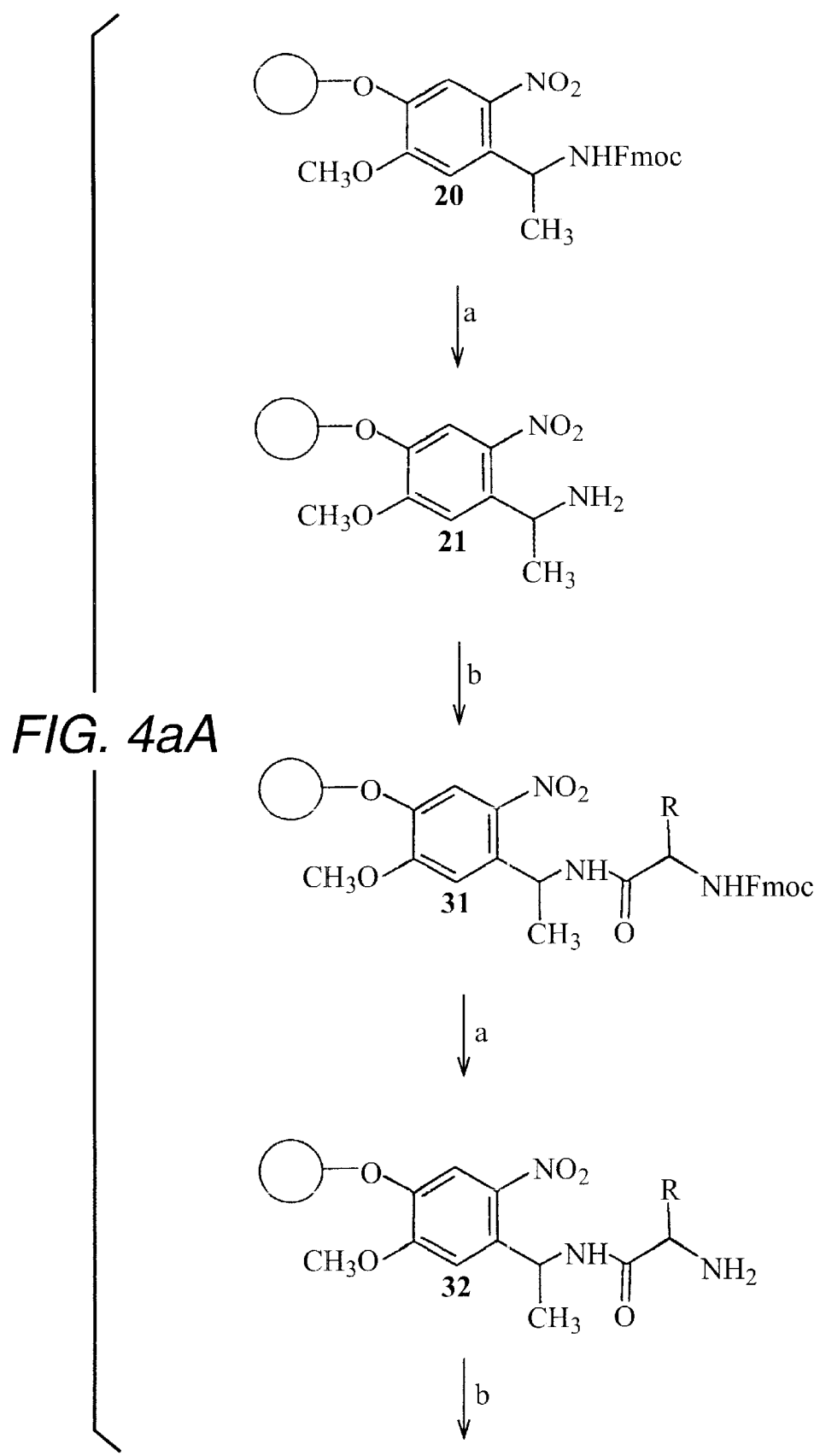
FIGS. 4a and 4b are a reaction scheme for the synthesis of further compounds of formulae V, IV, III, and II.
Figure 4A:
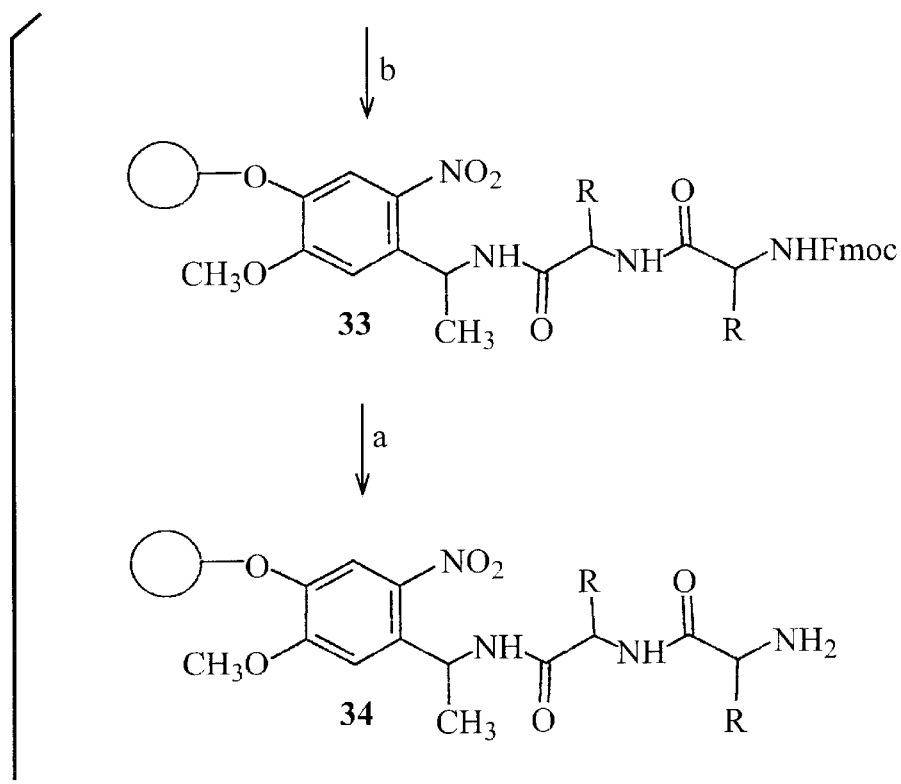
Figure 4A:
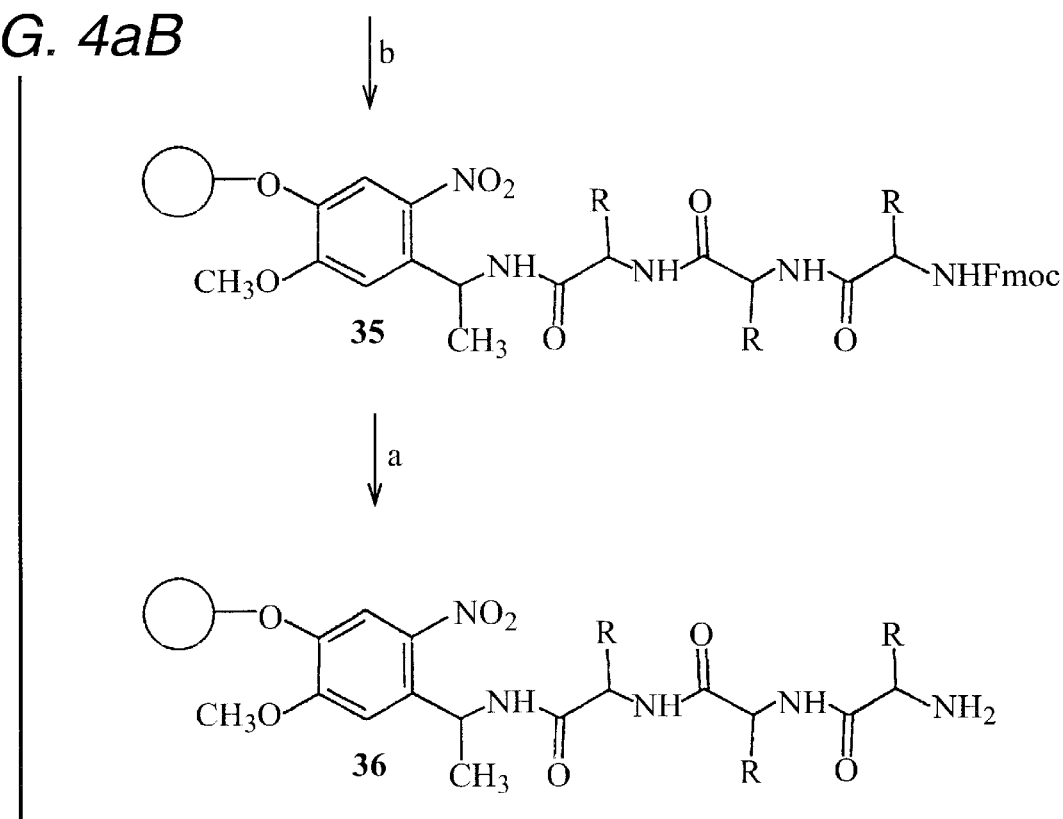
Figure 4B:
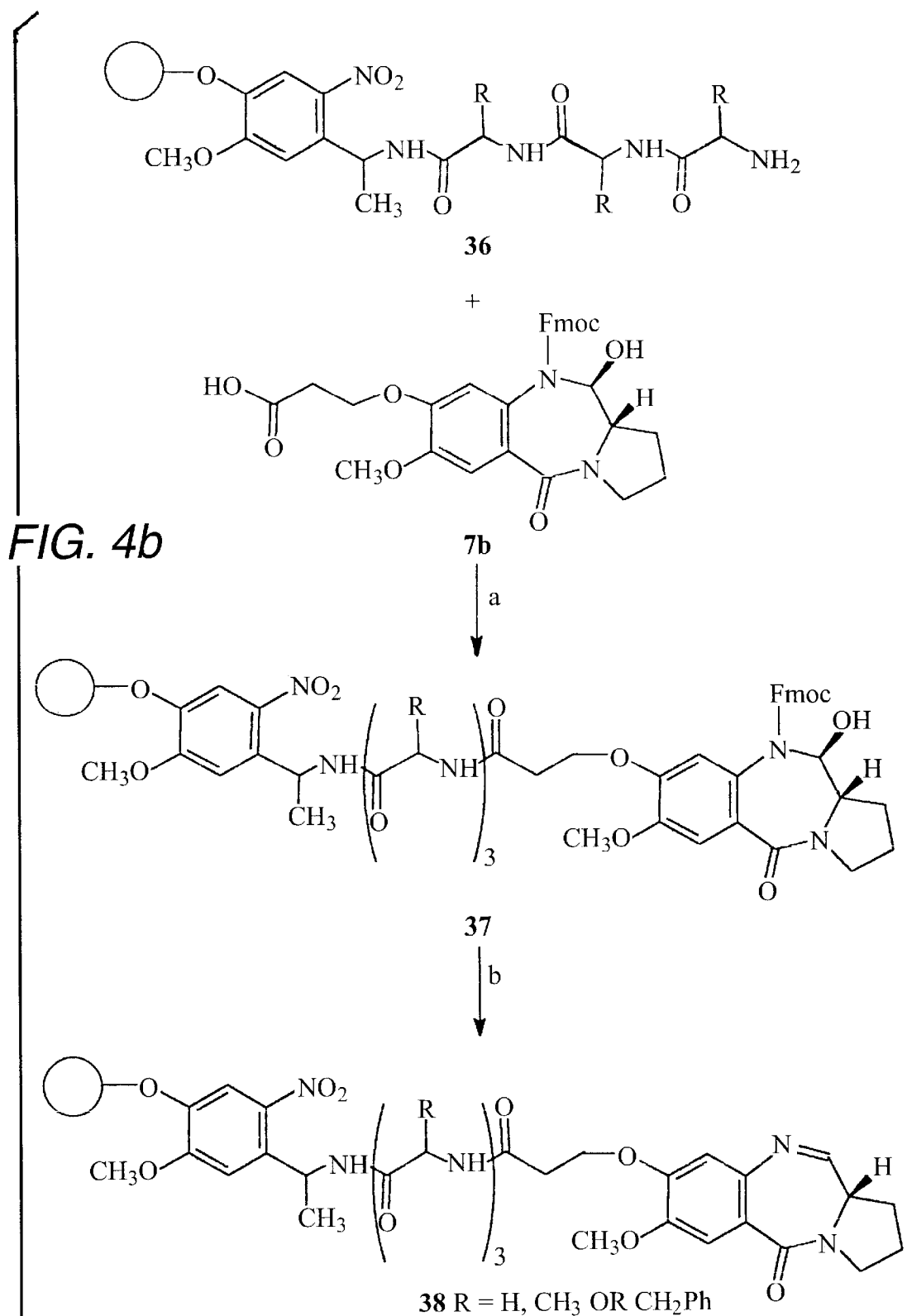

Synthesis of the Resin-bound Tripeptide Library (FIGS. 4a and 4b)

Following Example 3, this procedure was used to synthesize a tripeptide library.

Resin Deprotection

Fmoc-aminoethyl photolinker NovaSyn TG resin 20 (1.35 g, 0.23 mmol/g loading) was weighed into 27 Alltech tubes in 50 mg portions. Piperidine (20%) in DMF (0.5 ml) was added to each tube, and the tubes were then placed onto an orbital shaker for 3 hours. The deprotected resin 21 was collected by filtration using a Supelco Vacuum Manifold and rinsed with DMF (2 ml) and $CH_2Cl_2$ (2 ml). The whole procedure was repeated twice before drying the resin in vacuo.

Coupling Conditions

DMF (0.5 ml) was added to each Alltech tube containing resin 21, and the tubes were shaken for 30 min. Fmoc-glycine (0.306 g, 1.03 mmol) in DMF (3.4 ml) was added to the first 9 tubes; Fmoc-valine (0.36 g, 1.06 mmol) in DMF (3.54 ml) to the next 9 tubes and Fmoc-phenylalanine (0.396 g, 1.03 mmol) in DMF (3.4 ml) to the final 9 tubes. TBTU (0.972 g, 3.03 mmol) in DMF (10 ml) and DIPEA (540 μl 3.1 mmol) were added to all 27 tubes and shaking was continued for 20 hours. The coupled resin 31 was collected by filtration and rinsed with DMF (5 ml), $CH_2Cl_2$ (5 ml) and EtOH (5 ml). The whole procedure was repeated twice before drying the resin in vacuo. The coupling efficiency was monitored by the addition of a few drops of 10% DIPEA/DMF and 1% TNBS/DMF. The resin remained colourless when coupling was complete.

Acetylation (Endcapping) Conditions $Ac_2O$ (20%) and pyridine (30%) in $Ch_2Cl_2$ (1 ml) were added to each Alltech tube containing resin 31, and the tubes were shaken for 2 hours. The acetylated resin was filtered and washed with $CH_2Cl_2$ (5 ml), EtOH (5 ml) and further $CH_2Cl_2$ (2 ml). The whole procedure was repeated once before drying the resin in vacuo.

Deprotection Conditions

Piperidine (20%) in DMF (0.5 ml) was added to each tube of acetylated resin 31, and the tubes shaken for 12 hours. The deprotected resin 32 was collected by filtration and rinsed with DMF (5 ml) and $CH_2Cl_2$ (5 ml). The whole procedure was repeated twice before drying the resin in vacuo.

Coupling of Two Further Amino Acid Units

The previous coupling (21–31), acetylation and deprotection (31–32) steps were repeated twice using the appropriate Fmoc-protected Amino Acids in each Alltech tube (32–36) to achieve all possible combinations. This resulted in the resin-bound tripeptide library 36.

Coupling to the Fmoc-PBD Unit (FIG. 4b)

DMF (0.5 ml) was added to each Alltech tube containing resin 36 and the tubes were shaken for 30 min. Fmoc-PBD acid 7b (0.866 g, 1.55 mmol) in DMF (5.2 ml), TBTU (0.486 g, 1.55 mmol) in DMF (5 ml) and DIPEA (270 μl, 1.55 mmol) were added and shaking was continued for 20 hours. The coupled resin 37 was collected from each tube by filtration and rinsed with $CH_2Cl_2$ (5 ml), EtOH (5 ml) and further $CH_2Cl_2$ (2 ml). The whole procedure was repeated twice before drying the batches of resin in vacuo.

Acetylation (Endcapping) Conditions $Ac_2O$ (20%) and pyridine (30%) in $CH_2Cl_2$ (1 ml) were added to each tube of resin 37 and the tubes were shaken for 2 hours. Acetylated resin from each Alltech tube was collected by filtration and washed with $CH_2Cl_2$ (5 ml), EtOH (5 ml) and further $CH_2Cl_2$ (2 ml). The whole procedure was repeated once before drying the resin in vacuo. The effectiveness of acetylation was monitored by the addition of a few drops of 10% DIPEA/DMF and 1% TNBS/DMF.

Deprotection Conditions

Piperidine (20%) in DMF (0.5 ml) was added to each tube of acetylated resin 37 and the tubes were shaken for 12 hours. The batches of deprotected resin 38 were collected by filtration and rinsed with DMF (5 ml), $CH_2Cl_2$ (5 ml) and MeOH (5 ml). The whole procedure was repeated twice before drying the residue in vacuo to afford batches of resin 38.

Photolysis

A suspension of beads bearing the deprotected resin 38 were cleaved from the resin by irradiating at 365 nm for 2 hours (Spectrolinker XL 1000 UV Crosslinker, Spectronics Corporation) to afford a 1 mmol stock solution which was used directly in the MTT assay (EXAMPLE 4b).

Example 4(b)

Screening of a 27 Member Combinatorial Library Prepared on Beads

The combinatorial library synthesised in example 4(a) was screened using the MTT assay as previously described.

| Compound | Amino-acid Sequence of Combinatorial Units | $IC_{50}$ (μM) |
| --- | --- | --- |
| 1 | GGG | 0.59 |
| 2 | GGV | 0.63 |
| 3 | GGF | 0.56 |
| 4 | GVG | 0.55 |
| 5 | GVV | 0.52 |
| 6 | GVF | 0.64 |
| 7 | GFG | 0.63 |
| 8 | GFV | 0.78 |
| 9 | GFF | 0.63 |
| 10 | VGG | 0.59 |
| 11 | VGV | 0.33 |
| 12 | VGF | 0.58 |
| 13 | VVG | 0.58 |
| 14 | VVV | 0.58 |
| 15 | VVF | 0.53 |
| 16 | VFG | 0.46 |
| 17 | VFV | 0.56 |
| 18 | VFF | 0.56 |
| 19 | FGG | 0.54 |
| 20 | FGV | 0.54 |
| 21 | FGF | 0.57 |
| 22 | FVG | 0.58 |
| 23 | FVV | 0.54 |
| 24 | FVF | 0.69 |
| 25 | FFG | 0.54 |
| 26 | FFV | 0.40 |
| 27 | FFF | 0.59 |
| GW/613 | — | 0.33 |

G = GLYCINE
V = VALINE
F = PHENYLALANINE

These results demonstrate that varying the amino acid sequence affects the cytotoxicity of the PBDs.

Example 5(a)

Preparation of a 27-Member Tripeptide-PBD Library on Crowns for Solution Phase Testing

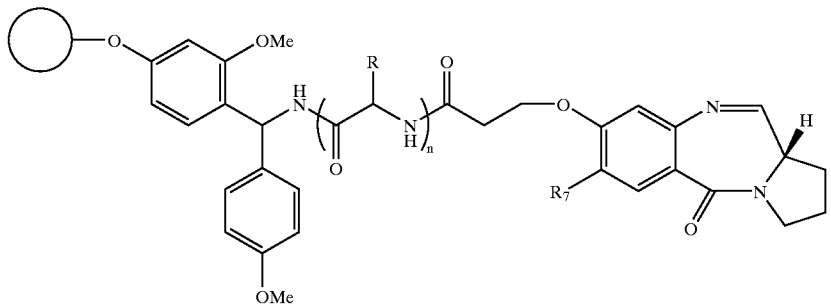

38: n = 3; R = H, CH₂CH(CH₃)₂ or CH₂Ph

A 27-member library was prepared on Chiron Technology crowns from Fmoc-protected Glycine, Leucine and Phenylalanine building blocks, and an NVOC-protected PBD unit using the Multipin™ Synthesis Kit and the same general reaction scheme as exemplified in Example 4(a).

Crown Deprotection

Twenty-seven Fmoc-Rink amide O-series crowns (loading: 2.2 μM per crown) were attached to the first twenty-seven pins of a 98-pin block. The block was inverted and placed in a vessel containing a solution of piperidine (20%) in DMF (50 mL, anhydrous) on a shaker (Heidolph, Titramax 100). After 30 min. the block was removed from the container and excess piperidine/DMF allowed to drain away. The block was then inverted, placed in a vessel containing fresh DMF (50 mL), and the whole assembly agitated for 5 min. Finally, the crowns were washed twice for 2 minutes with methanol before allowing to air-dry for 20 min.

Preparation of Activated Amino Esters

A solution of N-Fmoc-Glycine (128.4 mg, 0.43 mmol), DIC (55 mg, 0.43 mmol) and HOBt (70 mg, 0.52 mmol) in DMF (2160 μL) was agitated for 20 min, and aliquots (200 μL) were added to the first nine wells (H1–H9) of a deep 98-well microtitre plate. Similar solutions of active esters were prepared from N-Fmoc Leucine (152.7 mg) and N-Fmoc-Phenylalanine (167.4 mg), and aliquots (200 μL) were dispensed into wells H10-G6 and G7-F3, respectively (see Table 1 below).

TABLE 1

Distribution of N-Fmoc-protected Amino Acids into Wells H1 to F3.

|    | H | G | F |
|----|---|---|---|
| 1  | Glycine | Leucine | Phenylalanine |
| 2  | Glycine | Leucine | Phenylalanine |
| 3  | Glycine | Leucine | Phenylalanine |
| 4  | Glycine | Leucine | |
| 5  | Glycine | Leucine | |
| 6  | Glycine | Leucine | |
| 7  | Glycine | Phenylalanine | |
| 8  | Glycine | Phenylalanine | |
| 9  | Glycine | Phenylalanine | |
| 10 | Leucine | Phenylalanine | |
| 11 | Leucine | Phenylalanine | |
| 12 | Leucine | Phenylalanine | |

Coupling Reaction

Each well was doped with a small amount of bromophenol blue indicator (25 μL of 6.6 mg in 10 mL of DMF) and the crown array immersed in the wells. The crowns (previously colourless) instantly turned blue indicating the presence of free amines. The block/deep well plate assembly was agitated on a shaker for 18 hours after which time all of the crowns became virtually colourless indicating that the coupling reactions had gone to completion. The crown array was then removed from the microtitre plate, excess coupling reagent allowed to drain, and the crown array washed once with DMF (50 mL, five min) and twice with methanol (100 mL, 2 min). Finally, the crown array was allowed to air dry for 20 min.

Deprotection

The crown array was inverted and placed in a vessel containing a solution of piperidine (20%) in DMF (50 mL, anhydrous) on a shaker (Heidolph, Titramax 100). After 30 min, the block was removed from the container and excess piperidine/DMF allowed to drain away. The block was then inverted, placed in a vessel containing fresh DMF (50 mL) and the whole assembly agitated for 5 min. Finally, the crowns were washed twice for 2 minutes with methanol before allowing to air-dry for 20 min.

Coupling to the Second Amino Acid

The deprotected crown array was immersed in a deep well microtitre plate charged with freshly prepared solutions of the activated esters of N-Fmoc-Glycine, N-Fmoc-Leucine and Fmoc-Phenylalanine according to the pattern shown in Table 2 below. The block/deep well plate assembly was agitated on an orbital shaker for 18 hours after which time all of the crowns had become virtually colourless indicating that the coupling reactions had gone to completion. The crown array was then removed from the microtitre plate, excess coupling reagent allowed to drain, and the crown array washed once with DMF (50 mL, five min) and twice with methanol (100 mL, 2 min). Finally, the crown array was allowed to air dry for 20 min.

TABLE 2

Distribution of N-Fmoc-Protected Amino Acids into Wells H1 to F3.

|   | H | G | F |
|---|---|---|---|
| 1 | Glycine | Leucine | Phenylalanine |
| 2 | Glycine | Leucine | Phenylalanine |
| 3 | Glycine | Leucine | Phenylalanine |
| 4 | Leucine | Phenylalanine | |
| 5 | Leucine | Phenylalanine | |

TABLE 2-continued

Distribution of N-Fmoc-Protected Amino Acids into Wells H1 to F3.

| | H | G | F |
|---|---|---|---|
| 6 | Leucine | Phenylalanine | |
| 7 | Phenylalanine | Glycine | |
| 8 | Phenylalanine | Glycine | |
| 9 | Phenylalanine | Glycine | |
| 10 | Glycine | Leucine | |
| 11 | Glycine | Leucine | |
| 12 | Glycine | Leucine | |

Deprotection

The crown array was inverted and placed in a container charged with a solution of piperidine (20%) in DMF (50 mL, anhydrous) on a shaker (Heidolph, Titramax 100). After 30 min, the block was removed from the container and excess piperidine/DMF allowed to drain away. The block was then inverted, placed in a vessel containing fresh DMF (50 mL) and the whole assembly agitated for 5 min. Finally, the crowns were washed twice for 2 minutes with methanol before allowing to air-dry for 20 min.

Coupling of the Third Amino Acid Unit

The deprotected crown array was immersed in a deep well microtitre plate charged with freshly prepared solutions of the activated esters of N-Fmoc-Glycine, N-Fmoc-Leucine and Fmoc-Phenylalanine according to the pattern shown in Table 3 below. The block/deep well plate assembly was agitated on an orbital shaker for 18 hours after which time all of the crowns had become virtually colourless indicating that the coupling reactions had gone to completion. The crown array was then removed from the microtitre plate, excess coupling reagent allowed to drain, and the crown array washed once with DMF (50 mL, five min) and twice with methanol (100 mL, 2 min). Finally, the crown array was allowed to air dry for 20 min.

TABLE 3

Distribution of N-Fmoc-protected Amino Acids into Wells H1 to F3.

| | H | G | F |
|---|---|---|---|
| 1 | Glycine | Glycine | Glycine |
| 2 | Leucine | Leucine | Leucine |
| 3 | Phenylalanine | Phenylalanine | Phenylalanine |
| 4 | Glycine | Glycine | |
| 5 | Leucine | Leucine | |
| 6 | Phenylalanine | Phenylalanine | |
| 7 | Glycine | Glycine | |
| 8 | Leucine | Leucine | |
| 9 | Phenylalanine | Phenylalanine | |
| 10 | Glycine | Glycine | |
| 11 | Leucine | Leucine | |
| 12 | Phenylalanine | Phenylalanine | |

Deprotection

The crown array was inverted and placed in a vessel containing a solution of piperidine (20%) in DMF (50 mL, anhydrous) on a shaker (Heidolph, Titramax 100). After 30 min, the block was removed from the container and excess piperidine/DMF allowed to drain away. The block was then inverted, placed in a vessel containing fresh DMF (50 mL) and the whole assembly agitated for 5 min. Finally, the crowns were washed twice for 2 minutes with methanol before allowing to air-dry for 20 min.

Attachment of PBD Capping Unit

A solution of Nvoc-PBD acid (745 mg, 1.29 mmol), DIC (16 mg, 1.29 mmol) and HOBt (209 mg, 1.55 mmol) in DMF (6.48 ml) was agitated for 20 minutes and then dispensed into all twenty-seven wells. The block/deep well microtitre plate assembly was agitated on a shaker for 48 hours. The crown array was then removed from the microtitre plate, excess coupling reagent allowed to drain, and the crown array washed once with DMF (50 mL, five min) and twice with methanol (100 mL, 2 min). Finally, the crown array was allowed to air dry for 20 min.

Cleavage

Prior to cleavage, the crowns were washed successively with DMF, toluene, methanol and dichloromethane to remove any non-covalent contaminants. The crown array was then immersed in twenty-seven racked (but individual) 1 mL polypropylene tubes each containing TFA/H$_2$O (300 µL, 95:5, v/v), and the block/rack assembly was agitated on an orbital shaker for 2 hours at room temperature. Excess TFA was removed by parallel evaporation under nitrogen (supplied by a glass manifold with 8 outlets) followed by final drying in vacuo over 48 hours to afford the free N10-Nvoc-Protected PBD-tripeptides.

EXAMPLE 5(b)

Photolytic Cleavage and MTT Assay Method

The same assay method as Example 3(b) was used. Cells at a density of 5×10$^4$ cells/mL were continuously incubated with each member of the 27-mer library at a final concentration of 0.3 µM (6.6 µmoles/tube/ml). Aliquots of each of the compounds of the 27-member library were either left without UVA (365 nm) exposure or were exposed to UVA (365 nm) for 2 h prior to their addition to the cell suspension. Following addition of the compounds, the cells were transferred to 96-well microtitre plates, 10$^4$ cells per well, 8 wells per sample. Plates were incubated at 37° C. in a humidified atmosphere containing 5% CO$_2$. Following incubation of the plates for 4 days (to allow control cells to increase in number by 10-fold), 20 µL of a 5 mg/mL solution of MTT in phosphate-buffered saline was added to each well and the plates further incubated for 5 hours. The plates were then centrifuged for 5 minutes at 300 g and the bulk of the medium was removed from the cell pellet, leaving 10–20 µL per well. DMSO (200 µL) was added to each well, and the samples agitated to ensure complete mixing. The optical density was then read at a wavelength of 550 nm on a Titertek Multiscan ELISA plate reader and the dose-response curve constructed.

Results of In vitro Cytotoxicity Evaluation of the 27 Member PBD Library Synthesised on 'Crowns'

| Compound | Amino Acid Sequence | % Control at 0.3 µM |
|---|---|---|
| 1 | AAA | 104 |
| 2 | AAB | 106 |
| 3 | AAC | 93.8 |
| 4 | ABA | 86.2 |
| 5 | ABB | 89.6 |
| 6 | ABC | 91.7 |
| 7 | ACA | 87.8 |
| 8 | ACB | 100.6 |
| 9 | ACC | 107 |
| 10 | BAA | 112 |
| 11 | BAB | 88.2 |
| 12 | BAC | 99.3 |
| 13 | BBA | 93.9 |
| 14 | BBB | 79.2 |
| 15 | BBC | 95 |
| 16 | BCA | 69.6 |

-continued

| Compound | Amino Acid Sequence | % Control at 0.3 µM |
|---|---|---|
| 17 | BCB | 109 |
| 18 | BCC | 107.6 |
| 19 | CAA | 91.4 |
| 20 | CAB | 99.4 |
| 21 | CAC | 98.3 |
| 22 | CBA | 85.6 |
| 23 | CBB | 86.1 |
| 24 | CBC | 90.6 |
| 25 | CCA | 119 |
| 26 | CCB | 114 |
| 27 | CCC | 112 |
| Benzyl DC-81 | — | 47.4 |

A = glycine
B = leucine
C = phenylalanine

Table 4: In vitro Cytotoxicity of a 27 Member PBD Library Synthesised on 'Crowns'

As before, these results demonstrate that varying the amino acid sequence affects the cytotoxicity of the PBDs.

EXAMPLE 6

DNA Binding Assays

Labelling Double-stranded Oligonucleotides

Double-stranded oligonucleotides (10 pmol/µL) were 5'-end labelled with [$^{32}$P]-ATP using T4 polynucleotide kinase and incubated for 30 minutes at 37° C. The labelled oligonucleotides were purified through a mini-prep Bio-rad™ spin column containing P6 Bio-gel™ (40–90 µm).

On-bead Screening Assay

The beads were allowed to swell in DMF for approximately 1 h prior to the binding experiment. Labelled double-stranded oligonucleotides were incubated with the beads to which compound was attached for 24 h at 37° C. After 24 h incubation the samples were resuspended in TE buffer (10 mM tris, 1 mM EDTA), spun and supernatant removed 3 to 4 times. On the final wash the pellet was resuspended in 1 mL of EcoScint (Nat. Diagnostics, UK) scintillation fluid and counted on a Wallac 1400 scintillation counter.

```
              Labelled oligonucleotides

Oligonucleotide  5'-ACA CCT AIA GAT IAA ITC TI-3'
1(PuGPu)         3'-TIT IIA TCT CTA CTT CAI AC-5'
Oligonucleotide  5'-ACA CCT AIT GTT IAA ITC TI-3'
2(PyGPy)         3'-TIT IIA TCA CAA CTT CAI AC-5'
Oligonucleotide  5'-ACA CCT AIA IAT IAA ITC TI-3'
3(PuIPu)         3'-TIT IIA TCT CTA CTT CAI AC-5'
```

Oligonucleotide 1 contains the AGA sequence (highlighted in bold) which is the most preferred binding site for a PBD. Oligonucleotide 2 contains the TGT sequence which is the least preferred binding site for a PBD. Oligonucleotide 3 contains the AIA sequence, to which a PBD should not bind owing to the lack of an $NH_2$ group on the inosine moiety.

Compound JGB-285 is N10-protected and should not bond covalently to DNA:

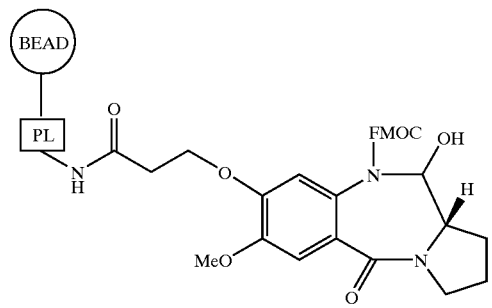

Compound JGB-285 is a free C10-N11 imine moiety and is able to interact with DNA:

TABLE 5

Binding of compounds JGB-285 and JGB-286 to Oligonucleotide 1 (counts corrected for background)

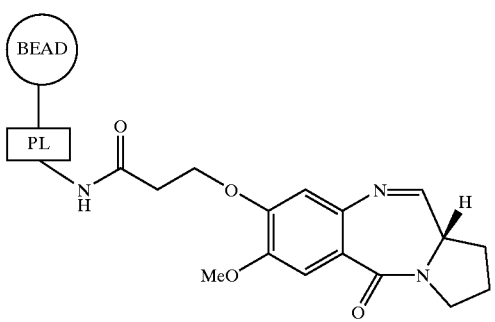

| Compounds | Counts per minute (CPM) |
|---|---|
| JGB-285 | 0 |
| JGB-286 | 50,394 |

TABLE 6

Binding of JGB-286 to double stranded oligonucleotides 1, 2, and 3 (counts corrected for background)

| Double-stranded oligonucleotide | Counts per minute (CPM) |
|---|---|
| — | 59.7 |
| 1 | 50,394 |
| 2 | 3,321 |
| 3 | 1,820 |

These tests were also carried out using oligonucleotide 1 labelled with Rhodamine or Fluorescein instead of [$^{32}$P]-ATP (the labelled oilgonucleotides are available from Genesis, Cambridge). The fluorescence was measured using a Tecan Spectrafluor Plus.

TABLE 7

Binding of compounds JGB-285 and JGB-286 to Rhodamine-labelled Oligonucleotide 1 (counts corrected for background).

| Compounds | Relative fluorescent units (RFU) |
|---|---|
| JGB-285 | 1,122 |
| JGB-286 | 16,539 |

TABLE 8

Binding of compounds JGB-285 and JGB-286 to Fluorescein-labelled Oligonucleotide 1 (counts corrected for background).

| Compounds | Relative fluorescent units (RFU) |
|---|---|
| JGB-285 | 1,217 |
| JGB-286 | 42,355 |

These results show that the PBD compound on-bead retains its ability to bind covalently to DNA—the protected PBD (JGB-285) did not bind at all, whereas the unprotected PBD (JGB-286) exhibited strong binding. More importantly, the unprotected PBD retained its selectivity for a PuGPu sequence, showing little binding activity towards the least preferred, and non-binding sites.

EXAMPLE 7

Figure 5A:
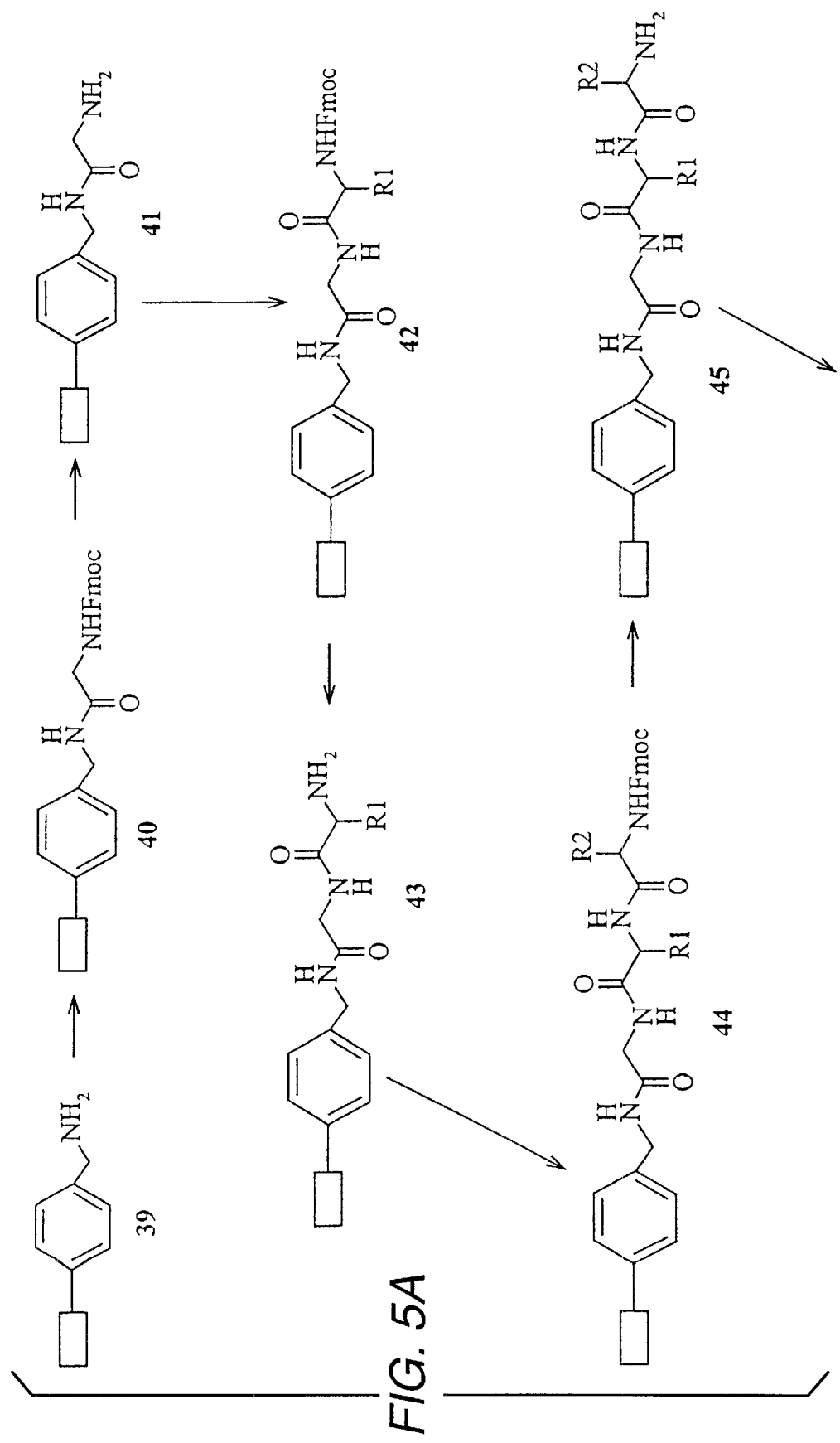
FIG. 5 is a reaction scheme for the synthesis of compounds of formula III and IV.
Figure 5B:
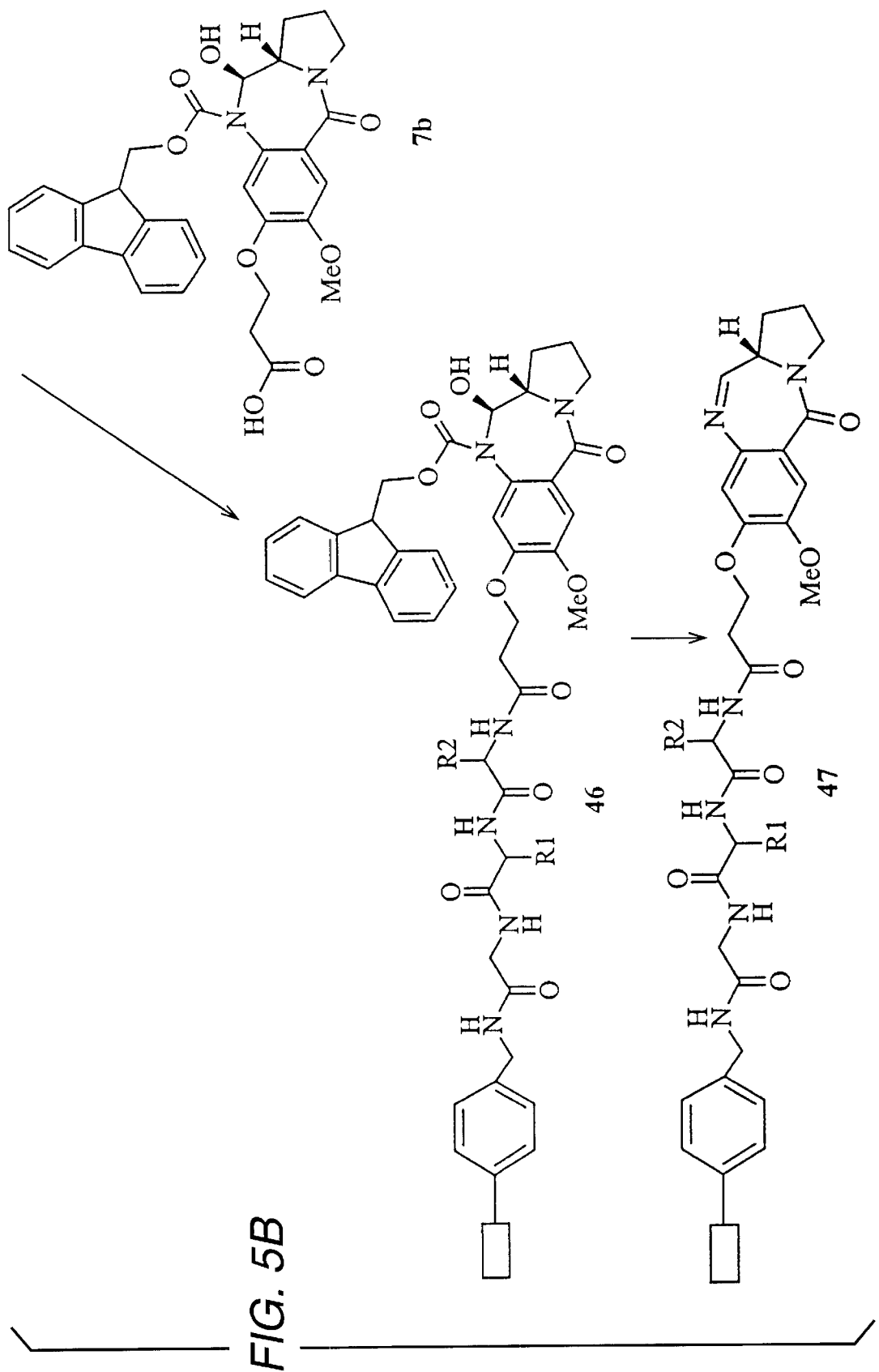

Synthesis and Screening of Irori™ Glycine PBD Sublibrary (FIG. 5)

Synthesis

Aminomethylated polystyrene resin 39 (5 g, 1.1 mmol/g loading) was suspended in DCE: $CH_2Cl_2$ (2:1, 102 ml) and dispensed equally into 289 Irori™ microkans. The resin was filtered and the kans were placed in a flask with DMF (70 ml) and shaken for 30 min.

A solution of Fmoc-glycine (4.91 g, 16.5 mmol), TBTU (5.3 g, 16.5 mmol) and DIPEA (2.9 ml, 16.5 mmol) in DMF (100 ml) was added to the combined kans and shaking continued for 20 hours. Resin 40 was filtered and rinsed with $CH_2Cl_2$ (3×10 ml), MeOH (3×10 ml), $Et_2O$ (3×10 ml) and dried in vacuo.

A solution of 20% $Ac_2O$, 30% pyridine in $CH_2Cl_2$ (200 ml) was added to the kans, which were shaken for 16 hours. The acetylated resin was filtered and washed with $CH_2Cl_2$ (3×10 ml), MeOH (3×10 ml), $Et_2O$ (3×10 ml) and dried in vacuo.

A solution of 20% piperidine in DMF (200 ml) was added to the acetylated resin 40 and the reaction flask was shaken for 16 hours. Resin 41 was filtered and rinsed with $CH_2Cl_2$ (3×10 ml), MeOH (3×10 ml), $Et_2O$ (3×10 ml) and dried in vacuo.

The kans were combined and sorted, using the Irori™ software into 17 flasks. Each flask contained a solution of an Fmoc-amino acid (0.97 mmol), TBTU (312 mg, 0.97 mmol) and DIPEA (170 ml, 0.97 mmol) in DMF (10 ml). [Fmoc-alanine (306 mg); Fmoc-asparagine (340 mg,); Fmoc-aspartic (O$^t$Bu) acid (391 mg); Fmoc-glutamine (357 mg); Fmoc-glutamic (O$^t$Bu) acid (408 mg); Fmoc-glycine (289 mg); Fmoc-isoleucine (340 mg); Fmoc-leucine (340 mg); Fmoc(Boc)-lysine (357 mg); Fmoc-methionine (459 mg); Fmoc-phenylalanine (374 mg); Fmoc-proline (323 mg); Fmoc-serine ($^t$Bu) (374 mg); Fmoc-threonine ($^t$Bu) (391 mg); Fmoc(Boc)-tryptophan (510 mg); Fmoc-tyrosine ($^t$Bu) (442 mg); Fmoc-valine (323 mg)].

The flasks were shaken for 16 hours and each batch of 17 kans was filtered and rinsed with DMF (3×10 ml), $CH_2Cl_2$ (3×10 ml), MeOH (3×10 ml), $Et_2O$ (3×10 ml) and dried in vacuo to give 42.

A solution of 20% $Ac_2O$, 30% pyridine in $CH_2Cl_2$ (200 ml) was added to all 289 kans and the reaction flask was shaken for 16 hours. Acetylated resin was filtered and washed with $CH_2Cl_2$ (3×10 ml), MeOH (3×10 ml), $Et_2O$ (3×10 ml) and dried in vacuo.

A solution of 20% piperidine in DMF (200 ml) was added to the acetylated resin and the vessel was shaken for 16 hours. Resin 43 was filtered and rinsed with $CH_2Cl_2$ (3×10 ml), MeOH (3×10 ml), $Et_2O$ (3×10 ml) and dried in vacuo.

This process was repeated again to produce a library of trimers 45 and the final step was carried out simultaneously on all 289 kans.

The kans were placed in a flask with DMF (70 ml) and shaken for 30 min. A solution of Fmoc-PBD acid 7b (Example 1/b) (9.2 g, 16.5 mmol), TBTU (5.3 g, 16.5 mmol) and DIPEA (2.9 ml, 16.5 mmol) in DMF (100 ml) was added to the kans and shaking continued for 20 hours. Resin 46 was filtered and rinsed with DMF (3×10 ml), $CH_2Cl_2$ (3×10 ml), MeOH (3×10 ml), $Et_2O$ (3×10 ml) and dried in vacuo.

A solution of 2% triisopropylsilane in TFA (100 ml) was added to the kans suspended in $CH_2Cl_2$ (100 ml) and the kans were shaken for 16 hours. The kans were filtered and washed with $CH_2Cl_2$ (3×10 ml), MeOH (3×10 ml), $Et_2O$ (3×10 ml) and dried in vacuo.

A solution of 20% piperidine in DMF (200 ml) was added to the kans and the reaction flask was shaken for 16 hours. The kans containing resin 47 were filtered and rinsed with $CH_2Cl_2$ (3×10 ml), MeOH (3×10 ml), $Et_2O$ (3×10 ml), and dried in vacuo.

Screening

The resulting library was screened against a double stranded DNA sequence to determine which members of the library bound most strongly to the DNA test sequence.

The DNA sequence used was annealed fluorescein labelled:
Label-5'-ACACCTAIAGATIAAITCTI-3'.

Approximately 10 mg of each library member was placed in a well of a 96 well plate and incubated with 5 pmol/µl annealed fluoroscein labelled double stranded DNA for 24 hours at 37° C. After 24 hours of incubation, each well was washed 4 times with TE buffer and the beads resuspended in 50 mL of TE or PBS.

The fluorescence of each well was measured using a Tecan Spectrafluor to determine which wells contained the most labelled DNA, and hence which compounds bound to the test DNA sequence most strongly.

Most active compounds from the library identified using the Iroriu™ software were found to be those with the following combinatorial chains: Gly-Gly-Gln-PBD; Gly-Pro-Iso-PBD; Gly-Thr-Asp-PBD; Gly-Leu-Val-PBD; Gly-Val-Asp-PBD; Gly-Val-Phen-PBD; Gly-Try-Asp-PBD; Gly-Lys-Ala-PBD; Gly-Gly-Asp-PBD; Gly-Gly-Pro-PBD.

EXAMPLE 8

Figure 6A:
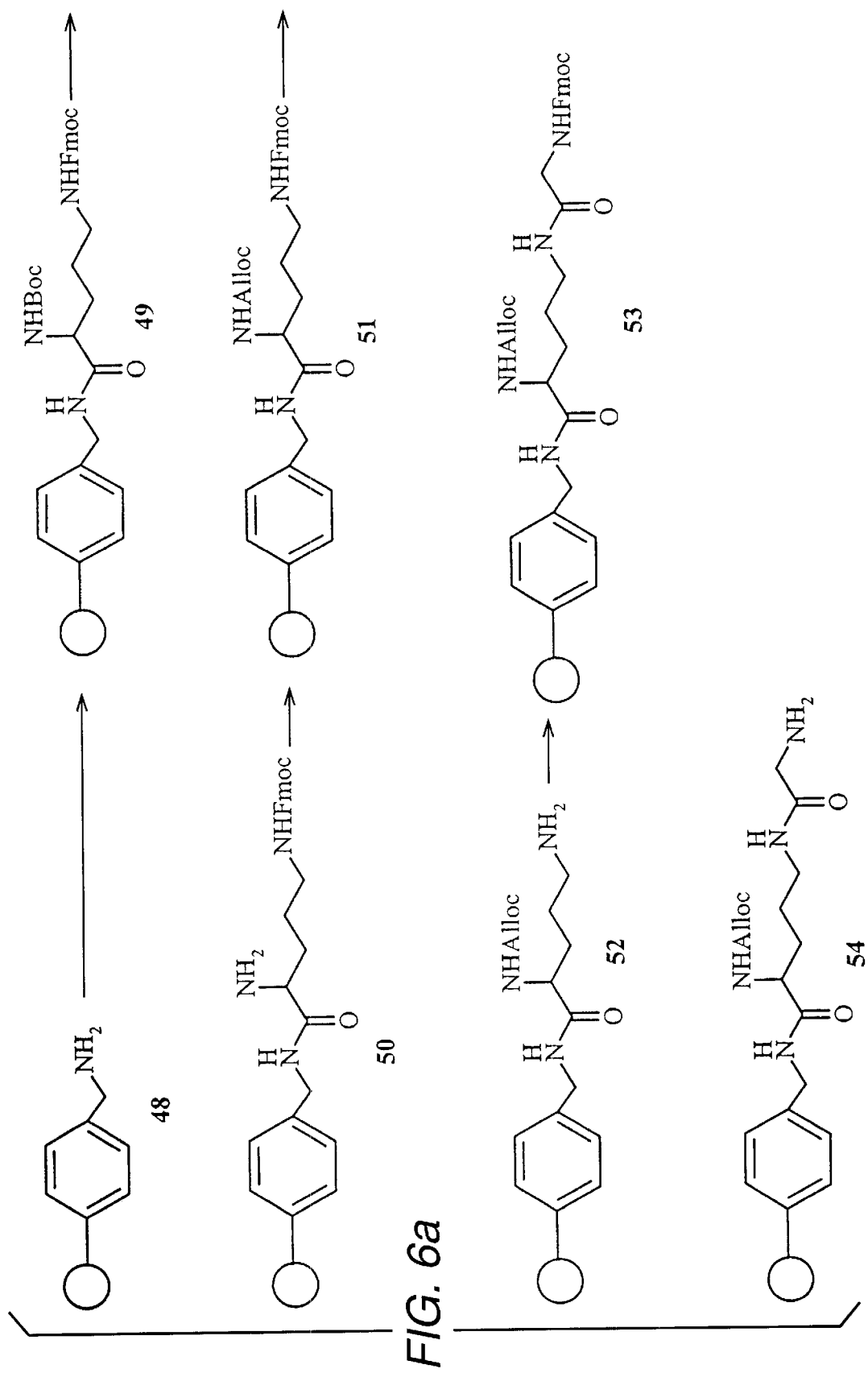
FIGS. 6a, 6b and 6c are a reaction scheme for the synthesis of compounds of formula VI and VII.
Figure 6B:
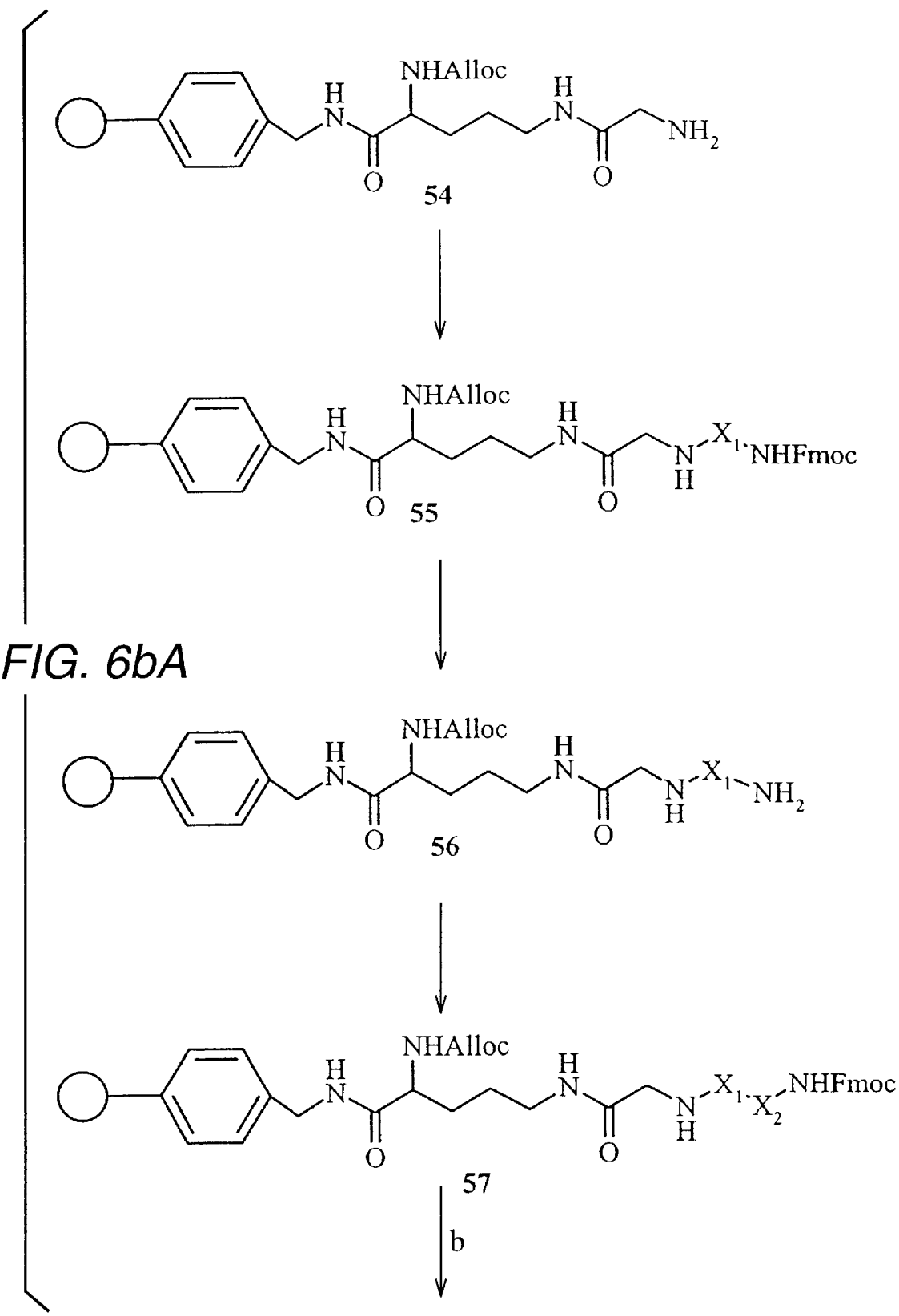
Figure 6B:
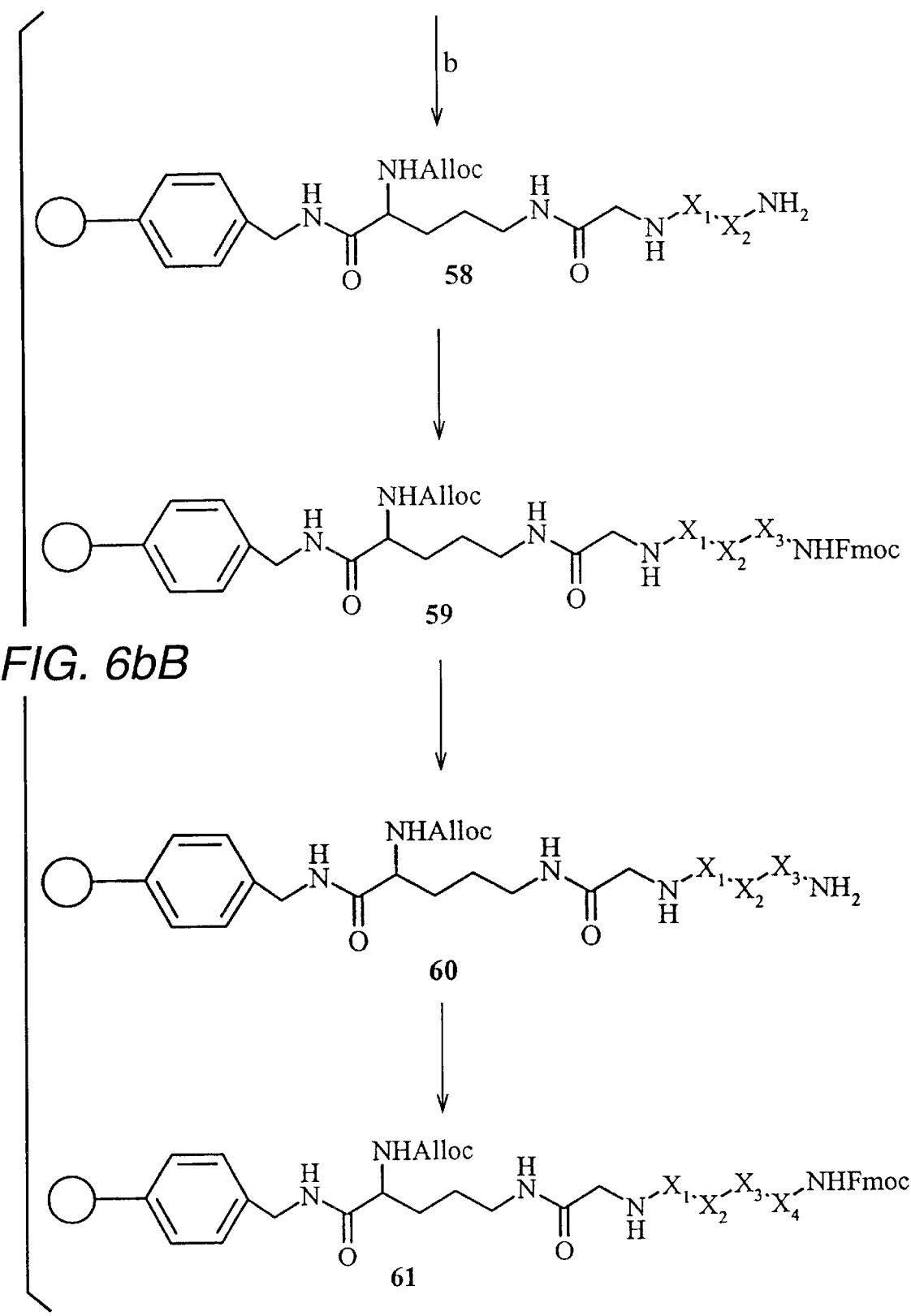
Figure 6C:
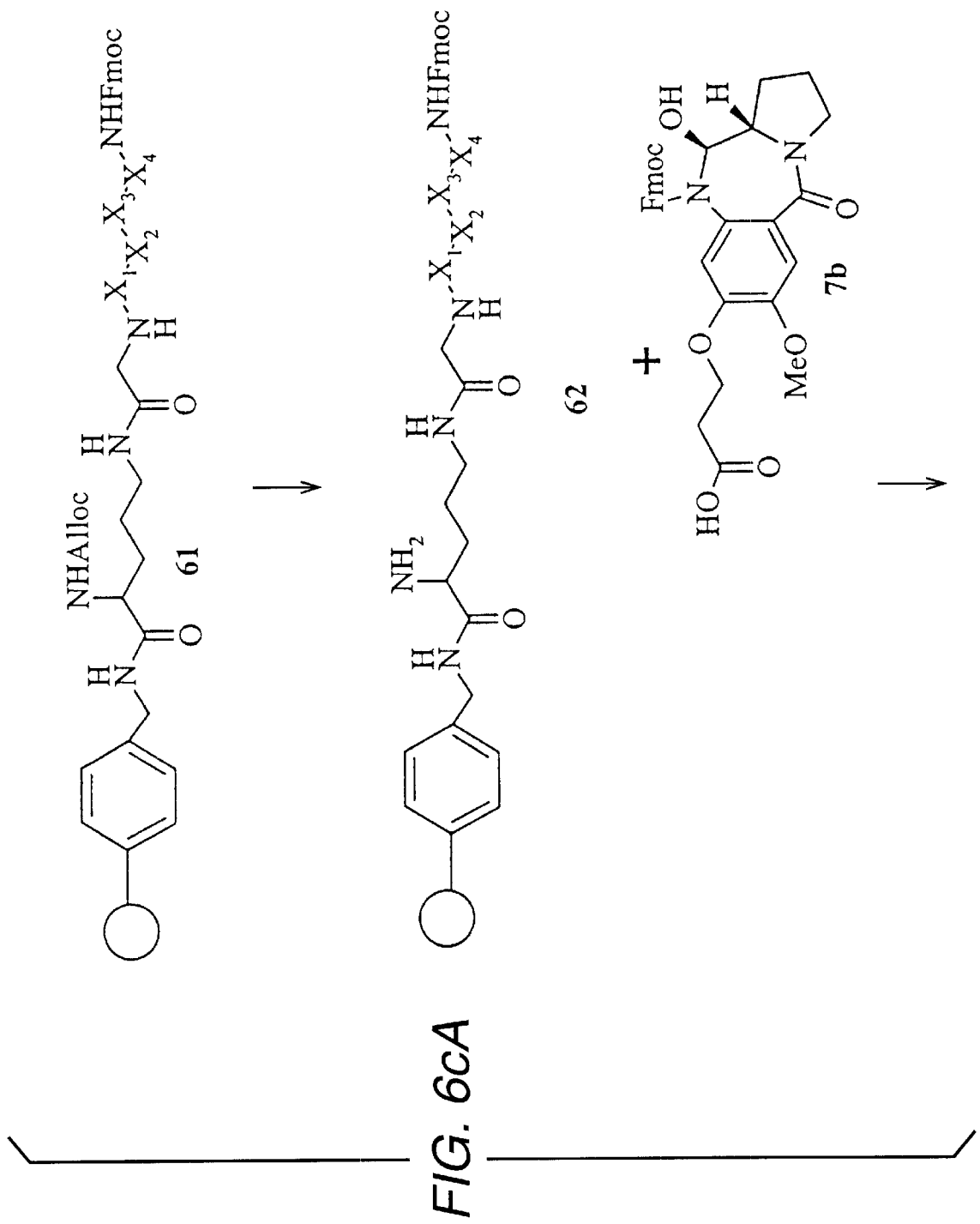
Figure 6C:
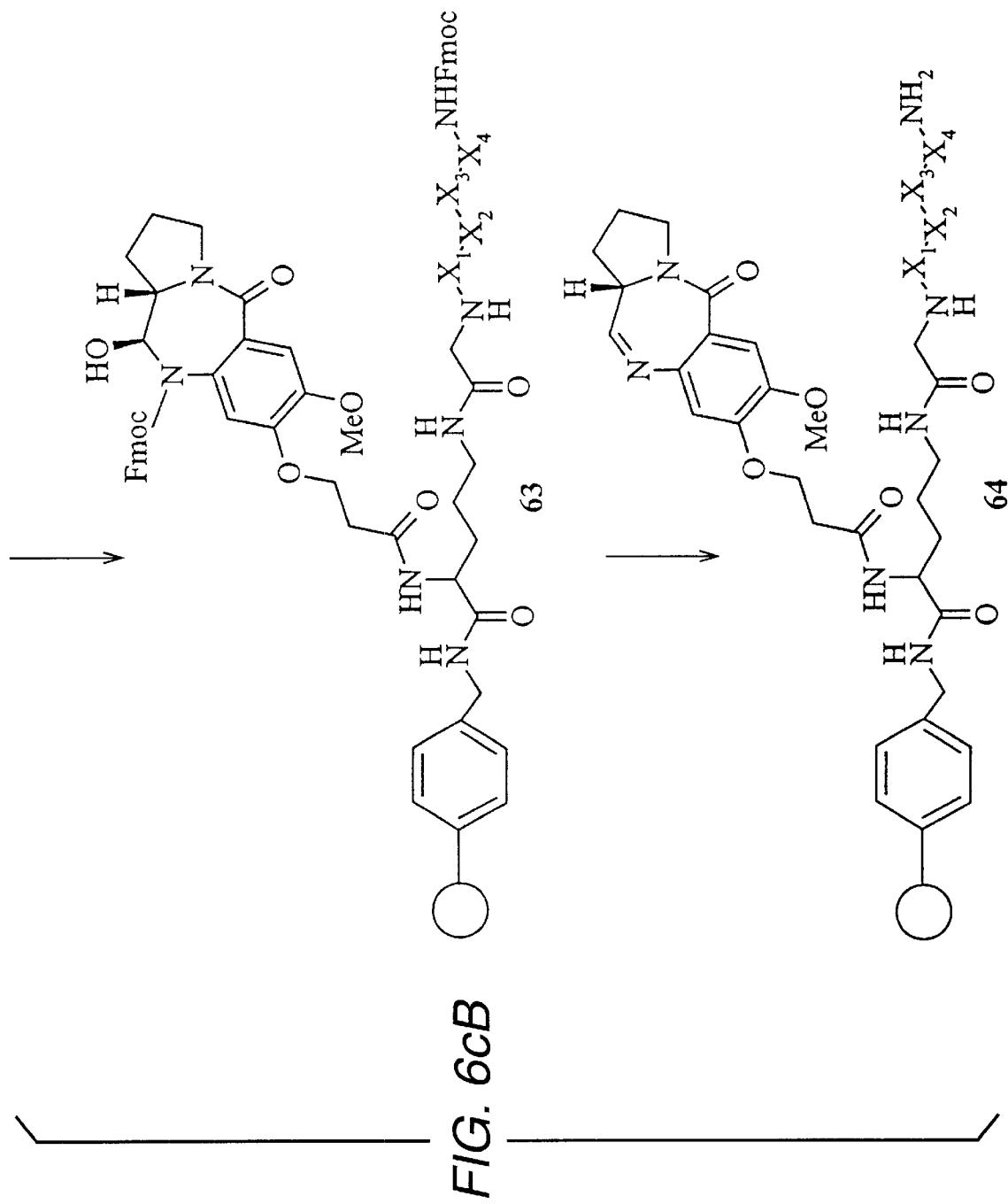

Synthesis of PBD—Glycine Sublibrary
(FIGS. 6a, 6b, 6c)

Synthesis of Lysine-Glycine Dimer 54 (FIG. 6a)

Tentagel M $NH_2$ resin 48 (58 mg, 0.3 mmol/g loading) was weighed into 17 Alltech tubes (4 ml volume) and DMF (250 µl) was added to each tube, which were then shaken for 30 min. A solution of Boc(Fmoc) lysine (416 mg, 0.88 mmol) in DMF (1.7 µl) and a solution of TBTU (285 mg, 0.88 mmol) and DIPEA (155 µl, 0.88 mmol) in DMF (3.4 ml) were equally dispensed into the tubes and shaking continued for 20 hours. Resin 49 was filtered and rinsed with DMF (3×2 ml), $CH_2Cl_2$ (3×2 ml), MeOH (3×2 ml) and dried in vacuo.

A solution of 20% Ac$_2$O, 30% pyridine in CH$_2$Cl$_2$ (500 μl) was added to each tube, and the tubes were shaken for 2 hours. The acetylated resin was filtered and washed with CH$_2$Cl$_2$ (3×2 ml), MeOH (3×2 ml), further CH$_2$Cl$_2$ (3×2 ml) and dried in vacuo.

A solution of 2% triisopropylsilane in TFA (250 μl) in CH$_2$Cl$_2$ (250 μl) was added to each tube, and the tubes were shaken for 2 hours. Resin 50 was filtered and washed with CH$_2$Cl$_2$ (3×2 ml), MeOH (3×2 ml), further CH$_2$Cl$_2$ (3×2 ml) and dried in vacuo.

Resin 50 was suspended in CH$_2$Cl$_2$ (250 μl) and shaken for 30 min. An ice cold solution of allyl chloroformate (100 μl, 0.88 mmol) and 4-methylmorpholine (90 mg, 0.88 mmol) in CH$_2$Cl$_2$ (1.7 ml) was equally dispensed to each tube and shaken for 16 hours. Resin 51 was filtered and washed with CH$_2$Cl$_2$ (3×2 ml), MeOH (3×2 ml), further CH$_2$Cl$_2$ (3×2 ml) and dried in vacuo.

A solution of 20% piperidine in DMF (500 μl) was added to resin 51 and the tubes were shaken for 12 hours. Resin 52 was filtered and rinsed with DMF (3×2 ml), CH$_2$Cl$_2$ (3×2 ml), MeOH (3×2 ml) and dried in vacuo.

Resin 52 was suspended in DMF (250 ml) and shaken for 30 min.

A solution of Fmoc-glycine (264 mg, 0.88 mmol) in DMF (1.7 ml) and a solution of TBTU (285 mg, 0.88 mmol) and DIPEA (155 μl, 0.88 mmol) in DMF (3.4 ml) were equally dispensed to the tubes and shaking continued for 20 hours. Resin 53 was filtered and rinsed with DMF (3×2 ml), CH$_2$Cl$_2$ (3×2 ml), MeOH (3×2 ml) and dried in vacuo.

A solution of 20% Ac$_2$O, 30% pyridine in CH$_2$Cl$_2$ (500 μl) was added to resin 53 and the tubes were shaken for 2 hours. The acetylated resin was filtered and washed with CH$_2$Cl$_2$ (3×2 ml), MeOH (3×2 ml), further CH$_2$Cl$_2$ (3×2 ml) and dried in vacuo.

A solution of 20% piperidine in DMF (500 μl) was added to the acetylated resin and the tubes were shaken for 12 hours. Resin 54 was filtered and rinsed with DMF (3×2 ml), CH$_2$Cl$_2$ (3×2 ml), MeOH (3×2 ml) and dried in vacuo.

Synthesis of Glycine Sublibrary 61 (FIG. 6b)
Coupling Conditions

A solution of an Fmoc-amino acid (0.052 mmol) in DMF (100 μl) was added to each tube containing resin 54. [Fmoc-alanine (16 mg); Fmoc-asparagine (18 mg,); Fmoc-aspartic (O$^t$Bu) acid (21 mg); Fmoc-glutamine (19 mg); Fmoc-glutamic (O$^t$Bu) acid (22 mg); Fmoc-glycine (16 mg); Fmoc-isoleucine (18 mg); Fmoc-leucine (18 mg); Fmoc (Boc)-lysine (24 mg); Fmoc-methionine (19 mg); Fmoc-phenylalanine (20 mg); Fmoc-proline (18 mg); Fmoc-serine ($^t$Bu) (20 mg); Fmoc-threonine ($^t$Bu) (21 mg); Fmoc(Boc)-tryptophan (27 mg); Fmoc-tyrosine ($^t$Bu) (24 mg); Fmoc-valine (18 mg)].

A solution of TBTU (285 mg, 0.88 mmol) and DIPEA (155 μl, 0.88 mmol) in DMF (3.4 ml) was equally dispensed into the 17 tubes and shaking continued for 20 hours. Resin 55 was filtered and rinsed with DMF (3×2 ml), CH$_2$Cl$_2$ (3×2 ml), MeOH (3×2 ml) and dried in vacua.
Acetylation Conditions A solution of 20% Ac$_2$O, 30% pyridine in CH$_2$Cl$_2$ (500 μl) was added to resin 55 and the tubes were shaken for 2 hours. The acetylated resin was filtered and washed with CH$_2$C$_2$ (3×2 ml), MeOH (3×2 ml), further CH$_2$C$_2$ (3×2 ml) and dried in vacuo.
Deprotection Conditions A solution of 20% piperidine in DMF (500 μl) was added to acetylated resin and the tubes were shaken for 2 hours. Resin 56 was filtered and rinsed with DMF (3×2 ml), CH$_2$Cl$_2$ (3×2 ml), MeOH (3×2 ml) and dried in vacuo.
Pool and Split Method The combined resin 56 was suspended in DCE: CH$_2$Cl$_2$ (2:1, 68 ml) in a round bottom flask, fitted with a sinter and was aspirated with nitrogen gas to ensure thorough mixing. The resin was re-dispensed into the 17 Alltech tubes, filtered and DMF (250 μl) was added to each tube, followed by shaking for 30 minutes.

This cycle of coupling, acetylation, deprotection and pooling/splitting was repeated a further three times, until a library of 6-mer peptides 61 had been synthesised.

Synthesis of PBD-Glycine Sublibrary 64 (FIG. 6c)

The resin 61 was suspended in CH$_2$Cl$_2$ (250 μl) and the tubes were shaken for 30 min. A solution of phenylsilane (876 μl, 7.1 mmol) in CH$_2$Cl$_2$ (1.7 ml) was equally dispensed into each tube and the tubes were shaken for 10 min. A solution of tetrakis(triphenylphosphine)palladium (34 mg, 0.03 mmol) in CH$_2$Cl$_2$ (1.7 ml) was equally dispensed into each tube and the tubes were shaken for a further 10 min. Resin 65 was filtered and rinsed with CH$_2$Cl$_2$ (3×2 ml), MeOH (3×2 ml), further CH$_2$Cl$_2$ (3×2 ml) and dried in vacuo. This procedure was repeated once.

A solution of Fmoc PBD acid 7b (Example 1b) (495 mg, 0.88 mmol) in DMF (3.4 ml) and a solution of TBTU (285 mg, 0.88 mmol) and DIPEA (155 μl, 0.88 mmol) in DMF (3.4 ml) were equally dispensed to the suspension of 6-mer peptide resin 62 in DMF (250 μl) and the tubes were shaken for 20 hours. Resin 63 was filtered and rinsed with DMF (3×2 ml), CH$_2$Cl$_2$ (3×2 ml), MeOH (3×2 ml) and dried in vacuo.

A solution of 2% triisopropylsilane in TFA (250 μl) in CH$_2$Cl$_2$ (250 μl) was added to resin 63 and the tubes were shaken for 2 hours. Resin was filtered and washed with CH$_2$Cl$_2$ (3×2 ml), MeOH (3×2 ml), further CH$_2$Cl$_2$ (3×2 ml) and dried in vacuo.

A solution of 20% piperidine in DMF (500 μl) was added to the resin and the tubes were shaken for 2 hours. Resin 64 was filtered and rinsed with DMF (3×2 ml), CH$_2$Cl$_2$ (3×2 ml), MeOH (3×2 ml) and dried in vacuo.

The resulting sublibrary was screened against rhodamine labelled annealed double strand DNA with the sequence:
Label-5'-ACACCTAIAGATIAAITCTI-3'

The sublibrary was mixed with the DNA sequence (5 pmol/mL) and incubated at 37° C. for 24 hours with occasional mixing. After 24 hours, the sublibrary was washed 4 times with TE buffer pH 7.6 or PBS. To identify the beads to which most labelled DNA had bound, agarose gel slides were prepared as follows. ~500 mL of 0.25% sea plaque agarose was layered onto a clean transparent slide and allowed to cool and set. The incubated beads were then mixed with another ~500 mL of 0.25% sea plaque agarose solution and layered onto the precoated slides, and allow to cool and set.

The reddest beads were identifed by eye under a dissecting light microscope, and then retrieved by adding ~1 mL of water to dried agarose slide to enable their removal using a p10 gilson pipette with a fine tip. The removed beads were then placed into a 1 mL Eppendorf PCR tube ready for identification.
Identification The identification of the sequences of the most active compounds was carried out using automated Edman degradation and reversed-phase HPLC.

Pulsed liquid-phase N-terminal sequencing was performed using an Applied Biosystems (ABI)477A automatic protein sequencer. The selected labelled beads were loaded onto a glass fibre disc which had previously been pre-cycled once. The disc was placed in the sequencer and pre-cycled once, then six cycles of Edman degradation were performed (Edman, P and Begg, G (1967) Eur. J. Biochem. 1, 80). The released phenylthiohydantoin (PTH-) amino acid derivatives were identified by reversed-phase HPLC analysis. The eight most active compounds were those with the following sequences:

PBD-KGNNNN; PBD-KGTESF; PBD-KGMPMA; PBD-KGGGMM; PBD-KGKGAS; PBD-KGANIA; PBD-KGMMGG; PBD-KGWYSP

EXAMPLE 9

Figure 7A:
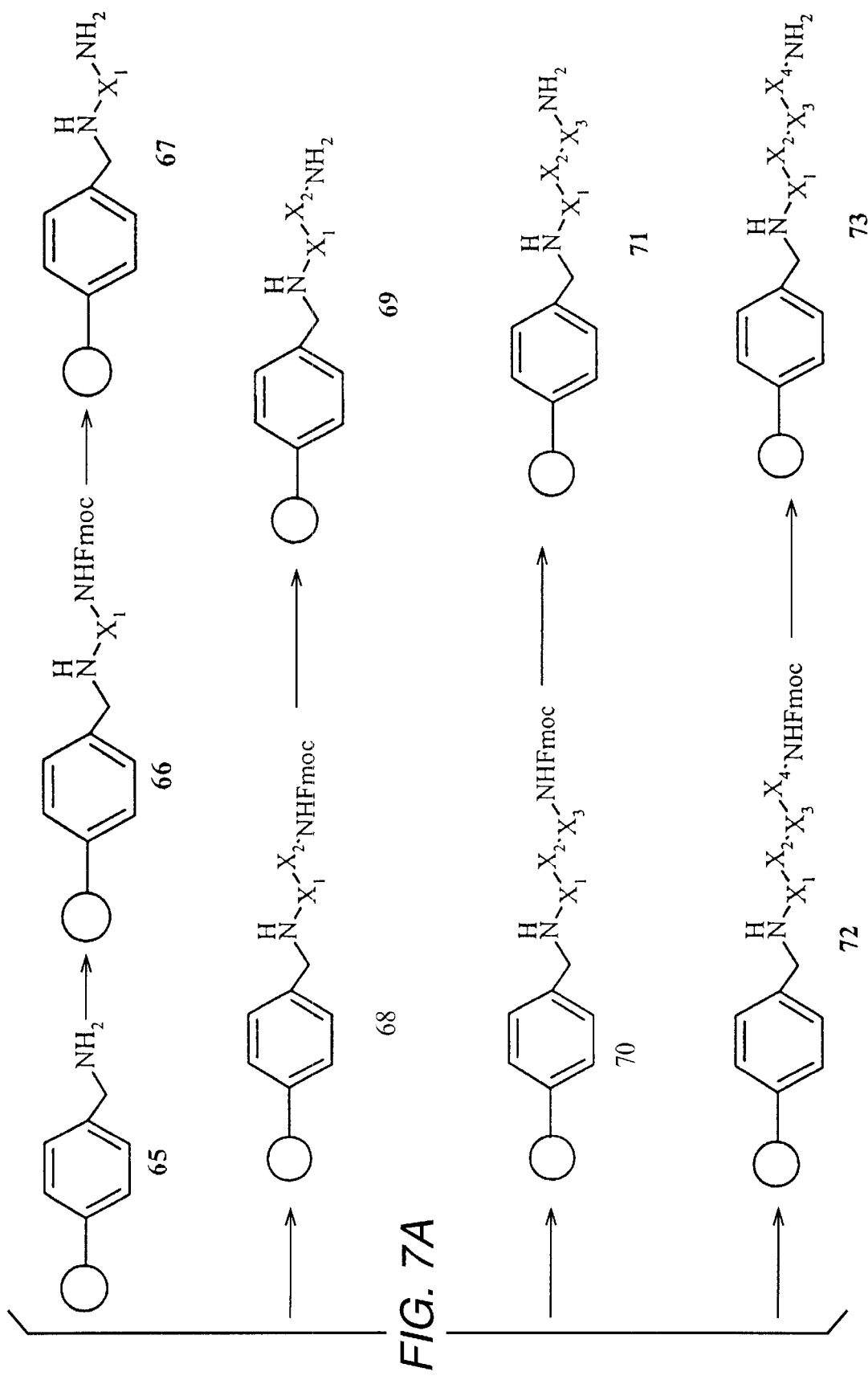
FIG. 7 is a reaction scheme for the synthesis of compounds of formula III and IV.
Figure 7B:
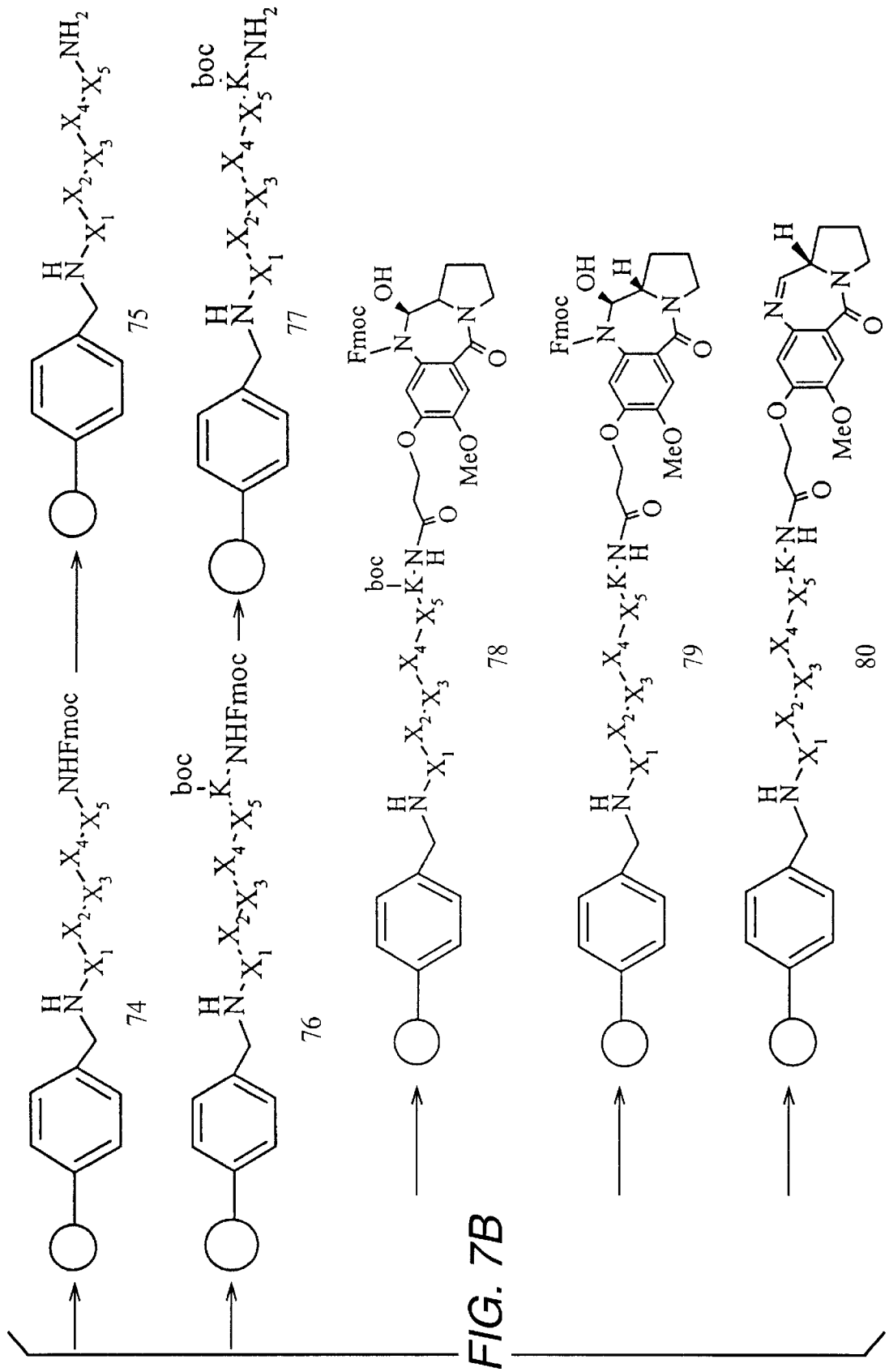

Synthesis of Split and Mix PED Peptide Library 80 (FIG. 7)

Aminomethylated polystyrene resin VHL 65 (3 g, 1.3 mmol/g loading) was suspended in DCE: $CH_2Cl_2$ (2:1, 102 ml) and dispensed equally into 17 Alltech tubes (8 ml volume). The resin was filtered and DMF (1.5 ml) was added to each tube and shaken for 30 min.

Coupling conditions: (→66)—same as Example 8, but using a solution of an Fmoc-amino acid (0.69 mmol) in DMF (250 μl) in each tube. (Fmoc-amino acids as example 8). The amounts of TBTU and DIPEA were increased in proportion to the amount of Fmoc-amino acid and were in 34 ml of DMF.

Acetylation conditions: same as Example 8, but using 1.5 ml of $CH_2Cl_2$ containing the $Ac_2O$ pyridine.

Deprotection conditions: (→67)same as Example 8, but using 1.5 ml solution of 20% piperidine in DMF.

Pool and Split method:—same as Example 8, but suspending resin in 102 ml of $DCE/CH_2Cl_2$.

The cycle was repeated a further four times, until a library of 5-mer peptides had been synthesised.

A solution of Boc(Fmoc) lysine (5.5 g, 11.7 mmol) in DMF (34 ml) and a solution of TBTU (3.76 g, 11.7 mmol) and DIPEA (2.04 ml, 11.7 mmol) in DMF (34 ml) were added to the suspension of 5-mer peptide resin 75 in DMF (17 ml) and the vessel was shaken for 20 hours. Resin 76 was filtered and rinsed with DMF (3×5 ml), $CH_2Cl_2$ (3×5 ml), MeOH (3×5 ml) and dried in vacuo.

A solution of 20% $Ac_2O$, 30% pyridine in $CH_2Cl_2$ (17 ml) was added to the resin and the vessel was shaken for 2 hours. The acetylated resin was filtered and washed with $CH_2Cl_2$ (3×5 ml), MeOH (3×5 ml), further $CH_2Cl_2$ (3×2 ml) and dried in vacuo.

A solution of 20% piperidine in DMF (17 ml) was added to the acetylated resin 76 and the vessel was shaken for 12 hours. Resin 77 was filtered and rinsed with DMF (3×5 ml), $CH_2Cl_2$ (3×5 ml), MeOH (3×5 ml) and dried in vacuo.

A solution of Fmoc PBD acid 7b (Example 1b) (6.55 g, 11.7 mmol) in DMF (34 ml) and a solution of TBTU (3.76 g, 11.7 mmol) and DIPEA (2.04 ml, 11.7 mmol) in DMF (34 ml) were added to the suspension of 6-mer peptide resin 77 in DMF (17 ml) and the vessel was shaken for 20 hours. Resin 78 was filtered and rinsed with DMF (3×5 ml), $CH_2Cl_2$ (3×5 ml), MeOH (3×5 ml) and dried in vacuo.

A solution of 2% triisopropylsilane in TFA (17 ml) in $CH_2Cl_2$ (17 ml) was added to the resin and the vessel was shaken for 2 hours. Resin 79 was filtered and washed with $CH_2Cl_2$ (3×5 ml), MeOH (3×5 ml), further $CH_2Cl_2$ (3×2 ml) and dried in vacuo.

A solution of 20% piperidine in DMF (17 ml) was added to the resin 79 and the vessel was shaken for 2 hours. Resin 80 was filtered and rinsed with DMF (3×5 ml), $CH_2Cl_2$ (3×5 ml), MeOH (3×5 ml) and dried in vacuo.

EXAMPLE 10

Figure 8A:
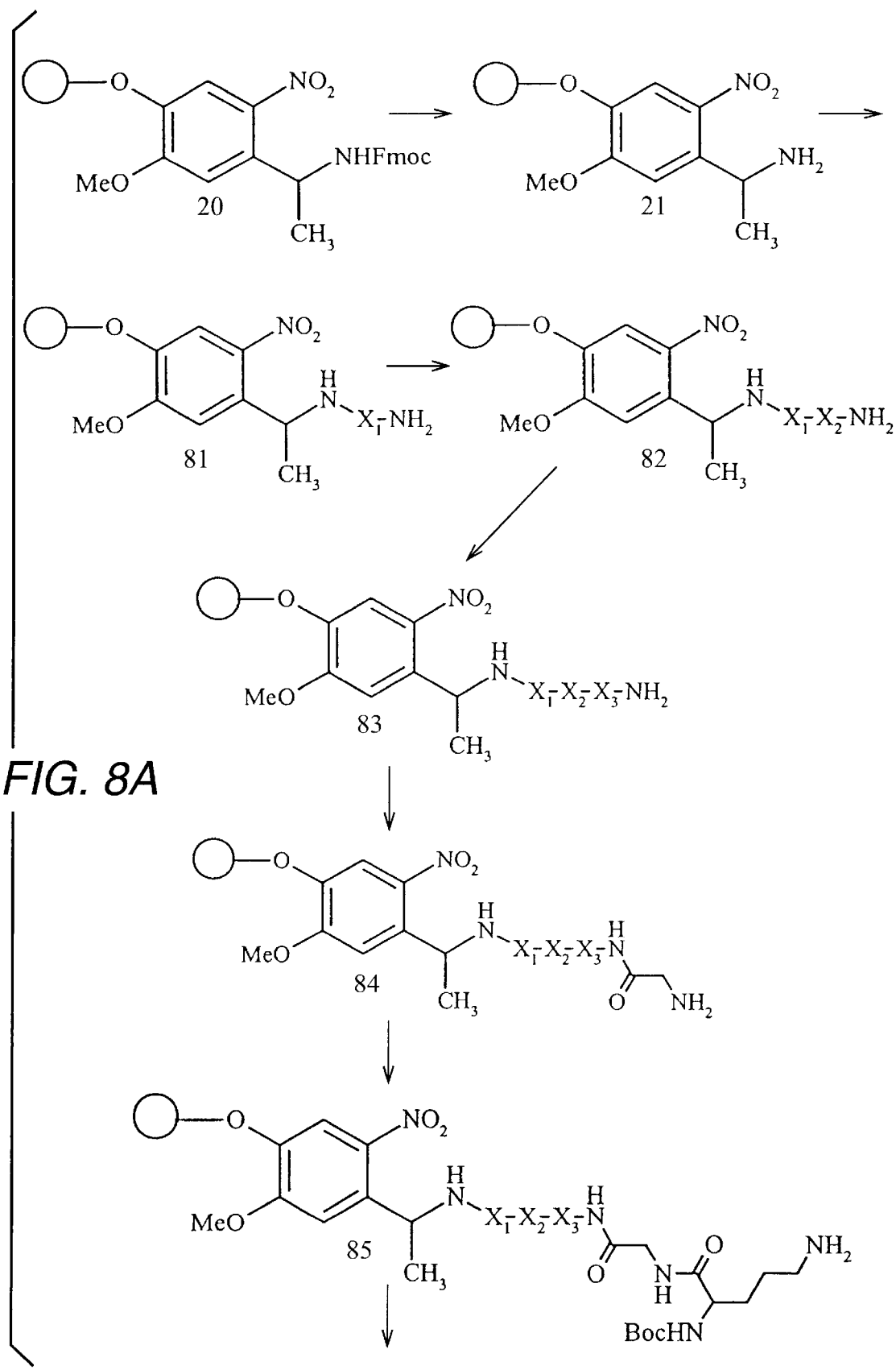
FIGS. 8 and 9 are reaction schemes for the synthesis of compounds of formula III and IV.
Figure 8B:
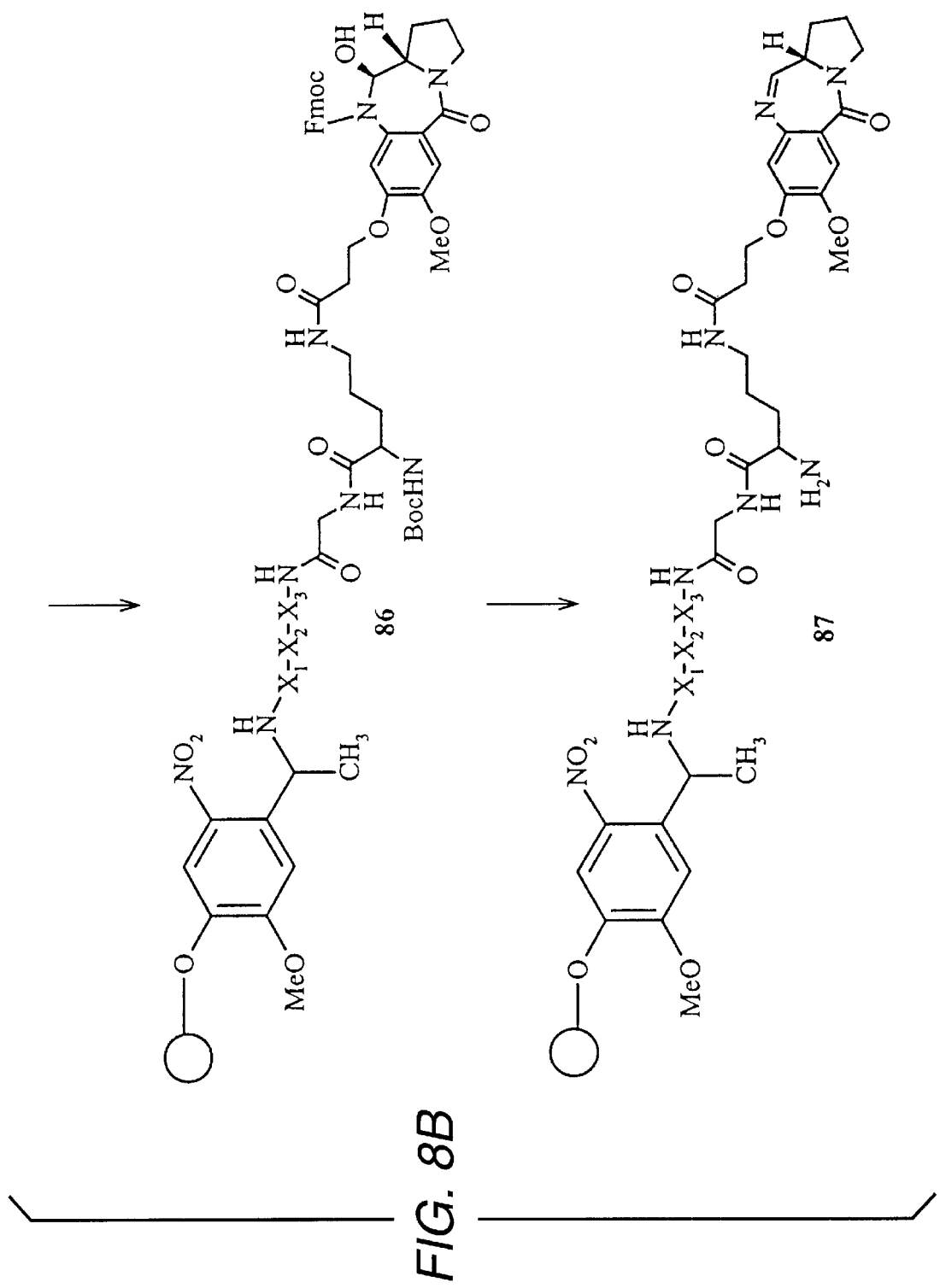

Synthesis of Glycine Sublibrary 87 (FIG. 8)

Fmoc-aminoethyl photolinker NovaSyn TG resin 20 (30 mg, 0.23 mmol/g loading) was weighed into 17 Alltech tubes (4 ml volume) and a solution of 20% piperidine in DMF (250 ml) was added to each tube, which were shaken for 16 hours. Resin 21 was filtered and rinsed with DMF (3×2 ml), $CH_2Cl_2$ (3×2 ml), MeOH (3×2 ml) and dried in vacuo. DMF (250 μl) was added to each tube and the tubes were shaken for 30 min.

Coupling Conditions:—Same as Example 8, but using solution of an Fmoc-amino acid (0.021 mmol) in DMF (150 μl) in each tube. The amounts of TBTU and DIPEA were increased in proportion to the amount of Fmoc-amino acid, and were in 1.7 ml DMF.

Acetylation Conditions:—Same as Example 8

Deprotection Conditions:—Same as Example 8

Pool and Split Method:—Same as Example 8

This cycle of coupling, acetylation, deprotection and pooling/splitting was repeated twice until a library of trimer peptides 83 had been synthesised, but after second repetition the resin was not pooled but kept as 17 separate sublibraries, allowing for the final amino acid to be known.

Coupling to Fmoc-glycine

Resin 83 was suspended in DMF (250 μl) and shaken for 30 min. A solution of Fmoc-glycine (105 mg, 0.35 mmol) in DMF (1.7 ml) and a solution of TBTU (112 mg, 0.35 mmol) and DIPEA (68 μl, 0.35 mmol) in DMF (1.7 ml) were dispensed equally to the tubes and shaking continued for 20 hours. Resin was filtered and rinsed with DMF (3×2 ml), $CH_2Cl_2$ (3×2 ml), MeOH (3×2 ml) and dried in vacuo.

A solution of 20% $Ac_2O$, 30% pyridine in $CH_2Cl_2$ (500 μl) was added to the tubes and were shaken for 2 hours. The acetylated resin was filtered and washed with $CH_2Cl_2$ (3×2 ml), MeOH (3×2 ml), further $CH_2Cl_2$ (3×2 ml) and dried in vacuo.

A solution of 20% piperidine in DMF (500 μl) was added to acetylated resin and the tubes were shaken for 2 hours. Resin 84 was filtered and rinsed with DMF (3×2 ml), $CH_2Cl_2$ (3×2 ml), MeOH (3×2 ml) and dried in vacuo.

Coupling to Boc(Fmoc)-lysine

A solution of Boc(Fmoc)-lysine (165 mg, 0.35 mmol) in DMF (1.7 ml) and a solution of TBTU (112 mg, 0.35 mmol) and DIPEA (68 μl, 0.35 mmol) in DMF (1.7 ml) were equally dispensed to the tubes and shaking continued for 20 hours. Resin was filtered and rinsed with DMF (3×2 ml), $CH_2Cl_2$ (3×2 ml), MeOH (3×2 ml) and dried in vacuo.

A solution of 20% $Ac_2O$, 30% pyridine in $CH_2Cl_2$ (500 μl) was added to the tubes and were shaken for 2 hours. The acetylated resin was filtered and washed with $CH_2Cl_2$ (3×2 ml), MeOH (3×2 ml), additional $CH_2Cl_2$ (3×2 ml) and dried in vacuo.

A solution of 20% piperidine in DMF (500 μl) was added to acetylated resin and the tubes were shaken for 2 hours. Resin 85 was filtered and rinsed with DMF (3×2 ml), $CH_2Cl_2$ (3×2 ml), MeOH (3×2 ml) and dried in vacuo.

Coupling to PBD Capping Unit

Resin 85 was suspended in DMF (250 μl) and shaken for 30 min. A solution of Fmoc-PBD acid 7b (196 mg, 0.35 mmol) in DMF (1.7 ml) and a solution of TBTU (112 mg, 0.35 mmol) and DIPEA (68 μl, 0.35 mmol) in DMF (1.7 ml) were dispensed equally to the tubes and shaking continued for 20 hours. Resin 86 was filtered and rinsed with DMF (3×2 ml), CH$_2$Cl$_2$ (3×2 ml), MeOH (3×2 ml) and dried in vacuo.

A solution of 2% triisopropylsilane in TFA (250 µl) and CH$_2$Cl$_2$ (250 ml) was added to the tubes which were shaken for 2 hours. Resin was filtered and rinsed with CH$_2$Cl$_2$ (3×2 ml), MeOH (3×2 ml) further CH$_2$Cl$_2$ (3×2 ml ) and dried in vacuo.

A solution of 20% piperidine in DMF (500 µl) was added to the tubes which were shaken for 2 hours. Resin 87 was filtered and rinsed with DMF (3×2 ml), CH$_2$Cl$_2$ (3×2 ml), MeOH (3×2 ml) and dried in vacuo.

EXAMPLE 11

Figure 9A:
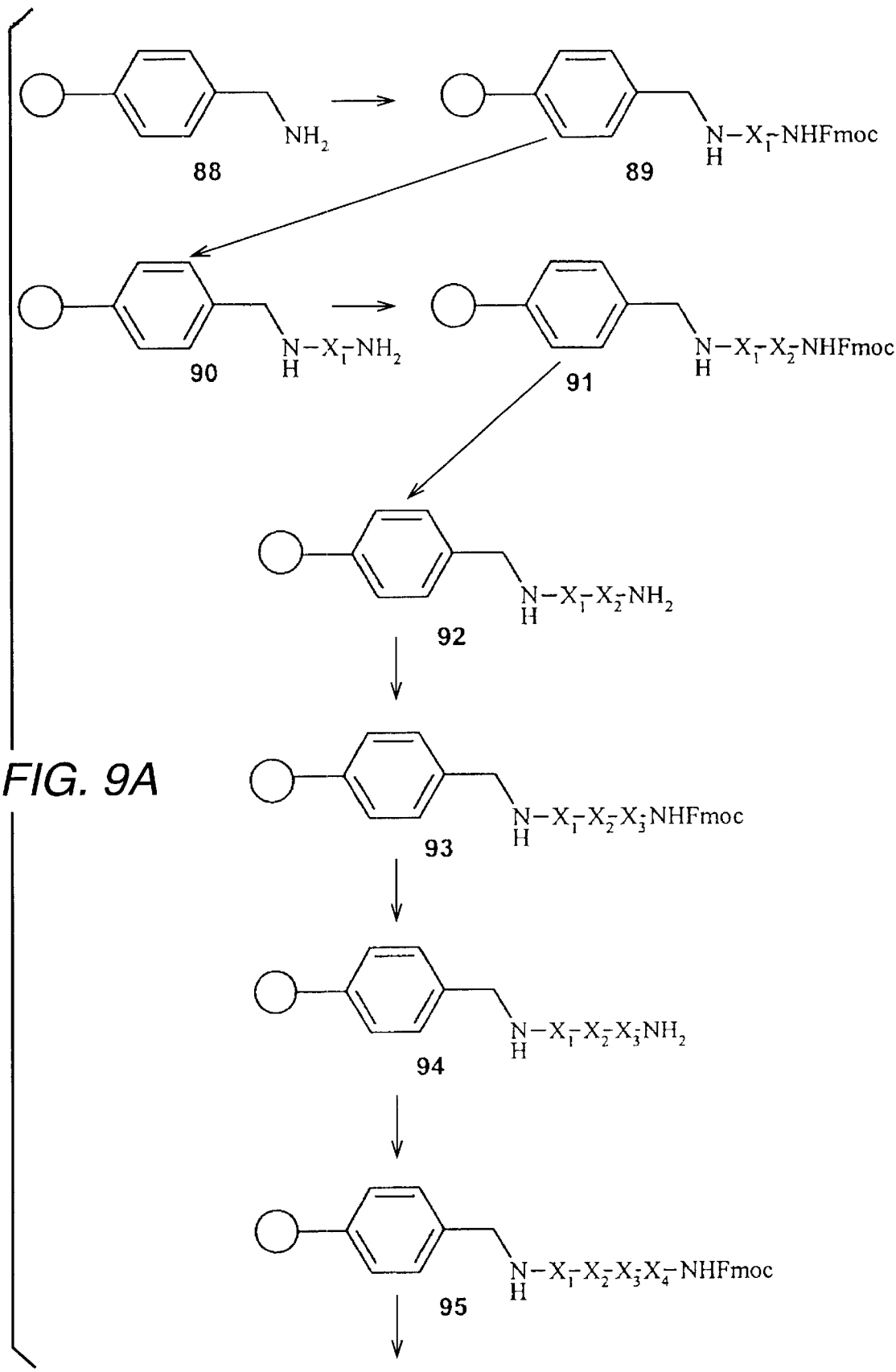
Figure 9B:
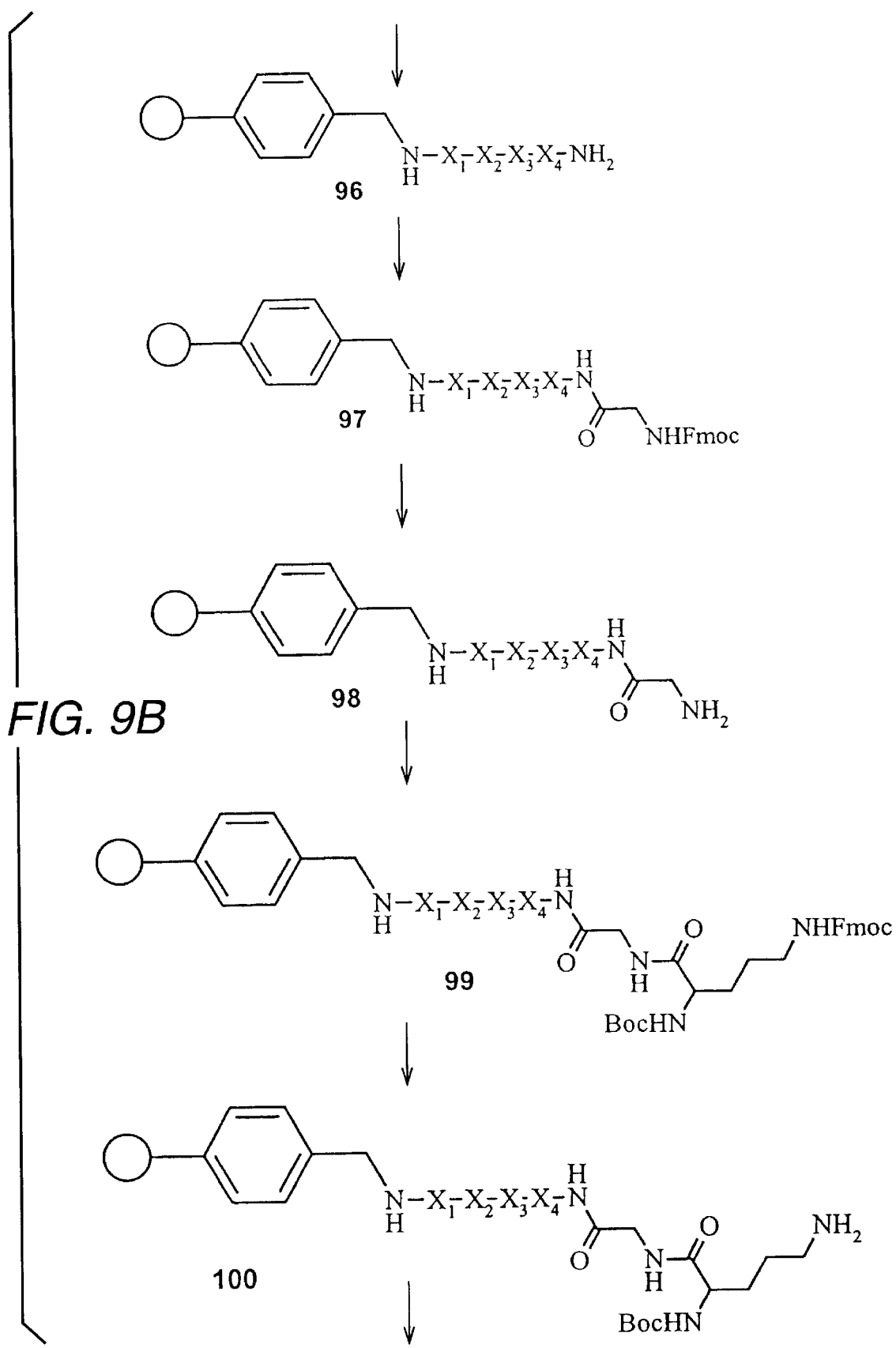
Figure 9C:
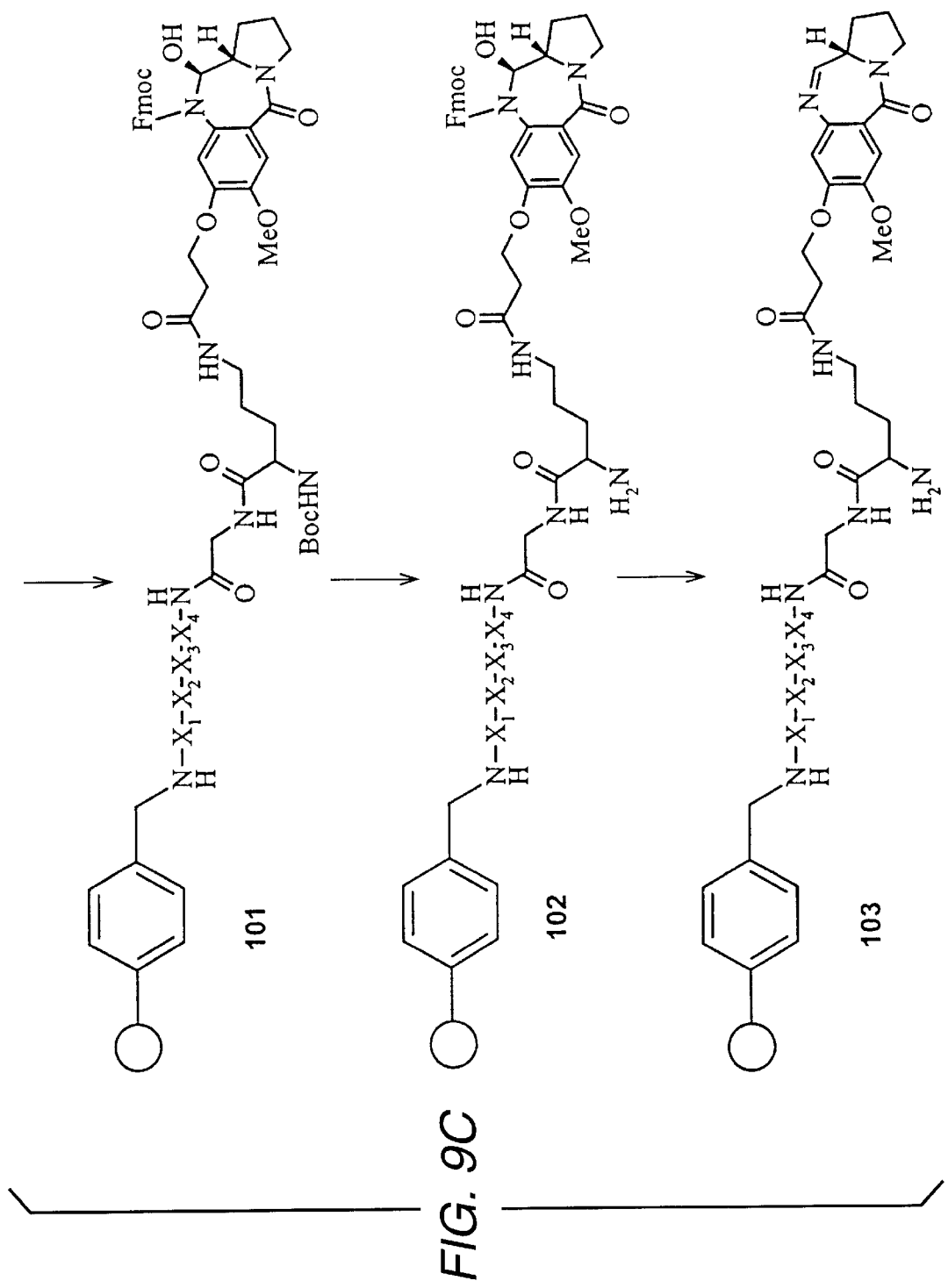

Synthesis of Glycine Sublibrary 103 (FIG. 9)

Aminomethylated resin 88 (30 mg, 0.97 mmol/g loading) was weighed into 17 Alltech tubes (4 ml volume). DMF (250 µl) was added to each tube and the tubes were shaken for 30 min.

Coupling Protocol:—Same as Example 8, but using a solution of an Fmoc-amino acid (0.087 mmol) in DMF (250 µl) in each tube. The amounts of TBTU and DIPEA were increased in proportion to the amount of Fmoc-amino acid.

Acetylation Condition:—Same as Example 8

Deprotection Condition:—Same as Example 8

Pool and Split method:—Same as Example 8

This cycle of coupling, acetylation, deprotection and pooling/splitting was repeated-a further three times until a library of tetramer peptides 96 had been synthesised, but after third repetition the resin was not pooled but kept as 17 separate sublibraries, allowing for the final amino acid to be known.

Coupling to Fmoc-glycine: (96→98)—Same as Example 10 but using 441 mg of Fmoc-glycine in 3.4 ml DMF with the amount of the other compounds increased in proportion.

Coupling to Boc(Fmoc)-lysine: (98→100)—Same as Example 10 but using 695 mg of TBTU and DIPEA with the amounts of Boc(Fmoc)-lysine in 3.4 ml DMF.

Coupling to PBD Capping Unit: (100→103)—same as Example 10 but using a solution of 828 mg Fmoc PBD acid 7b in 3.4 ml DMF.

EXAMPLE 12

Synthesis of a Bis-PBD Pentapeptide Library
Synthesis of Lysine-Glycine Dimer 109 (FIG. 10a)

Aminomethylated resin 88 (510 mg, 0.97 mmol/g loading) was weighed into a round bottom flask, fitted with a sinter. DMF (20 ml) was added and the vessel was shaken for 30 min.

A solution of Boc(Fmoc)-lysine (695 mg, 1.48 mmol) in DMF (10 ml) and a solution of TBTU (480 mg, 1.48 mmol) and DIPEA (260 µl, 1.48 mmol) also in DMF (10 ml) were added to the vessel and shaking continued for 20 hours. Resin 104 was filtered and rinsed with DMF (3×10 ml), CH$_2$Cl$_2$ (3×10 ml), MeOH (3×10 ml), Et$_2$O (2×10 ml) and dried in vacuo.

A solution of 20% Ac$_2$O, 30% pyridine in CH$_2$Cl$_2$ (20. ml) was added to resin 104 and the vessel was shaken for 2 hours. The acetylated resin was filtered and washed with CH$_2$Cl$_2$ (3×10 ml), MeOH (3×10 ml), Et$_2$O (2×10 ml) and dried in vacuo.

A solution of 2% triisopropylsilane in TFA (10 ml) and CH$_2$Cl$_2$ (10 ml) was added to the vessel, which was shaken for 2 hours.

Resin 105 was filtered and rinsed with CH$_2$Cl$_2$ (3×10 ml), MeOH (3×10 ml), Et$_2$O (2×10 ml) and dried in vacuo.

Resin 105 was suspended in CH$_2$Cl$_2$ (5 ml) and shaken for 30 min. An ice cold solution of allyl chloroformate (157 µl, 1.48 mmol) and 4-methylmorpholine (150 mg, 1.48 mmol) in CH$_2$Cl$_2$ (10 ml) was added and the vessel was shaken for 16 hours. Resin 106 was filtered and rinsed with CH$_2$Cl$_2$ (3×10 ml), MeOH (3×10 ml), Et$_2$O (2×10 ml) and dried in vacuo.

A solution of 20% piperidine in DMF (20 ml) was added to resin 106 and the tubes were shaken for 2 hours. Resin 107 was filtered and rinsed with DMF (3×10 ml), CH$_2$Cl$_2$ (3×10 ml), MeOH (3×10 ml), Et$_2$O (2×10 ml) and dried in vacuo.

Resin 107 was suspended in DMF (20 ml) and shaken for 30 min. A solution of Fmoc-glycine (441 mg, 1.48 mmol) in DMF (10 ml) and a solution of TBTU (480 mg, 1.48 mmol) and DIPEA (260 µl, 1.48 mmol) in DMF (10 ml) were added to the vessel and shaking continued for 20 hours. Resin 108 was filtered and rinsed with DMF (3×10 ml), CH$_2$Cl$_2$ (3×10 ml), MeOH (3×10 ml), Et$_2$O (2×10 ml) and dried in vacuo.

A solution of 20% Ac$_2$O, 30% pyridine in CH$_2$Cl$_2$ (20 ml) was added to resin 108 and the vessel was shaken for 2 hours. The acetylated resin was filtered and washed with CH$_2$Cl$_2$ (3×10 ml), MeOH (3×10 ml), Et$_2$O (2×10 ml) and dried in vacuo.

A solution of 20% piperidine in DMF (20 ml) was added to acetylated resin and the vessel was shaken for 2 hours. Resin 109 was filtered and rinsed with DMF (3×10 ml), CH$_2$Cl$_2$ (3×10 ml), MeOH (3×10 ml), Et$_2$O (2×10 ml) and dried in vacuo.

Figure 10B:
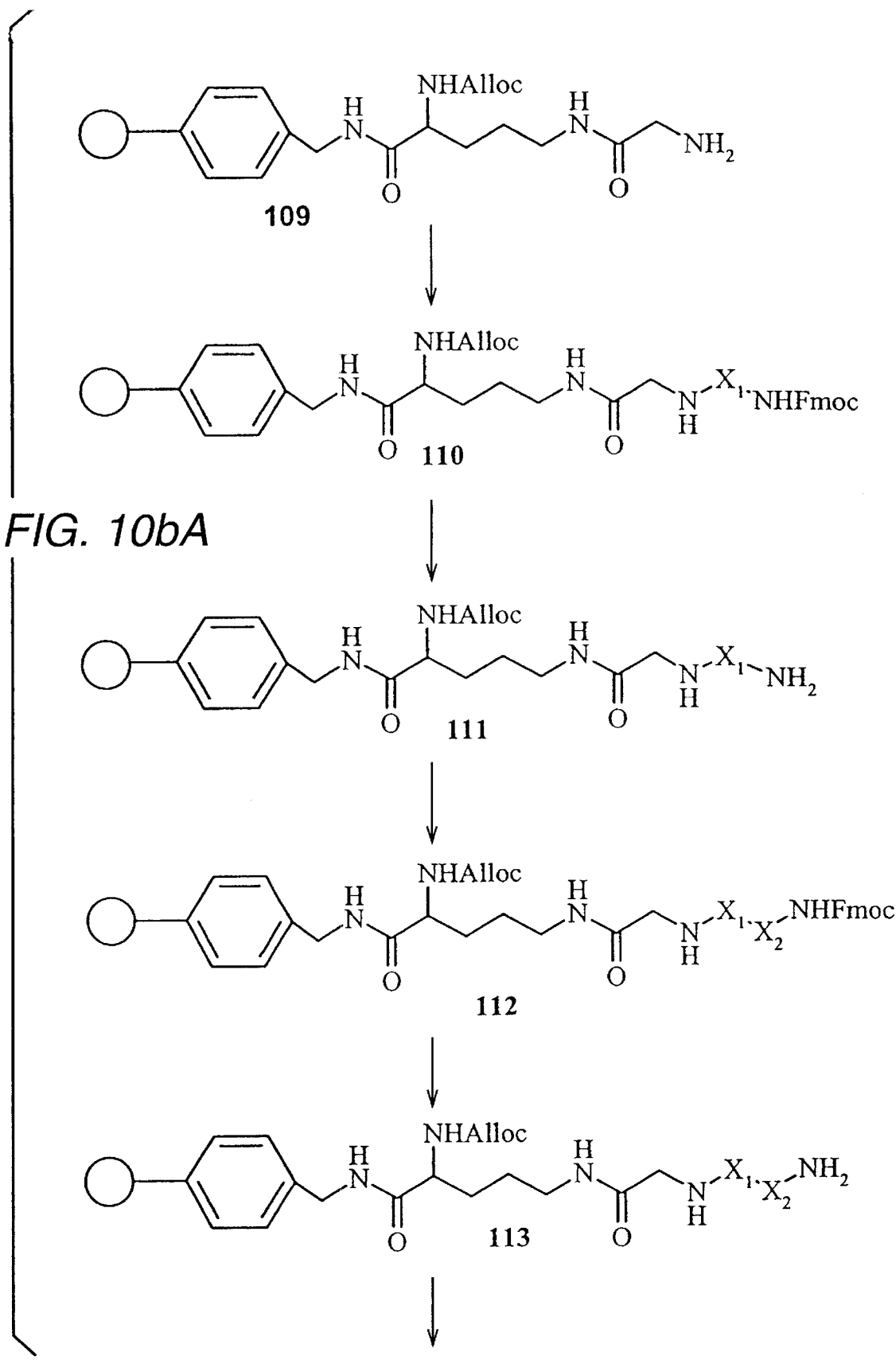
Figure 10B:
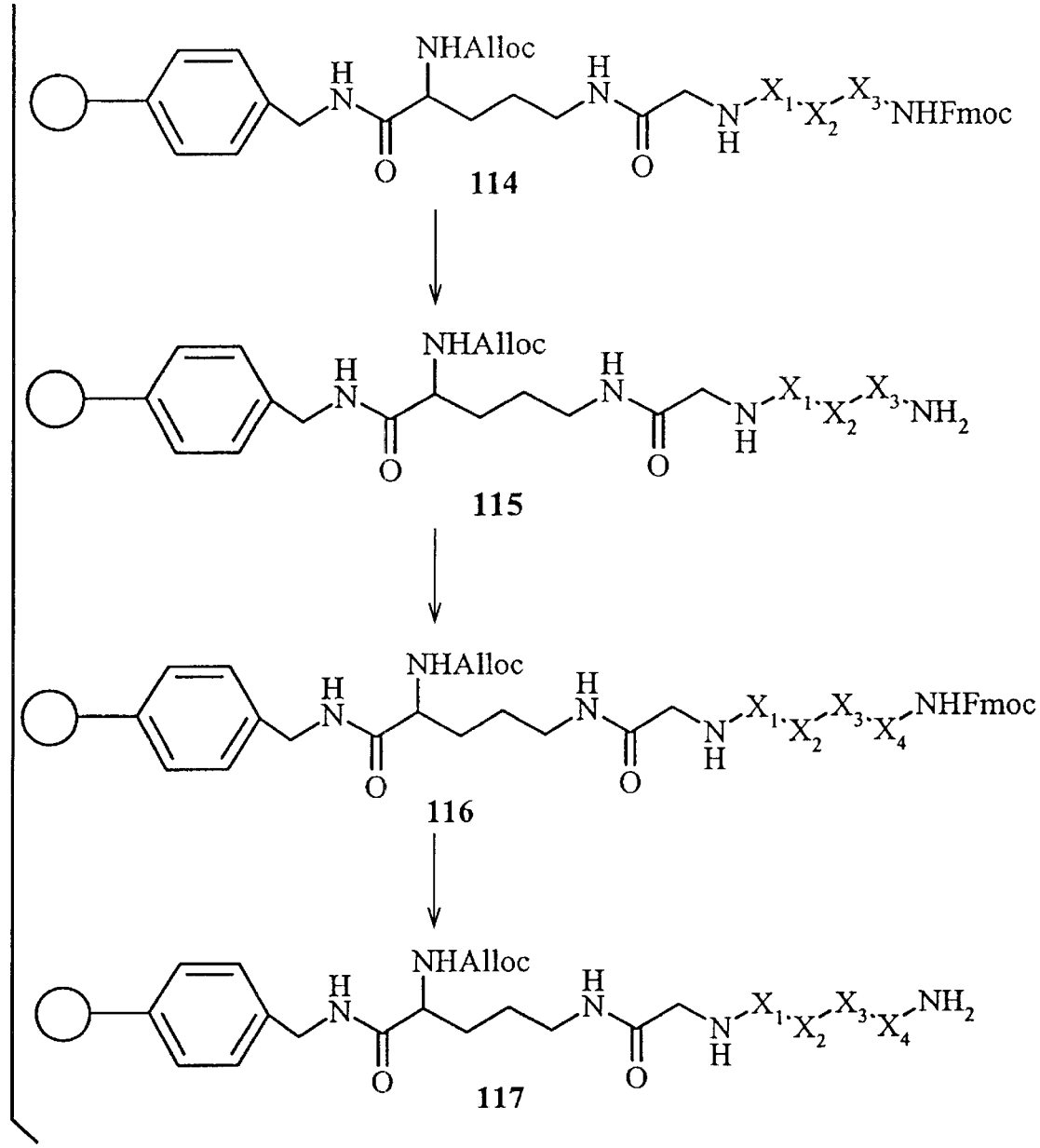

Synthesis of Glycine Sublibrary 117 (FIG. 10b)

Pool and Split Method:—Same as Example 8, starting with resin 109.

Coupling Conditions:—Same as Example 8 but using a solution of an Fmoc-amino acid (0.087 mmol) in DMP (250 µl) in each tube.

Instead of TBTU and DIPEA a solution of diisopropyl-carbodiimide (232 µl, 1.48 mmol) and HOBt (200 mg, 1.48 mmol) in DMF (3.4 ml) was dispensed equally into the 17 tubes and shaken for 20 hours.

Acetylation Protocol:—Same as Example 8

Deprotection Protocol:—Same as Example 8

This cycle of pooling/splitting, coupling, acetylation and deprotection was repeated a further three times until a library of 6-mer peptides 117 had been synthesised, but after the third repetition the resin was not pooled but kept as 17 separate sublibraries, allowing for the final amino acid to be known.

Figure 10C:
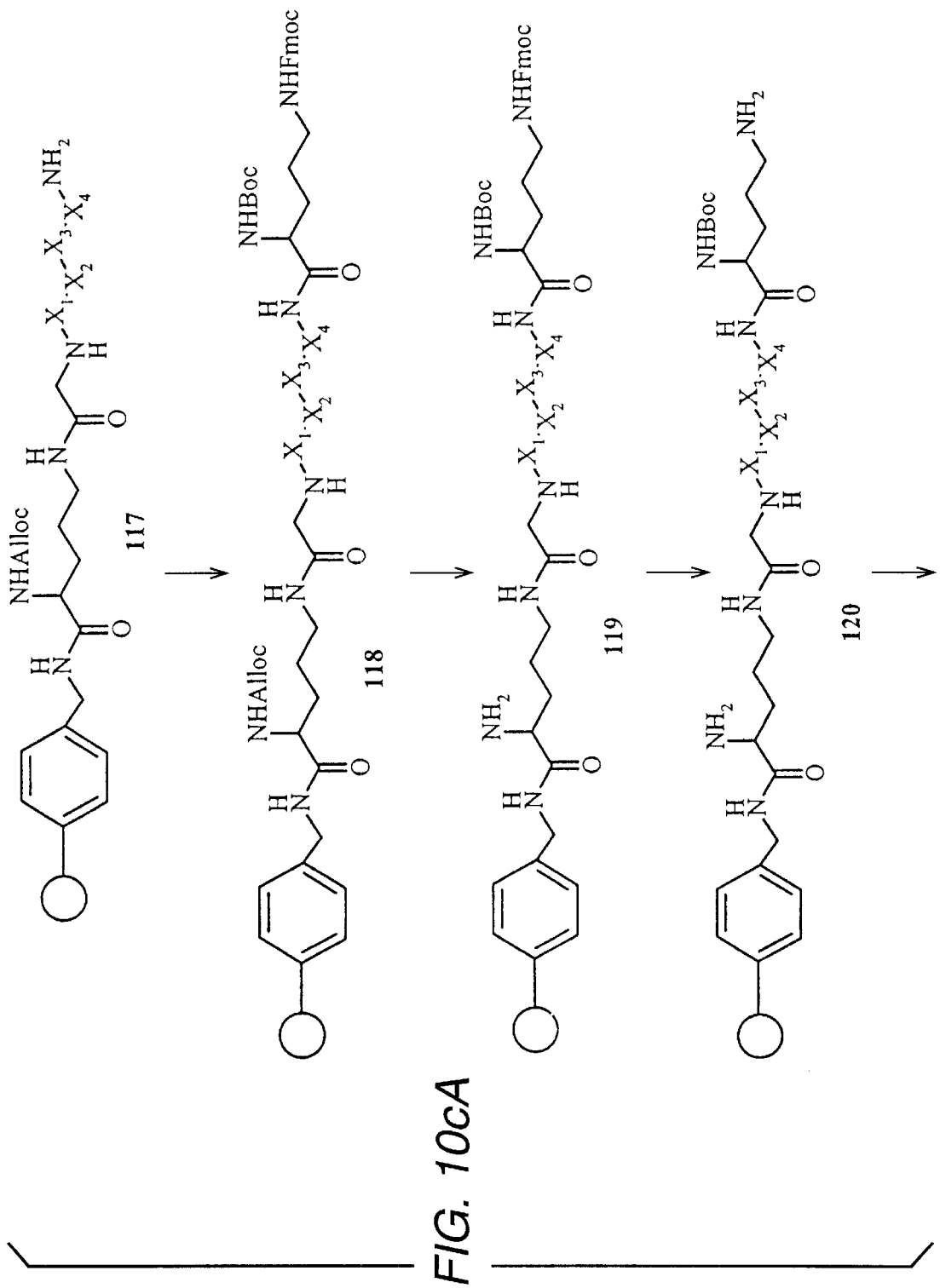
Figure 10C:
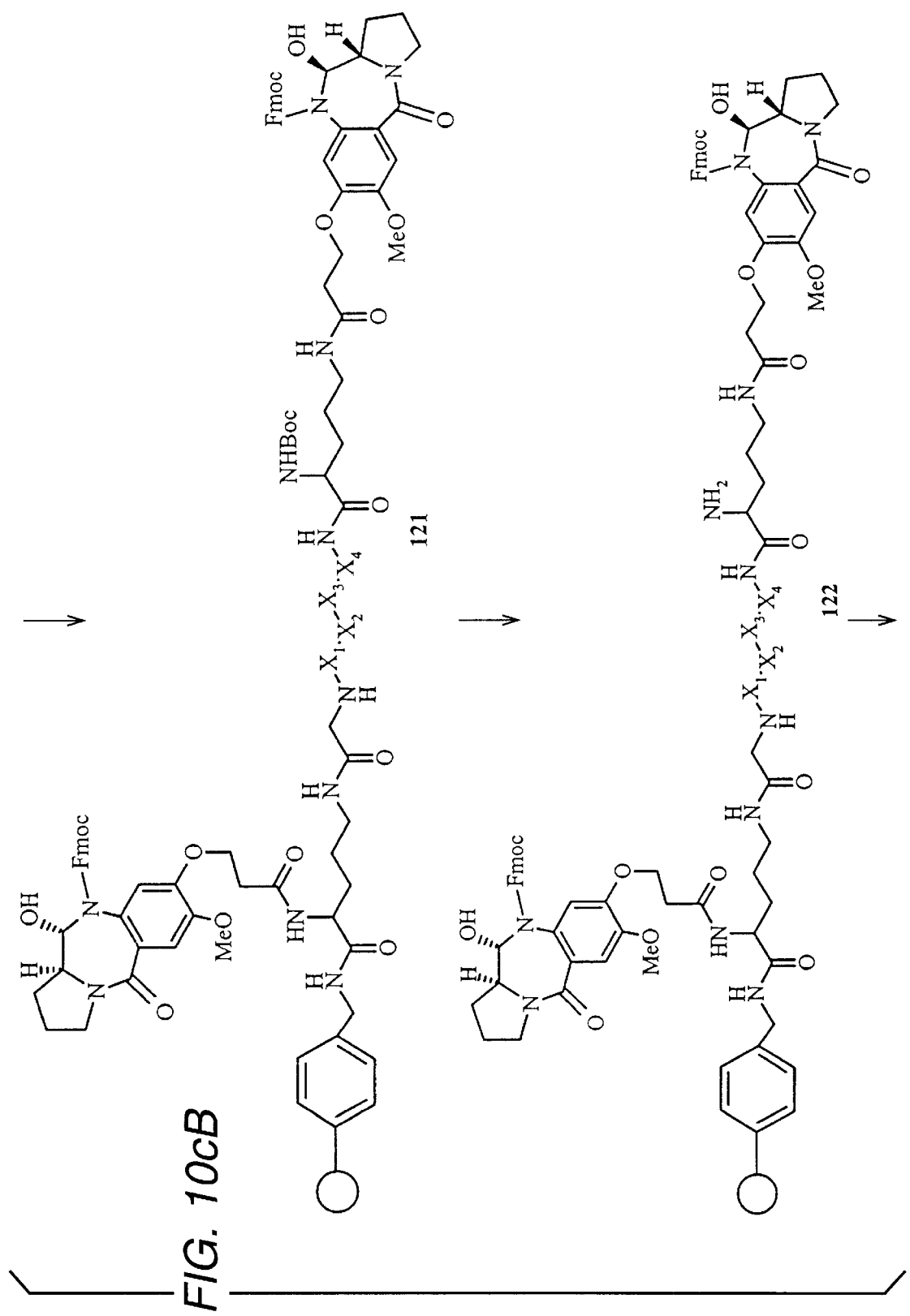
Figure 10C:
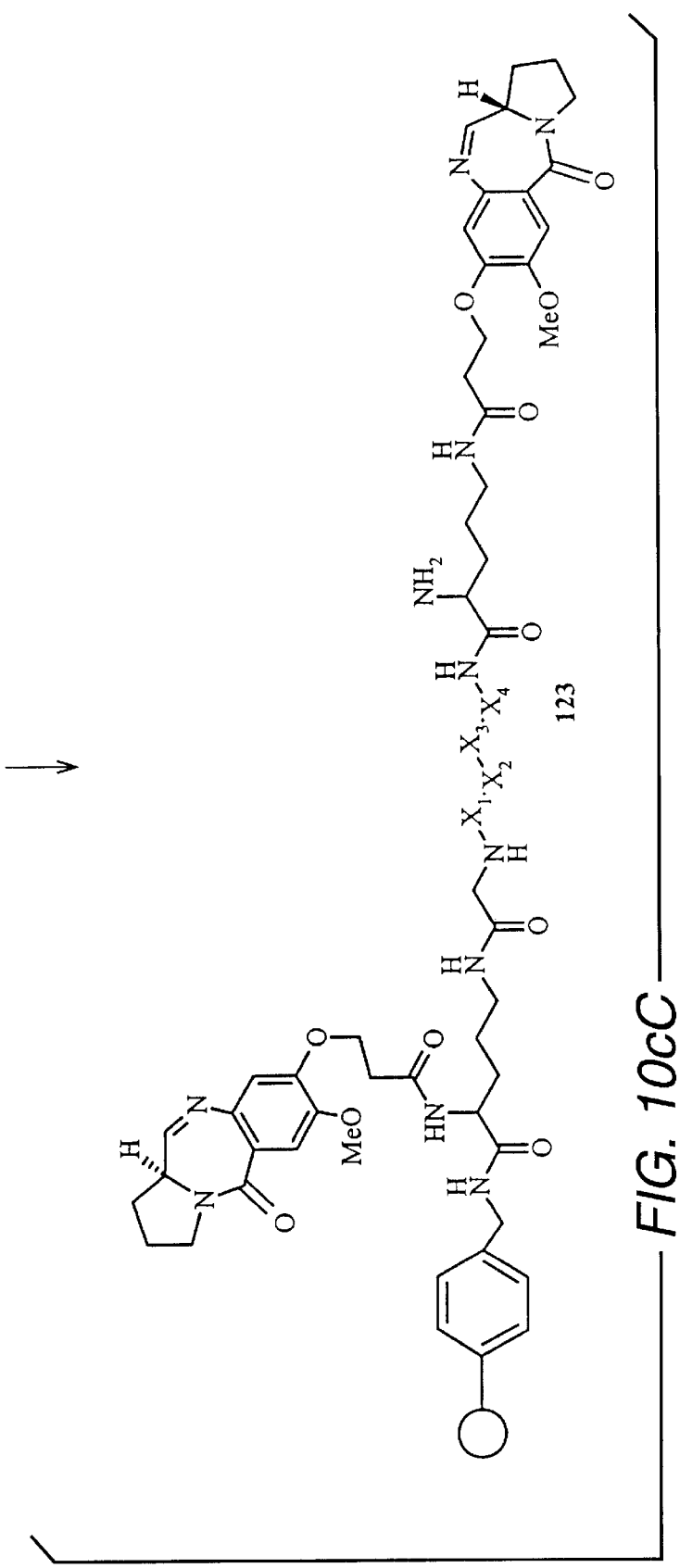

Synthesis of Bis PBD-Glycine Sublibrary 123 (FIG. 10C)

A solution of Boc(Fmoc)-lysine (695 mg, 1.48 mmol) in DMF (3.4 ml) and a solution of TBTU (480 mg, 1.48 mmol) and DIPEA (260 µl, 1.48 mmol) in DMF (3.4 ml) were dispensed equally to resin 117 and shaking was continued for 20 hours. Resin 118 was filtered and rinsed with DMF (3×2 ml), CH$_2$Cl$_2$ (3×2 ml), MeOH (3×2 ml) and dried in vacuo.

A solution of 20% Ac$_2$O, 30% pyridine in CH$_2$Cl$_2$ (500 µl) was added to resin 118 and the tubes were shaken for 2 hours. The acetylated resin was filtered and washed with CH$_2$Cl$_2$ (3×2 ml), MeOH (3×2 ml), further CH$_2$Cl$_2$ (3×2 ml) and dried in vacuo.

Resin 118 was suspended in $CH_2Cl_2$ (250 µl) and the tubes were shaken for 30 min. A solution of phenylsilane (1.5 ml, 11.9 mmol) in $CH_2Cl_2$ (3.4 ml) was dispensed equally into each tube and shaken for 10 min.

A solution of tetrakis(triphenylphosphine)palladium (57 mg, 0.05 mmol) in $CH_2Cl_2$ (3.4 ml) was dispensed equally into each tube and shaken for a further 10 min. Resin 119 was filtered and rinsed with $CH_2Cl_2$ (3×2 ml), MeOH (3×2 ml) and dried in vacuo. This procedure was repeated once.

A solution of 20% piperidine in DMF (500 µl) was added to resin 119 and the tubes were shaken for 2 hours. Resin 120 was filtered and rinsed with DMF (3×2 ml), $CH_2Cl_2$ (3×2 ml), MeOH (3×2 ml) and dried in vacuo.

Resin 120 was suspended in DMF (250 µl) and shaken for 30 min. A solution of Fmoc-PBD acid 7b (1.66 g, 2×1.48 mmol) in DMF (3.4 ml) and a solution of TBTU (960 mg, 2×1.48 mmol) and DIPEA (520 µl, 2×1.48 mmol) in DMF (3.4 ml) were equally dispensed to the tubes and shaking continued for 20 hours. Resin 121 was filtered and rinsed with DMF (3×2 ml), $CH_2Cl_2$ (3×2 ml), MeOH (3×2 ml) and dried in vacuo.

A solution of 2% triisopropylsilane in TFA (250 µl) and $CH_2Cl_2$ (250 µl) was added to resin 122 and the tubes were shaken for 2 hours. Resin 122 was filtered and rinsed with $CH_2Cl_2$ (3×2 ml), MeOH (3×2 ml) further $CH_2Cl_2$ (3×2 ml) and dried in vacuo.

A solution of 20% piperidine in DMF (500 ml) was added to resin 122 and the tubes were shaken for 2 hours. Resin 123 was filtered and rinsed with DMF (3×2 ml), $CH_2Cl_2$ (3×2 ml), MeOH (3×2 ml) and dried in vacuo.

EXAMPLE 13

Synthesis of Fmoc-Glu-OAll-Amino-Resin (171) (FIG. 11)

The TentaGel amine resin 169 (3.0 g, 0.8 mmol) in the form of beads was allowed to swell for 2 hours in dry DMF (12 mL) and shaken gently in a siliconised randomisation round bottom flask, equipped with a sintered glass filter tube. The suspension was filtered by suction from below. The beads were washed twice with dry DMF as follows: DMF (20 mL) was added from the top of the vessel (to wash down any resin adhering to the sides of the vessel), nitrogen gas was gently bubbled from below through the sintered glass for 2 minutes, and excess DMF was removed by suction. A threefold molar excess of HOBt (7.7 mL, 0.3 M in DMF, 2.32 mmol) ("coupling reagent" was added to a threefold molar excess of Fmoc-Glu-OAll (0.95 g, 2.32 mmol) and the resulting solution was added to the resin. A threefold molar excess of PyBOP (1.2 g, 2.32 mmol) and a threefold molar excess of DIPEA (0.4 mL, 0.3 g, 2.32 mmol) in a minimal volume of DMF (1.2 mL) were added to the reaction flask to initiate the coupling reaction. The reaction flask was capped tightly and allowed to shake gently for 1 hour at room temperature and excess coupling reagent was removed by suction. The coupling procedure was repeated once, from from the addition of coupling reagent to ensure complete reaction. The resulting resin 171 was washed 6 times with DMF (4×20 mL), DCM (1×20 mL) and MeOH (1×20 mL), on each occasion the resin was shaken for 2 minutes and then filtered. The washing cycle was then repeated and the resin was dried in vacuo.

Synthesis of Pentapeptide Library (172)

In order to cap any remaining free amino groups the resin (in the randomisation flask), was suspended in a mixture of $Ac_2O$/pyridine/DMF (0.2:0.3:0.5, 10 mL) and allowed to shake for 2 hours. The supernatant was removed by suction, the beads were washed with DCM (1×10 mL), MeOH (1×10 mL) and again with DCM (1×10 mL). The washing cycle was then repeated and the resin was dried in vacuo.

The Fmoc protecting groups were removed by treating the resin with 50% piperidine in DMF (10.7 mL) whilst being shaken. After 10 minutes, the supernatant was removed by suction and fresh 50% piperidine in DMF (10.7 mL) was added and shaking continued. After another 10 minutes, the beads were washed 6 times with DMF (4×20 mL), DCM (1×20 mL) and MeOH (1×20 mL), on each occasion the resin was shaken for 2 minutes and then filtered. The washing cycle was then repeated and the resin was dried in vacuo.

The beads were suspended in an isopycnic mixture of DCE/DMF (2:1, 32 mL) and nitrogen gas was gently bubbled from below. Equal aliquots (470 µL) of the suspension were added in sequence to each of the 17 Alltech tubes, previously marked with a letter corresponding to a specific amino acid. This was repeated 4 times. The beads remaining in the randomisation flask were resuspended in the isopycnic mixture (32 mL) and the distribution process was then repeated twice.

The Glu-OAll-resin M1(45.6 mmol) in each Alltech tube was allowed to swell in dry DMF (710 µL) accompanied by gently shaking for 2 hours. Excess DMF was removed by suction on a vacuum manifold.

The resin was washed with dry DMF (1.18 mL) which was added from the top in order to wash down any resin adhering to the side of the Alltech tubes. The tubes were allowed to shake for 2 minutes and excess DMF was removed by suction on a vacuum manifold.

A threefold molar excess of HOBt (460 µL, 0.3 M in DMF, 0.137 mmol) was added to a threefold molar excess of a each Fmoc-amino-acid (0.137 mmol) and the resulting mixture was shaken for 10 minutes and then added to appropriate Alltech tube.

|  | Amount | | |
| --- | --- | --- | --- |
| Substance | mg | mol | TUBE |
| Fmoc-Ala-OH | 42.56 | 0.137 | 1 |
| Fmoc-Asn-OH | 48.5 | 0.137 | 2 |
| Fmoc-Asp(O $^t$Bu)-OH | 56.3 | 0.137 | 3 |
| Fmoc-Glu(O $^t$Bu)-OH | 58.2 | 0.137 | 4 |
| Fmoc-Gln-OH | 50.4 | 0.137 | 5 |
| Fmoc-Gly-OH | 40.7 | 0.137 | 6 |
| Fmoc-Ile-OH | 48.3 | 0.137 | 7 |
| Fmoc-Leu-OH | 48.3 | 0.137 | 8 |
| Fmoc-Lys(Boc)-OH | 64.1 | 0.137 | 9 |
| Fmoc-Met-OH | 50.8 | 0.137 | 10 |
| Fmoc-Phe-OH | 51.8 | 0.137 | 11 |
| Fmoc-Pro-OH | 46.2 | 0.137 | 12 |
| Fmoc-Ser($^t$Bu)-OH | 52.4 | 0.137 | 13 |
| Fmoc-Thr($^t$Bu)-OH | 54.4 | 0.137 | 14 |
| Fmoc-Trp(Boc)-OH | 72.0 | 0.137 | 15 |
| Fmoc-Tyr($^t$Bu)-OH | 62.8 | 0.137 | 16 |
| Fmoc-Val-OH | 46.4 | 0.137 | 16 |

A threefold molar excess of PyBOP (71 mg, 0.137 mmol) and threefold molar excess of DIPEA (24 µL, 18 mg, 0.137 mmol) in a minimal volume of DMF (70 µL), were added to each of the Alltech tubes to initiate the coupling reaction.

The Alltech tubes were capped tightly and allowed to shake gently for 1 hour at room temperature. After this time, excess coupling reagent was removed by suction on a vacuum manifold. The coupling procedure was repeated once to ensure complete reaction.

The resin was washed 6 times with DMF (4×2 mL), DCM (1×2 mL), MeOH (1×2 mL), on each occasion the resin was shaken for 2 minutes and then filtered on a vacuum manifold. The washing cycle was then repeated and the resin was dried in vacuo.

In order to cap any remaining free amino groups in the peptide resin, the resin in each Alltech tube was suspended in a mixture of $Ac_2O$/pyridine/DMF (0.2:0.3:0.5, 460 μL) and allowed to shake for 2 hours. The supernatant was removed by suction on a vacuum manifold and the beads were washed 3 times with DCM (1×2 mL), MeOH (1×2 mL) and again with DCM (1×2 mL), on each occasion the resin was shaken for 2 minutes and then filtered on a vacuum manifold. The washing cycle was then repeated and the resin was dried in vacuo.

The Fmoc protecting groups were removed by treating the resin with 50% piperidine in DMF (0.62 mL) over 10 minutes on a shaker. The supernatant was removed and fresh 50% piperidine in DMF (620 μL) was added. After another 10 minutes, the beads were washed 3 times with DMF (4×2 mL), DCM (1×2 mL) and MeOH (1×2 mL), on each occasion the resin was shaken for 2 minutes and then filtered on a vacuum manifold. The washing cycle was then repeated and the resin was dried in vacuo.

The beads in each of the 17 Alltech tubes were suspended in DCE/DMF (2:1, 1.9 mL), transferred by pipette to the siliconised randomisation flask and excess isopycnic solution removed by suction. The process was repeated twice to ensure that all the resin was returned to the randomisation flask.

Once the resin was returned to the randomisation vessel it was redistributed amongst the 17 Alltech reaction tubes as described above.

The coupling protocol was repeated 4 more times to generate a pentapeptide library 172. At the end of the last coupling cycle the resin was not recombined so as to obtain 17 sublibraries, in which the identity of the N-terminus amino acid was known.

Coupling Library Members to PBD-Capping Unit (172→174)

The peptide resin 172 (45.6 mmol) in each of the Alltech tubes was washed with DCM (2×2 mL); on each occasion the resin was shaken for 2 minutes and then filtered on a vacuum manifold. The resin was then dried in vacuo.

A mixture of $CHCl_3$/HOAc/NMM (37:2:1, 650 μL) was added to the reaction tubes and shaken for 30 minutes. The deprotected peptide resin was washed with DCM (4×2 mL), on each occasion the resin was shaken for 2 minutes and then filtered on a vacuum manifold. The resin was then allowed to dry in vacuo.

The peptide resin (45.6 μmol) in each Alltech tubes was allowed to swell in dry DMF (0.8 mL) shaken gently for 2 hours and then filtered using the vacuum manifold.

The beads were washed twice with dry DMF as follows: DMF (1.18 mL) was added from the top followed by gentle shaking for 2 minutes and excess DMF was removed by filtration on a vacuum manifold.

A threefold molar excess of HOBt (18 mg, 0.137 mmol) in a minimal volume of DMF (0.3 molar, 700 μL) and threefold molar excess of Alloc-PBD 173 synthesised in an analogous manner to example 2 (55 mg, 0.137 mmol) in DMF were added to the resin.

A threefold molar excess of PyBOP (71 mg, 0.137 mmol) and threefold molar excess of DIPEA (24 μL, 18 mg, 0.137 mmol) in a minimal volume of DMF (150 μL), were added to the reaction tube to initiate the coupling reaction.

The reaction tube was capped tightly and allowed to shake gently for 16 hours at room temperature. Excess reagents were removed by filtration on a vacuum manifold.

The beads were washed 4 times with DMF (4×2 mL), DCM (1×2 mL) and MeOH (1×2 mL), on each occasion the resin 174 was shaken for 2 minutes and then filtered on a vacuum manifold. The washing cycle was then repeated and the resin was dried in vacuo.

Removal of Side Chain, Fmoc and Alloc Protecting Groups (174→175)

The Boc and tBu protecting groups were removed by treating the PBD-peptide resin 174 (45.6 μmol) in each Alltech tubes with a solution of TFA/triisopropylsilane/DCM (48:2:50, 800 μL). The reaction tubes were allowed to shake for 30 minutes and excess reagents were removed by filtration on a vacuum manifold. The procedure was repeated once and the beads were washed 3 times with DCM (1×2 mL), MeOH (1×2 mL) and again with DCM (1×2 mL), on each occasion the resin was shaken for 2 minutes and then filtered on a vacuum manifold. The washing cycle was then repeated and the resin was dried in vacuo.

The resin was washed with DCM (5×2 mL) on each occasion the resin was shaken for 30 seconds and then filtered on a vacuum manifold.

Alloc protecting groups were removed by treating the resin (45.6 μmol) with a solution of phenylsilane ($PhSiH_3$, 130 μL, 0.118 g, 1.09 mmol) in DCM (300 μL) and the resin was stirred manually. A solution of $Pd(PPh_3)_4$ (5.3 mg, 4.56 μmol) in DCM (500 μL) was added, and the Alltech tubes were shaken mechanically for 10 min. Excess reagents were removed by filtration on a vacuum manifold and the process was repeated once.

The peptide resin was washed with DCM (8×2 mL), on each occasion the resin was shaken for 30 seconds and then filtered on a vacuum manifold. The washing cycle was repeated and the resin was dried in vacuo.

The Fmoc groups were removed by treating the resin (45.6 μmol) with 50% piperidine/DMF (800 μL) during 2 hours on a shaker. The supernatant was removed by filtration on a vacuum manifold.

The beads 175 were washed 6 times with DMF (4×2 mL), DCM (1×2 mL) and MeOH (1×2 mL), on each occasion the resin was shaken for 2 minutes and then filtered on a vacuum manifold. The washing cycle was repeated twice and the resin was dried and stored in vacuo.

EXAMPLE 14

Cellulose Paper as a Laminar Support
A. Attachment of an Fmoc-PBD (7b) to Cellulose Paper

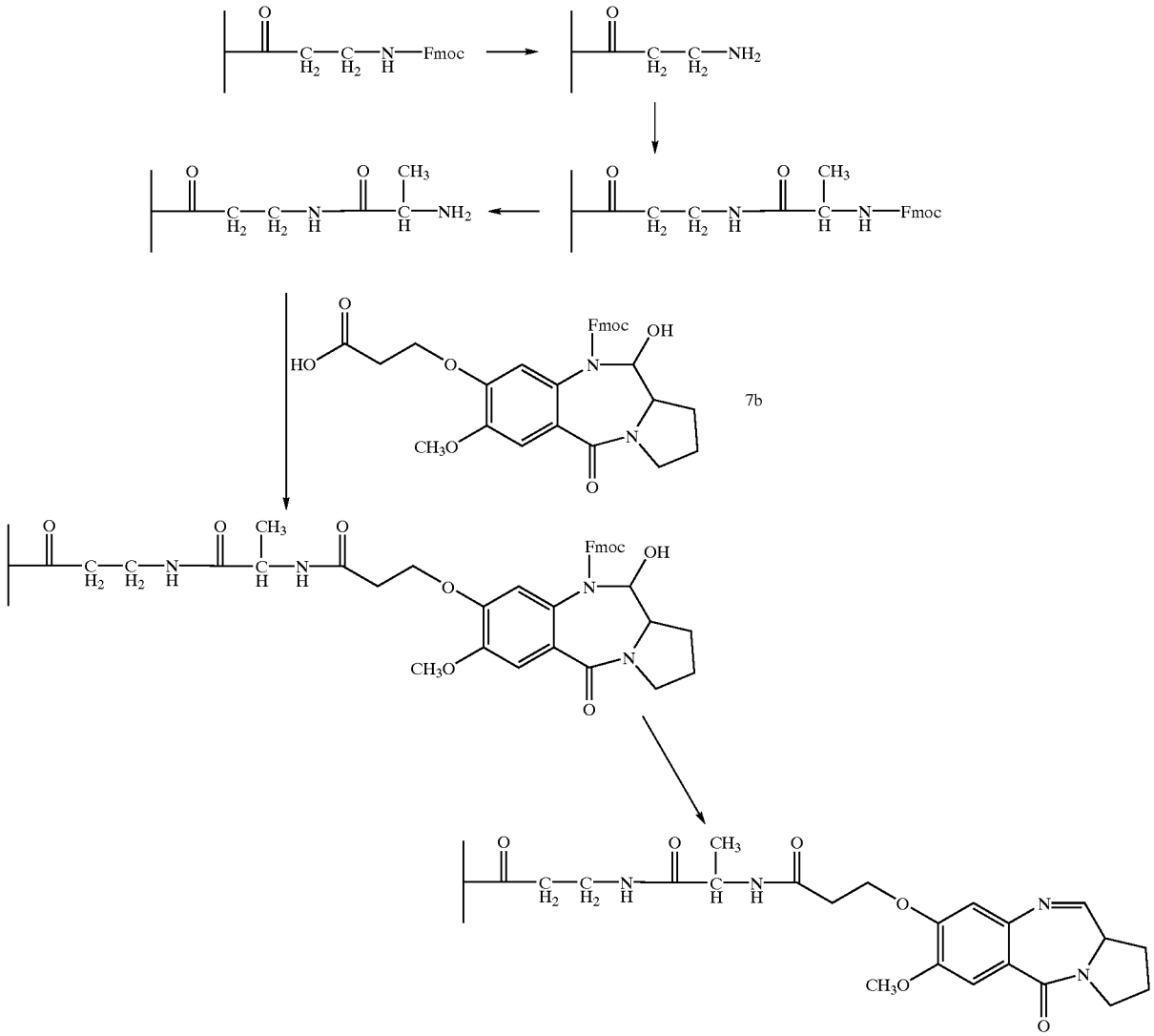

Modification of the Cellulose Paper—(General Method)

The required number of points were marked onto a square of cellulose paper, using a graphite pencil, before the dry paper was incubated with activated β-alanine solution (12 mL, [0.2 M Fmoc-β-alanine activated with 0.24M DIC and 0.4M N-methylimidazole]), for 3 hrs in a sealed vessel. The membrane was washed with DMF (3×50 mL for 3 minutes) and then treated with piperidine solution for 20 minutes (20% piperidine in DMF, 50 mL).

The membrane was washed with DMF (5×50 mL for 3 minutes) and MeOH (2×50 mL, for 3 minutes) and dried.

Fmoc-β-Alanine-OPfp solution (0.3 M Fmoc-βAla-OPfp in DMSO, 1 mL) was coupled to the pre-defined positions on the membrane. After 15 minutes, the coupling was repeated once again.

The membrane was then acetylated (2 minutes, face-down, in acetic anhydride solution A, 2 mL [2% acetic anhydride in DMF], followed by 30 minutes, face-up in acetic anhydride solution B, 50 mL [2% acetic anhydride, 1% DIPEA in DMF], with shaking. After washing with DMF (3×50 mL for 3 minutes), the membrane was treated with piperidine solution for 20 minutes (20% piperidine in DMF, 50 mL), washed with DMF (5×50 mL for 3 minutes) and MeOH (2×50 mL for 3 minutes).

The membrane was stained with bromophenol blue solution (0.01% w/v bromophenol blue in methanol, 50 mL), washed with methanol for 3 minutes and dried.

Coupling of the Fmoc-PBD

A solution of Fmoc-PBD 7b, HOBt and DIC (0.3M, 1.5 mL) in NMP was spotted at the marked points on the membrane. This was left to couple for 1 hour and repeated (6×) until the blue colour of the spot was discharged. The membrane was washed once with DMF (50 mL) and incubated with acetic anhydride solution B, 50 mL for 30 minutes [2% acetic anhydride, 1% DIPEA in DMF].

The membrane was washed with DMF (5×50 mL) for 3 minutes, followed by methanol (2×50 mL) and dried.

N-Fmoc Deprotection

The Fmoc-protecting group was cleaved by treating the membrane with piperidine solution (20% in DMF, 20 mL) for 20 minutes.

The membrane was then washed with DMF (5×50 mL) for 3 minutes and MeOH (2×50 mL) for 3 minutes, stained with bromophenol blue solution (50 mL), washed with MeOH (50 mL) for 3 minutes and dried.

[The bromophenol blue colouration was removed by destaining with piperidine solution, washing with DMF and MeOH and drying.]

B. Attachment of Nvoc-PBD to Cellulose Paper

Coupling of the Nvoc-PBD (7a) (Example 1a)

The general method for modification and attachment of the Fmoc-PBD 7b was employed. The Nvoc-PBD (7a) was coupled as a 0.3 M solution for 30 minutes and repeated (4×) until the bromophenol blue stain was discharged. The membrane was washed and dried as previously described.

Deprotection of the Nvoc-protecting Group

The membrane was incubated for several hours in a solution of DMSO containing 1% ethanolamine at a wavelength of 365 nm. After washing with DMF (3×50 mL) for 3 minutes and MeOH (2×50 mL) for 3 minutes, the membrane was allowed to dry.

EXAMPLE 15

Synphase Crowns as Solid Support

A. Attachment of Fmoc-PBD to Synphase Crowns

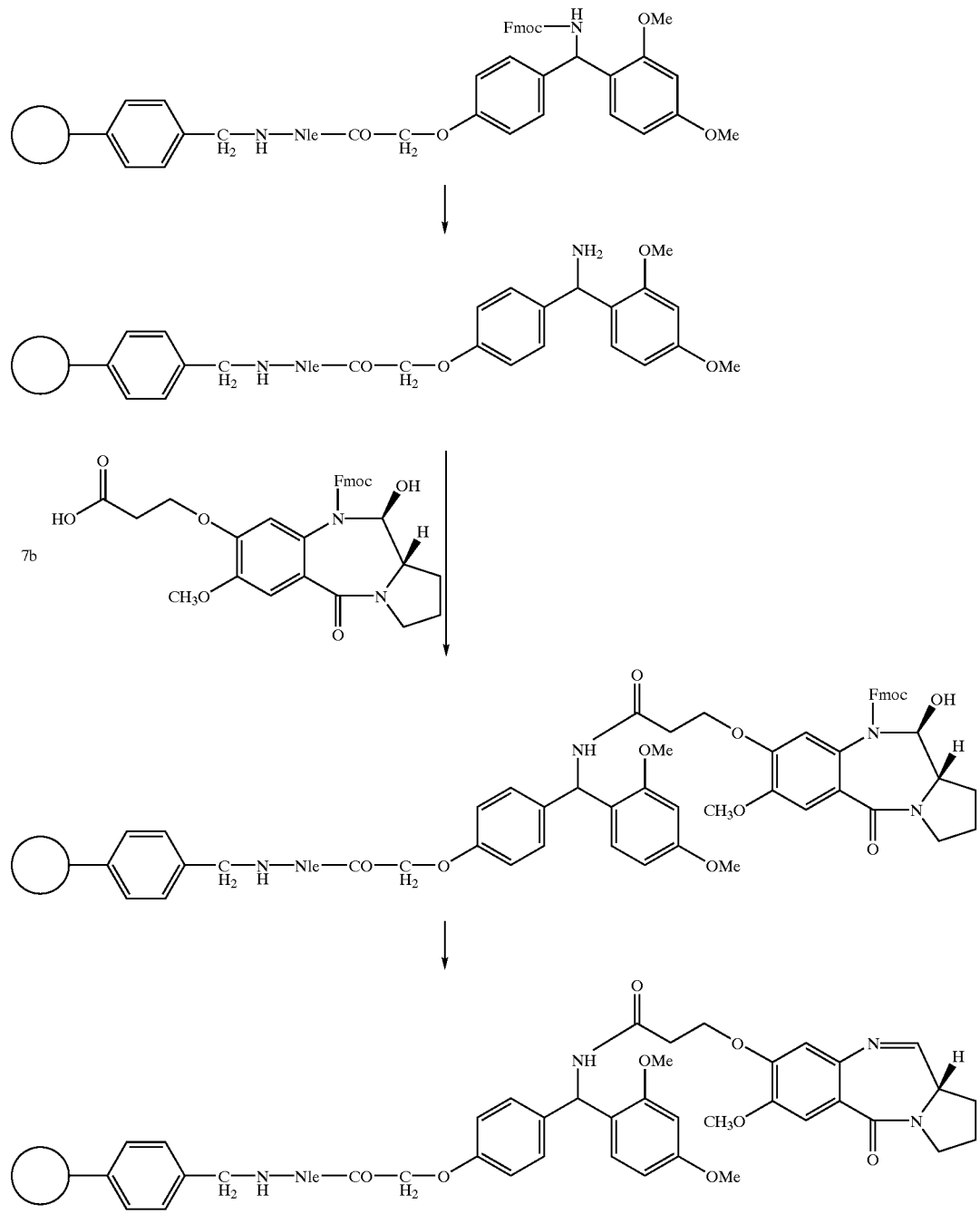

Deprotection of the Fmoc-protecting Group

Two Fmoc-protected Rink-amide crowns (loading 7.7 mM/g), were placed in a scintillation vial and immersed in piperidine solution (20% in DMF, 2 mL) for 20 minutes, with shaking. After rinsing with DMF (3×2 mL) and DCM (3×2 mL), the crowns were immersed in a solution of bromophenol blue (0.01% w/v bromophenol blue in MeOH, 5 mL), until equal colouration was achieved and the crowns were then rinsed in MeOH and dried.

Coupling of the Fmoc-PBD

A solution of Fmoc-PBD 7b (17.18 mg, $3.08 \times 10^{-5}$ mol), HOBt (8.32 mg, $6.16 \times 10^{-5}$ mol) and diisopropylcarbodiimide (10.62 mL, $6.16 \times 10^{-5}$ mol) in NMP (500 mL) was added to the scintillation vial with the crowns.

Coupling was monitored by the loss of the bromophenol blue colouration on the crowns. The reaction was allowed to proceed overnight and was repeated until complete colour loss had occurred. The crowns were then washed with DMF (3×2 mL), DCM (3×2 mL), MeOH (1×2 mL) and allowed to air-dry.

N-Fmoc Deprotection

A single crown was immersed in the piperidine solution (20% in DMF, 1 mL) for 20 minutes with shaking. After rinsing with DMF (3×1 mL), and DCM (3×1 mL), the crown was rinsed in MeOH (1×1 mL) and allowed to air-dry.

B. Attachment of Nvoc-PBD (7a) to Synphase Crowns

Coupling of the Nvoc-PBD (7a)

The general method for modification and attachment of the Fmoc-PBD 7b was employed. The Nvoc-PBD 7a was coupled as a 0.62M solution overnight.

Deprotection of the Nvoc-protecting Group

A single crown was immersed in DMSO containing 1% ethanolamine (2 mL) and irradiated at λ=365 nm for 2 hours, with shaking. After rinsing with DMF (3×1 mL), and DCM (3×1 mL), the crown was rinsed in MeOH (1×1 mL) and allowed to air-dry.

EXAMPLE 16

Figure 12A:
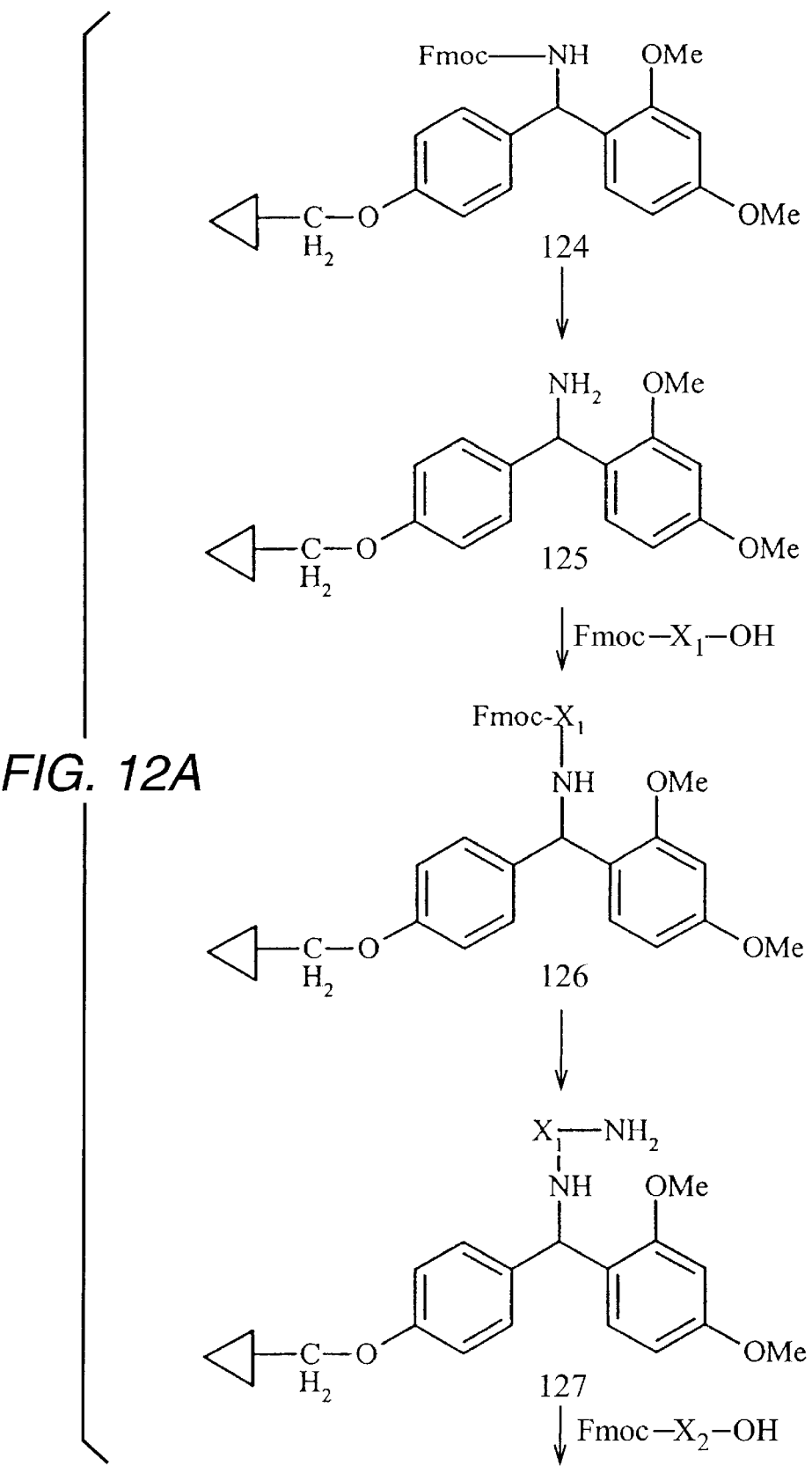
Figure 12B:
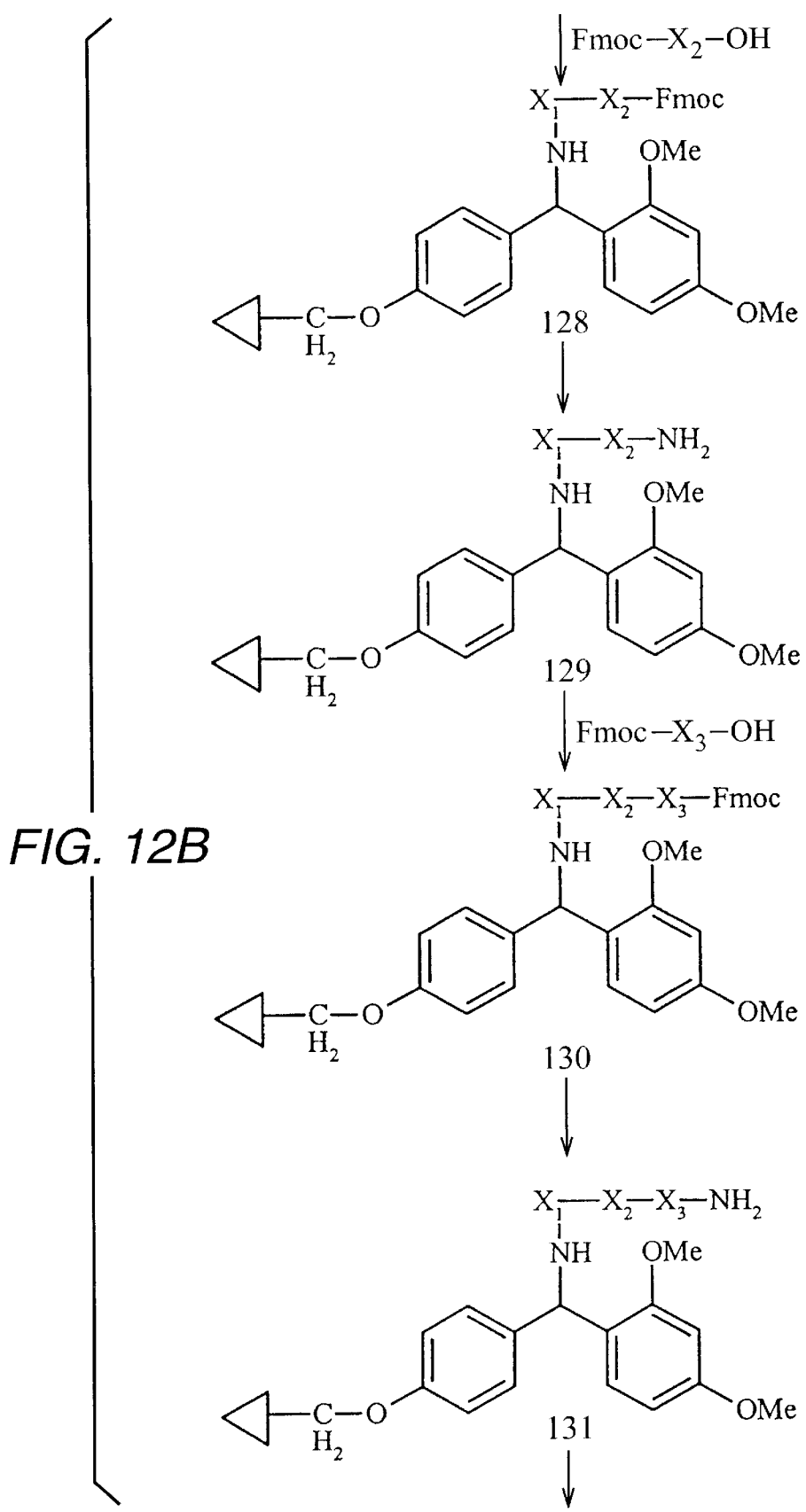
Figure 12C:
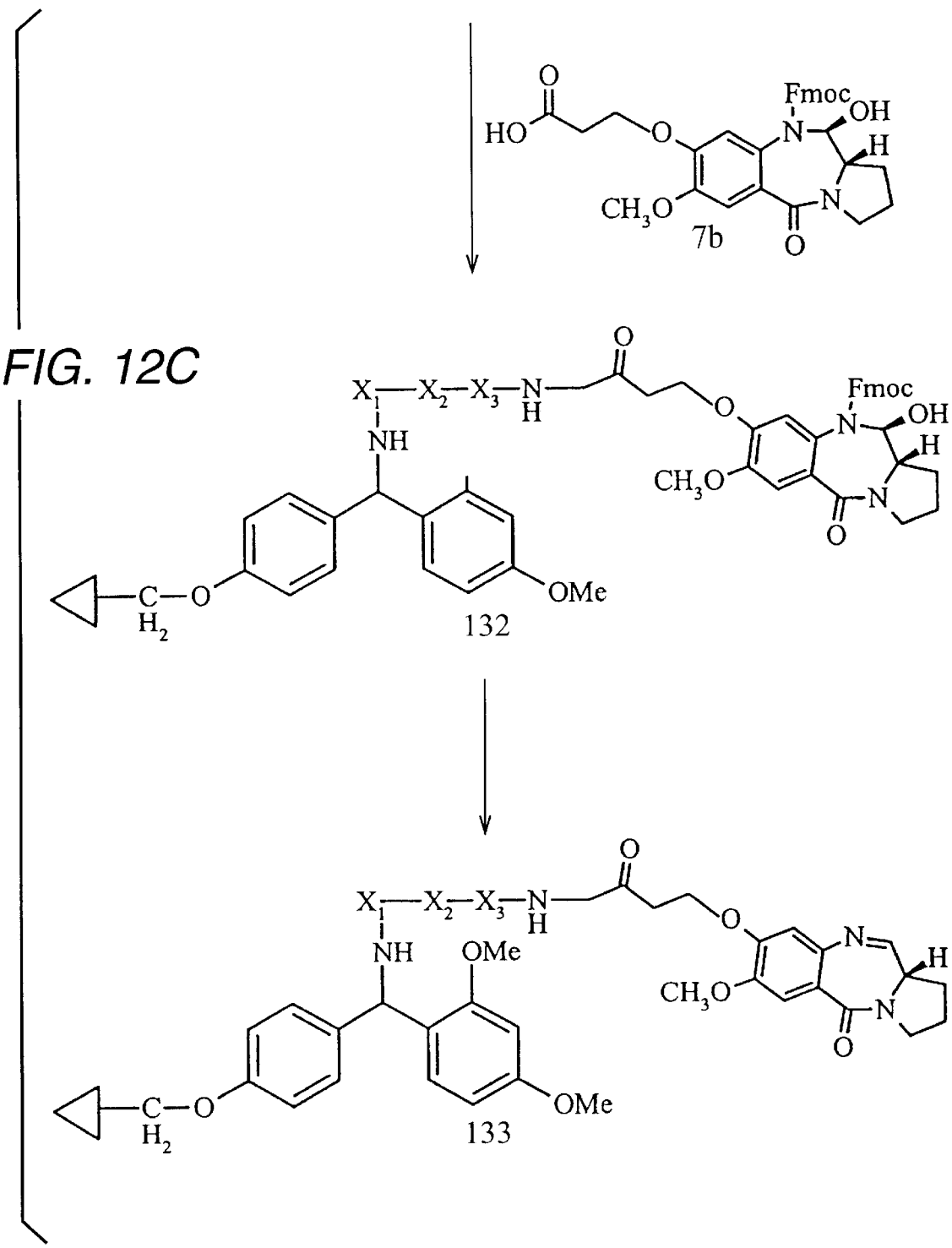
Figure 13A:
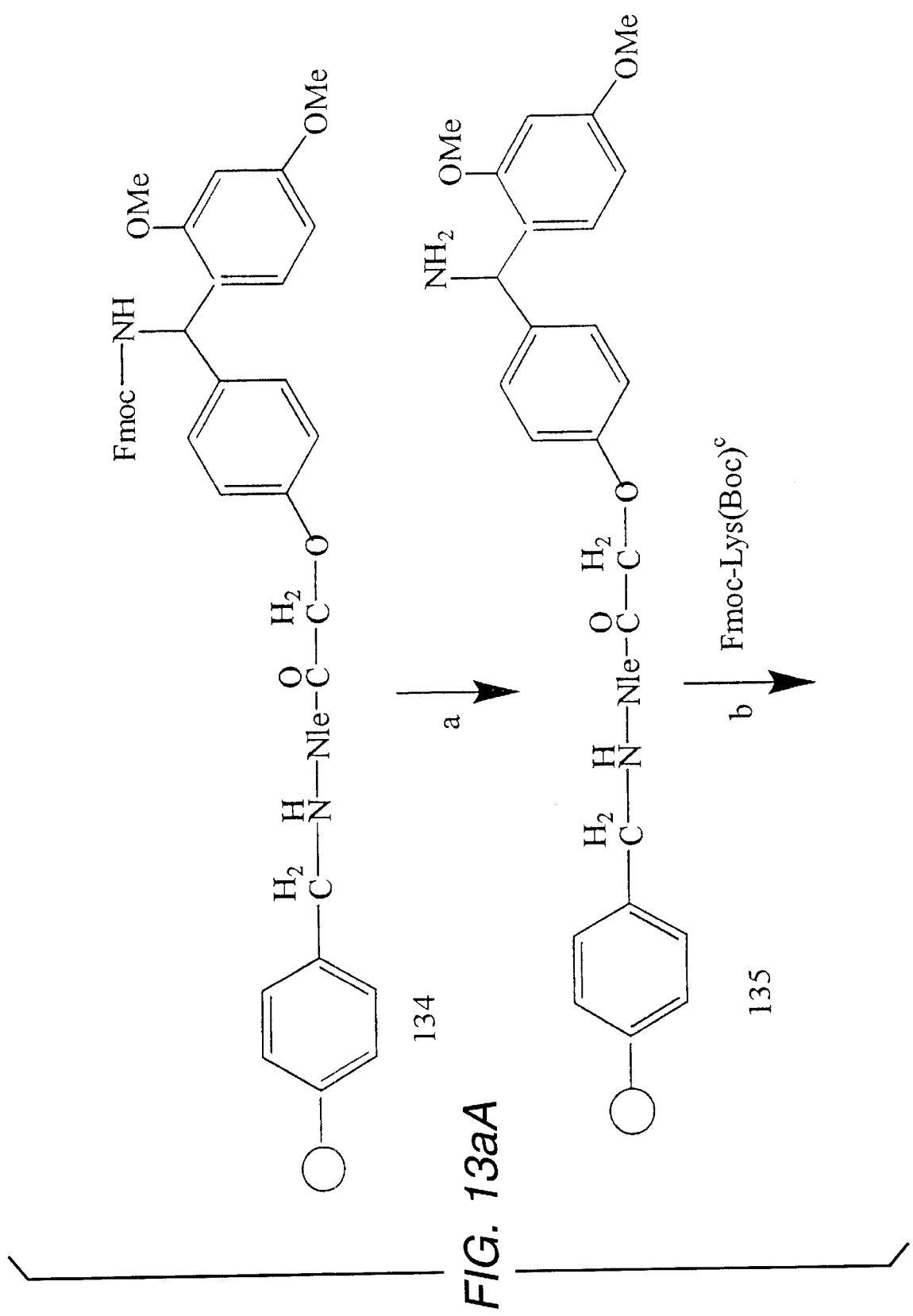
Figure 13A:
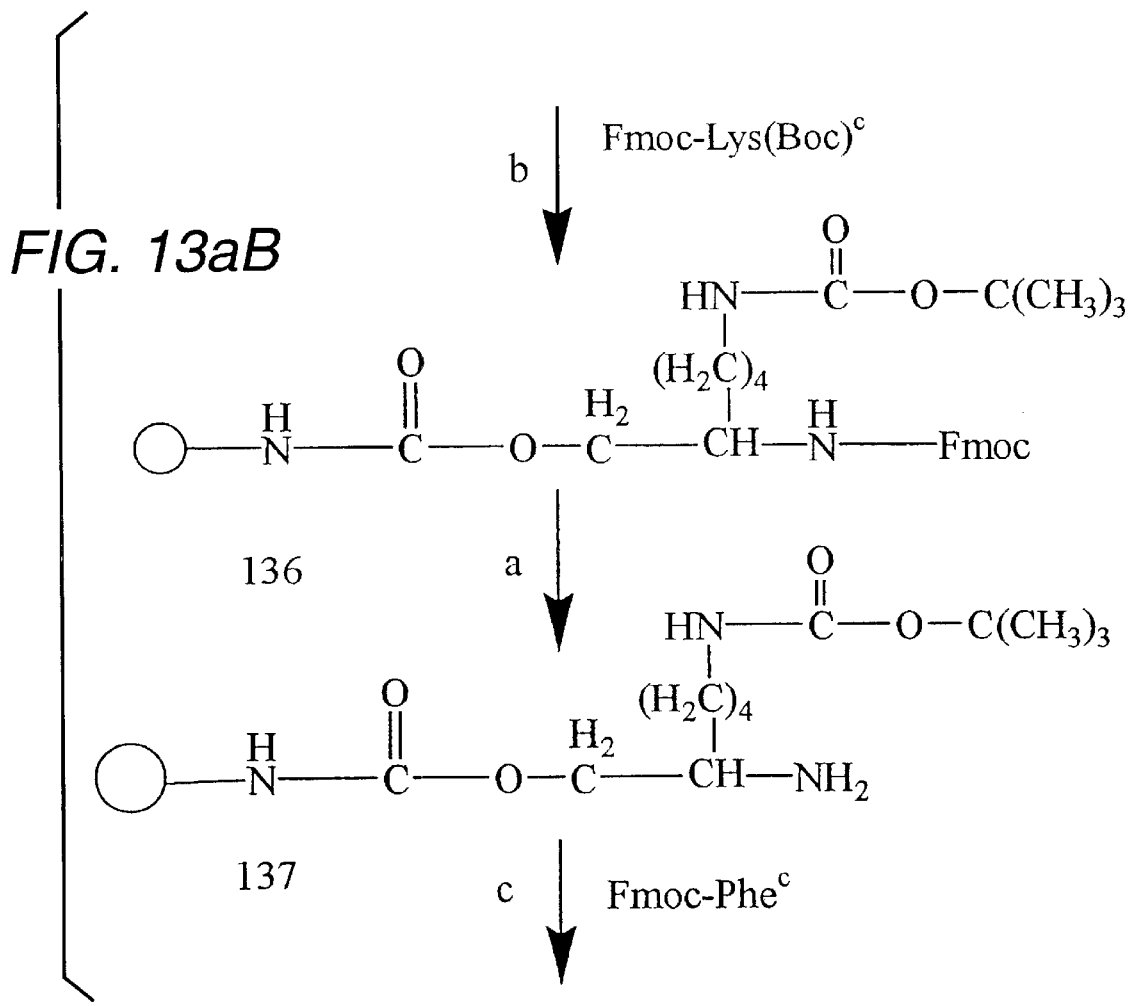
Figure 13A:
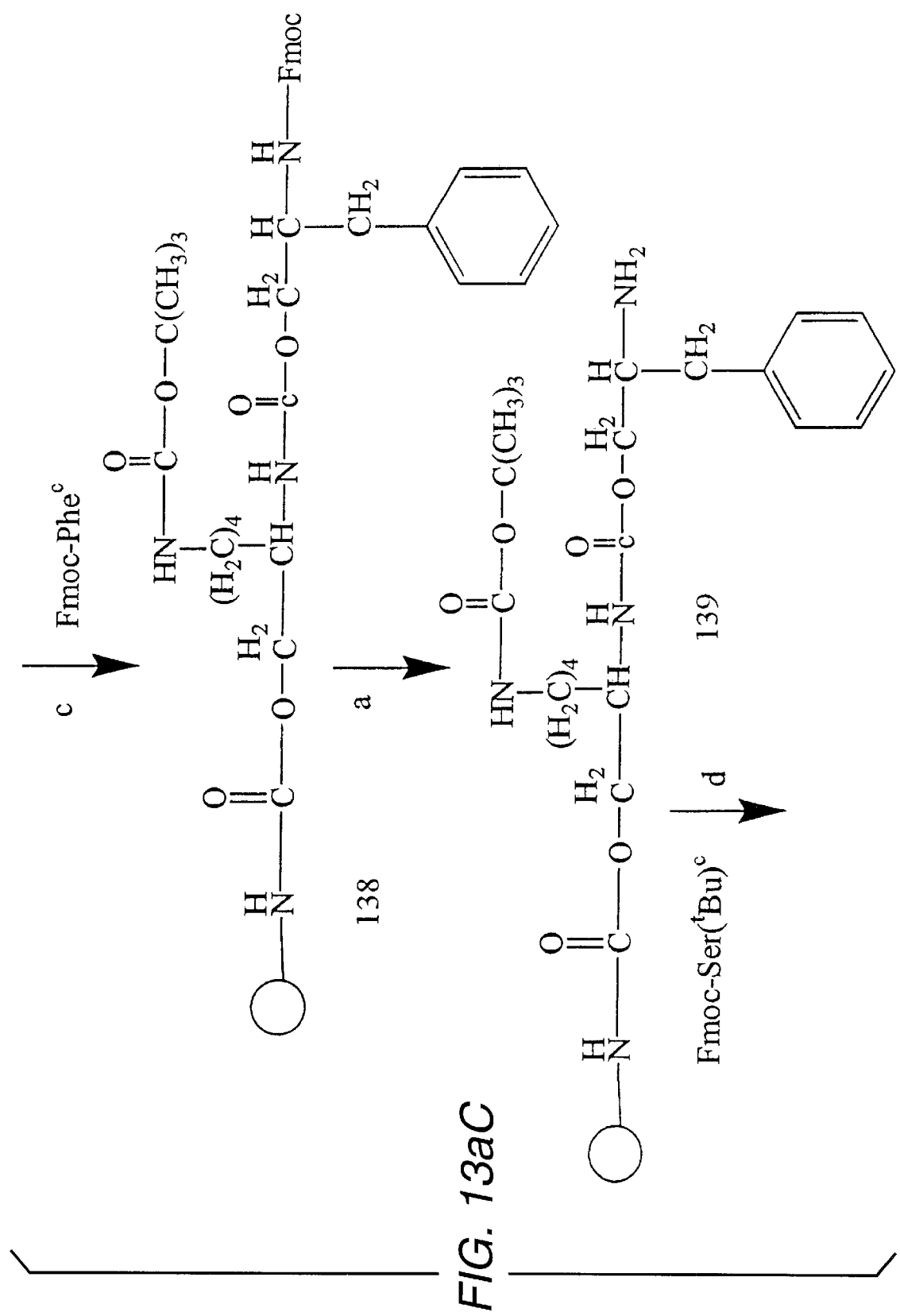
Figure 13B:
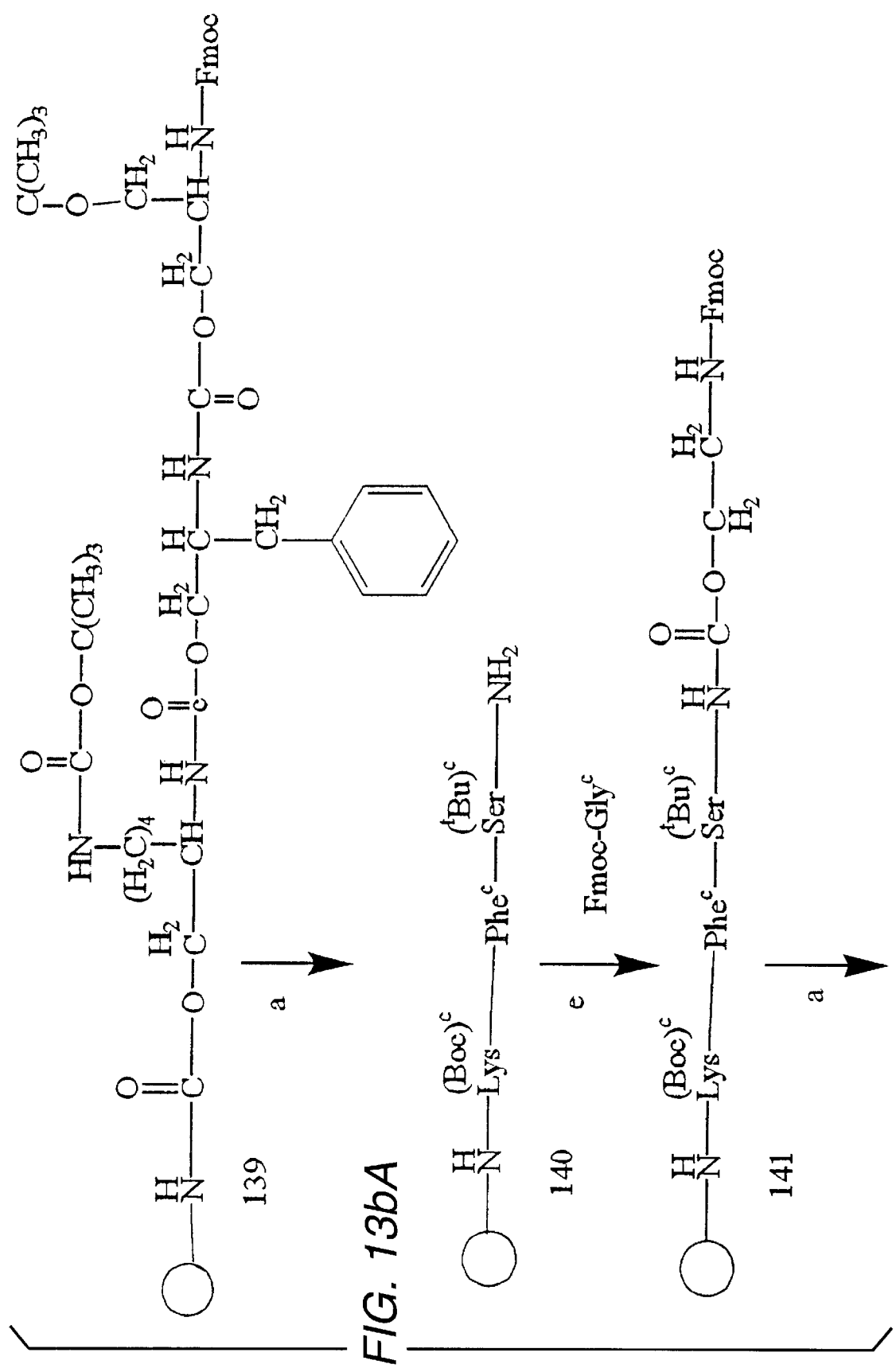
Figure 13B:
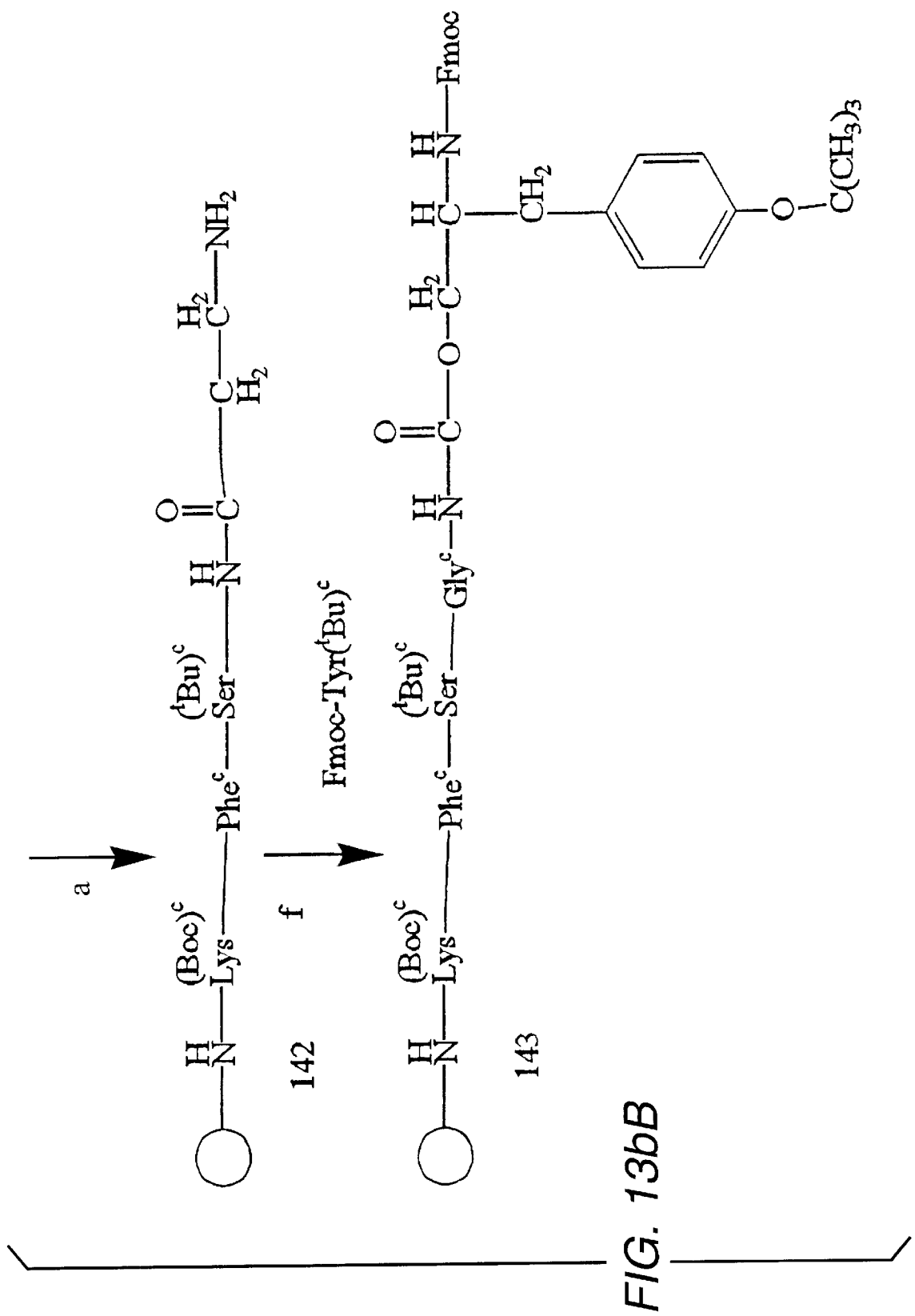
Figure 13C:
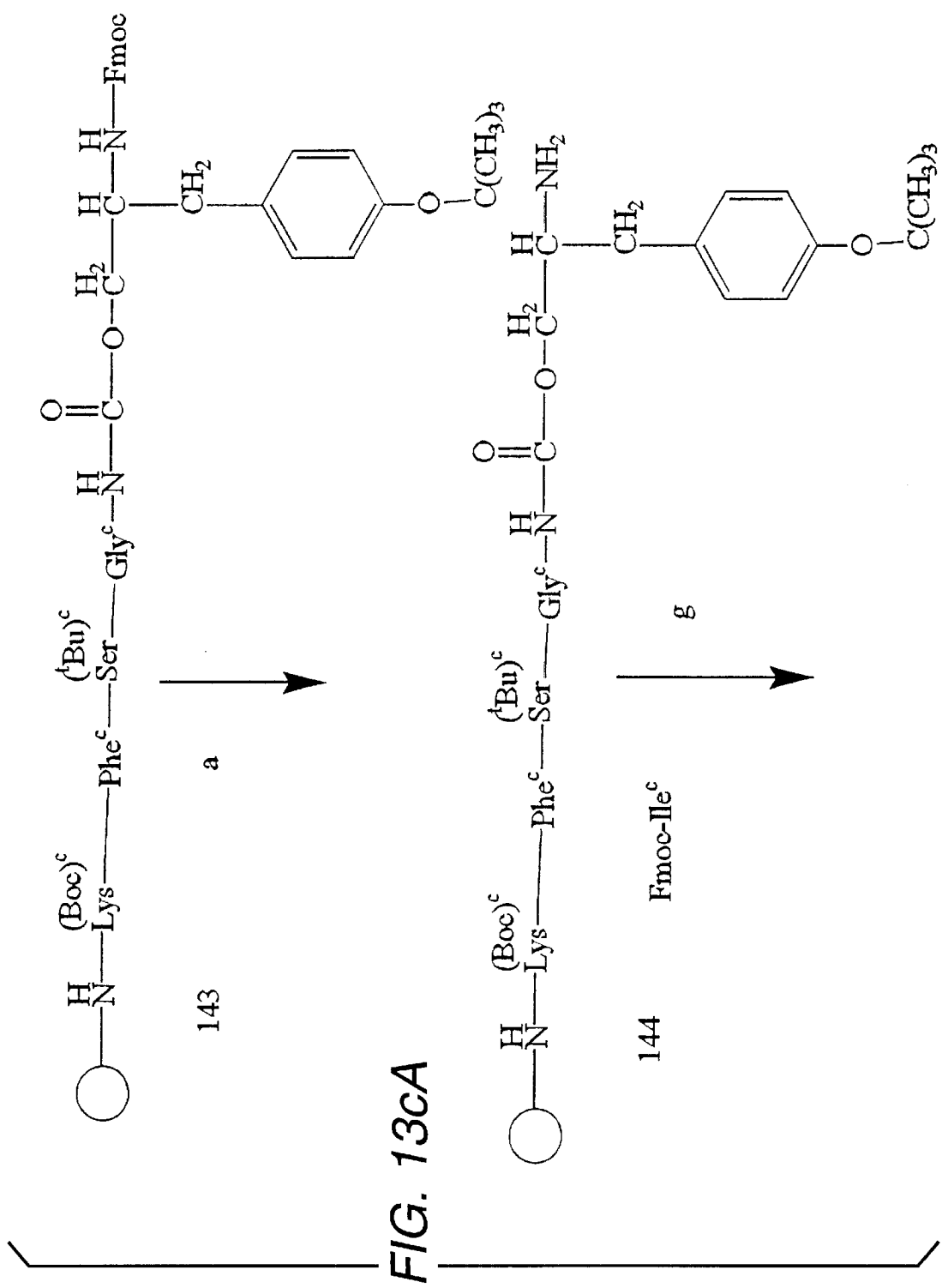
Figure 13C:
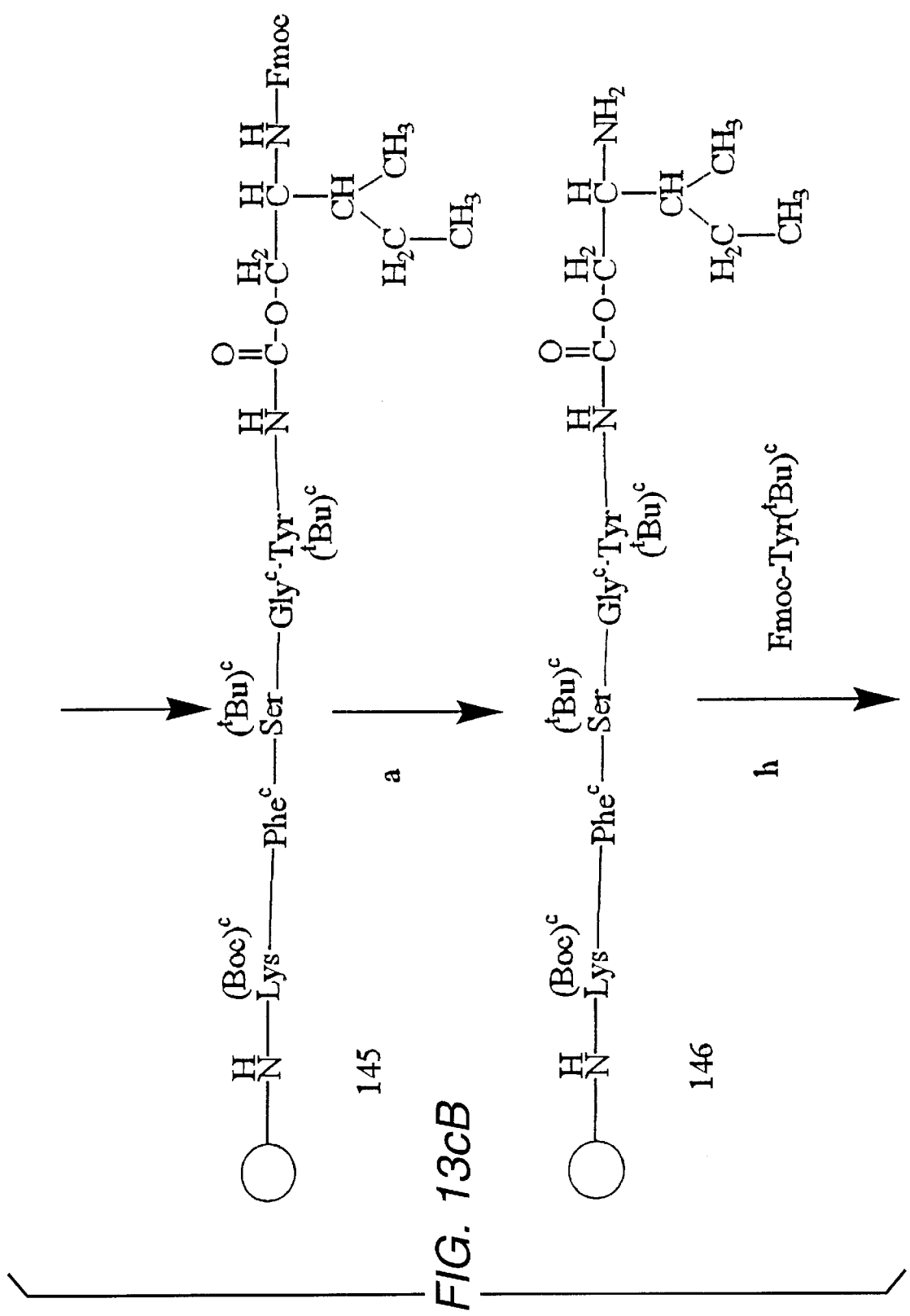
Figure 13D:
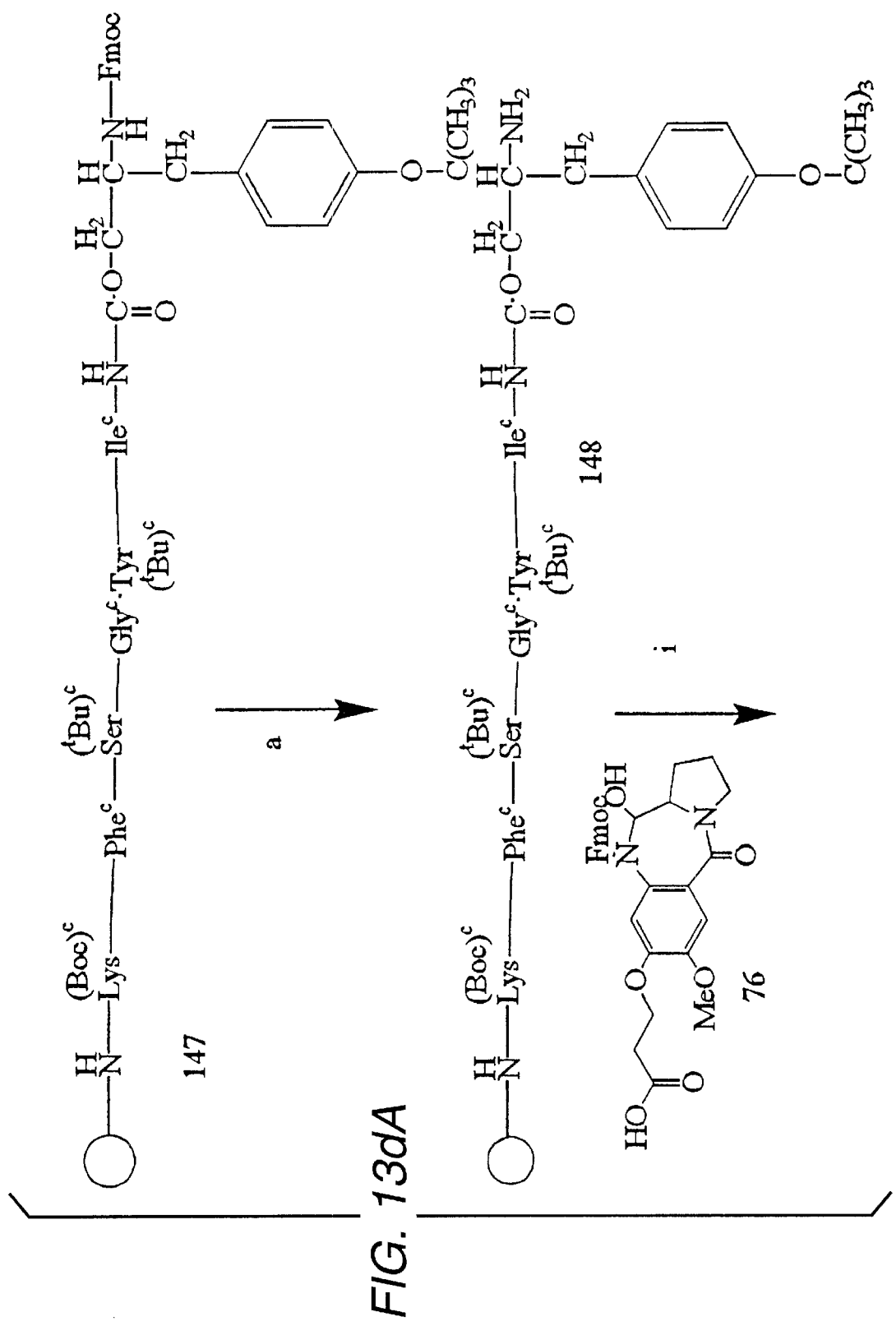
Figure 13D:
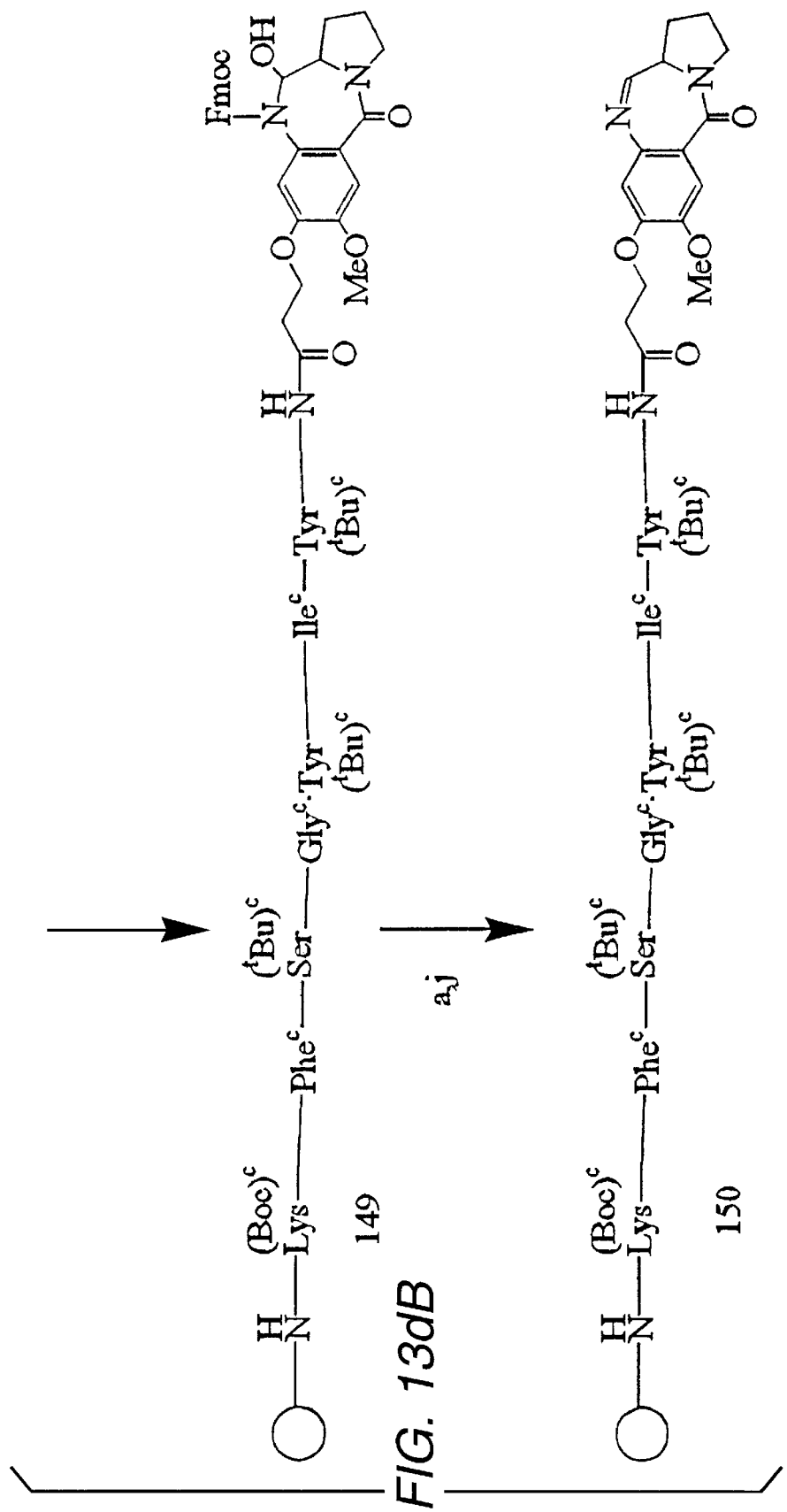

Synthesis of a 175 Membered Library Utilising Synphase Crowns as the Solid Support (FIG. 12)

Preparation of the Crowns—N-Fmoc Deprotection

175 Rink amide-handle O-series polystyrene crowns 124 were placed into two multipin blocks, arranged in a 8×12 format.

The crowns were immersed in the piperidine solution (20% in DMF, 50 mL) for 20 minutes, with shaking. After rinsing with DMF (3×50 mL) and DCM (3×50 mL), the crowns were immersed in a solution of bromophenol blue (0.01% w/v bromophenol blue in methanol, 50 mL), until equal staining was achieved and the deprotected crowns 125 were then rinsed in MeOH and dried.

| Coupling the first amino acid residue | | | |
|---|---|---|---|
| Amino Acid | M. Wt. | Reagent Mass (mg) | Solvent Vol. (mL) |
| Fmoc-Arg(Pbf)-OH | 648.8 | 545.0 | 8.40 |
| Fmoc-Gly-OH | 297.3 | 254.8 | 8.40 |
| Fmoc-Lys(Boc)-OH | 468.5 | 393.5 | 8.40 |
| Fmoc-Met-OH | 371.5 | 312.1 | 8.40 |
| Fmoc-Val-OH | 339.4 | 285.1 | 8.40 |

| Coupling Reagent (used for all couplings in example 16) | | | |
|---|---|---|---|
| Reagent | M. Wt. | Reagent Mass | Solvent Vol |
| DIC | 126.2 | 0.530 g | 42.0 |
| HOBt | 135.1 | 567.4 mg | 42.0 |

Solutions of the amino acids and coupling reagents detailed above in NMP (200 mL) were dispensed into the deep-well microtiter plates. Couplings were monitored by the loss of the bromophenol blue staining on the crowns and were generally allowed to proceed overnight. The crowns 126 were then washed in DMF (3×50 mL), DCM (3×50 mL) and allowed to air-dry.

N-Fmoc Deprotection

The crowns 126 were immersed in piperidine solution (20% in DMF, 50 mL) for 20 minutes, with shaking. After rinsing with DMF (3×50 mL) and DCM (3×50 mL), the deprotected crowns 127 were immersed in a solution of bromophenol blue (0.01% w/v bromophenol blue in methanol, 50 mL), until equal staining was achieved and then rinsed in MeOH and dried.

| Coupling the second amino acid residue | | | |
|---|---|---|---|
| Amino Acid | M. Wt. | Reagent Mass (mg) | Solvent Vol. (mL) |
| Fmoc-Arg(Pbf)-OH | 648.8 | 389.3 | 6.0 |
| Fmoc-Gly-OH | 297.3 | 182.0 | 6.0 |
| Fmoc-Lys(Boc)-OH | 468.5 | 281.1 | 6.0 |
| Fmoc-Gln-OH | 368.4 | 221.0 | 6.0 |
| Fmoc-His(Trt)-OH | 619.7 | 379.4 | 6.0 |
| Fmoc-Leu-OH | 353.4 | 212.0 | 6.0 |
| Fmoc-Tyr(2-ClTrt)-OH | 680.2 | 408.1 | 6.0 |

Solutions of the amino acids and coupling reagents detailed above (in NMP, 200 mL) were dispensed into the deep-well microtiter plates. Couplings were monitored by the loss of the bromophenol blue staining on the crowns 127 and were generally allowed to proceed overnight. The coupled crowns 128 were then washed in DMF (3×50 mL), DCM (3×50 mL) and were allowed to air dry. N-Fmoc deprotection was carried as above, to give crowns 129.

| Coupling the third amino acid residue | | | |
|---|---|---|---|
| Amino Acid | M. Wt. | Reagent Mass (mg) | Solvent Vol. (mL) |
| Fmoc-Arg(Pbf)-OH | 648.8 | 545.0 | 8.40 |
| Fmoc-Lys(Boc)-OH | 468.5 | 393.5 | 8.40 |
| Fmoc-Gly-OH | 297.3 | 254.8 | 8.40 |
| Fmoc-Gln-OH | 368.4 | 309.5 | 8.40 |
| Fmoc-Trp-OH | 426.5 | 358.3 | 8.40 |

Solutions of the amino acids and coupling reagents detailed above (in NMP, 200 mL) were dispensed into the deep-well microtiter plates. Couplings were monitored by the loss of the bromophenol blue staining on the crowns and were generally allowed to proceed overnight. The coupled crowns 130 were then washed in DMF (3×50 mL), DCM (3×50 mL) and allowed to air dry overnight.

N-Fmoc deprotection was carried out as above to give crowns 131.

| Coupling the Fmoc-PBD | | | |
|---|---|---|---|
| Reagent | M. Wt. | Reagent Mass (g) | Solvent Vol. (mL) |
| Fmoc-PBD 7b | 558 | 2.346 | 42.0 |

Fmoc-PBD 7b (2.346 g in 42 ml NHP) and the coupling reagents detailed above (in NMP, 200 mL) were dispensed into the deep-well microtiter plates. Couplings were monitored by the loss of the bromophenol blue staining on the crowns 132 and repeated until complete colour loss had occurred. The crowns were then washed in DMF (3×50 mL), DCM (3×50 mL) and allowed to air dry.

N-Fmoc Deprotection

The crowns 132 were immersed in piperidine solution (20% in DMF, 50 mL) for 20 minutes, with shaking. After rinsing with DMF (3×50 mL) and DCM (3×50 mL), the crowns 133 were allowed to air dry.

EXAMPLE 17

Use of Rink-amide Resin as Solid Support

A. Attachment of Fmoc-PBD (7b) to Rink-amide Resin

Preparation of the resin—N-Fmoc Deprotection

Fmoc-rink amide resin 200(50 mg, loading 0.63 mmol/g) was

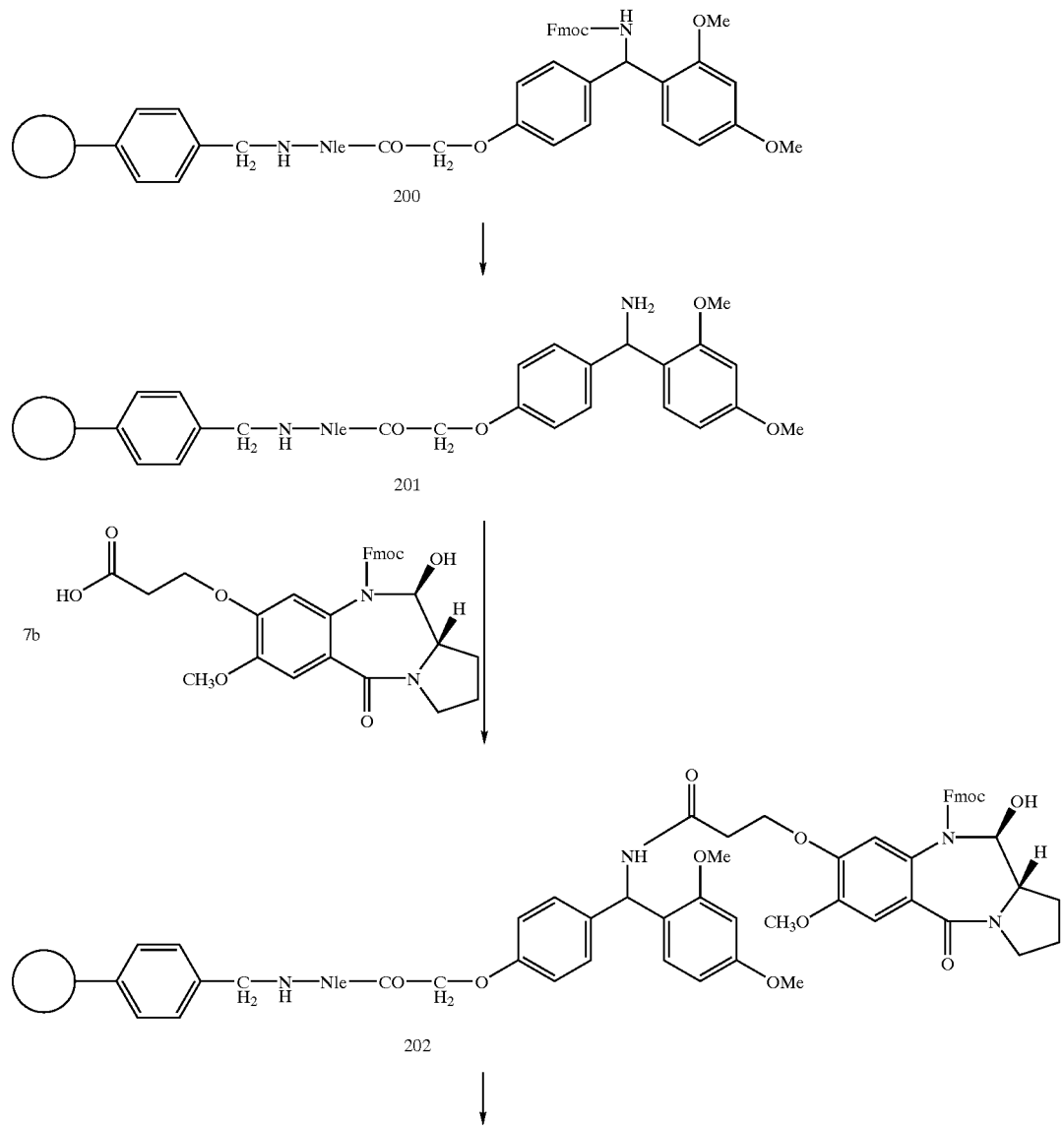

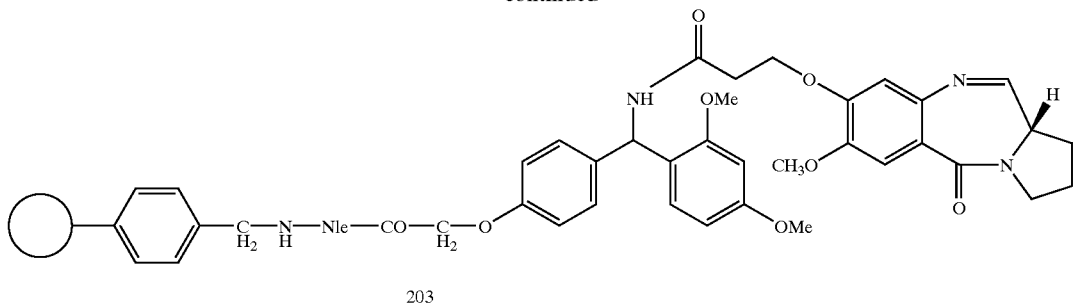

203 suspended in DCM:DMF (1:1, 1 mL) and shaken for 2 minutes. The resulting solution was removed under vacuum and the resin resuspended in DMF (1 mL) and shaken for 5 minutes.

The DMF was drained from the resin and the Fmoc-group was removed by treatment with piperidine solution (20% in DMF, 1 mL) for 20 minutes. Excess piperidine solution was removed by suction and the deprotected resin 201 was washed with DMF and DCM and allowed to dry.

Coupling of the Fmoc-PBD

A solution of Fmoc-PBD propanoic acid 7b (70.3 mg, $1.26 \times 10^{-4}$ mol) diisopropylcarbodiimide (20.1 mL $1.26 \times 10^{-4}$ mol) and HOBt (17.02 mg, $1.26 \times 10^{-4}$ mol) in DMF (0.5 mL) was added to the resin 201, and the resulting slurry shaken overnight.

The solution was drained and the coupled resin 202 washed with DMF and DCM. The resin was resuspended in DMF/DCM (DCM) (1 mL) and split into two portions. The solutions were removed from both tubes and the resin in the first tube was washed with DCM, methanol and dried under vacuum overnight.

N-Fmoc Deprotection

The resin 202 in the second tube was suspended in piperidine solution (20% in DMF, 0.5 mL) and shaken for 20 minutes. Excess piperidine solution was drained and the deprotected resin 203 washed with DMF, DCM and methanol, and dried under vacuum overnight.

B. Attachment of Nvoc-PBD (7a)

Preparation of the Resin—N-Fmoc Deprotection

Coupling of the Nvoc-PBD (7a)

The general method for modification and attachment of the Fmoc-PBD 7b was employed. The Nvoc-PBD 7a was coupled as a 0.25M solution in DMF.

EXAMPLE 18

Attachment of Fmoc-PBD (7b) to Aminoethyl Photolinker AM Resin (210)

Preparation of the Resin—N-Fmoc Deprotection

Aminoethyl photolinker AM resin 210(50 mg, 0.21 mmol/g) was placed into two Alltech tubes. The resin was suspended in NMP (2 mL) and swelled for 2 hours.

After draining excess solvent, the deprotected resin 211 was suspended in piperidine solution (20% in DMF, 0.5 mL) and shaken for 20 minutes. Excess solvent was drained and the resin washed with DMF, DCM and NMP.

Coupling Protocol of Fmoc-PBD (7b)

A solution of Fmoc-PBD propanoic acid 7b(32.22 mg, $5.78 \times 10^{-5}$

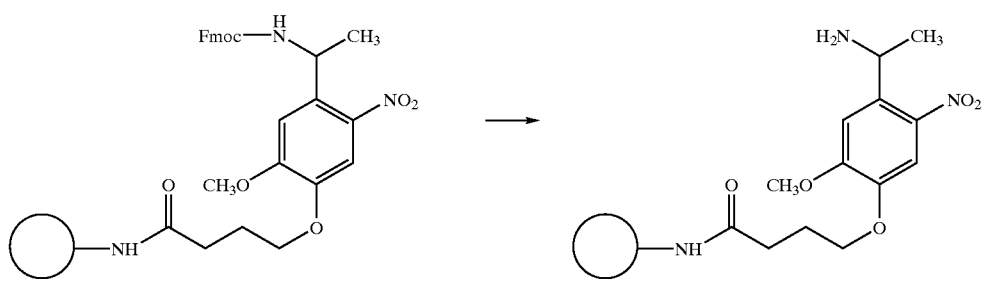

210 211

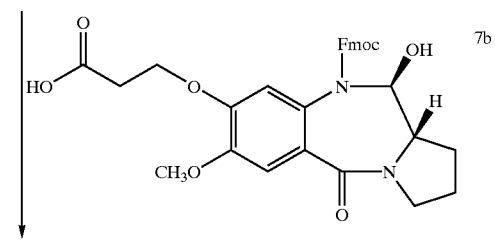

7b

-continued

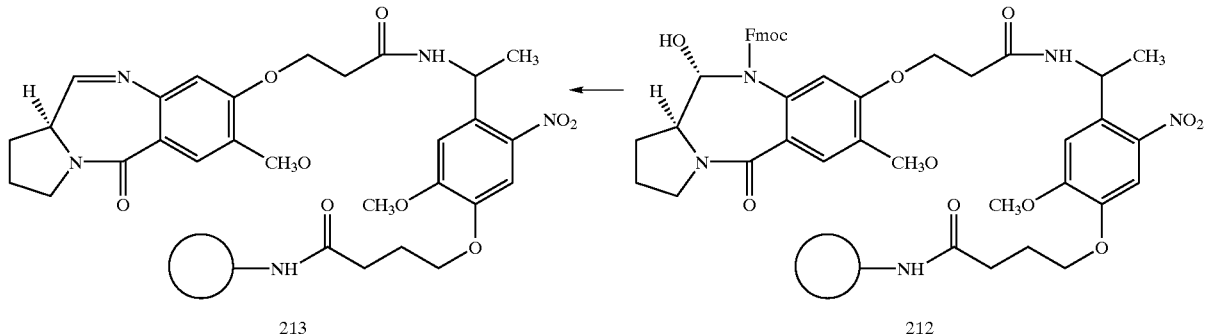

213    212 mol, 5.5 equivalents), PyBop (11.4 mg, $2.2 \times 10^{-5}$ mol) and DIPEA (0.05 mL) in NMP (0.5 mL) was added to the resin 211 which was shaken for 1 hour.

After draining, the coupled resin 212 was washed with DCM (5×1 mL), methanol (5×1 mL) and NMP (5×1 mL). The coupling reaction was repeated 3 times. The resin in the first tube was then washed with DCM (3×1 mL), methanol (3×1 mL) and water (3×1 mL) and dried in vacuo overnight.

N-Fmoc Deprotection

The Fmoc-PBD resin 212 in the second Alltech tube was re-suspended in piperidine solution (20% in DMF, 1 mL) and shaken for 20 minutes. After draining, the deprotected resin 213 was washed with NMP (3×1 mL), DCM (3×1 mL), methanol (3×1 mL) and finally water (3×1 mL) and dried in vacuo overnight.

EXAMPLE 19

Tentagel-Amino Resin

A. Attachment of Fmoc-PBD (7b) to Novasyn Tentagel Amino Resin (220)

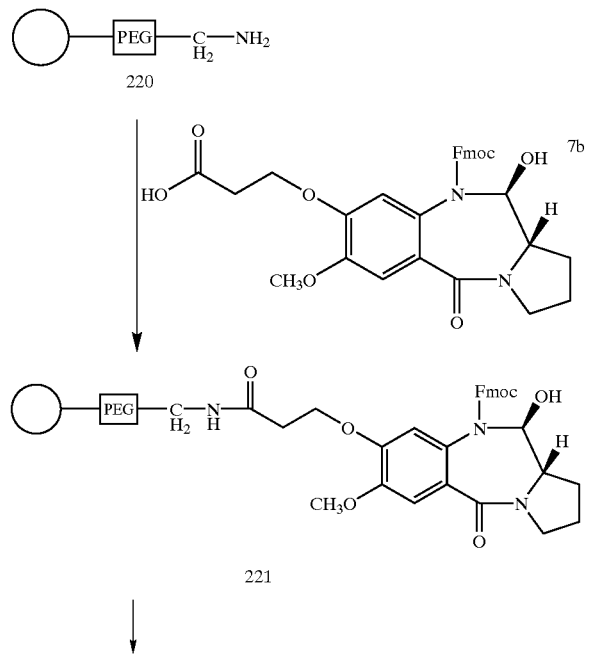

-continued

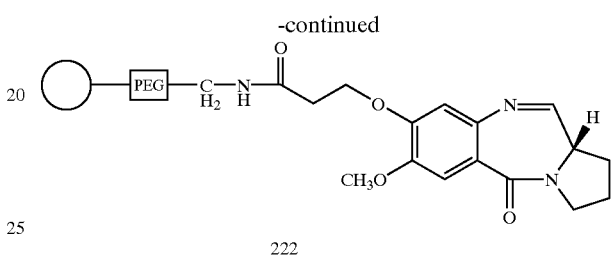

222

Preparation of the Resin

Novasyn Tentagel amino resin 220 (50 mg, loading 0.28 mmol/g), was placed into two Alltech tubes and suspended in DCM:DMF (1:1, 1 mL) and shaken for 2 minutes. Excess solvent was removed by suction and the resin resuspended in DMF (1 mL), shaken for 5 minutes and then drained.

Coupling of FMOC-PBD (7b)

A solution of Fmoc-PBD propanoic acid 7b (23.44 mg, $4.2 \times 10^{-5}$ mol, 3×excess), TBTU (13.4 mg, $4.2 \times 10^{-5}$ mol) and DIPEA (7.3 mL, $4.2 \times 10^{-5}$ mol) in DMF (500 mL) was added to the resin 220 and the resulting slurry shaken overnight.

The solution was drained and the resin washed with DMF and DCM. The coupling was repeated a second time and the coupled resin 221 washed as before. The resin in the first tube was washed further with methanol and dried in vacuo, overnight.

Fmoc Deprotection

The resin 221 in the second tube was suspended in piperidine solution (20% in DMF, 0.5 mL) and shaken for 20 minutes. This solution was drained and the deprotected resin 222 washed with DMF, DCM and methanol, and dried under vacuum overnight.

B. Attachment of Nvoc-PBD (7a) to Tentagel Resin

Coupling of the Nvoc-PBD (7a)

The general method for modification and attachment of the Fmoc-PBD 7b was employed. The Nvoc-PBD 7a was coupled as a 0.085M solution.

Deprotection of the Nvoc-protecting Group

The resin was incubated for several hours in a solution of DMSO containing 1% ethanolamine at a wavelength of 365 nm. After washing with DMF (3×50 mL) for 3 minutes and MeOH (2×50 mL) for 3 minutes, the membrane was allowed to dry.

EXAMPLE 20

Synthesis of an PBD-Oligocarbamate Sequence
(FIG. 13)

Preparation of the Resin (N-Fmoc Deprotection)

Fmoc-Rink amide resin 134 (53.43 mg, loading 0.63 mmol/g, $3.37 \times 10^{-5}$ mol) was suspended in DCM:DMF (1:1, 1 mL) and shaken for 2 minutes. Excess solvent was removed by suction, the resin resuspended in DMF (1 mL) and shaken for 5 minutes.

Excess DMF was removed by suction and the Fmoc-group was removed by treating with piperidine solution (20% in DMF, 1 mL) for 20 minutes. The resin 135 was then washed with DMF and DCM.

Coupling Protocol

| | Fmoc aminoalkyl carbonate | M. Wt | No of moles 4× excess | Mass required/ mg |
|---|---|---|---|---|
| 1 | Fmoc-Lys(Boc)$^c$ | 619 | $1.35 \times 10^{-4}$ | 83.6 |
| 2 | Fmoc-Phe$^c$ | 539 | $1.35 \times 10^{-4}$ | 72.8 |
| 3 | Fmoc-Ser($^t$Bu)$^c$ | 535 | $1.35 \times 10^{-4}$ | 72.2 |
| 4 | Fmoc-Gly$^c$ | 448 | $1.35 \times 10^{-4}$ | 60.5 |
| 5 | Fmoc-Tyr($^t$Bu)$^c$ | 610 | $1.35 \times 10^{-4}$ | 82.4 |
| 6 | Fmoc-Ile$^c$ | 504 | $1.35 \times 10^{-4}$ | 68.0 |
| 7 | Fmoc-Tyr($^t$Bu)$^c$ | 610 | $1.35 \times 10^{-4}$ | 82.4 |

A solution of the required 4-nitrophenyl Fmoc-aminoalkyl carbonate, HOBt (36.3 mg) and DIPEA (11 ml), in NMP (200 ml) was added to the free amino resin 135 and allowed to couple for 4 hours. After draining, the resin 136 was washed with NMP and DCM and dried under vacuum.

Deprotection and coupling cycles were repeated until the aminolkyl sequence was complete (137–148).

Fmoc-protected PBD (7b) (75.3 mg), HOBt (36.3 mg) and diisopropylcarbodiimide (21.5 ml) were dissolved in NMP (300 ml) and added to the free amino resin 148. The slurry was shaken for 24 hours, drained and washed with NMP, DCM and dried overnight, under vacuum to give PBD resin 149. This was deprotected as above to give unprotected PBD resin 150.

Cleavage from the Resin

The resins (149 and 150) were treated with a solution of 95% TFA:5% water:2.5% triisopropylsilane (1 mL) at RT for 2 hours. The resins were removed by filtration, washed with a small amount of TFA and DCM. The solvent was removed in vacuo and the residue dissolved in acetonitrile:water 1:2 and lyophilised twice.

EXAMPLE 21

Figure 14A:
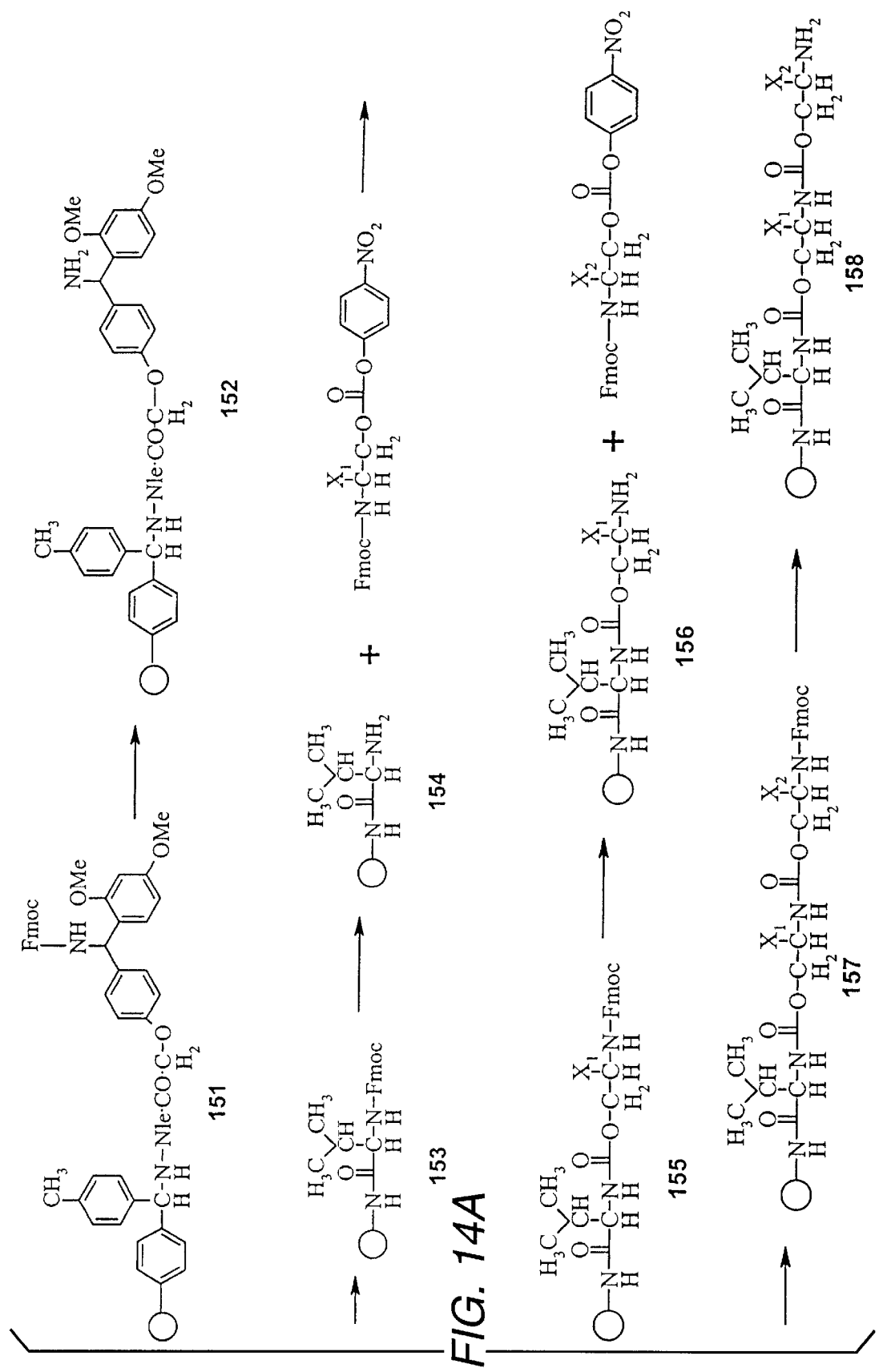
Figure 14B:
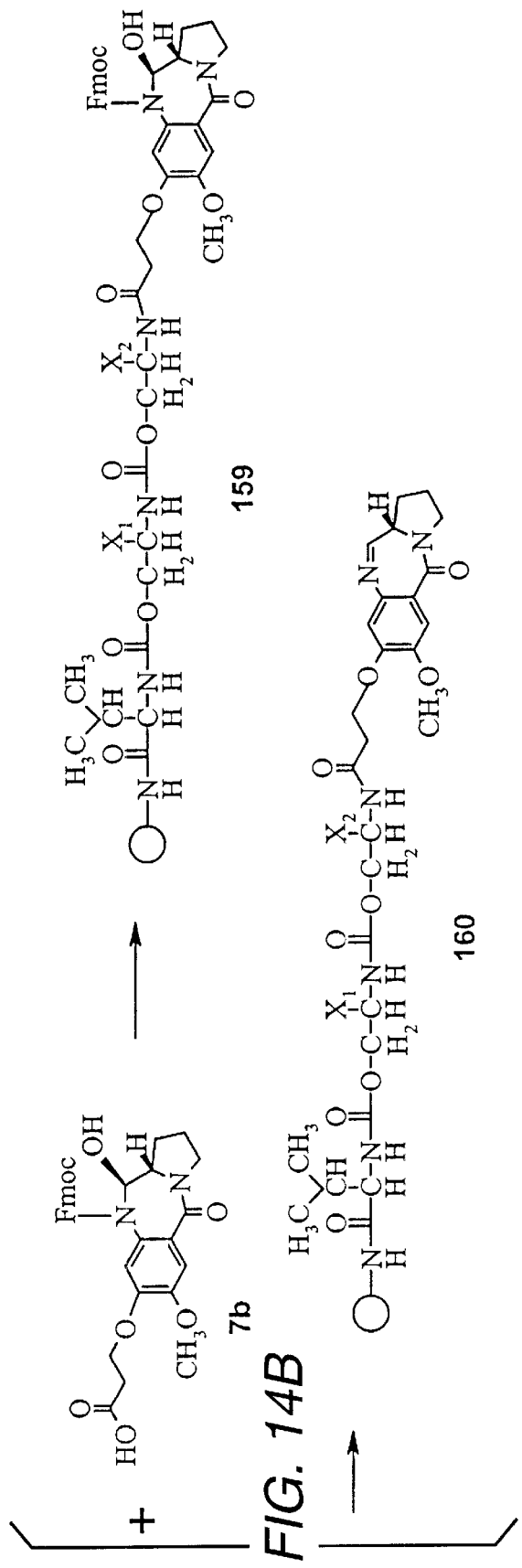

Synthesis of a 289 Member Library Using 4-nitrophenyl N-Fmoc Aminoalkyl Carbonates
(FIG. 14)

Formation of N-(9-fluorenylmethoxycarbonyl) amino alcohols. (General method of Cho et al: *Synthesis and Screening of Linear and Cyclic Oligocarbamate Libraries. Discovery of High Affinity Ligands for GPIIb/IIIa, J. Am. Chem. Soc.*, (1998), 120, 7706–7718., C. Y. Cho, R. S. Youngquist, S. J. Paikoff, M. H. Beresini, A. R. Herbert. L. T. Berleau, C. W. Liu, D. E. Wemmer, T. Keouah and P. G. Schultz.)

The appropriate N-Fmoc-protected amino acid (10 mmol) and dimethoxyethane were stirred under nitrogen, in an ice/salt bath. N-methylmorpholine (1.11 mL, 10 mmol) and isobutylchloroformate (1.36 mL, 10 mmol) was added to the solution.

After stirring for 1 min, under nitrogen, the solid was removed by filtration and sodium borohydride (570 mg, 15 mmol) in water (20 mL), was added to the filtrate. Additional water (150 mL) was added after 20 minutes, and the solution allowed to stir for 1 hour at room temp.

The precipitated product was filtered and washed with a small amount of water followed by hexane. The solid was redissolved in ethyl acetate, dried using $MgSO_4$ and the solvent removed in vacuo.

For those amino alcohol derivatives that did not precipitate from solution, the solution was extracted with ethyl acetate (5×300 mL). The organic extract was dried, over $MgSO_4$ and the solvent removed in vacuo.

Fmoc-amino alcohols were used without further purification—the data for the amino alcohols are shown in Appendix 1

Formation of 4-nitrophenyl N-(9-fluorenylmethoxycarbonyl)-aminoalkyl Carbonates (General Method of Cho et al.)

To the appropriate N-Fmoc-amino alcohol (10 mmol) was added pyridine (11 mmol) and DCM (50 mL). A solution of 4-nitrophenyl chloroformate (11 mmol) in DCM (10 mL) was added dropwise to the reaction mixture. The mixture was stirred for at least 24 hours. The mixture was diluted with DCM (100 mL) and washed with 1.0 M sodium bisulfate (3×75 mL) and 1.0 M sodium bicarbonate (10×100 mL). The organic layer was dried, using $MgSO_4$ and the solvent removed in vacuo.

The crude product was purified using silica gel chromatography (9:1 DCM:hexane DCM). The data for the amino alkyl nitrophenyl carbonate is shown in Appendix 2.

Library Synthesis

Preparation of the Resin

Rink amide MBHA resin 151 (8.67 g, loading 0.54 mMol/g) was suspended in a solution of DCM/DMF (3:1) and distributed between 289 Irori MicroKan reactors containing RF tags.

The Kans were immersed in a solution of DCM/DMF (1:1, 300 mL) and shaken vigorously for 1 min. The solvent was removed under vacuum and the Kans were re-immersed in DMF and shaken vigorously for 10 minutes.

The DMF was drained and the Fmoc-group was removed by adding piperidine solution (20% in DMF, 300 mL) to the Kans followed by shaking for 5 minutes and draining. Additional piperidine solution was added (20% in DMF) and the Kans were shaken for 1 hour. The Kans with deprotected resin 152 were drained and washed with DMF (6×300 mL) and DCM (3×300 mL).

Coupling of the First 4-nitrophenyl Fluorenylmethoxy Aminoalkyl Carbonate

A solution of Fmoc-Valine$^c$ (6.88 g, $4.86 \times 10^{-5}$ mol, 3×excess), HOBt (3.795 g, $9.72 \times 10^{-5}$ mol) and DIPEA (1.22 mL, $2.43 \times 10^{-5}$ mol) in NMP (300 mL) was added to the Kans and allowed to couple for 4 hours.

After draining the Kans with coupled resin 153 were washed with NMP (3×300 mL) and DCM (3×300 mL).

Fmoc-deprotection

The Fmoc-protecting group was removed by adding piperidine solution to the Kans (20% in DMF; 300 mL) followed by shaking for 1 hour. The Kans with deprotected resin 154 were drained and washed with DMF (3×300 mL) and DCM (3×300 mL).

Coupling of the second 4-nitrophenyl fluorenylmethoxy aminoalkyl carbonate

| Fmoc-Amino alkyl nitrophenyl carbonate | Mass (mg) |
| --- | --- |
| Ala | 382 |
| Asn | 417 |
| Asp(O$^t$Bu) | 467 |
| Arg(Pbf) | 673 |
| Gln | 428 |
| Glu(O$^t$Bu) | 449 |
| Gly | 370 |
| Ile | 416 |
| Leu | 416 |
| Lys(Boc) | 511 |
| Met | 430 |
| Phe | 445 |
| Pro | 477 |
| Ser($^t$Bu) | 442 |
| Thr($^t$Bu) | 453 |
| Trp | 477 |
| Tyr($^t$Bu) | 504 |

The Kans with the resin 154 were sorted using their Rf tags into 17 flasks containing solutions of the appropriate 4-nitrophenyl Fmoc-amino alkyl carbonate ($8.262 \times 10^{-4}$ mol), HOBt (223 mg, $1.6524 \times 10^{-3}$ mol) and DIPEA (71.4 mL, $4.131 \times 10^{-4}$ mol) in NMP (15 mL). The Kans were agitated four 4 hours, drained and washed with NMP (3×100 mL) and DCM (3×100 mL), and then contained coupled resin 155).

N-Fmoc Deprotection

The 289 Kans with coupled resin 155 were pooled in one flask and the Fmoc-protecting group was removed by treatment with piperidine solution (20% in DMF, 300 mL) for 1 hour. The Kans with deprotected resin 156 were drained and washed with DMF (3×300 mL) and DCM (3×300 mL).

Coupling of the third 4-nitrophenyl fluorenylmethoxy aminoalkyl carbonate

| Fmoc-Amino alkyl nitrophenyl carbonate | Mass (mg) |
| --- | --- |
| Ala | 382 |
| Asn | 417 |
| Asp(O$^t$Bu) | 467 |
| Arg(Pbf) | 673 |
| Gln | 428 |
| Glu(O$^t$Bu) | 449 |
| Gly | 370 |
| Ile | 416 |
| Leu | 416 |
| Lys(Boc) | 511 |
| Met | 430 |
| Phe | 445 |
| Pro | 477 |
| Ser($^t$Bu) | 442 |
| Thr($^t$Bu) | 453 |
| Trp | 477 |
| Tyr($^t$Bu) | 504 |

The Kans with resin 156 were sorted via their Rf tags into 17 flasks containing solutions of the appropriate 4-nitrophenyl Fmoc-amino alkyl carbonate ($8.262 \times 10^{-4}$ mol), HOBt (223 mg, $1.6524 \times 10^{-3}$ mol) and DIPEA (71.4 ml, $4.131 \times 10^{-4}$ mol) in NMP (15 mL). The resin in the Kans was allowed to couple for 4 hours to from coupled resin 157. After draining, the Kans were washed with NMP (3'100 mL) and DCM (3×100 mL).

N-Fmoc Deprotection was carried out as above to give resin 158 in the Kans.

Coupling of the Fmoc-PBD (7b)

A solution of Fmoc-PBD (7b) (7.84 g, $1.40 \times 10^{-2}$ mol, 3×excess), HOBt (1.896 g, $1.40 \times 10^{-2}$ mol) and diisopropylcarbodiimide (2.18 mL, $1.40 \times 10^{-2}$ mol) in NMP (300 mL) was added to the 289 Kans with resin 158. The Kans were stirred vigorously for 24 hours and drained. The Kans which then contained coupled resin 159 were washed with NMP (3×300 mL) and DCM (3×300 mL).

N-Fmoc deprotection was carried out as before to give resin 160 in the Kans.

EXAMPLE 22

Figure 15A:
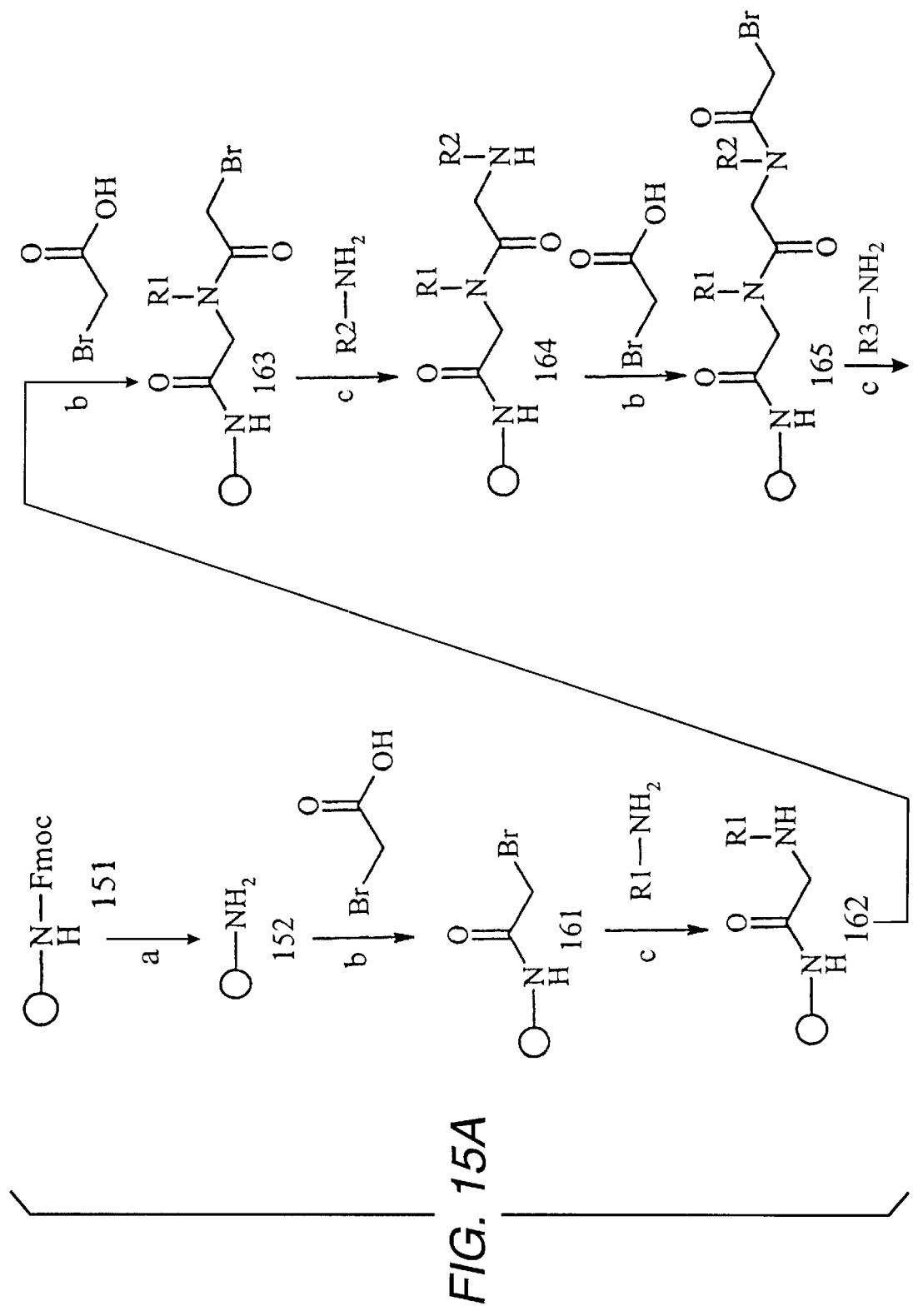
Figure 15B:
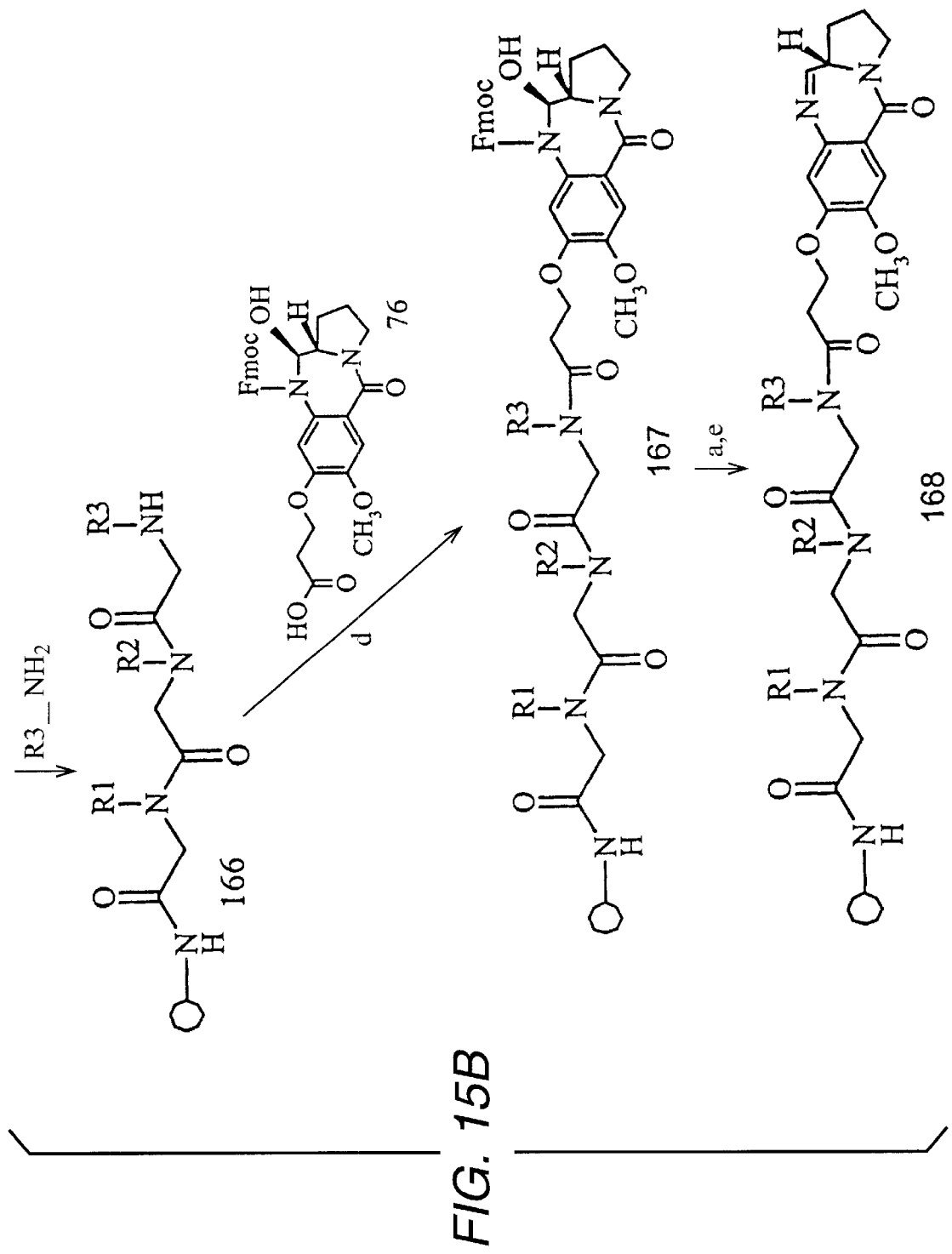

Synthesis of a 27 Member Library Using Peptoids (Irori Method) (FIG. 15)

Preparation of the Resin

Rink amide MBHA resin 151 (810 mg, loading 0.54 mMol/g) was suspended in a solution of DCM/DMF (3:1, 5.4 mL) and distributed between 27 Irori MicroKan reactors containing RF tags.

The Kans were immersed in a solution of DCM/DMF (1:1, 50 mL) and shaken vigorously for 1 min. This solution was removed under vacuum and the Kans were re-immersed in DMF and shaken vigorously for 10 minutes.

The DMF was drained and the Fmoc-group of resin 151 was removed by adding piperidine solution (20% in DMF, 50 mL) to the Kans. This was shaken for 5 minutes and drained. Further piperidine solution was added (20% in DMF, 50 mL) and the Kans shaken for 1 hour. The Kans with deprotected resin 152 were drained and washed with DMF (6×50 mL).

Acylation Step

Bromoacetic acid solution (0.6M in DMF, 60 mL) was added to the Kans with resin 152, followed by diisopropylcarbodiimide solution (3.2M in DMF, 14.1 mL). This was shaken for 2 hours at room temperature, drained and repeated. The Kans with bromoacetamide resin 161 were then washed with DMF (2×50 mL) and DMSO (1×50 mL).

Displacement Step

The 27 Kans were sorted via their RF tags into 3 flasks. The first set were suspended in aq. methylamine solution (40% w/v, 20 mL), the second set in piperonylamine solution (2M in DMSO, 20 mL) and the third set in 2-methoxyethylamine (2M in DMSO, 20 mL). These were shaken vigorously for 4 hours and then drained. The Kans with amino-coupled resin 162 were washed with DMSO (2×20 mL),and DMF (1×20 ml).

The acylation and displacement steps were repeated twice to give resin 166 (which is a library of 27 resins with all combinations of 3 values for $R_1$, $R_2$ and $R_3$)

Coupling of the Fmoc-PBD (7b)

The 27 Kans with the peptoid bearing resin 166 were re-combined and a solution of the Fmoc-PBD (7b) (976.3 mg, 1.75 mmol, 4×excess), HOBt (236.4 mg, 1.75 mmol) and diisopropylcarbodiimide (22.08 mg, 1.75 mmol) in DMF (20 mL) added. This was stirred vigorously for 24 hours and drained. The Kans with the Fmoc-PBD coupled resin 167 were washed with DMF (3×50 mL) and DCM (3×50 mL).

N-Fmoc Deprotection

The Fmoc-protecting group was removed from the PBD resin 167 by adding piperidine solution (20% in DMF, 50 mL) to the Kans. This was shaken for 5 minutes and drained. Further piperidine solution was added (20% in DMF, 50 mL) and the Kans shaken for 1 hour. The Kans with the deprotected resin 168 were drained and washed with DMF (3×50

Amines used in library

H₃C—NH₂    1

CH₃O—CH₂—CH₂—NH₂    2

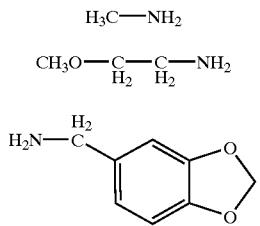    3

APPENDIX 1
Data for Amino Alcohols Incl Yield (%) &NMR

Ala:-74%
¹H NMR (270 MHz, d₆-acetone): δ7.88 (d, 2, J=7.1 Hz), 7.71 (d, 2, J=7.3 Hz), 7.31–7.42 (dt, 4), 7.09 (d, 1, J=8.1 Hz), 4.28 (m, 4), 3.54 (m, 1), 3.36 (m, 1), 3.26 (m, 1), 1.04 (d, 3, J=6.6 Hz).
¹³C NMR (67.8 MHz, d₆-acetone): δ155.5, 143.9 140.7 127.5, 127.0, 0.1, 120.0, 65.1 64.4, 48.4 46.7 17.3

Arg(Pbf):
¹H NMR (270 MHz, d₆-acetone): δ, 7.81 (d, 2, J=7.7 Hz), 7.66 (d, 2, J=7.3 Hz), 7.29–7.38 (dt, 4), 6.54 (s, br, 1), 4.31 (m, 2), 4.18 (t, 1, J=6.95 Hz), 4.06 (q, 2, J=6.95 Hz), 3.63 (m, 1), 3.53 (m, 2), 3.21 (m, 2), 2.94 (m, 2), 2.60 (s, 4), 2.51 (s, 3), 1.96 (s, 2), 1.38 (m, 10), 1.19 (t, 2, J=7 Hz), 0.89 (m,1).
¹³C NMR (67.8 MHz, d₆-acetone): δ, 158.9, 157.3, 145.1 145.0, 138.7, 135.3, 132.8, 128.4, 127.9, 126.1, 125.3, 120.7, 117.5, 86.9, 66.8, 62.3, 60.5, 53.7, 48.1, 43.6, 41.6, 20.8, 19.5, 18.2, 14.5, 12.5.

Asp(OtBu):-84%
¹H NMR (270 MHz, d₆-acetone): δ, 7.88 (d, 2, J=7.5 Hz), 7.69 (d, 2, J=7.3 Hz), 7.30–7.45 (dt, 4), 7.16 (d, 1, J=8.8 Hz), 4.84 (m, 1), 4.31 (m, 3), 3.87 (m,1), 3.39 (m, 2), 2.26 (m,1), 1.37 (s, 9).
¹³C NMR (67.8 MHz, d₆-acetone): δ, 170.4, 155.5, 143.8, 140.7, 127.5, 127.0, 125.1,120.0, 79.6,65.2, 62.9, 50.2, 46.7, 27.6.

Asn:-56%
¹H NMR (270 MHz, d₆-acetone): δ, 7.96, 7.88 (s, d, 2, J=7.5 Hz), 7.70, (m, 2), 7.31–7.43 (dt, 4), 4.34 (m, 4), 3.74 (m, 3), 3.62 (t, 1, J=4.6 Hz), 3.44 (m, 1), 2.52 (m, 2).
¹³C NMR (67.8 MHz, d₆-acetone): δ, 162.3, 155.6, 143.7, 140.6, 127.6, 125.2, 125.0, 120.0, 65.2, 54.1, 46.6, 46.5.

Gln:-86%
¹H NMR (270 MHz, d₆-acetone): δ, 7.96, 7.87 (s, d, 3, J=7.3 Hz), 7.70 (d, 2, J=7.1 Hz), 7.30–7.42 (dt, 4), 7.13 (d, 1, J=8.6 Hz), 4.74 (s, br, 1), 4.24 (m, 3), 3.43 (m, 5), 2.89 (s, 2), 2.73 (s, 2), 2.45 (m, 3), 2.03 (s, 3), 1.80 (m, 1), 1.59 (m,1).
¹³C NMR (67.8 MHz, d₆-acetone): δ, 162.2, 155.9, 143.9, 143.8, 140.7, 127.5, 126.9, 125.1, 124.7, 120.0, 65.1, 63.2, 52.0, 46.7, 35.7, 30.5, 29.9, 14.6.

Glu(OtBu):-71%
¹H NMR (270 MHz, d₆-acetone) δ, 7.88 (d, 2, J=7.3 Hz), 7.71 (d, 2, J=7.3 Hz), 7.31–7.45 (dt, 4), 7.05 (d, 1, J=8.6 Hz), 4.24 (m, 3), 4.02 (q, 1, J=7.1 Hz), 3.37 (m ,2), 2.20 (m, 2), 1.40 (s, 9).
¹³C NMR (67.8 MHz, d₆-acetone): δ, 172.1, 155.9, 143.9, 143.8, 140.7, 127.5, 126.7, 125.0, 120.0, 79.3, 65.1, 63.3, 52.1, 46.8, 31.5, 27.7, 26.3

Gly:-79%
¹H NMR (270 MHz, d₆-acetone): δ, 7.88 (d, 2, J=7.1 Hz), 7.69 (d, 2, J=7.1 Hz), 7.24–7.42 (m, 5), 4.66 (t, 1, J=5.5 Hz), 4.29 (m, 3), 3.38 (m, 2), 3.09 (q, 2, J=6 Hz).
¹³C NMR (67.8 MHz, d₆-acetone): δ, 156.2, 143.9, 140.7, 127.5, 127.0, 125.1, 120.0, 65.2, 59.8, 46.7, 43.0.

Ile:-72%
¹H NMR (270 MHz, d₆-acetone): δ, 7.88 (d, 2, J=7.1 Hz), 7.73 (d, 2, J=7.3 Hz), 7.29–7.42 (m, 4), 7.03 (d, 1, J=8.4 Hz), 4.51 (m, 1), 4.23 (m, 3), 3.42 (m, 3), 0.84 (m, 6).
¹³C NMR (67.8 MHz, d₆-acetone): δ, 156.1, 144.0, 143.8, 140.7, 127.5, 126.9, 125.2, 120.0, 65.1, 61.1, 57.0, 46.8, 35.3, 24.6, 15.4, 11.3.

Leu:-88%
¹H NMR (270 MHz, d₆-acetone): δ, 7.88 (d, 2, J=7.5 Hz), 7.71 (d, 2, J=7.3 Hz), 7.30–7.44 (dt, 4), 6.99 (d, 1, J=8.8 Hz), 4.24 (m, 3), 3.54 (m, 1), 3.35 (m, 2), 1.62 (m, 1), 1.30 (m, 2), 0.87 (m, 6).
¹³C NMR (67.8 MHz, d₆-acetone): δ, 155.9, 144.0, 143.8, 140.7, 127.5, 126.9, 125.2, 125.2, 120.0, 65.0, 64.1, 50.9, 46.8, 24.2, 23.4, 21.7.

Lys(Boc):-95%
¹H NMR (270 MHz, d₆-acetone): δ, 7.88 (d, 2, J=7.7 Hz), 7.72 (d, 2, J=7.0 Hz), 7.30–7.42 (dt, 4), 4.23 (m,3), 4.01 (q, 1, J=7.0 Hz), 2.89 (m, 2), 1.37 (m, 12), 1.17 (t, 2, J=7.1 Hz), 0.89 (d, 1, J=6.6 Hz).
¹³C NMR (67.8 MHz, d₆-acetone): δ, 155.9, 155.5, 143.9, 143.9, 143.3, 140.7, 127.7, 127.5, 127.0, 125.1, 120.0, 77.2, 65.1, 63.5, 59.7, 52.8, 46.7, 46.6, 29.5, 28.2, 22.8, 20.7, 18.7, 14.0.

Met:-52%
¹H NMR (270 MHz, d₆-acetone): δ, 7.91, 7.72 (m, d, 4, J=6.6 Hz), 7.34 (m, 4), 7.08 (d, 1, J=8,1 Hz), 6.75 (m, 1), 4.28 (m, 3), 3.42 (m, 3), 2.89 (s, 2), 2.74 (s, 2), 2.11 (m, 2), 1.81 (m, 1), 1.56 (m, 1).
¹³C NMR (67.8 MHz, d₆-acetone): δ, 162.2, 155.9, 143.9, 140.7, 127.6, 127.0, 125.2, 120.0, 119.9, 65.2, 63.3, 52.6, 46.7, 26.8.

Phe:-94%
¹H NMR (270 MHz, d₆-acetone): δ, 7.87 (d, 2, J=7.3 Hz), 7.65 (m, 2), 7.24–7.41 (m, 10), 4.81 (t, 1, J=5.5 Hz), 4.16 (m, 3), 3.67 (m, 1), 3.39 (m, 2), 2.87 (dd, 1, J=4.9, 8.6 Hz), 2.67 (m, 1).
¹³C NMR (67.8 MHz, d₆-acetone): δ, 155.6, 143.8, 140.6, 139.2, 1291, 128.0, 127.5, 127.0, 125.8, 125.2, 125.1, 120.0, 65.1, 62.9, 54.6, 46.6.

Pro:-73%
¹H NMR (270 MHz, d₆-acetone): δ, 7.88 (d, 2, J=6.7 Hz), 7.65 (d, 2, J=7.3 Hz), 7.31–7.43 (dt, 4), 4.74 (m, 1), 4.30 (m, 3,), 3.73 (m, 1), 3.27 (m, 3,), 1.86 (m, 4), 1.17 (t, 1, J=7.1).
¹³C NMR (67.8 MHz, d₆-acetone): δ, 154.1, 143.9, 140.8, 127.6, 127.0, 125.0, 120.0, 66.4, 66.2, 61.8, 61.1, 59.7, 58.9, 58.3, 46.8, 46.3, 27.7, 26.9, 23.2, 22.4, 20.7, 14.0.

Ser(tBu):-76%
¹H NMR (270 MHz, d₆-acetone): δ, 7.88 (d, 2, J=7.5 Hz), 7.11 (d, 2, J=7.3 Hz), 7.30–7.45 (dt, 4), 6.99 (d, 1, J=8.1 Hz), 4.24, 3.74, 3.30–3.56 (m, m, m, 11), 1.12 (s, 9).
¹³C NMR (67.8 MHz, d₆-acetone): δ, 155.9, 144.0, 143.9, 140.8, 127.6, 127.1, 125.3, 125.3, 120.1, 72.4, 65.3, 60.7, 53.6, 46.8, 27.4, 18.9.

Thr(tBu ):
¹H NMR (270 MHz, d₆-acetone): δ, 7.90 (d, 2, J=7.3 Hz), 7.70 (d, 2, J=7.3 Hz), 7.28–7.44 (dt, 4), 6.89 (d, 1, J=8.1 Hz), 4.23 (m, 3), 3.68 (m, 1), 3.29 (m, 1), 2.73 (m, 1), 1,15 (m, 12).
¹³C NMR (67.8 MHz, d₆-acetone): δ, 155.6, 143.9, 143.7, 140.8, 127.5, 127.1, 125.2, 125.2, 120.2, 72.3, 65.3, 60.7, 53.6, 46.8, 27.3, 18.6, 17.9.

Trp:−89%

¹H NMR (270 MHz, d₆-acetone): δ, 10.81 (s, 1), 7.86 (d, 2, J=7.3 Hz), 7.67 (m, 3), 7.34 (m, 5), 6.96–7.14 (m, 4), 4.76 (t, 1, J=5.3 Hz), 4.24 (m, 3), 3.77 (m, 1), 3.41 (m, 2), 2.94, 2.5 (m, 2).

¹³C NMR (67.8 MHz, d₆-acetone): δ, 155.8, 143.9, 140.6, 136.1, 127.5, 127.5, 127.0, 125.2, 125.2, 123.1, 120.7, 112.0, 118.4, 118.1, 111.4, 111.2, 65.2, 62.8, 53.8, 46.7, 26.7.

Tyr(tBu):−88%

¹H NMR (270 MHz, d₆-acetone): δ, 7.87 (d, 2, J=7.3 Hz), 7.66 (d, 2, J=7.3 Hz), 7.31–7.41 (m, 4), 7.11 (m, 3), 6.82 (d, 2, J=8.2 Hz), 4.79, (t, 1, J=5.5 Hz), 4.13 (m, 3), 3.64 (m, 1), 3.38 (m, 1), 2.82 (dd, 1, J=4.8, 9.0 Hz), 1.19 (s, 9).

¹³C NMR (67.8 MHz, d₆-acetone): δ, 155.6, 153.0, 143.9, 143.8, 140.6, 133.8, 129.5, 127.5, 126.9, 125.2, 125.1, 123.3, 112.0, 77.4, 65.2, 63.0, 54.6, 46.6, 28.4.

Val:−96%

¹H NMR (270 MHz, d₆-acetone) δ, 7.88 (d, 2, J=7.3 Hz), 7.73 (d, 2, J=7.3 Hz), 7.32–7.41 (dt, 4), 4.24 (m, 3), 3.89 9d, 1, J=6.2 Hz), 3.39 (m, 2), 0.86 (m, 6), 0.54 (t, 1, J=7.1 Hz).

¹³C NMR (67.8 MHz, d₆-acetone): δ, 156.3, 152.7, 143.9, 143.9, 140.7, 127.5, 126.9, 125.2, 120.0, 65.2, 61.4, 57.9, 46.8, 46.2, 28.4, 19.5, 18.6, 17.9.

APPENDIX 2

Data for Amino Alkyl Nitrophenyl Carbonates Incl Yield (%), NMR (d/ppm, d₆-acetone).

Ala:,

¹H NMR (270 MHz, d₆-acetone): δ, 8.32 (d, 2, J=9.1 Hz), 7.85 (d, 2, J=7.3 Hz), 7.71 (d, 2, J=7.3 Hz), 7.56 (d, 2, J=9.3 Hz), 7.30–7.41 (m, 7), 4.07–4.44 (m, 6), 1.24 (d,3, J=6.6 Hz).

¹³C NMR (67.8 MHz, d₆-acetone): δ, 206.4, 156.7, 156.5, 153.1, 146.1, 145.0, 144.9, 141.9, 128.3, 127.8, 126.0, 125.9, 123.1, 120.7, 72.1, 66.5, 47.7, 46.3, 17.1.

Arg(Pbf):

¹H NMR (270 MHz, d₆-acetone): δ, 8.13 (d, 2, J=4.9 Hz), 7.68 (d, 4, 7.7 Hz), 7.52 (d, 4, J=7.8 Hz), 7.24–7.37 (d, 10, J=9.3 Hz), 4.07–4.22 (m, 6), 3.87 (m, 9, 1), 3.37 (m, 2), 2.47 (d, 6, J=3.1 Hz), 1.26 (m, 12).

¹³C NMR (67.8 MHz, d₆-acetone): δ, 207.3, 160, 158.3, 157.7, 154.3, 147.4, 146.2, 146.1, 145.9, 143.1, 139.8, 136.5, 133.9, 129.5, 129.5, 128.9, 127.0, 124.1, 121.8, 121.8, 88.0, 80.2, 72.5, 67.9, 67.8, 66.1, 49.2, 49.1, 44.6, 29.7, 27.8, 20.5, 19.3, 19.2, 13.6.

Asp(OtBu):−74%

¹H NMR (270 MHz, d₆-acetone): δ, 8.31 (d, 2, J=9.5 Hz), 7.86 (d, 2, J=7.7 Hz), 7.54 (d, 2, J=9.1 Hz), 7.39 (m, 6), 4.37 (m, 4), 4.24 (m, 1), 4.06 (q, 1, J=6.9 Hz), 2.66 (m, 1), 1.46 (s, 9).

¹³C NMR (67.8 MHz, d₆-acetone): δ, 206.1, 170.3, 156.7, 153.2, 146.4, 145.0, 142.1, 128.5, 126.8, 126.0, 123.1, 120.8, 81.3, 70.7, 67.1, 48.2, 37.9, 28.2.

Asn:10%

¹H NMR (270 MHz, d₆-acetone): δ, 8.31 (d, 1, J=9.5 Hz), 8.14 (m, 2), 7.98 (m, 1), 7.83 (d, 1, J=7.3 Hz), 7.67 (t, 1, J=8.1 Hz), 7.53 (d, 1, J=9.2 Hz), 73.0–7.39 (dt, 3), 6.99 (m, 2), 4.41 (m, 2), 4.24 (m, 1), 2.94 (m, 2), 2.79 (s, 2).

¹³C NMR (67.8 MHz, d₆-acetone): δ, 206.3, 164.4, 163.1, 156.8, 156.6, 153.1, 144.9, 142.1, 141.6, 128.5, 127.9, 127.8, 126.1, 123.1, 120.8, 116.5, 79.2, 73.8, 69.6, 67.3, 48.0, 36.3, 20.6.

Gln:−17%

¹H NMR (270 MHz, d₆-acetone): δ, 8.31 (dd, 2, J=2.7 Hz, 5.5 Hz), 8.16 9dd, 1, J=2.2 Hz, 4.8 Hz), 7.83 (d, 2, J=7.3 Hz), 7.68 (m, 2), 7.27–7.54 (dt, m, 6), 7.03 (dd, 1, J=2.2 Hz, 4.8 Hz), 6.65 (d, 1, J=8.4 Hz), 4.21–4.46 (m, 5), 2.59 (m, 2), 1.92 (m, 2).

¹³C NMR (67.8 MHz, d₆-acetone): δ, 206.2, 157.1, 156.7, 153.3, 145.1, 144.9, 142.1, 128.5, 127.9, 126.8, 126.3, 123.1, 120.8, 116.6, 71.3, 66.9, 50.2, 48.1, 15.3.

Glu(OtBu):−76%

¹H NMR (270 MHz, d₆-acetone): δ, 8.30 (d, 2, J=9.1 Hz), 7.83 (d, 2, J=7.3 Hz), 7.69 (m, 2), 7.50 (d, 1, J=6.9 Hz), 7.39 (m, 4), 4.39 (m, 2), 4.26 (m, 2), 4.06 (m, 1), 2.38 (m ,1), 1.44 (s, 9).

¹³C NMR (67.8 MHz, d₆-acetone): δ, 206.2, 172.6, 157.1, 156.7, 153.2, 146.3, 145.1, 144.9, 142.1, 128.5, 127.9, 126.0, 123.1, 120.8, 80.5, 71.4, 66.9, 50.4, 49.0, 32.3, 27.0.

Gly:−30%

¹H NMR (270 MHz, d₆-acetone): δ, 8.29 (d, 2, J=9.1 Hz), 7.84 (d, 2, J=7.3 Hz), 7.68, (d, 2, J=7.3 Hz), 7.54, (d, 2, J=9.1 Hz), 7.31–7.4, (dt, 4), 4.39 (m, 4), 4.24, (t, 1, J=6.9 Hz), 3.56, (q, 2, J=5.1 Hz).

¹³C NMR (67.8 MHz, d₆-acetone): δ, 206.1, 157.4, 156.7, 153.3, 146.4, 145.1, 142.1, 128.5, 127.9, 126.3, 126.0, 123.1, 120.8, 68.8, 67.1, 48.1, 40.4.

Ile:−91%

¹H NMR (270 MHz, d₆-acetone): δ, 8.26 (d, 2, J=9.2 Hz), 7.82 (d, 2, J=7.5 Hz), 7.68 (m, 2), 7.50 (d, 2, J=9.1 Hz), 7.26–7.47 (dt, 3), 4.20–4.51 (m, 3), 3.92 (m, 1), 1.60 (m, 1), 1.19 (m, 1), 1.01, 0.92 (d, t, 3, J=6.8 Hz, 7.3 Hz).

¹³C NMR (67.8 MHz, d₆-acetone): δ, 206.3, 156.7, 153.3, 145.4, 144.1, 142.1, 128.5, 127.9, 127.8, 126.1, 126.0, 123.1, 120.8, 70.2, 66.9, 54.9, 54.8, 48.1, 36.7, 15.7, 11.4.

Leu:−88%

¹H NMR (270 MHz, d₆-acetone): δ, 8.27(d, 2, J=9.1 Hz), 7.83 (d, 2, J=7.3 Hz), 7.67 (t, 2, J=5.8 Hz), 7.51 (m, 2,), 7.29–7.49 (dt, 4), 4.38 (m, 3), 4.22 (m, 3), 1.77 (m, 1), 1.55 (m, 1), 1.37 (m, 1), 0.94 (m, 6).

¹³C NMR (67.8 MHz, d₆-acetone): δ, 205.4, 156.4, 155.9, 152.5, 145.6, 144.4, 144.2, 141.3, 127.7, 127.1, 127.1, 125.2, 122.3, 112.0, 71.3, 66.1, 48.2, 47.3, 24.5, 22.7, 21.3.

Lys(Boc):−64%

¹H NMR (270 MHz, d₆-acetone): δ, 8.30 (m ,1), 7.86 (m, 2), 7.52 (m, 2), 7.31–7.40 (m, 5), 4.23–4.37 (m, 3), 3.08 (m, 2), 1.39 (m, 14).

¹³C NMR (67.8 MHz, d₆-acetone): δ, 206.2, 157.2, 156.7, 146.4, 145.1, 145.0, 142.1, 128.5, 127.9, 126.8, 126.0, 123.7, 123.1, 120.8, 116.5, 78.4, 71.6, 67.3, 66.9, 50.9, 48.1, 48.0, 40.8, 40.7, 23.8.

Met:−13%

¹H NMR (270 MHz, d₆-acetone): δ, 8.29 (d, 2, J=9.1 Hz), 7.83 (d, 2, J=7.3 Hz), 7.69 (d, 2, J=7.3 Hz), 7.39 (m, 4), 4.17–4.42 (m, 3), 3.60–3.71 (m, 2).

¹³C NMR (67.8 MHz, d₆-acetone): δ, 205.5, 156.4, 144.4, 144.2, 141.3, 127.7, 127.7, 125.3, 125.3, 122.3, 120.0, 70.6, 66.0, 50.8, 47.4, 29.3, 29.1, 13.5.

Phe:−36.%

¹H NMR (270 MHz, d₆-acetone): δ, 8.28 (d, 2, J=9.1 Hz), 7.82 (d, 2, J=7.5 Hz), 7.62 (m, 2), 7.51, 7.38–7.18 (d, m, m, 10, J=9.1 Hz), 6.75 (d, 1, J=7.9 Hz), 4.46 (d, 1, J=6.59), 4.31 (m, 3), 4.18 (m, 1), 2.97 (m, 2).

¹³C NMR (67.8 MHz, d₆-acetone): δ, 206.2, 156.9, 156.7, 153.2, 146.4, 145.0, 142.0, 138.8, 130.1, 129.2, 128.4, 127.9, 127.3, 126.8, 126.0, 123.1, 120.7, 70.9, 66.9, 52.4, 48.0, 37.7.

Pro:−50.%

¹H NMR (270 MHz, d₆-acetone): δ, 8.30 (d, 2, J=8.8 Hz), 7.84, (d, 2, J=7.7 Hz), 7.67 (d, 2, J=7.7 Hz), 7.54 (d, 2, J=9.1 Hz), 7.31–7.40 (m, 4), 4.37, 4.29, 4.04 (m, 6), 3.45 (m, 2), 2.05 (m, 1), 1.96 (m, 3).

¹³C NMR (67.8 MHz, d₆-acetone): δ, 205.4, 155.9, 154.8, 152.5, 145.6, 144.4, 141.4, 127.7, 127.2, 125.2, 125.0, 122.4, 120.0, 69.0, 66.8, 55.9, 47.4, 27.4, 23.7, 20.0.

Ser(tBu):−53%

$^1$H NMR (270 MHz, d$_6$-acetone): δ, 8.31 (m, 1), 7.84 (d, 2, J=7.7 Hz), 7.69 (d, 2, J=7.5 Hz), 7.53 (d, 1, J=9.4 Hz), 7.42–7.31 (m, 5), 4.35 (m, 4), 3.65 (m, 4), 2.93 (d, 1, J=3.3 Hz), 1.17 (m, 11), 0.92 (d, 1, J=6.6 Hz).

$^{13}$C NMR (67.8 MHz, d$_6$-acetone): δ, 206.1, 156.9, 156.7, 153.2, 145.1, 142.1, 128.5, 128.4, 127.9, 126.1, 126.0, 120.7, 116.5, 79.2, 73.7, 73.4, 69.2, 67.0, 66.9, 62.4, 61.7, 54.2, 51.3, 48.1, 48.0, 47.9, 27.2, 19.2.

Thr(tBu):−45%

$^1$H NMR (270 MHz, d$_6$-acetone): δ, 8.30 (d, 2, J=9.1 Hz), 7.84 (d, 2, J=7.7 Hz), 7.68 (d, 2, J=7.3 Hz), 7.51 (d, 2, J=9.1 Hz), 7.28–7.49 (dt, 4), 6.4 (d, 1, J=9.2 Hz), 4.46, 4.39, 4.24 (dd, d, m, 5, J=4.8 Hz, 10.9 Hz, 7.3 Hz), 3.96–4.03 (m, 2), 1.21 (m, 12).

$^{13}$C NMR (67.8 MHz, d$_6$-acetone): δ, 205.4, 156.6, 155.9, 152.5, 145.6, 144.4, 144.2, 141.3, 127.7, 127.1, 125.2, 122.3, 120.0, 73.7, 68.3, 66.3, 65.9, 60.6, 55.4, 54.9, 54.1, 47.3, 18.7.

Trp:−64%

$^1$H NMR (270 MHz, d$_6$-acetone): δ, 8.30 (d, 2, J=9.1 Hz), 7.85 (d, 2, J=7.7 Hz), 7.69 (m, 3), 7.52 (d, 2, J=8.8 Hz), 7.24–7.42 (m, 2), 4.35 9m, 6), 3.08 (d, 2, J=4.0 Hz).

$^{13}$C NMR (67.8 MHz, d$_6$-acetone): δ, 206.4, 156.9, 156.4, 153.0, 146.1, 144.1, 144.8, 141.8, 137.4, 128.3, 127.7, 126.0, 125.7, 124.2, 123.1, 121.7, 120.6, 119.2, 119.0, 112.2, 70.8, 66.5, 51.5, 47.8, 27.5.

Tyr(tBu):−50%

$^1$H NMR (270 MHz, d$_6$-acetone): δ, 8.30 (d, 2, J=9.1 Hz), 7.84 (d, 2, J=7.7 Hz), 7.64 (d, 2, J=7.3 Hz), 7.52 (d, 2, J=9.1 Hz), 7.29–7.38 9m, 6), 6.90 (d, 2, J=8.42 Hz), 4.14–4.45 (m, 7), 2.89 (m, 4), 1.24 (s, 10).

$^{13}$C NMR (67.8 MHz, d$_6$-acetone): δ, 206.2, 156.9, 156.7, 155.1, 153.2, 146.3, 145.0, 142.0, 133.3, 130.8, 130.5, 128.4, 127.9, 126.0, 124.7, 123.1, 120.7, 78.4, 70.9, 66.9, 52.5, 52.4, 48.0, 37.0.

Val:−62%

$^1$H NMR (270 MHz, d$_6$-acetone): δ, 8.30 (d, 2, J=9.1 Hz), 7.83 (d, 2, J=7.3 Hz), 7.70 (d, 2, J=7.1 Hz), 7.54 (d, 2, J=9.2 Hz), 7.30–7.44 (m, 4), 4.10–4.44 (m, 6), 3.89 (d, 1, J=6.2 Hz), 0.86 (m, 6).

$^{13}$C NMR (67.8 MHz, d$_6$-acetone) δ NMR (67.8 MHz, d$_6$-acetone): d, 206.2, 156.4, 155.8, 152.3, 146.1, 145.3, 141.9, 128.5, 127.9, 127.1, 125.9, 123.1, 119.9, 71.2, 66.2, 48.1, 47.5, 24.3, 22.7.

What is claimed is:

1. A compound of formula (I):

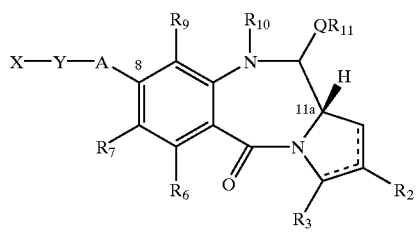

(I)

wherein:
X is selected from COOH, NHZ, SH, or OH, where Z is either H or an amine protecting group;
A is O, S, NH, or a single bond;
$R_2$ and $R_3$ are independently selected from: H, R, OH, OR, =O, =CH—R, =CH$_2$, CH$_2$—CO$_2$R, CH$_2$—CO$_2$H, CH$_2$—SO$_2$R, O—SO$_2$R, CO$_2$R, COR, CN and there is optionally a double bond between C1 and C2 or C2 and C3;

$R_6$, $R_7$, and $R_9$ are independently selected from H, R, OH, OR, halo, nitro, amino, and Me$_3$Sn;
$R_{11}$ is either H or R;
Q is S, O or NH;
$R_{10}$ is a nitrogen protecting group;
where R is selected from the group consisting of a lower alkyl group having 1 to 10 carbon atoms and optionally contains one or more carbon-carbon double or triple bonds, which may form part of a conjugated system; an alkyl-C(O)-alkyl group having 3 to 10 carbon atoms; an alkyl-O-alkyl group having 2 to 10 carbon atoms; an alkyl-S-alkyl group having 2 to 10 carbon atoms; an aralkyl group of up to 12 carbon atoms, wherein an alkyl group of the aralkyl group optionally contains one or more carbon-carbon double or triple bonds, which may form part of a conjugated system; and an aryl group of up to 12 carbon atoms; and where R is optionally substituted by one or more halo, hydroxy, amino, or nitro groups; and
Y is a divalent group selected from the group consisting of a lower alkylene group having 1 to 10 carbon atoms, which optionally contains one or more carbon-carbon double or triple bonds, which may form part of a conjugated system; an alkylene-C(O)- alkylene group having 3 to 10 carbon atoms; an alkylene-O-alkylene group having 2 to 10 carbon atoms; an alkylene-S-alkylene group having 2 to 10 carbon atoms; an aralkylene group of up to 12 carbon atoms wherein an alkylene portion of the aralkylene group optionally contains one or more carbon-carbon double or triple bonds which may form part of a conjugated system; or an arylene group of up to 12 carbon atoms; and wherein Y is optionally substituted by one or more halo, hydroxy, amino or nitro groups.

2. A compound according to claim 1, wherein R and HY are independently selected from lower alkyl group having 1 to 10 carbon atoms, or an aralkyl group, of up to 12 carbon atoms, or an aryl group, of up to 12 carbon atoms, optionally substituted by one or more halo, hydroxy, amino, or nitro groups.

3. A compound according to claim 2, wherein R and HY are independently selected from lower alkyl groups having 1 to 10 carbon atoms optionally substituted by one or more halo, hydroxy, amino, or nitro groups.

4. A compound according to claim 3, wherein R or HY are independently selected from unsubstituted straight or branched chain alkyl groups, having 1 to 10 carbon atoms.

5. A compound according to claim 1, wherein $R_{10}$ is selected from the group consisting of Fmoc, Nvoc, Teoc, Troc, Boc, CBZ, Alloc, and Psec.

6. A compound according to claim 1, wherein $R_7$ is selected from the group consisting of R, OH, OR and amino.

7. A compound according to claim 1, wherein Q is 0, and/or $R_{11}$ is H.

8. A compound according to claim 1, wherein $R_6$ and $R_9$ are H.

9. A compound according to claim 8, wherein $R_7$ is an alkoxy group.

10. A compound according to claim 1, wherein $R_2$ and $R_3$ are H.

11. A compound according to claim 1, wherein there is no double bond between C2 and C3.

12. A compound according to claim 1, wherein —Y—A— is an alkoxy chain.

* * * * *